United States Patent
Marcotte et al.

(10) Patent No.: US 11,435,358 B2
(45) Date of Patent: *Sep. 6, 2022

(54) SINGLE MOLECULE PEPTIDE SEQUENCING

(71) Applicant: BOARD OF REGENTS, THE UNIVERSITY OF TEXAS SYSTEM, Austin, TX (US)

(72) Inventors: Edward Marcotte, Austin, TX (US); Eric V. Anslyn, Austin, TX (US); Andrew Ellington, Austin, TX (US); Jagannath Swaminathan, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/491,797

(22) Filed: Oct. 1, 2021

(65) Prior Publication Data
US 2022/0091130 A1   Mar. 24, 2022

Related U.S. Application Data

(63) Continuation of application No. 17/491,485, filed on Sep. 30, 2021, which is a continuation of application No. 16/572,194, filed on Sep. 16, 2019, now Pat. No. 11,162,952, which is a continuation of application No. 15/510,962, filed as application No. PCT/US2015/050099 on Sep. 15, 2015, now Pat. No. 10,545,153, application No. 17/491,797, which is a continuation-in-part of application No. 17/384,118, filed on Jul. 23, 2021, which is a continuation of application No. 15/461,034, filed on Mar. 16, 2017, now Pat. No. 11,105,812, which is a continuation of application No. 14/128,247, filed as application No. PCT/US2012/043769 on Jun. 22, 2012, now Pat. No. 9,625,469.

(60) Provisional application No. 61/500,525, filed on Jun. 23, 2011, provisional application No. 62/050,462, filed on Sep. 15, 2014.

(51) Int. Cl.
*G01N 33/68* (2006.01)
*G01N 33/58* (2006.01)
*C07K 17/08* (2006.01)

(52) U.S. Cl.
CPC ......... *G01N 33/6824* (2013.01); *C07K 17/08* (2013.01); *G01N 33/582* (2013.01); *G01N 33/58* (2013.01); *G01N 33/6818* (2013.01); *G01N 2570/00* (2013.01)

(58) Field of Classification Search
CPC .... C07K 17/08; G01N 2570/00; G01N 33/58; G01N 33/582; G01N 33/68; G01N 33/6818; G01N 33/6824

USPC .............................................. 436/86, 89, 172
See application file for complete search history.

(56) References Cited

U.S. PATENT DOCUMENTS

| | | |
|---|---|---|
| 5,591,646 A | 1/1997 | Hudson et al. |
| 5,605,809 A | 2/1997 | Komoriya et al. |
| 5,902,723 A | 5/1999 | Dower et al. |
| 5,914,313 A | 6/1999 | Bouffard et al. |
| 6,156,527 A | 12/2000 | Schmidt et al. |
| 6,902,936 B2 | 6/2005 | Qui et al. |
| 7,329,505 B2 | 2/2008 | Marme |
| 7,468,258 B2 | 12/2008 | Owen |
| 8,569,481 B2 | 10/2013 | Koster et al. |
| 8,609,423 B2 | 12/2013 | Diller et al. |
| 8,778,685 B2 | 7/2014 | Diller et al. |
| 9,175,035 B2 | 11/2015 | Konno et al. |
| 9,435,810 B2 | 9/2016 | Havranek et al. |
| 9,470,680 B2 | 10/2016 | Gonzalez et al. |
| 9,566,335 B1 | 2/2017 | Emili et al. |
| 9,625,469 B2 | 4/2017 | Marcotte et al. |
| 9,689,868 B2 | 6/2017 | Kelts et al. |
| 9,983,211 B2 | 5/2018 | Diller et al. |
| 10,302,591 B2 | 5/2019 | Bogoev et al. |
| 10,473,654 B1 | 11/2019 | Mallick |

(Continued)

FOREIGN PATENT DOCUMENTS

| | | |
|---|---|---|
| WO | WO 2007/104219 | 9/2007 |
| WO | WO 2007/120805 | 10/2007 |

(Continued)

OTHER PUBLICATIONS

"The catalog for Molecular Probes", downloaded from: https://web.archive.org/web/20101217092018/http://www.mobitec.de/probes/docs/sections/0101.pdf, available 2010.

(Continued)

*Primary Examiner* — Maureen Wallenhorst
(74) *Attorney, Agent, or Firm* — Parker Highlander PLLC

(57) ABSTRACT

Identifying proteins and peptides, and more specifically large-scale sequencing of single peptides in a mixture of diverse peptides at the single molecule level is an unmet challenge in the field of protein sequencing. Herein are methods for identifying amino acids in peptides, including peptides with unnatural amino acids. In one embodiment, the N-terminal amino acid is labeled with a first label and an internal amino acid is labeled with a second label. In some embodiments, the labels are fluorescent labels. In other embodiments, the internal amino acid is Lysine. In other embodiments, amino acids in peptides are identified based on the fluorescent signature for each peptide at the single molecule level.

21 Claims, 62 Drawing Sheets

Specification includes a Sequence Listing.

(56) References Cited

U.S. PATENT DOCUMENTS

| | | | |
|---|---|---|---|
| 10,481,162 B2 | 11/2019 | Emili et al. | |
| 10,545,153 B2 | 1/2020 | Marcotte et al. | |
| 11,105,812 B2* | 8/2021 | Marcotte | G01N 33/6824 |
| 11,162,952 B2* | 11/2021 | Marcotte | G01N 33/582 |
| 2002/0168682 A1 | 11/2002 | Goodlett et al. | |
| 2004/0053356 A1 | 3/2004 | Duewel et al. | |
| 2005/0003558 A1 | 1/2005 | Zuckermann et al. | |
| 2005/0020810 A1 | 1/2005 | Ternansky et al. | |
| 2008/0206141 A1 | 8/2008 | Johannesen | |
| 2008/0242838 A1 | 10/2008 | Peters et al. | |
| 2009/0264300 A1 | 10/2009 | Franch et al. | |
| 2010/0047170 A1 | 2/2010 | Denmeade et al. | |
| 2010/0233095 A1 | 9/2010 | Duan et al. | |
| 2011/0027300 A1 | 2/2011 | Ugurbil et al. | |
| 2012/0100559 A1 | 4/2012 | Hell et al. | |
| 2014/0024124 A1 | 1/2014 | Shinohara et al. | |
| 2014/0273004 A1 | 9/2014 | Havranek et al. | |
| 2014/0349860 A1 | 11/2014 | Marcotte et al. | |
| 2015/0087526 A1 | 3/2015 | Hesselberth | |
| 2015/0185199 A1 | 7/2015 | Joo | |
| 2016/0238612 A1 | 8/2016 | Sims | |
| 2017/0212126 A1 | 7/2017 | Emili et al. | |
| 2017/0242024 A1 | 8/2017 | Marcotte et al. | |
| 2017/0343545 A1 | 11/2017 | Hadrup et al. | |
| 2019/0145982 A1 | 5/2019 | Chee et al. | |
| 2020/0018768 A1 | 1/2020 | Marcotte et al. | |
| 2020/0123593 A1 | 4/2020 | Rothberg et al. | |
| 2020/0123594 A1 | 4/2020 | Rothberg et al. | |
| 2020/0124613 A1 | 4/2020 | Marcotte et al. | |

FOREIGN PATENT DOCUMENTS

| | | |
|---|---|---|
| WO | WO 2010/044892 | 4/2010 |
| WO | WO 2010/065322 | 6/2010 |
| WO | WO 2010/065531 | 6/2010 |
| WO | WO 2012/178023 | 12/2012 |
| WO | WO 2013/112745 | 8/2013 |
| WO | WO 2014/106957 | 7/2014 |
| WO | WO 2016/069124 | 5/2016 |
| WO | WO 2016/164530 | 10/2016 |
| WO | WO 2017/063093 | 4/2017 |
| WO | WO 2017/219027 | 12/2017 |
| WO | WO 2019/063827 | 4/2019 |
| WO | WO 2019/089836 | 5/2019 |
| WO | WO 2019/089846 | 5/2019 |
| WO | WO 2019/089851 | 5/2019 |
| WO | WO 2020/023488 A1 | 1/2020 |
| WO | WO 2020/037046 A1 | 1/2020 |
| WO | WO 2020/102741 | 5/2020 |

OTHER PUBLICATIONS

Aitken, C. E. et al. (2008) "An Oxygen Scavenging System for Improvement of Dye Stability in Single-Molecule Fluorescence Experiments()," *Biophysical Journal* 94(5), 1826-1835.

Altman, R. B. et al. (2012) "Enhanced photostability of cyanine fluorophores across the visible spectrum," *Nature Methods* 9(5), 428-429.

Axelrod, D. (1981) "Cell-substrate contacts illuminated by total internal reflection fluorescence," *Journal of Cell Biology* 89(1), 141.

Bailey and Shively, "Carboxy-Terminal Sequencing: Formation and Hydrolysis of C-Terminal Peptidylthiohydantoins," *Biochemistry*, 29(12):3145-3156, 1990.

Basle, E. et al. (2010) "Protein Chemical Modification on Endogenous Amino Acids," *Chemistry & Biology* 17(3), 213-227.

Bethell et al., "Kinetics and Mechanism of the Edman Degradation," *Chem. Comm.*, (0):189-190, 1965.

Billingsley, Daniel J. et al., "Single molecule studies of dna transcriptionusing atomic force microscopy." *Phys. Biol.* (2012) 9 021001.

Borgo et al., "Computer-Aided Design of a Catalyst for Edman Degradation Utilizing Substrate-Assisted Catalysis," *Protein Sci.*, 24(4):571-579, 2015.

Bradski, G. (2000) "Open CV: an open source computer vision library," Dr. Dobb's Journal of Software Tools.

Bradski, G. (2000) "OpenCV: an open source computer vision library," Dr. Dobb's Journal of Software Tools.

Brandt, M. (downloaded Feb. 18, 2016) Quenching processes, https://www.rose-hulman.edu/-brandt/Fluorescence/Quenching_processes.pdf.

Branton et al., "The Potential and Challenges of Nanopore Sequencing," *Nat. Biotechnol.*, 26(10): 1146-1153, 2008.

Braslavsky, I. et al. (2003) "Sequence information can be obtained from single DNA molecules," *Proceedings of the National Academy of Sciences of the United States of America* 100(7), 3960-3964.

Cang, H. et al. (2013) "Giant suppression ofphotobleaching for single molecule detection via the Purcell effect," *Nano Letters* 13(12), 5949-5953.

Cannon, B. et al. (2013) "A Dual-Mode Single-Molecule Fluorescence Assay for the Detection of Expanded CGG Repeats in Fragile X Syndrome," *Molecular Biotechnology* 53(1), 19-28.

Chalker, J. M. et al. (2009) "Chemical Modification of Proteins at Cysteine: Opportunities in Chemistry and Biology," *Chemistry—An Asian Journal* 4(5), 630-640.

Chang, "Manual Solid Phase Sequence Analysis of Polypeptides Using 4-N,N-Dimethylaminoazobenzene 4'-Isothiocyanate," *Biochim. Biophys. Acta*, 578(1):188-195, 1979.

Chen, et al. Reactivity of functional groups on the protein surface: development of epoxide probes for protein labeling. Journal of the American Chemical Society 125.27 (2003): 8130-8133.

Chen, X. et al. (2012) "An efficient and versatile approach for the preparation of a rhodamine B ester bioprobe library," *Dyes and Pigments* 94(2), 296-303.

Cline, G. W. et al. (1988) "Kinetics and mechanisms of the aminolysis of N-hydroxysuccinimide esters in aqueous bnffers," Journal of Organic Chemistry 53(15), 3583-3586.

Cockrill, S. L. et al. (2005) "Efficient micro-recovery and guanidination of peptides directly from MALDI target spots," *BioTechniques* 38(2), 301-304.

Colombani, Oliver et al., "Polymerization kinetics: monitoring monomer conversion using an internal standard and the key role of sample to." *J. Chem, Ed*, (2011) 88(1) p116-121.

Co-pending U.S. Appl. No. 17/155,298, inventors Marcotte; Edward et al., filed Jan. 22, 2021.

Cordes and Blum, "Opportunities and Challenges in Single-Molecule and Single-Particle Fluorescence Microscopy for Mechanistic Studies of Chemical Reactions," *Nat. Chem.*, 5(12):993-999, 2013.

Czaplyski, W. L. et al. (2014) "Substituent effects on the tum-on kinetics of rhodamine-based fluorescent pH probes," *Organic & Biomolecular Chemistry* 12(3), 526-533.

Declaration of Dr. Edward Marcotte filed in U.S. Appl. No. 14/128,247, filed Jul. 7, 2016.

Declaration of Dr. Edward Marcotte filed in U.S. Appl. No. 14/128,247, filed Sep. 2, 2016.

Declaration of Dr. Jagannath Swaminathan filed in U.S. Appl. No. 14/128,247, filed Jan. 26, 2016.

Dempsey et al., "Evaluation of Fluorophores for Optimal Performance in Localization-Based Super-Resolution Imaging." *Nat. Methods*, 8(12): 1027-1036, 2011.

Doll, et al. Visualization of Protein-Specific Glycosylation inside Living Cells. Angewandte Chemie International Edition 55.6 (2016): 2262-2266. Supporting Information.

Edman, P. (1949) "A method for the determination of amino acid sequence in peptides," *Archives of Biochemistry* 22(3), 475.

Edman, P. (1950) "Method for determination of the amino acid sequence in peptides," *Acta Chemica Scandinavica* 4, 283-293.

Edman, P. et al. (1967) "A Protein Sequenator," *European Journal of Biochemistry* 1(1), 80-91.

Eid, J. et al. (2009) "Real-time DNA sequencing from single polymerase molecules," *Science* 323(5910), 133-138.

Eliason, Robert et al., "Temperature effect on reaction rates." *J. Chem. Ed.* (1981) 58(4) p354.

Fredkin, E. (1960) "Trie memory," *Communications of the ACM* 3(9), 490-499.

(56) References Cited

OTHER PUBLICATIONS

Frey, B. L. et al. (2013) "Chemical derivatization of peptide carboxyl groups for highly efficient electron transfer dissociation," *Journal of the American Society for Mass Spectrometry* 24(11), 1710-1721.
Fukuzaki, Satoshi et al., "Adsorption of protein onto stainles steel surfaces." *J. Ferm. Bioeng.* (1995) 80(1) p6-11.
Garcia-Parajo, M. F. et al. (2001) "The nature of fluorescence emission in the red fluorescent protein DsRed, revealed by single-molecule detection," *Proceedings of the National Academy of Sciences* 98(25), 14392-14397.
Gilmore, Joshua M. et al., "N-terminal protein modification through a biomimetic transamination reaction." *Angew. Chem. Int. Ed.* (2006) 45 p5307-5311.
Gooley, A. A. et al. (1991) "Glycosylation sites identified by detection of glycosylated amino acids released from Edman degradation: The identification of Xaa-Pro-Xaa-Xaa as a motif for Thr-O-glycosylation," *Biochemical and Biophysical Research Communications* 178(3), 1194-1201.
Haab, B. B. (2006) "Applications of antibody array platforms," *Current Opinion in Biotechnology* 17(4), 415-421.
Han, K.-K. et al. (1985) "Current developments in stepwise edman degradation of peptides and proteins," *International Journal of Biochemistry* 17(4), 429-445.
Hanay, M. S. et al. (2012) "Single-protein nanomechanical mass spectrometry in real time," *Nature Nanotechnology* 7(9), 602-608.
Harris, T. D. et al. (2008) "Single-Molecule DNA Sequencing of a Viral Genome," *Science* 320(5872), 106-109.
Herbrink, P. (197 5) "Solid phase Edman degradation. High yield attachment of tryptic protein fragments to aminated supports," *FEBS Letters* 60(2), 313-316.
Hernandez, Erik T., et al. "Solution-phase and solid-phase sequential, selective modification of side chains in KDYWEC and KDYWE as models for usage in single-molecule protein sequencing." *New Journal of Chemistry* 41.2 (2017): 462-469.
Hoebe, R. A. et al., (2007) "Controlled light-exposure microscopy reduces photobleaching and phototoxicity in fluorescence live-cell imaging," *Nature Biotechnology* 25(2), 249-253.
Horton, H. R. et al. (1965) "A Highly Reactive Colored Reagent with Selectivity for the Tryptophan Residue in Proteins. 2-Hydroxy-5-nitrobenzyl Bromidel," *Journal of the American Chemical Society* 87(5), 1126-1132.
Imakyure et al., "A Fluorogenic Reagent for Amino Acids in Liquid Chromatography, 4-(2-Cyanoisoindolyl)Phenylisothiocyanate," *Anal. Chim. Acta*, 291(1-2):197-204, 1994.
Inglis, "Chemical Procedures for C-Terminal Sequencing of Peptides and Proteins." *Anal. Biochem.*, 195(2): 183-96, 1991.
Ingolia, N. T. et al. (2009) "Genome-Wide Analysis in Vivo of Translation with Nucleotide Resolution Using Ribosome Profiling," *Science* 324(5924), 218-223.
Ireland et al., "Double Coupling Edman Chemistry for High-Sensitivity Automated Protein Sequencing," *J. Protein Chem.*, 16(5):491-93, 1997.
Isidro-Llobet, A. et al. (2009) "Amino Acid-Protecting Groups," *Chemical Reviews* 109(6), 2455-2504.
Jameson, David M. and Ross, Justin A, "Fluorescence polarization/anisotropy in diagnostics and imaging." *Chem. Rev.* (2010) 110 (5) 2685-2708.
Jin, S.-W. et al. (1989) "Study on New Edman-type Reagents," in Methods in Protein Sequence Analysis (Wittmann-Liebold, B., Ed.), pp. 34-41, Springer Berlin Heidelberg, Berlin, Heidelberg.
Joo, C. et al. (2008) "Advances in single-molecule fluorescence methods for molecular biology," *Annual Review of Biochemistry* 77, 51-76.
Julka, S. et al. (2004) "Quantification in Proteomics through Stable Isotope Coding: A Review," *Journal of Proteome Research* 3(3), 350-363.
Jungmann et al., "Quantitative Super-Resolution Imaging with QPAINT," *Nat. Methods*, 13(5):439 442, 2016.
Kelly, K. A. et al. (2008) "Targeted Nanoparticles for Imaging Incipient Pancreatic Ductal Adenocarcinoma," *PLoS Medicine* 5(4), e85.
Keough, T. et al. (2000) "Derivatization procedures to facilitate de novo sequencing of lysine-terminated tryptic peptides using postsource decay matrix-assisted laser desorption/ionization mass spectrometry," *Rapid Communications in Mass Spectrometry* 14(24), 2348-2356.
Kinraide, "Use of a Gouy-Chapman-Stern Model for Membrane-Surface Electrical Potential to Interpret Some Features of Mineral Rhizotoxicity," *Plant Physiol.*, 106(4):1583-1592, 1994.
Ko, B. J. et al. (2012) "Enhanced electron transfer dissociation of peptides modified at C-terminus with fixed charges," *Journal of American Society for Mass Spectrometry* 23(11), 1991-2000.
Koide, Y. et al. (2012) "Development of NIR Fluorescent Dyes Based on Si-rhodamine for in Vivo Imaging," *Journal of the American Chemical Society* 134(11), 5029-5031.
Krusemark, C. J. et al. (2011) "Complete chemical modification of amine and acid functional groups of peptides and small proteins," *Methods in molecular biology* (Clifton, NJ) 7 5 3, 10.1007/1978-1001-61779-61148-61772 61776.
Kuyama, H. et al., (2003) "An approach to quantitative proteome analysis by labeling tryptophan residues," *Rapid Communications in Mass Spectrometry* 17(14), 1642-1650.
Lakowicz, ed., "Mechanisms and Dynamics of Fluorescence Quenching," In: *Principles of Fluorescence Spectroscopy*, 331-351. Boston, MA: Springer US, 2006.
Laursen, R. A. (1971) "Solid-Phase Edman Degradation," *European Journal of Biochemistry* 20(1), 89-102.
Li, Z.-S. et al. (2013) "Synthesis and biological evaluation of nonsymmetrical aromatic disulfides as novel inhibitors of acetohydroxy acid synthase," *Bioorganic & Medicinal Chemistry Letters* 23(13), 3723-3727.
Lukina Vicius, G. et al. (2013) "A near-infrared fluoropbore for live-cell super-resolution microscopy of cellular proteins," *Nature Chemistry* 5(2), 132-139.
Macbeath, G. et al. (1999) "Printing Small Molecules as Microarrays and Detecting Protein-Ligand Interactions en Masse," *Journal of the American Chemical Society* 121 (34), 7967-7968.
MacDonald et al., "One-Step Site-Specific Modification of Native Proteins with 2-Pyridinecarboxyaldehydes," *Nat. Chem. Biol.*, 11(5):326-331, 2015.
Matsunaga et al., "Proton: A Major Factor for the Racemization and the Dehydration at the Cyclization/Cleavage Stage in the Edman Sequencing Method," *Anal. Chem.*, 68(17):2850-2856, 1996.
McAlpine, S. R. et al. (1999) "Visualizing Functional Group Distribution in Solid-Support Beads by Using Optical Analysis," *Chernistry—A European Journal* 5(12), 3528-3532.
Millington, C. R. et al. (1998) "Arvl hvdrazides as linkers for solid phase synthesis which are cleavable under mild oxidative conditions." *Tetrahedron Letters* 39(39), 7201-7204.
Miyashita et al., "Attomole Level Protein Sequencing by Edman Degradation Coupled with Accelerator Mass Spectrometry," *Proc. Natl. Acad. Sci.*, 98(8):4403-4408, 2001.
Moffett, J. R. et al. (2003) "Tryptophan and the immune response." *Immunology and Cell Biology* 81(4), 247-265.
Muramoto et al., "The Application of Fluorescein Isothiocyanate and High-Performance Liquid Chromatography for the Microsequencing of Proteins and Peptides," *Anal. Biochem.*, 141(2):446-450,1984.
Nagaraj, N. et al. (2011) "Deep proteome and transcriptome mapping of a human cancer cell line," *Molecular Systems Biology* 7, 548-548.
Niall, H. D. (1973) "[36] Automated edman degradation: The protein sequenator," *Methods in Enzymology* 27, 942-1010.
Nikon. (2010) Nikon microscopes educational literature, https://www.microscopyu.com/references/photobleaching.html.
Nivala, J. et al. (2013) "Unfoidase-mediated protein translocation through an a-hemolysin nanopore," *Nature Biotechnology* 31(3), 247-250.
Office Communication issued in GB1322371.4, dated Nov. 26, 2018.
Office Communication issued in GB1322371.4, dated Jul. 29, 2019.

(56) References Cited

OTHER PUBLICATIONS

Office Communication issued in GB1322371.4, dated Nov. 8, 2019.
Office Communication issued in GB1912227.4, dated Nov. 11, 2019.
Office Communication issued in U.S. Appl. No. 15/461,034, dated Jun. 29, 2018.
Office Communication issued in U.S. Appl. No. 15/461,034, dated Nov. 20, 2018.
Office Communication issued in U.S. Appl. No. 15/510,962, dated Dec. 6, 2018.
Office Communication issued in U.S. Appl. No. 15/510,962, dated May 3, 2019.
Office Communication issued in U.S. Appl. No. 15/510,962, dated Sep. 11, 2019.
Oquare, "Design and Synthesis of Peptide Nucleic Acid (PNA) Agents", Dissertation, Washington University, 2007.
PCT International Search Report of International Application No. PCT/US2012/043769 dated Oct. 4, 2012.
PCT/US19/46507 International Search Report dated Dec. 10, 2019.
PCT/US2019/042998 International Search Report dated Oct. 31, 2019.
Perron, Y. G. et al. (1961) "Derivatives of 6-Aminopenicillanic Acid. II. Reactions with Isocyanates, Isothiocyanates, and Cyclic Anhydrides," Journal of Organic Chemistry 26(9), 3365-3367.
Pickens et al., "Practical Considerations, Challenges, and Limitations of Bioconjugation via Azide-Alkyne Cycloaddition," *Bioconj. Chem.*, 29(3):686-701, 2018.
Pieroni et al. (1975) "Reaction of diazonium salt with tyrosine residues in polypeptides," *Die Makromolekulare Chemie* 176(11), 3201-3209.
Powell and Tempst, "Microflow-Based Automated Chemistries: Application to Protein Sequencing," *Anal. Chem.*, 73(4):776-786, 2001.
Previero, A. et al. (1973) "Solid phase sequential analysis: Specific linking of acidic peptides by their carboxyl ends to insoluble resins," *FEBS Letters* 33(1), 135-138.
Romond, E. H. et al. (2005) "Trastuzumab plus Adjuvant Chemotherapy for Operable HER2-Positive Breast Cancer," *New England Journal of Medicine* 353(16), 1673-1684.
Roper Scientific. (2015) Datasheet for 1-pentarnax camera, http://www.spectracore.coru/cameras/pdf/ipgeniii.pdf.
Rosenbaum, C. et al. (2001) "Solid phase synthesis of cyclic peptides by oxidative cyclative cleavage of an aryl hydrazide linker—synthesis of stylostatin 1," *Tetrahedron Letters* 42, 5677-5680.
Sawyers, C. L. (2008) "The cancer biomarker problem," *Nature* 452(7187), 548-552.
Scangarello, F. A. (2012) Application of mulivalent displays on metalloprotease-dependent cleavage of semaphorin 4d in synapse development, in Department of Biochemistry, Brandeis University.
Scoffone, E. et al. (1966) "Selective modification of the tryptophan residue in peptides and proteins using sulfenyl halides," *Biochemical and Biophysical Research Communications* 25(2), 170-174.
Scoffone, E. et al. (1968) "Sulfenyl halides as modifying reagents for polypeptides and proteins. I. Modification of tryptophan residues," *Biochemistry* 7(3), 971-979.
Song, L. et al. (1995) "Photobleaching kinetics of fluorescein in quantitative fluorescence microscopy," *Biophysical Journal* 68(6), 2588-2600.
Supplemental Search Report issued in European Application No. 15854171.4, dated Feb. 12, 2018.
Swaminathan, Jagannath, Alexander A. Boulgakov, and Edward M. Marcotte. "A theoretical justification for single molecule peptide sequencing." *PLoS computational biology* 11.2 (2015): e1004080.
Taylor, "Aminopeptidases: Structure and Function." *FASEB*, 7(2):290-298, 1993.

Thakur, S. S. et al. (2011) "Deep and Highly Sensitive Proteome Coverage by LC-MS/MS Without Prefractionation," *Molecular & Cellular Proteomics* 10(8).
The Scientist Solution Forum (2009), http://www.scientistsolutions.coru/tl1153-keratin+contamination.html.
The University of Cambridge. (2009) Michaelis-Menten equation, http://wwwjmg.ch.cam.ac.uk/tools/magnus/michmenten.html.
Thermo Scientific. (2005) "Thermo Scientific Pierce Cross-Linking Reagents Technical Handbook," 1-48.
Thoma et al., "The ABRF Edman Sequencing Research Group 2008 Study: Investigation into Homopolymeric Amino Acid N-Terminal Sequence Tags and Their Effects on Automated Edman Degradation." *J. Biomol. Tech.*, 20(4):216-225, 2009.
Tokeshi, Manabu et al., "Single and countable moleucle detection of non-fluorescent molecules in liquid phase." *J. Luminesce.* (1999) 83-84 p261-264.
Toseland, Christopher P. "Fluorescent labeling and modification of proteins." *Journal of chemical biology* 6.3 (2013): 85-95.
Tulla-Puche, J. et al. (2008) "The (classic concept of) solid support," in the power of functional resins in organic synthesis (Tulla-Puche, J., et al., Eds.), pp. 3-14, Wiley, Weinheim.
Tung et al., "Preparation of a Cathepsin D Sensitive Near-Infrared Fluorescence Probe for Imaging," *Bioconj. Chem.*, 10(5):892-896, 1999.
Tyler et al., "Evaluation of Oxford Nanopore's MinION Sequencing Device for Microbial Whole Genome Sequencing Applications," *Sci. Rep.*, 8(1):10931, 2018.
U.S. Appl. No. 14/128,247 Notice of Allowance dated Dec. 6, 2016.
U.S. Appl. No. 14/128,247 Office Action dated Mar. 9, 2016.
U.S. Appl. No. 14/128,247 Office Action dated Oct. 28, 2015.
U.S. Appl. No. 15/461,034 Office Action dated Jun. 29, 2018.
U.S. Appl. No. 15/461,034 Office Action dated May 8, 2020.
U.S. Appl. No. 15/461,034 Office Action dated Nov. 20, 2018.
U.S. Appl. No. 15/510,962 Notice of Allowance dated Sep. 11, 2019.
U.S. Appl. No. 16/572,194 Office Action dated Aug. 17, 2020.
U.S. Appl. No. 16/709,903 Office Action dated Dec. 30, 2020.
U.S. Appl. No. 16/709,903 Office Action dated Jul. 16, 2020.
U.S. Appl. No. 16/709,903 Office Action Feb. 5, 2020.
Ulbrich, M. H. et al. (2007) "Subunit counting in membrane-bound proteins," *Nature Methods* 4(4), 319-321.
Wainaina, M. N. et al. (2008) "Fluorescence detection of amino acids in the postcleavage conversions for manual sequencing of a peptide," Analytical Biochemistry 3 7 4(2), 423-425.
Wang, Tracy Y. et al. (2014) "The Covalent Trimethoprim Chemical Tag Facilitates Single Molecule Imaging with Organic Fluorophores," *Biophysical Journal* 106(1), 272-278.
Wittmann, V. et al. (2000) "Combinatorial Solid-Phase Synthesis of Multivalent Cyclic Neoglycopeptides," *Angewandte Chemie International Edition* 39(23), 4348-4352.
Yuan, L. et al. (2011) "A rational approach to timing the pKa values of rhodamines for living cell fluorescence imaging," *Organic & Biomolecular Chemistry* 9(6), 1723-1726.
Zervas, L. et al. (1963) "New Methods in Peptide Synthesis. I. Tritylsulfenyl and o-Nitrophenylsulfenyl Groups as N-Protecting Groups," *Journal of the American Chemical Society* 85(22), 3660-3666.
Zhao, Y. et al. (2014) "Single-molecule spectroscopy of amino acids and peptides by recognition tunnelling," *Nature Nanotechnology* 9(6), 466-473.
Zheng, Q. et al. (2014) "The Contribution of Reactive Oxygen Species to the Photobleaching of Organic Fluorophores," *Photochemistry and Photobiology* 90(2), 448-454.
Zheng, Q. et al. (2014) "Ultra-stable organic fluorophores for single-molecule research," *Chemical Society Reviews* 43(4), 1044-1056.
Office Communication issued in U.S. Appl. No. 16/709,903, dated Jan. 27, 2022.

\* cited by examiner

FIGURE 6
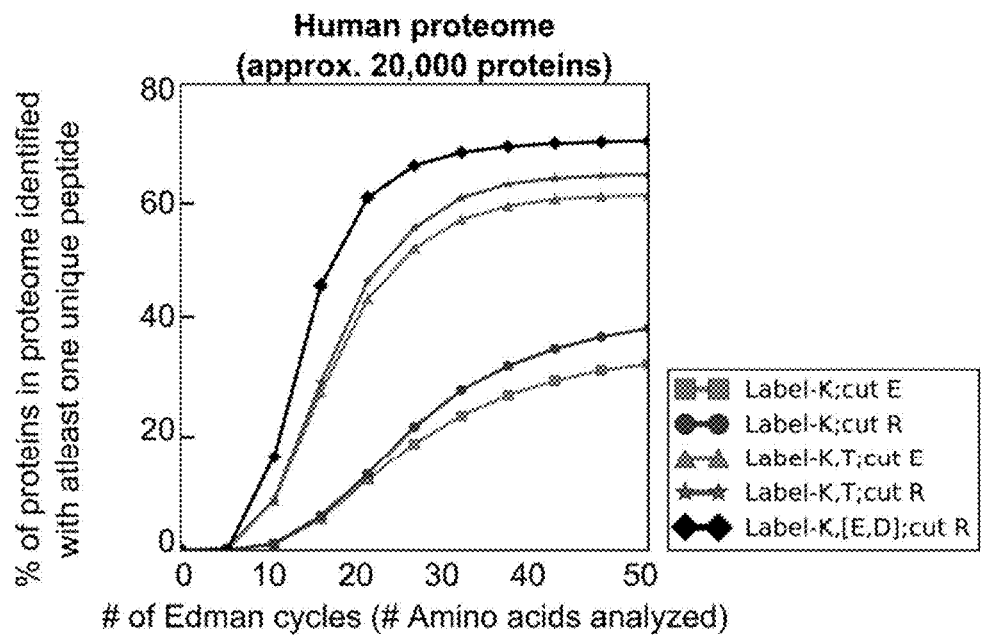
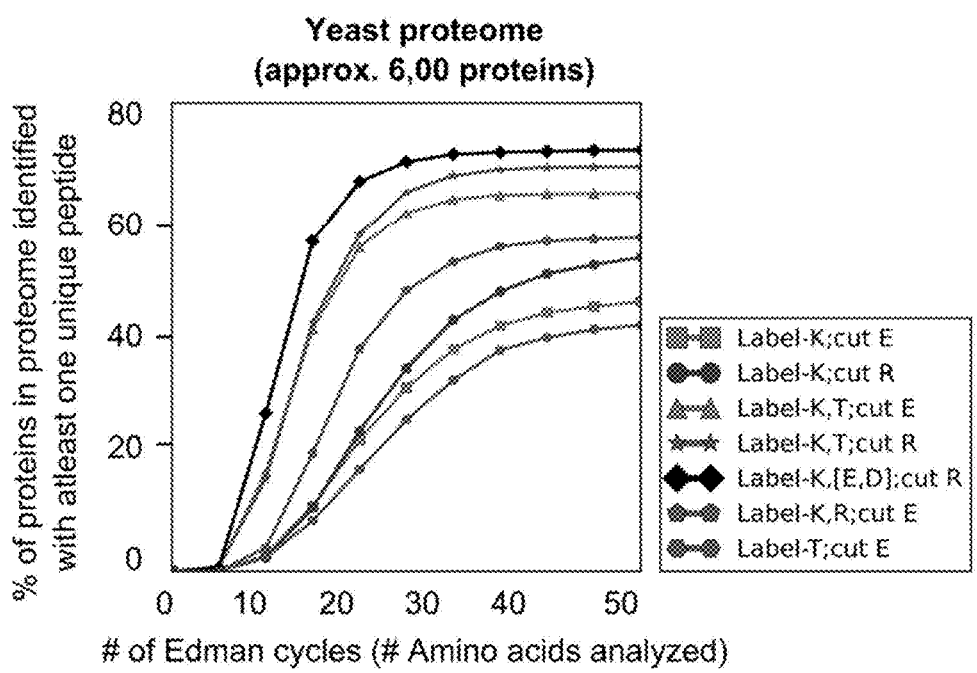

FIGURE 7
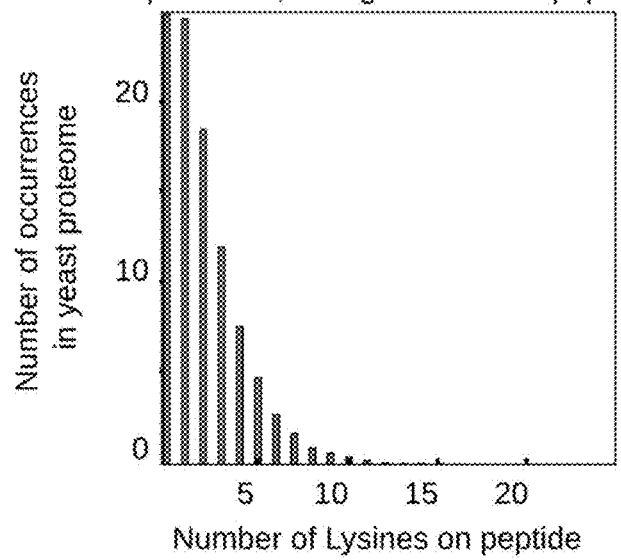
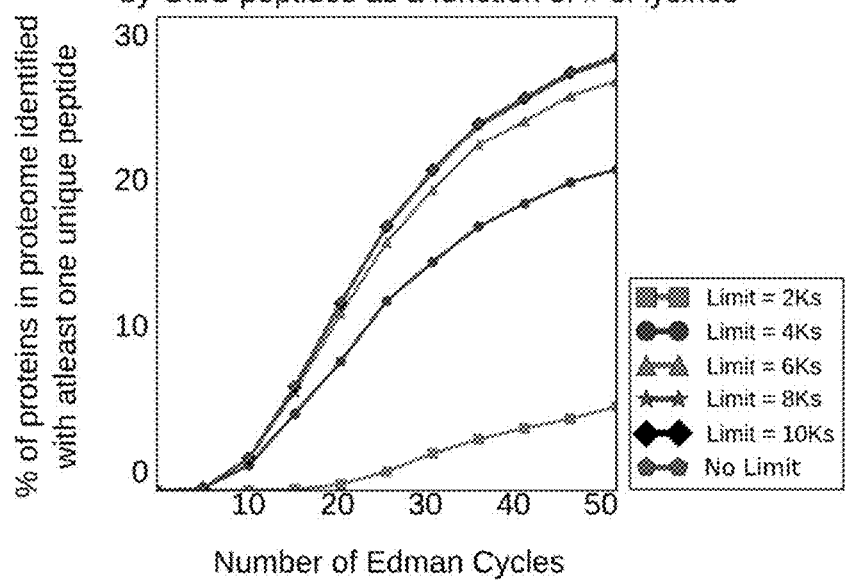

Structures of Cyanine Dyes Cy3 and Cy5

FIGURE 9
Scheme for synthesis of Cyanine dyes Cy3 and Cy5
Synthesis of indoles:
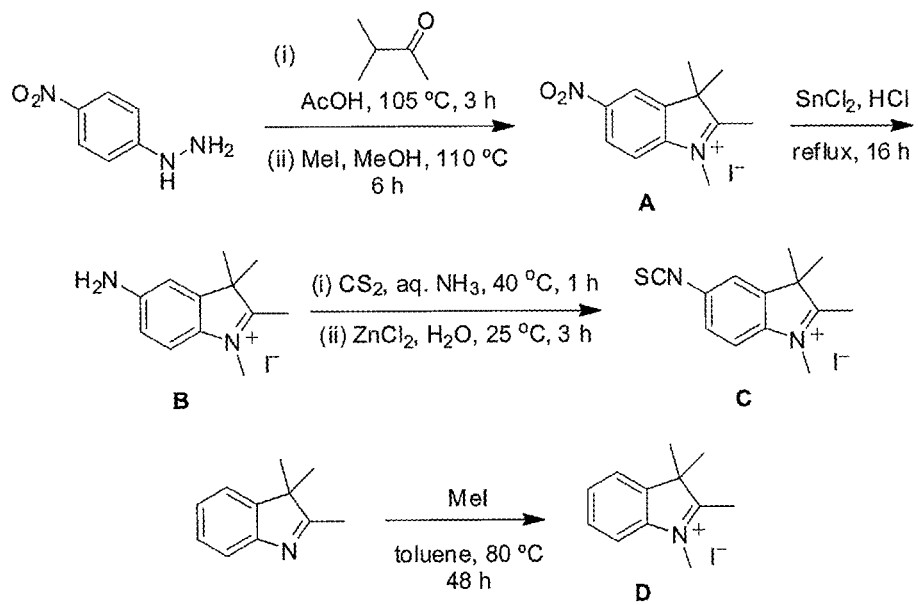
Synthesis of cyanine dyes Cy3 and Cy5:
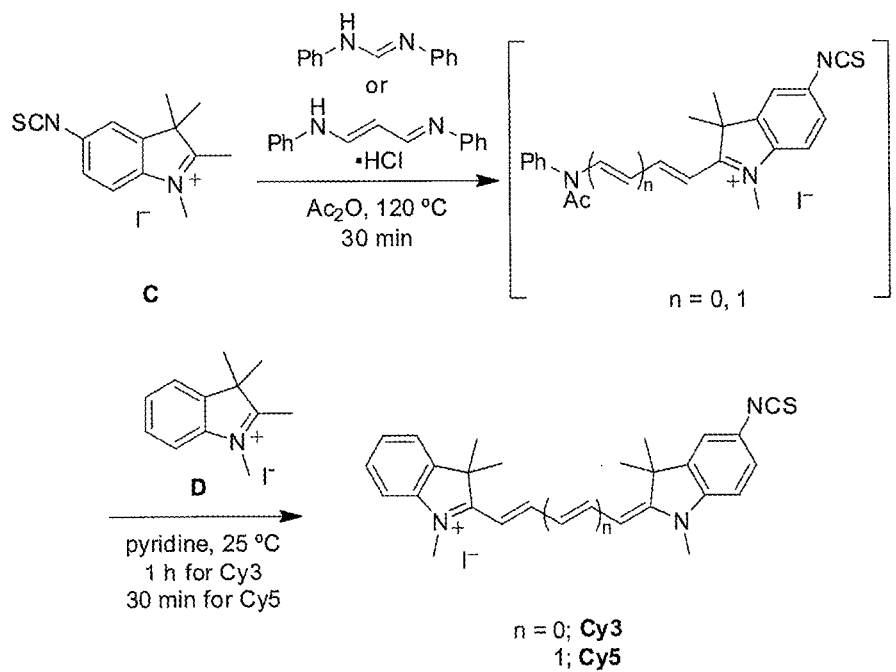
Procedures for preparing A, B, C, and D are reported in the literature.

Fluorescently labeled <u>lysines</u> (amine-reactive dye Hilyte 647)
Attached by <u>cysteines</u> to maleimide-PEG quartz surface Single fluorescently-labeled peptides Alternate fluorescent channel (here unused, shows low background)

FIGURE 19

A) Synthesis a) synthesize from the C-terminus to the N-terminus
    b) single pot combinatorial libraries of unnatural amino acids (X) via amide bonds (-)
    c) each 10-mer has a Cys at its C-terminus for sequencing purposes
    d) the union between the 10-mers is an alkene (=) from olefin metathesis

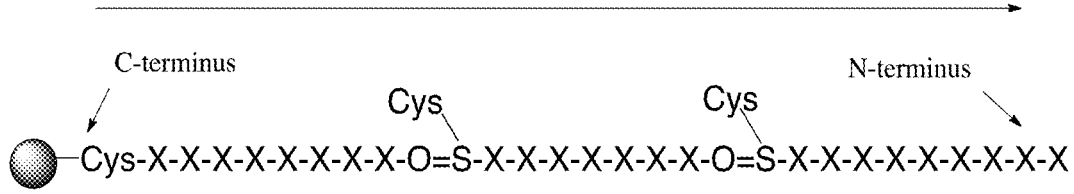

C-terminus      Cys      Cys      N-terminus

●—Cys-X-X-X-X-X-X-X-O=S-X-X-X-X-X-X-X-O=S-X-X-X-X-X-X-X-X

B) Clipping 30-mers into 10-mers clip from the resin    cleave 30-mer into three 10-mers
deprotect side chains   via addition of ethylene and
         ⟶     olefin metathesis ⟶

Cys-X-X-X-X-X-X-X-O
C-terminal 10-mer carries an
O as the first amino acid

Cys-S-X-X-X-X-X-X-X-O
Central 10-mer carries an
O as the first amino acid and
an S as the last amino acid Cys-S-X-X-X-X-X-X-X-X
N-terminal 10-mer carries
an S as the last amino acid C) Preparation for sequencing add all the
appropriate    Cys-X'-X'-X'-X'-X'-X'-X'-O
fluorophore
tags        Cys-S-X'-X'-X'-X'-X'-X'-X'-O
⟶

Cys-S-X'-X'-X'-X'-X'-X'-X'-X'
     C-terminals       N-terminals

D) Clipping via olefin metathesis and ethylene

Immobilization on Glass Cover Slip: Cysteine Immobilization

Immobilization on Glass Cover Slip

Use a protease that digests proteins at the carboxylates

FIGURE 25
Current Orthogonal Reactions
Boronic acid + α-hydroxyacid
Thiol + conjugate acceptor
Acyl hydrazine + aldehyde
Salen complex
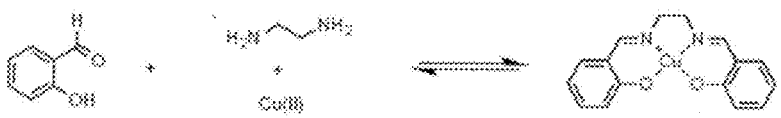

FIGURE 26
Alternative Orthogonal Reactions
Disulfide exchange
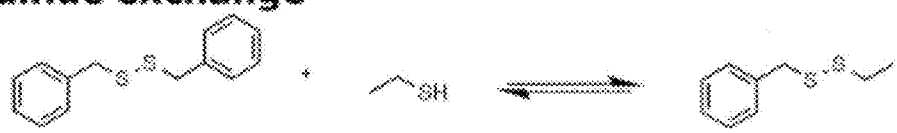
Diels-Alder reaction
Tripodal complex
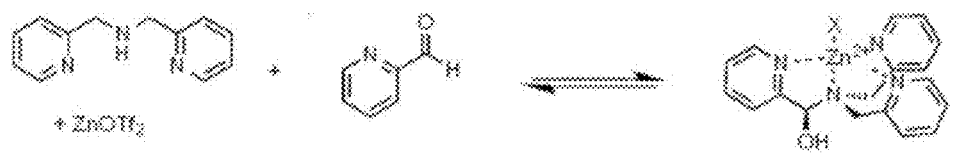
Copper terpyridine complex
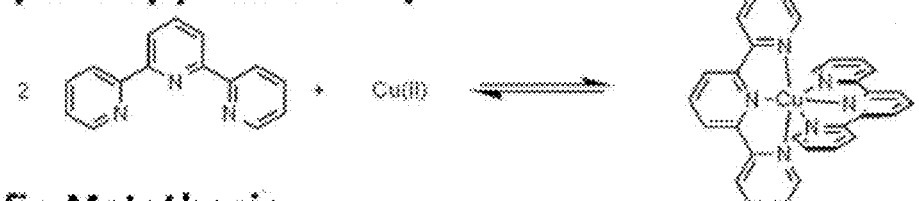
Olefin Metathesis
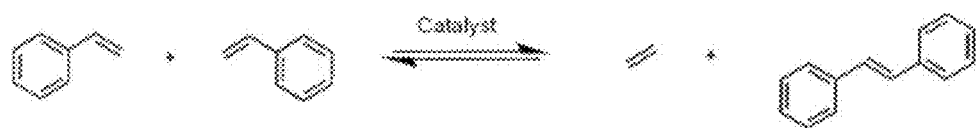

FIGURE 27
Alternative Side Chains
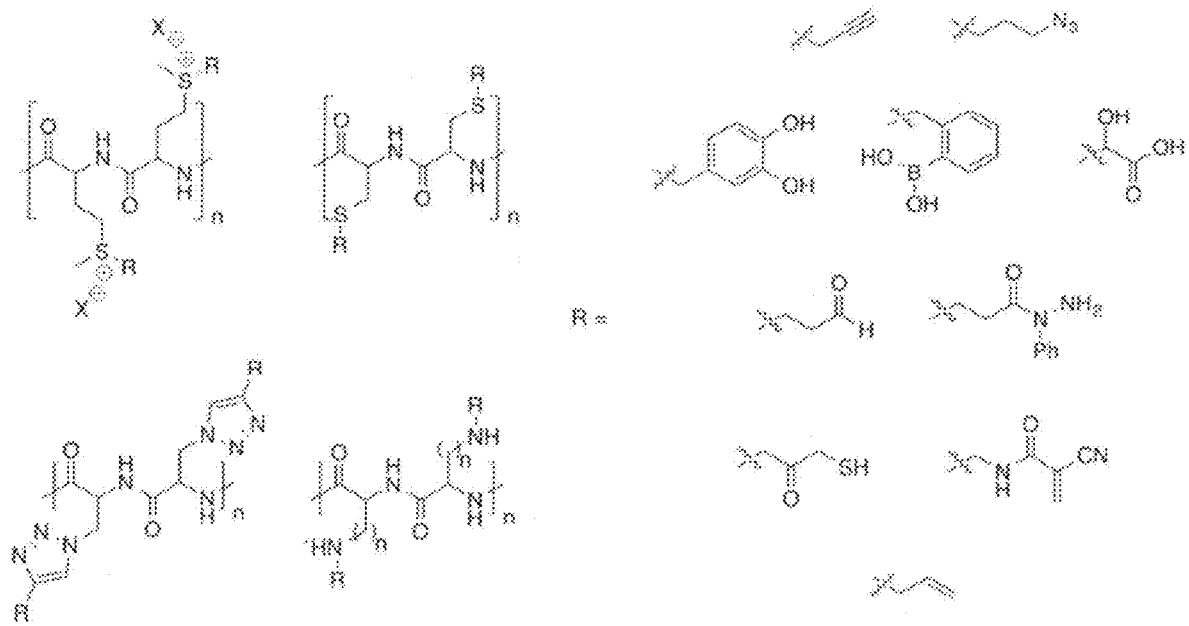
FIGURE 28
Methionine Alkylation
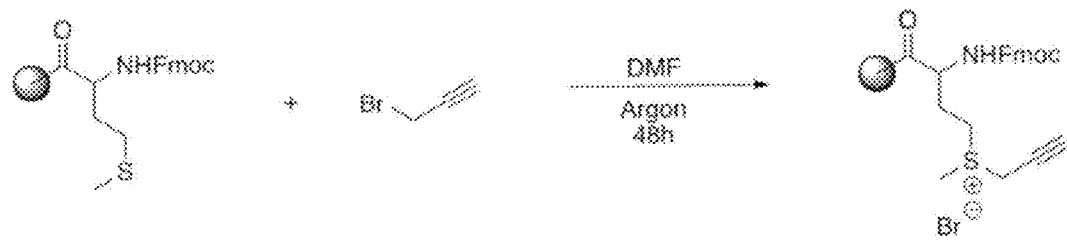
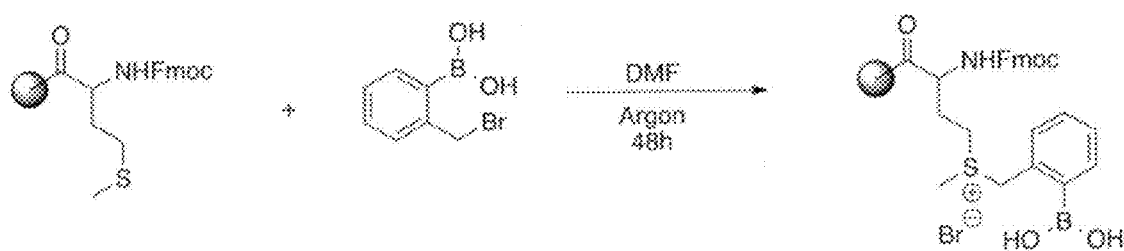

Simplified Alternating Polymers

Amino Acid Fluorophores

R = Conjugating handle

Conjugating Handle and Target Functional Groups

Screening Dyes

Use of Polymer For Nerve Agent Detoxification

FIGURES 36A-B

FIGURES 38A-B
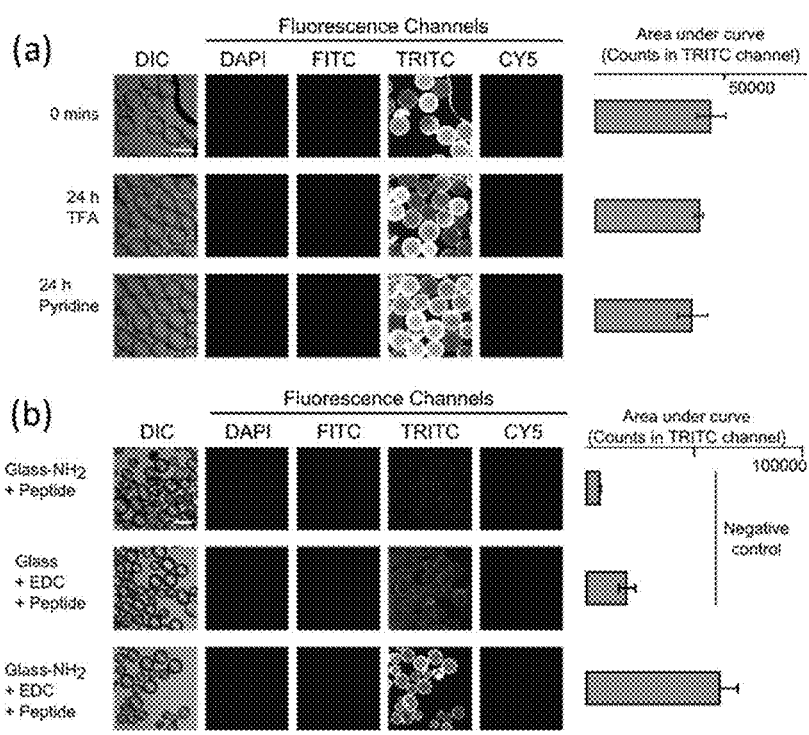
FIGURE 39
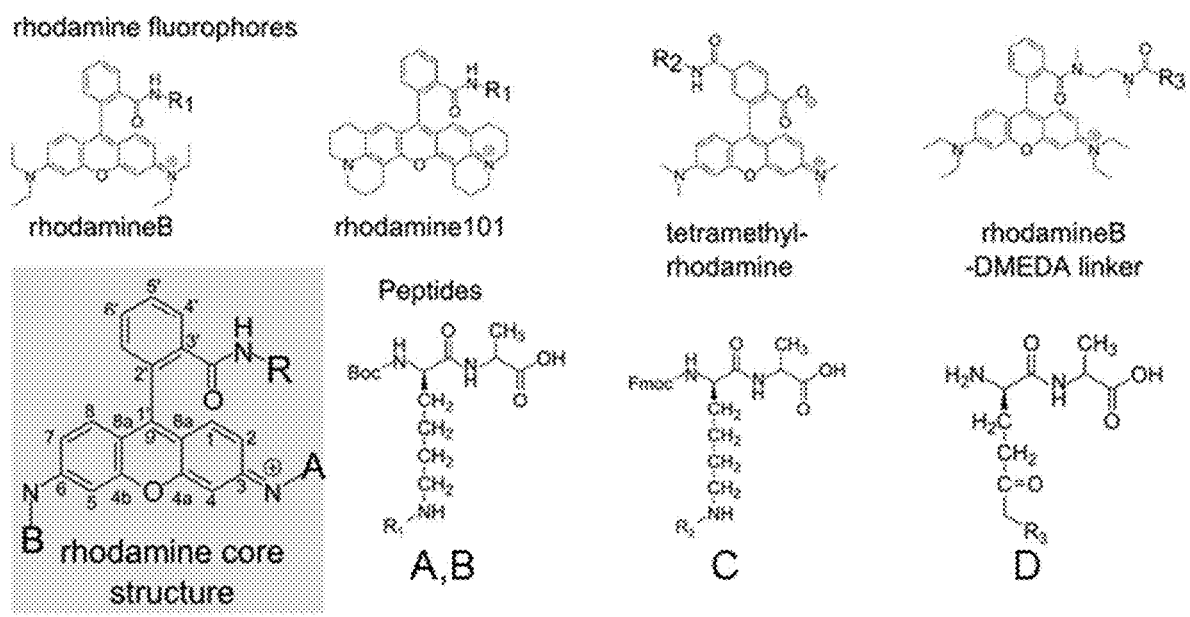

FIGURES 40A-B
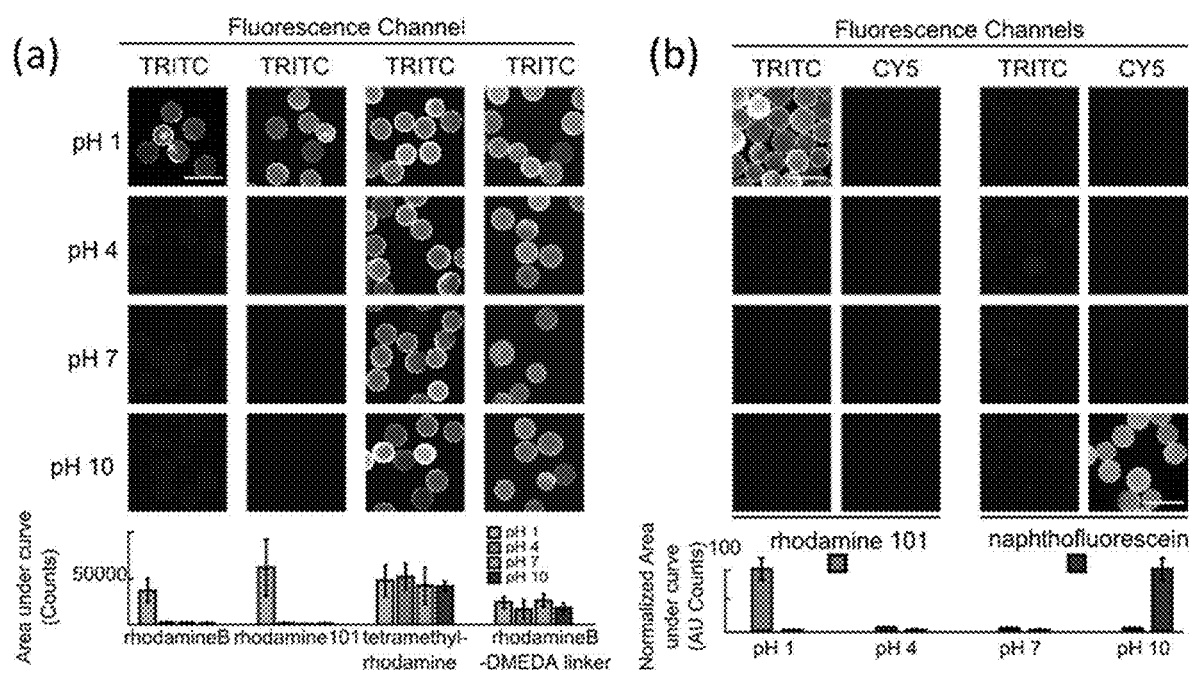

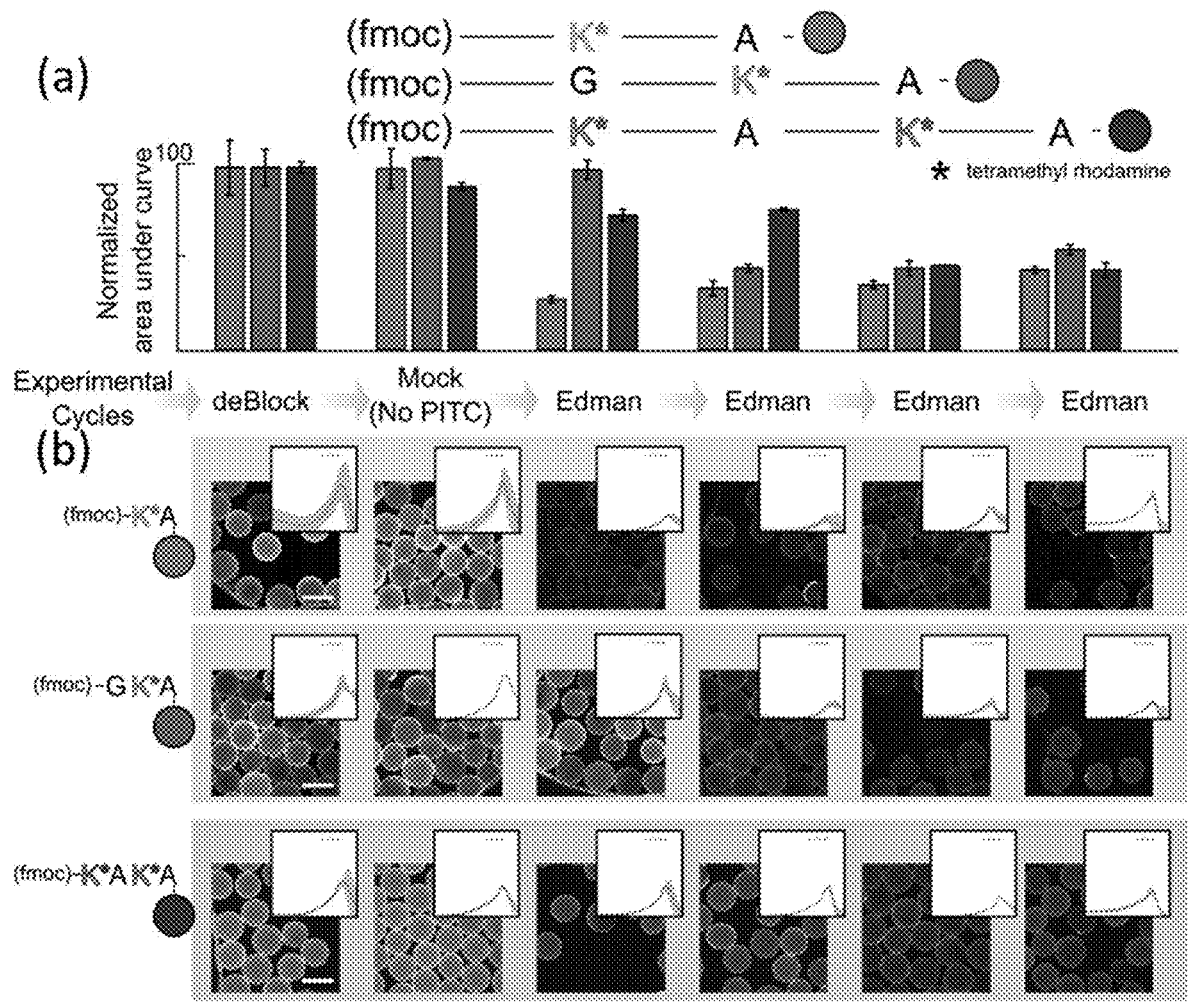
FIGURES 41A-B

FIGURES 42A-B
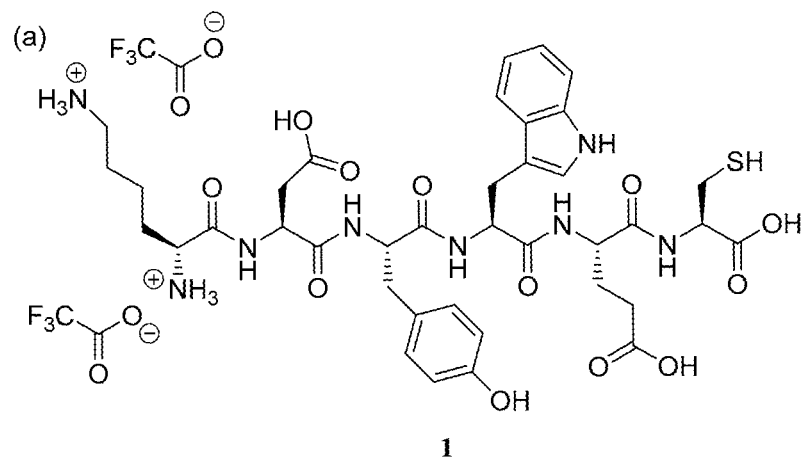
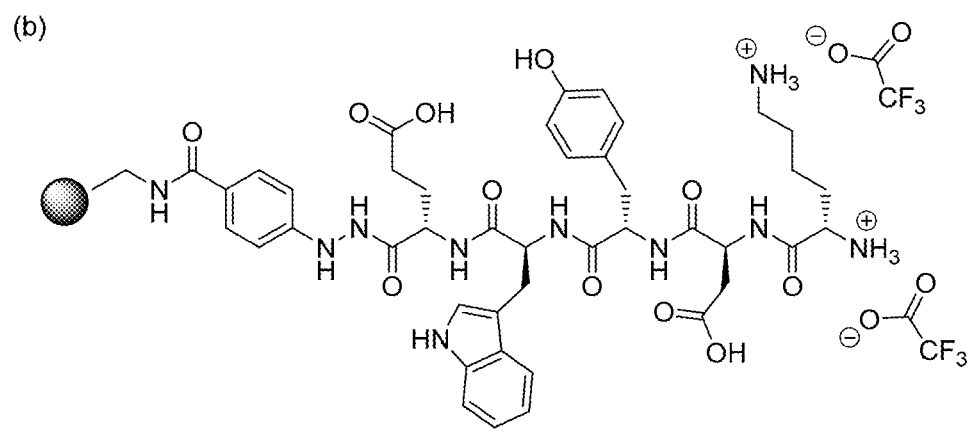

FIGURE 45
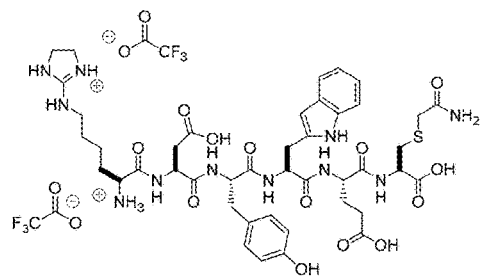
3
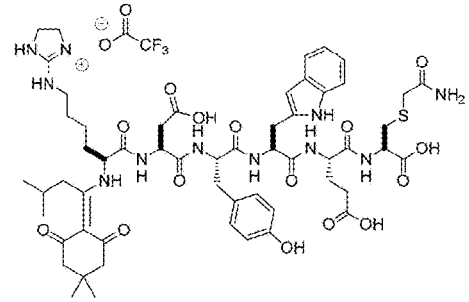
4
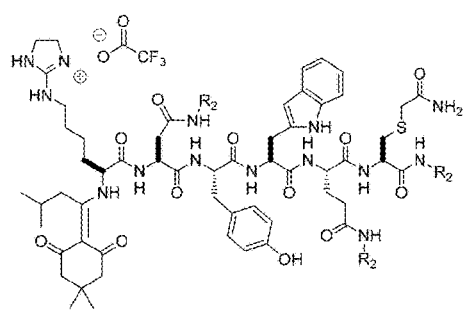
5 R$_2$ = -CH$_2$(C$_6$H$_5$)
6 R$_2$ = -CH$_2$CH$_2$CH$_2$N(CH$_3$)$_2$
7 R$_2$ = -CH$_2$CH(CH$_3$)$_2$
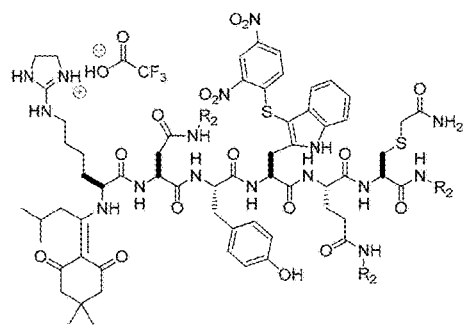
8 R$_2$ = -CH$_2$CH$_2$CH$_2$N(CH$_3$)$_2$
9 R$_2$ = -CH$_2$CH(CH$_3$)$_2$
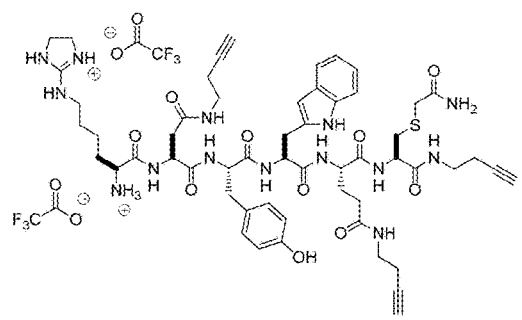
10

FIGURE 46A
Peptide 3
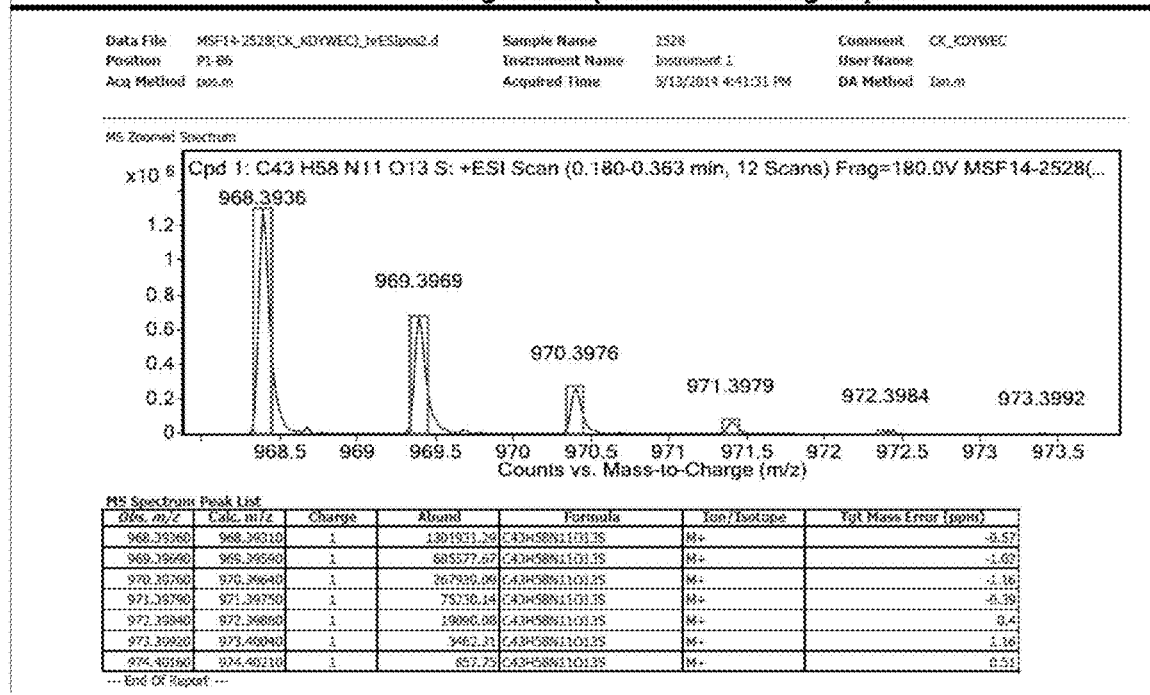
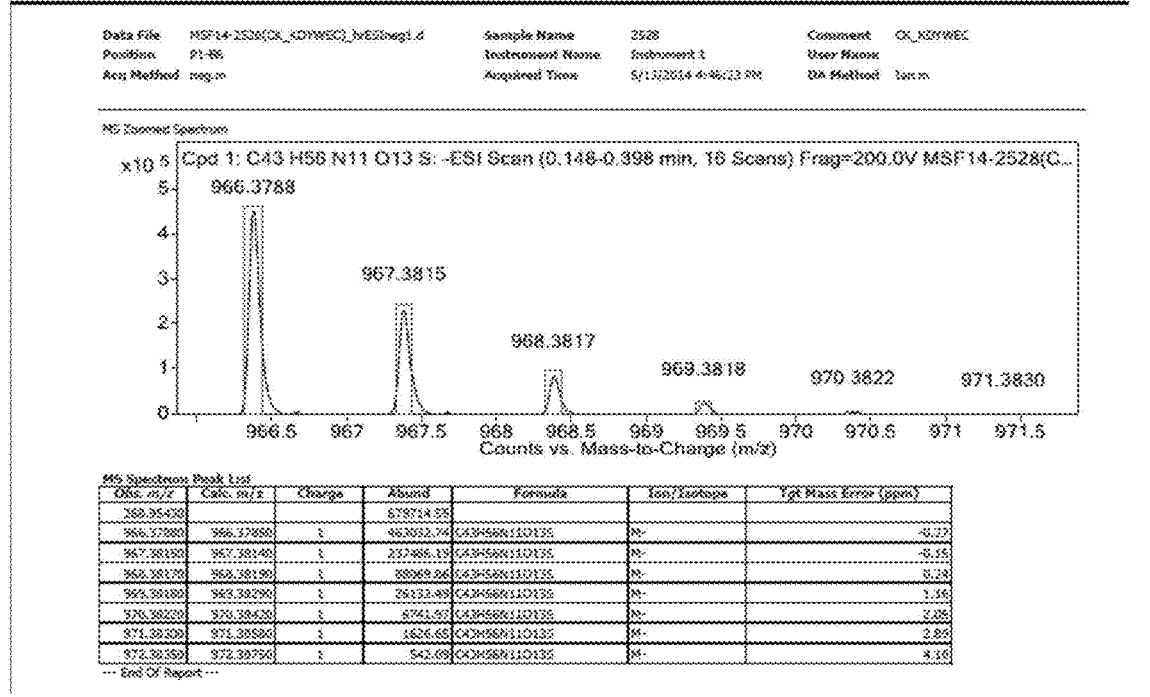

FIGURE 46A, Continued
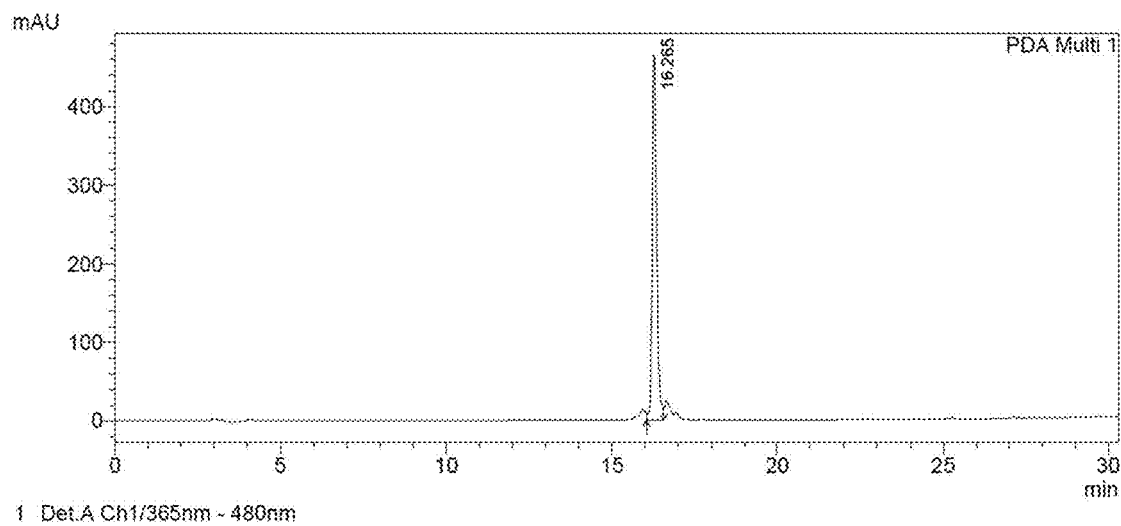
1 Det.A Ch1/365nm - 480nm
2 PDA Multi 1/254nm 4nm
FIGURE 46B
Peptide 4
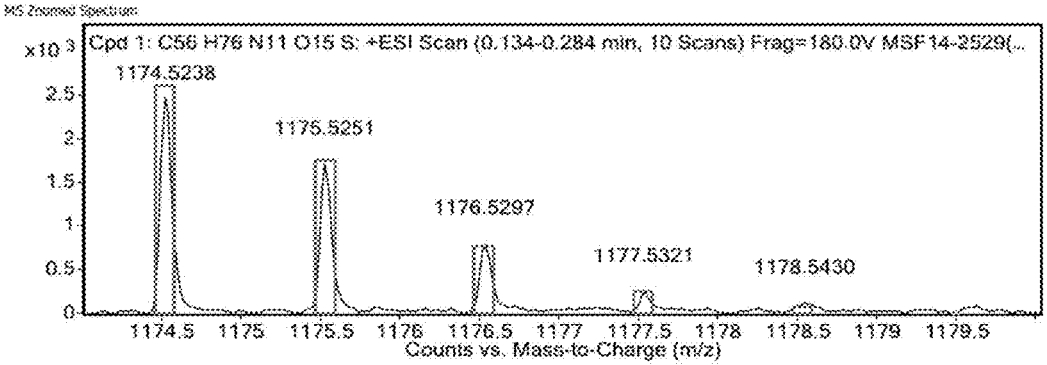

FIGURE 46B, Continued
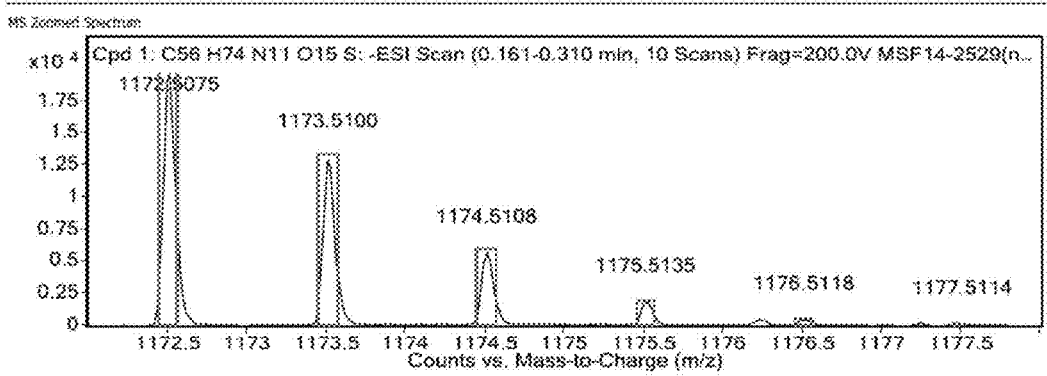
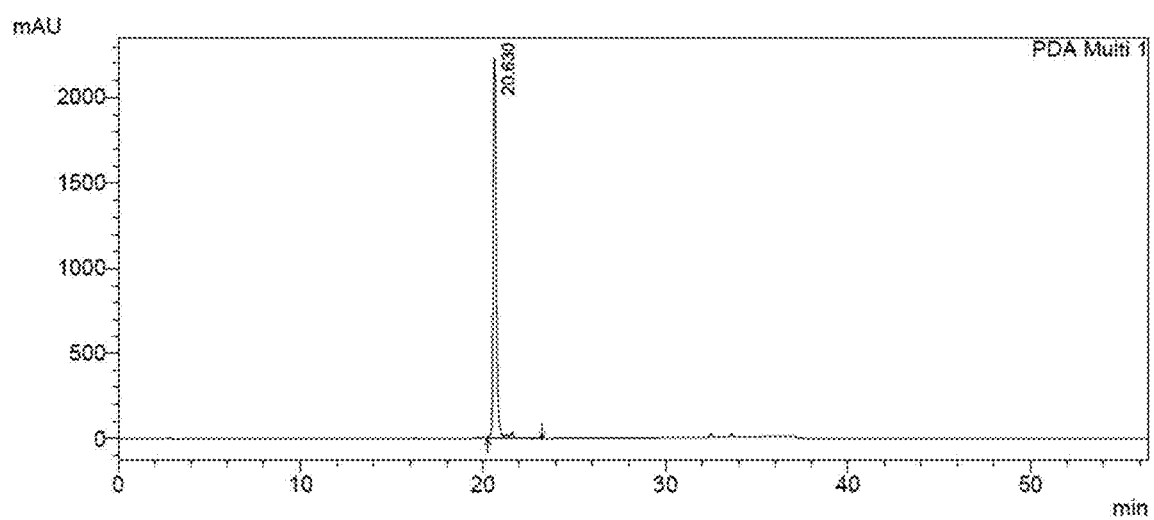
1  Det.A Ch1/365nm - 480nm
2  PDA Multi 1/254nm 4nm FIGURE 46C
Peptide 5
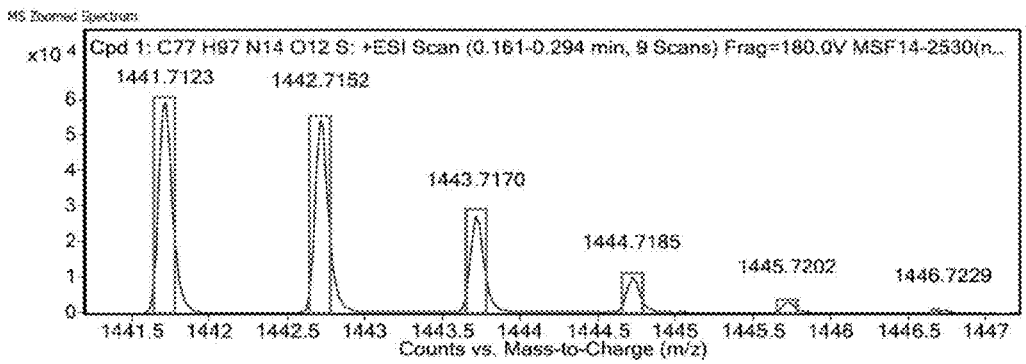
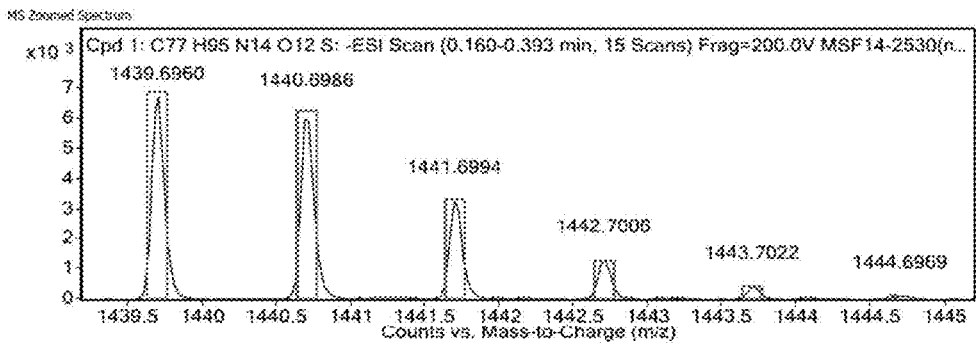

FIGURE 46C, Continued
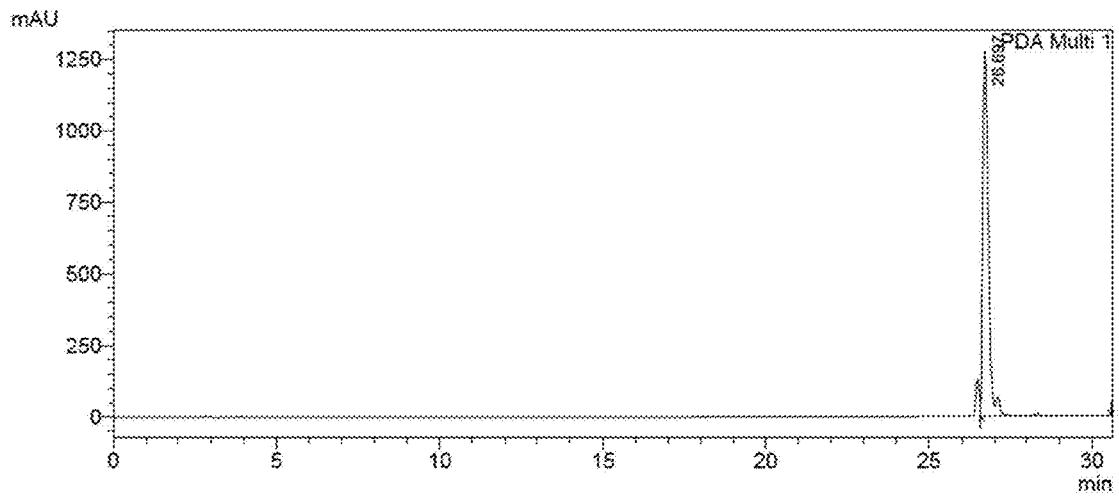
1 Det.A Ch1/365nm - 480nm
2 PDA Multi 1/254nm 4nm
FIGURE 46D
Peptide 6
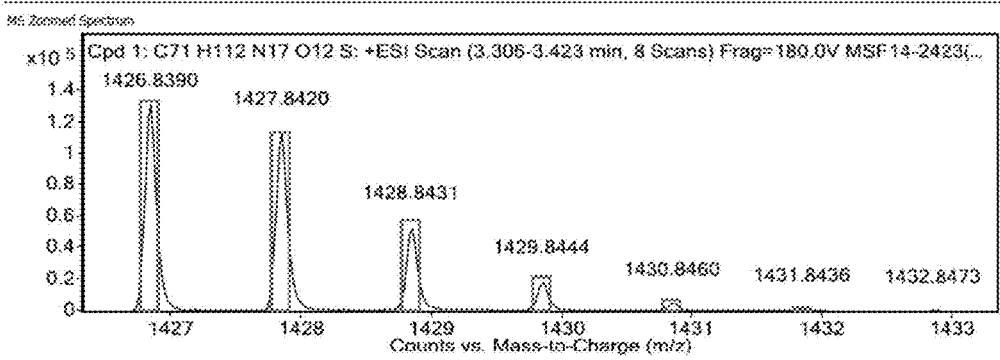

FIGURE 46D, Continued
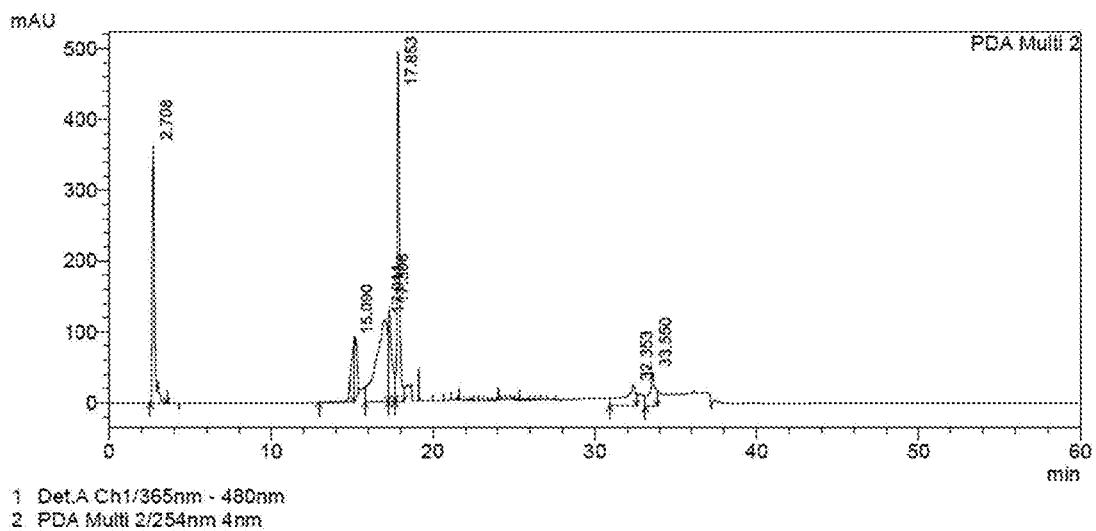
FIGURE 46E
Peptide 8
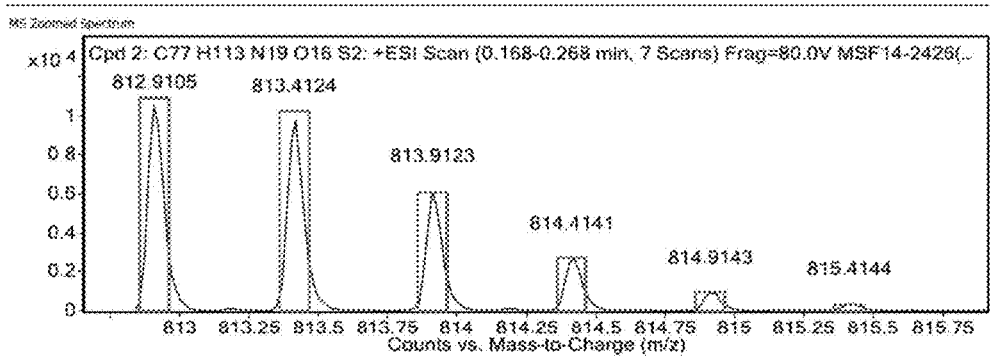

FIGURE 46E, Continued
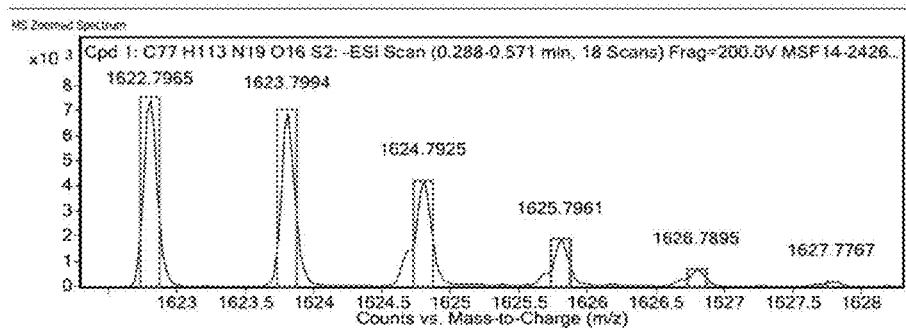
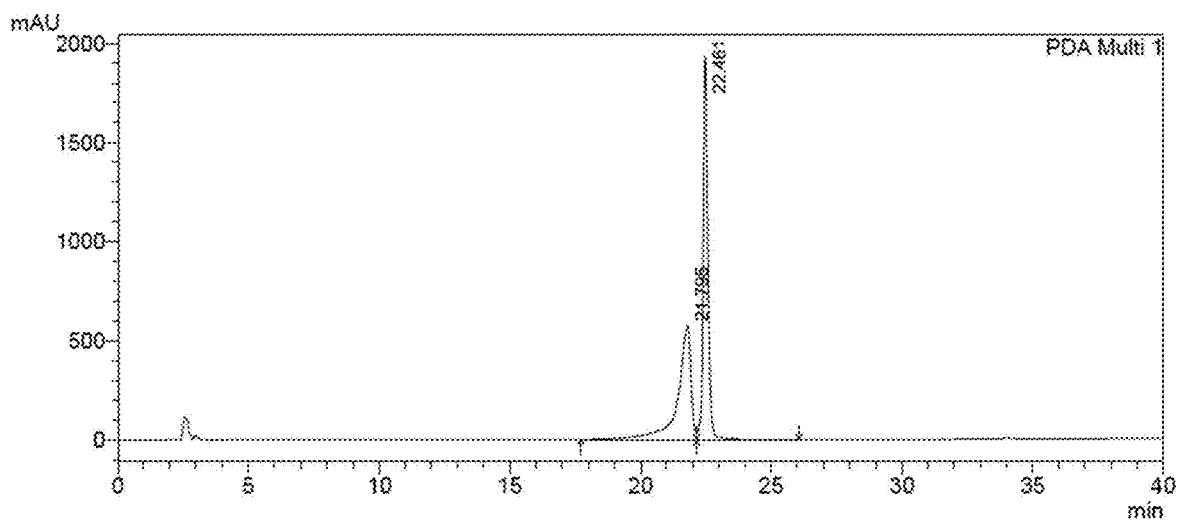

FIGURE 46F
Peptide 9
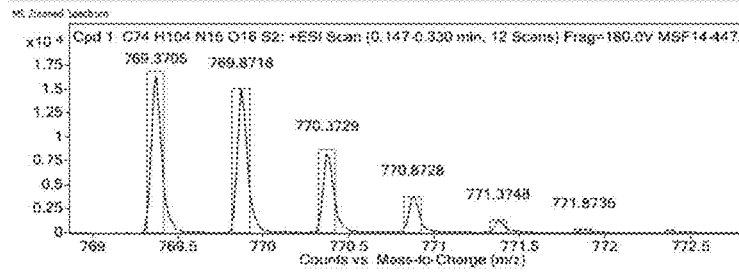
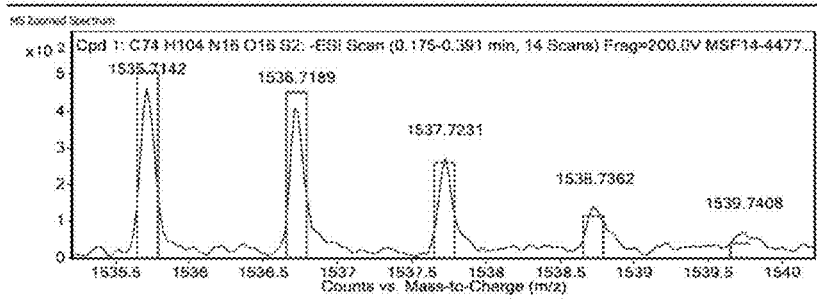

FIGURE 46F, Continued
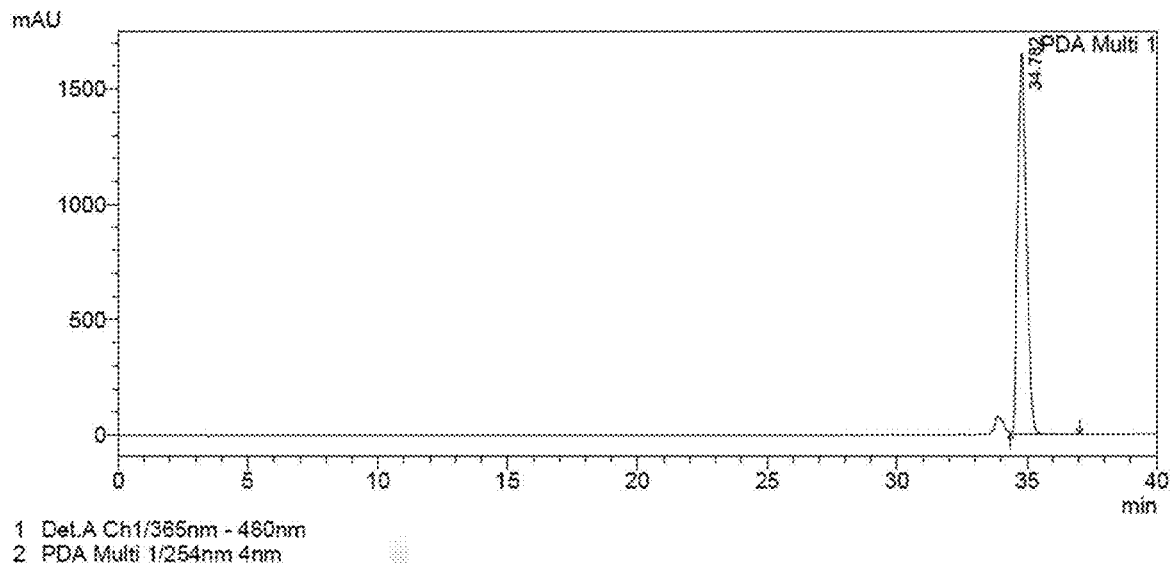
1  Det.A Ch1/365nm - 460nm
2  PDA Multi 1/254nm 4nm
FIGURE 46G
Peptide 10
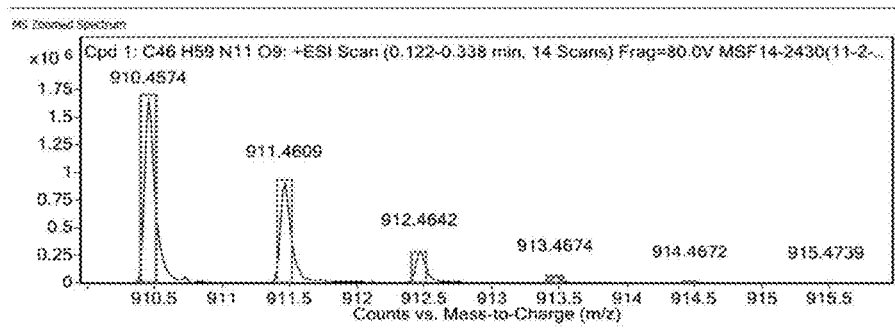

FIGURE 46G, Continued
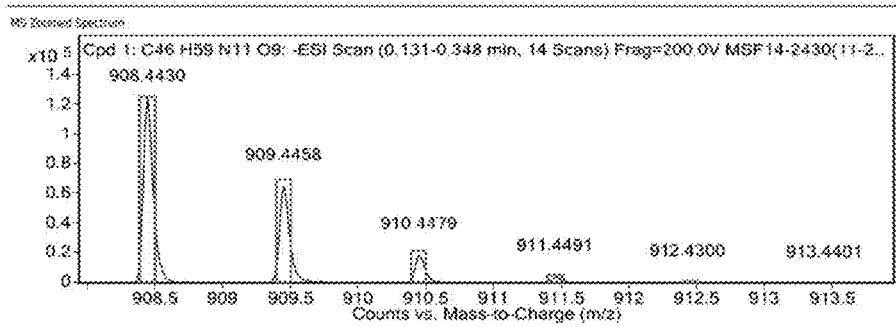
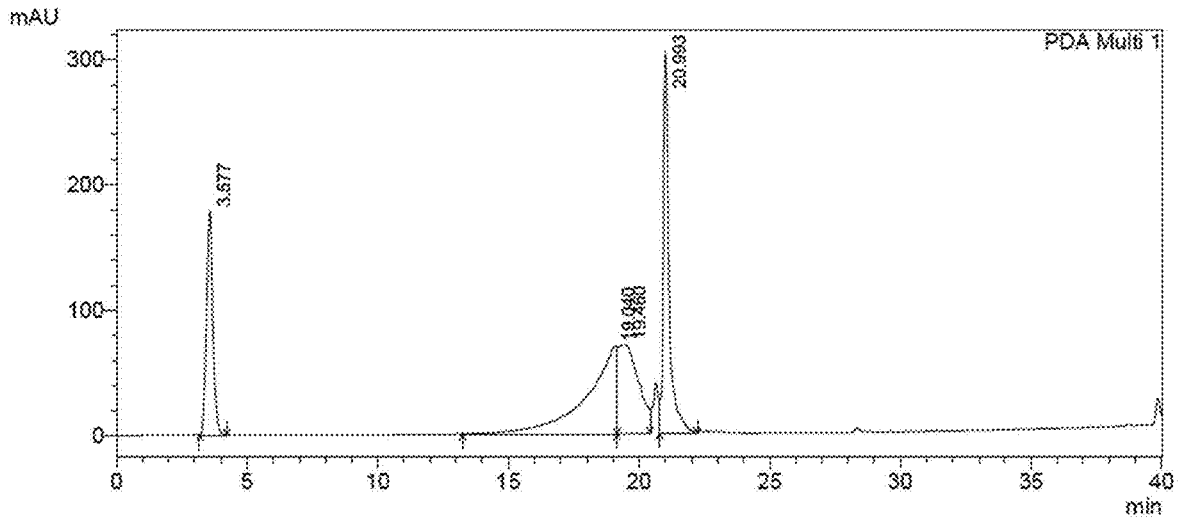

FIGURE 46H
Peptide 11
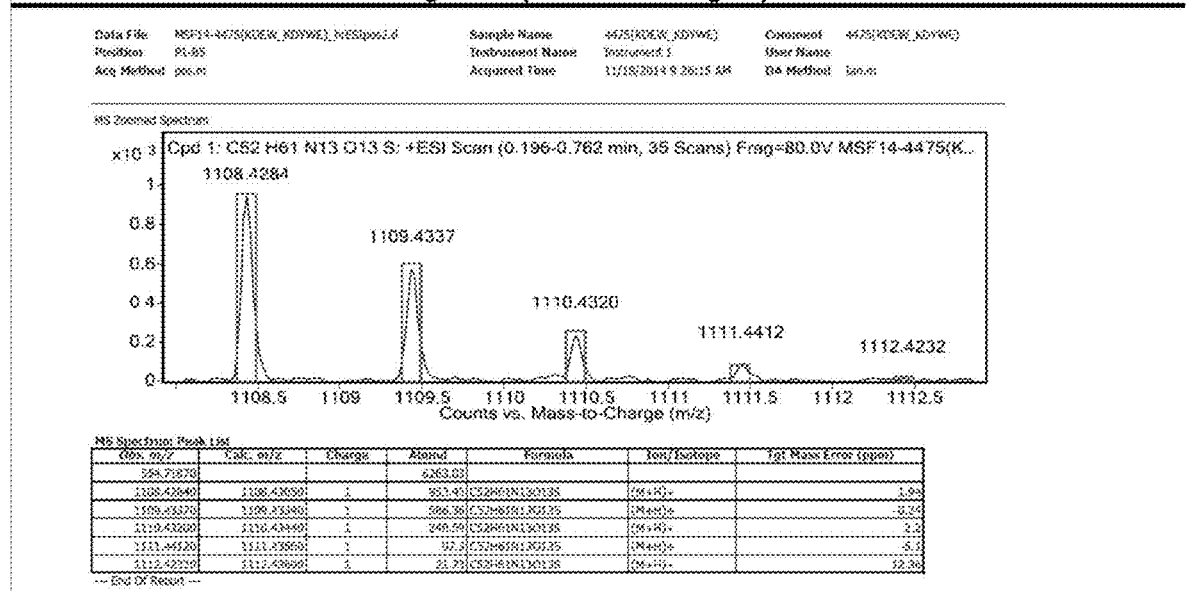
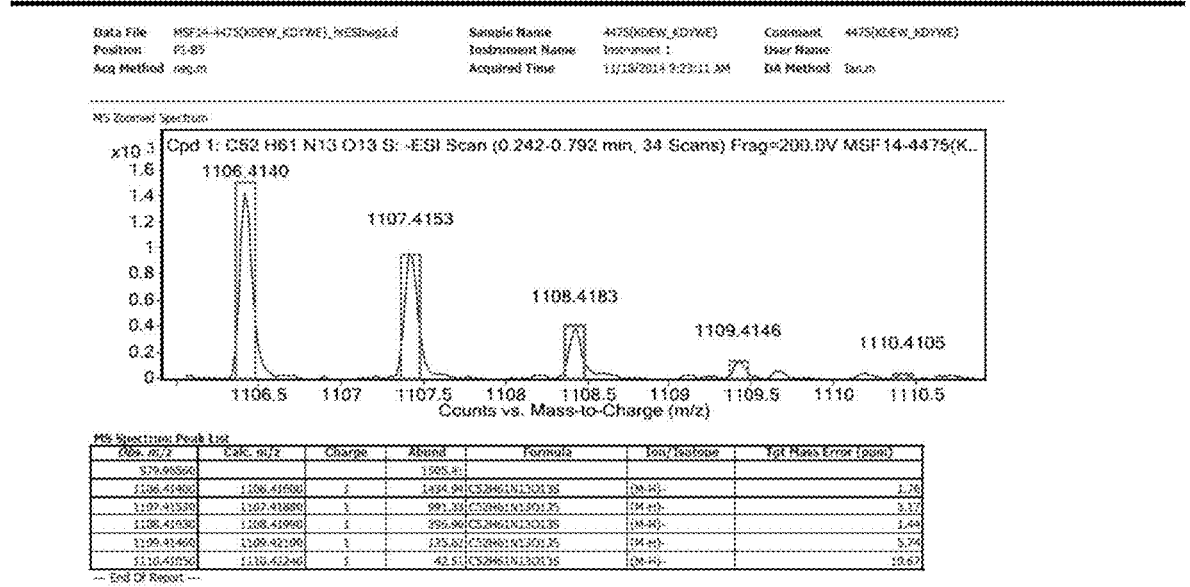

FIGURE 46H, Continued
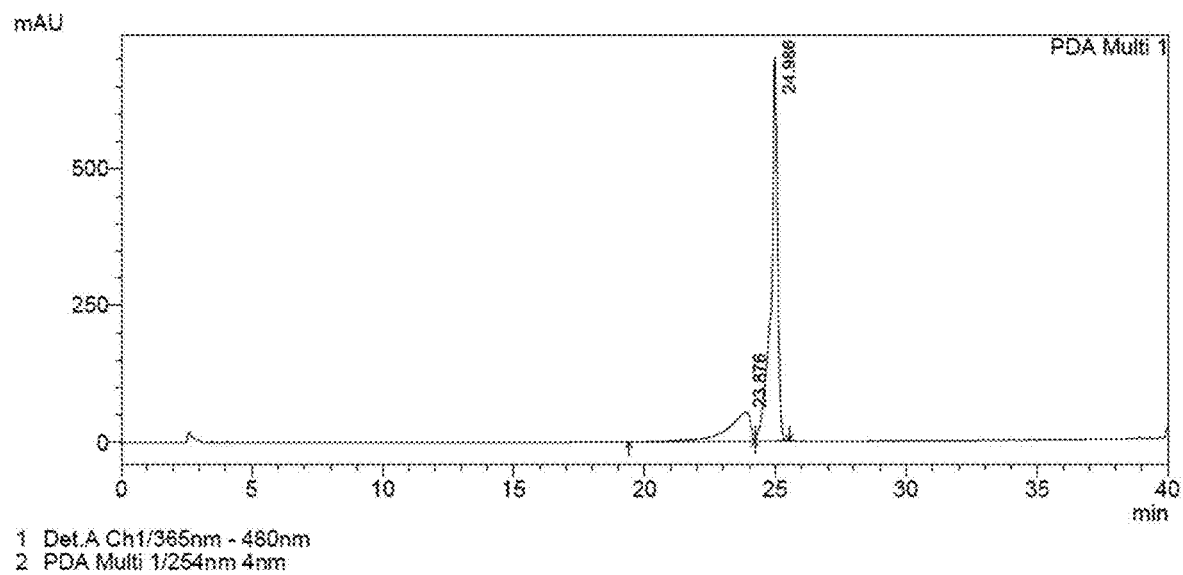
FIGURE 46I
Peptide 12
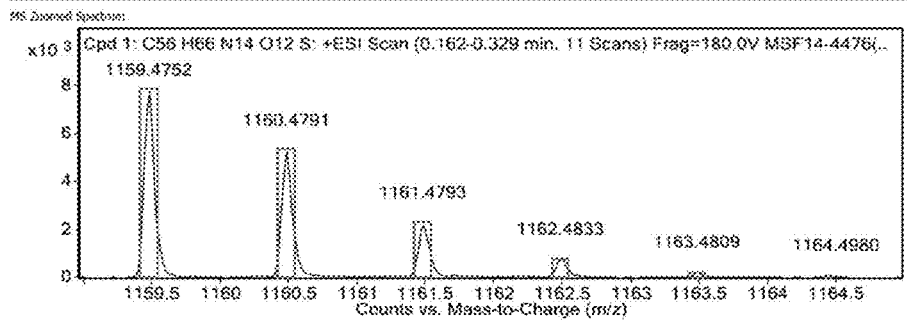

FIGURE 46I, Continued
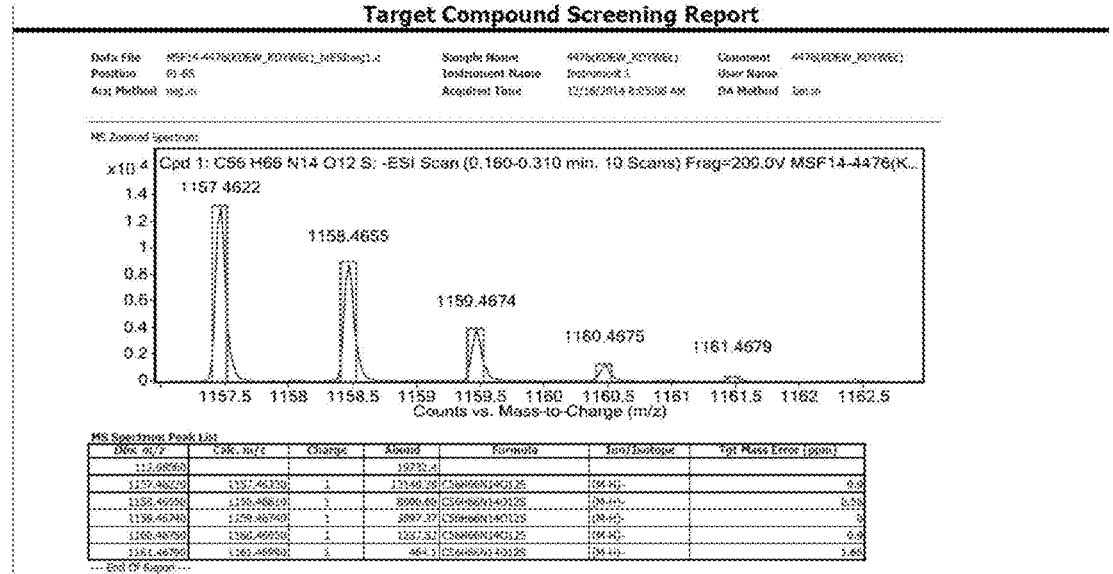
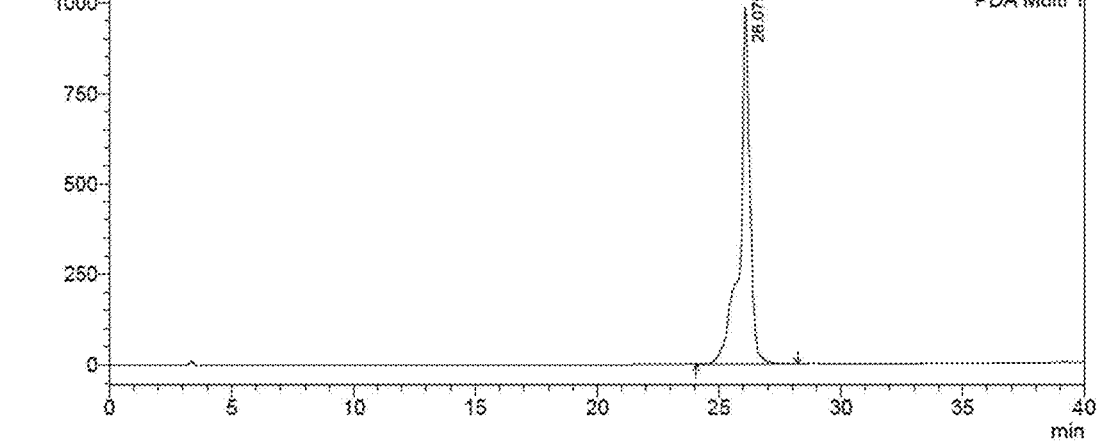
1  Det.A Ch1/365nm - 480nm
2  PDA Multi 1/254nm 4nm

FIGURES 48A-C

FIGURE 49
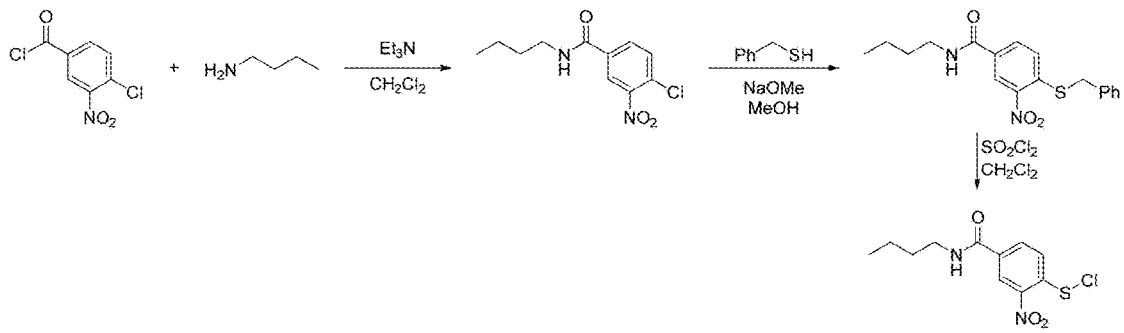
FIGURE 50
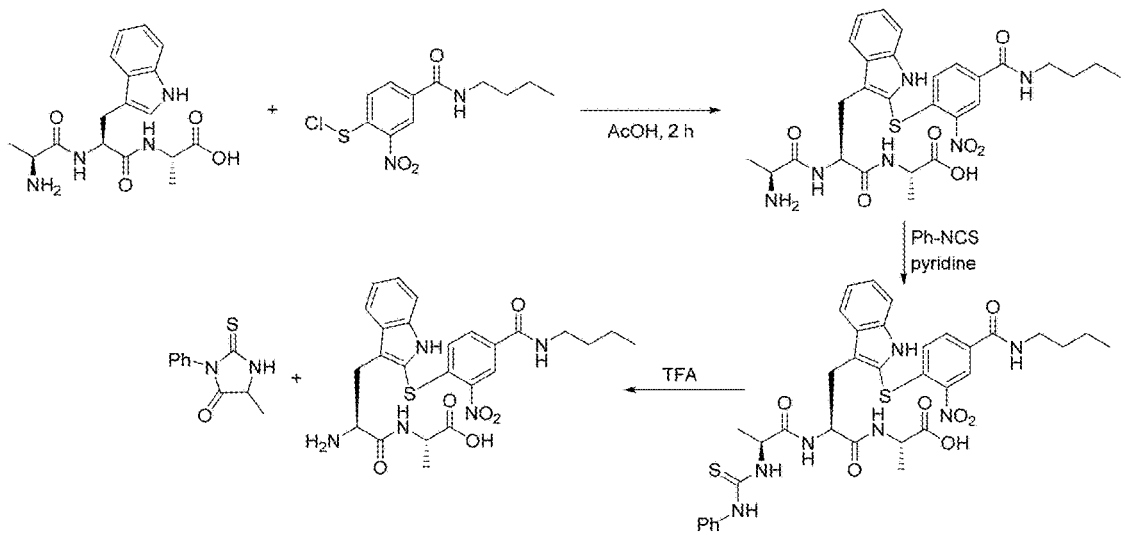
FIGURES 51A-B
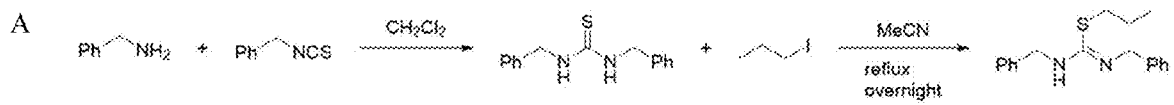
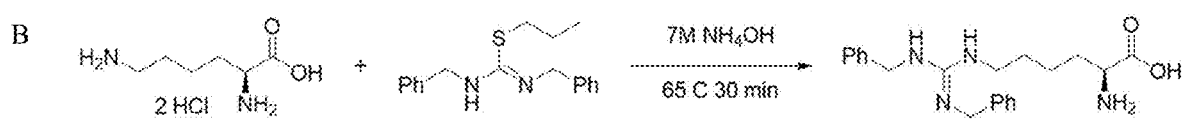

FIGURES 52A-B
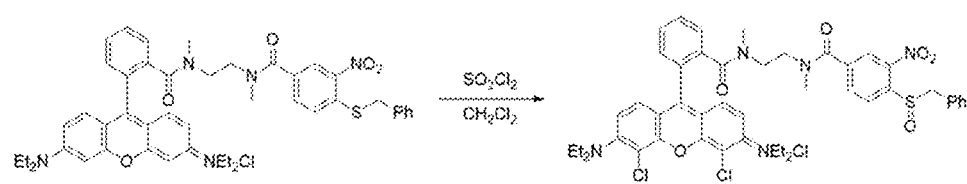
A
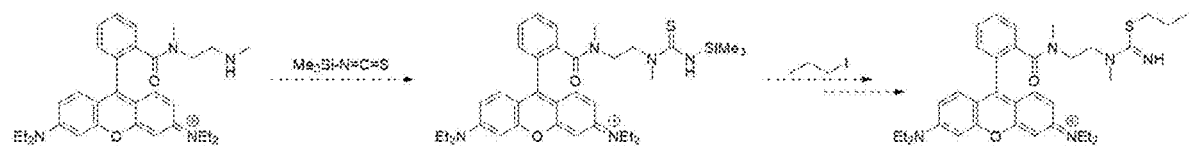
B

FIGURES 53A-B
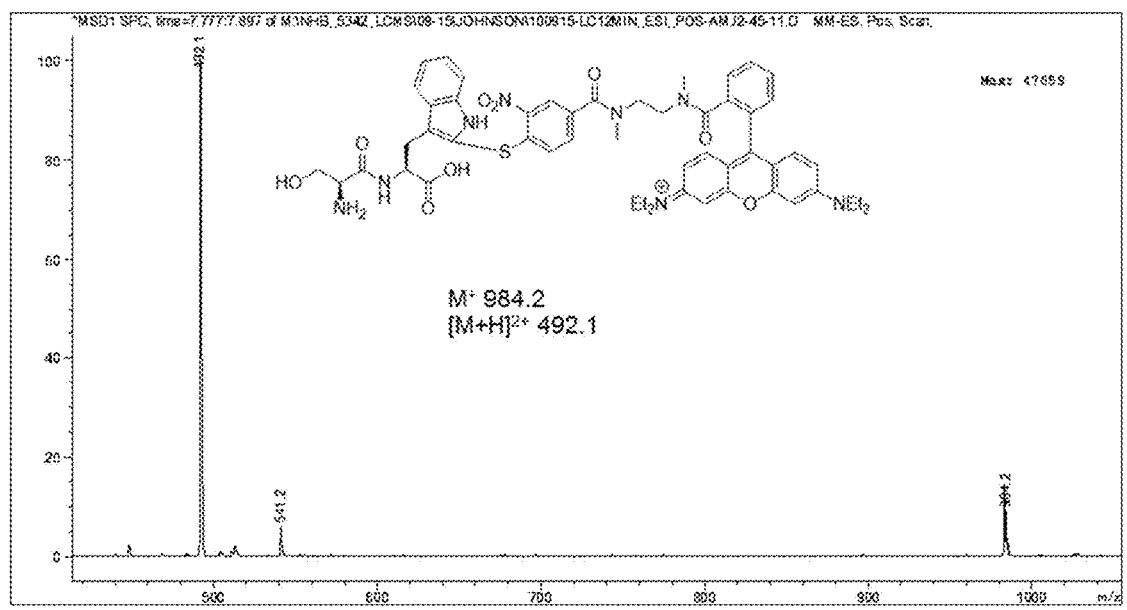
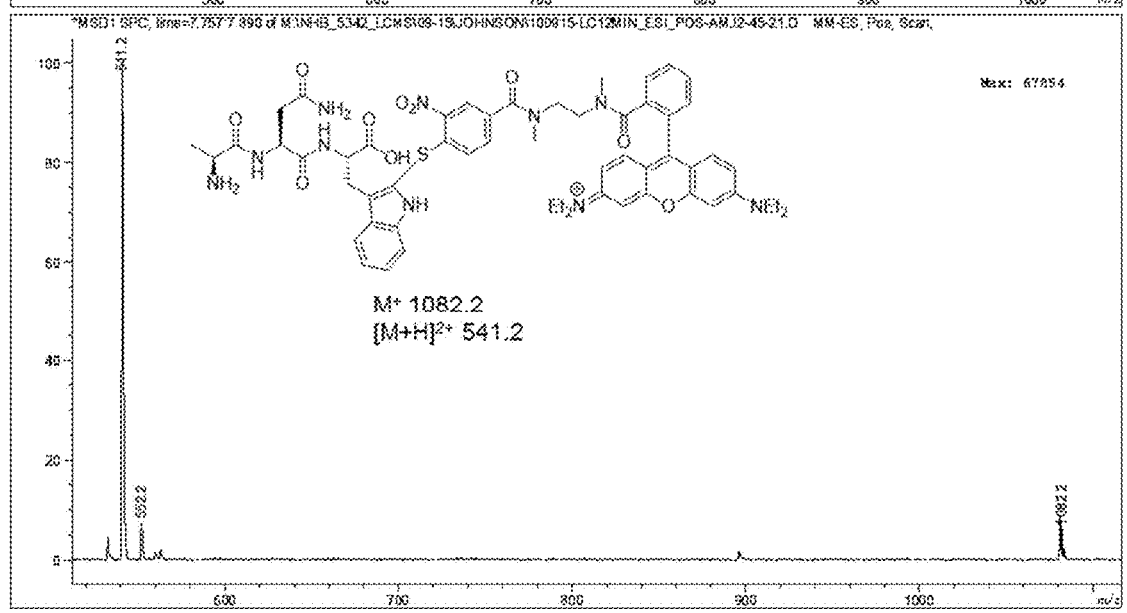

FIGURES 56A-D

FIGURES 58A-C
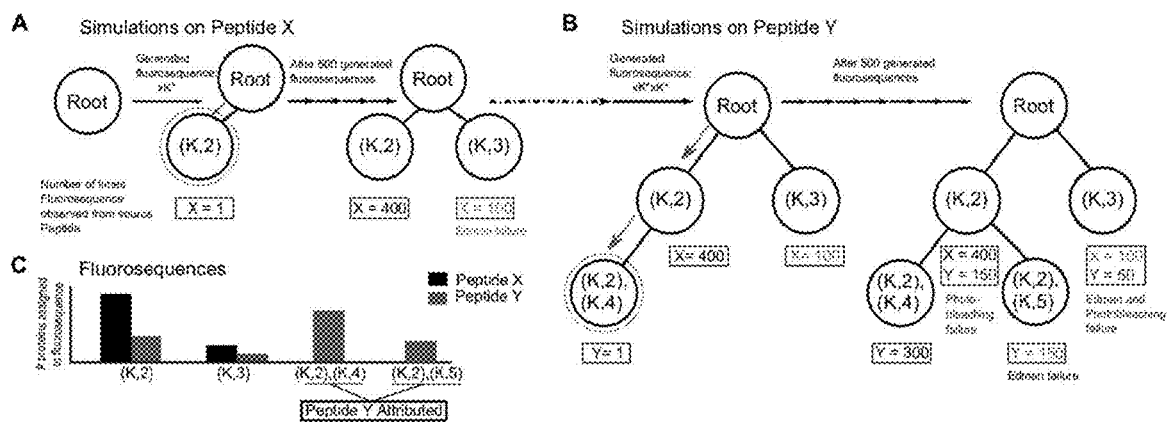
FIGURES 59A-B
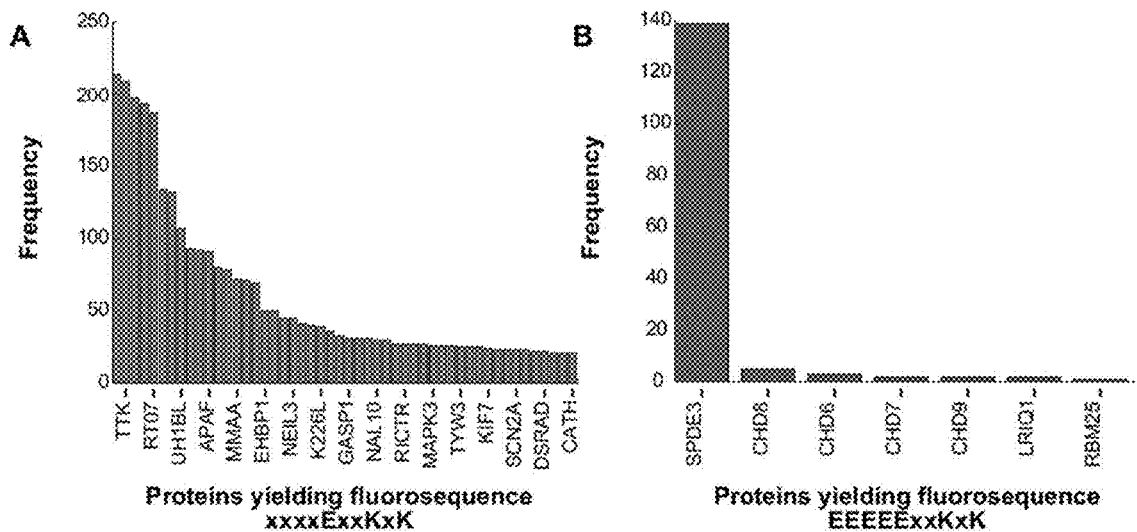

FIGURES 63A-B
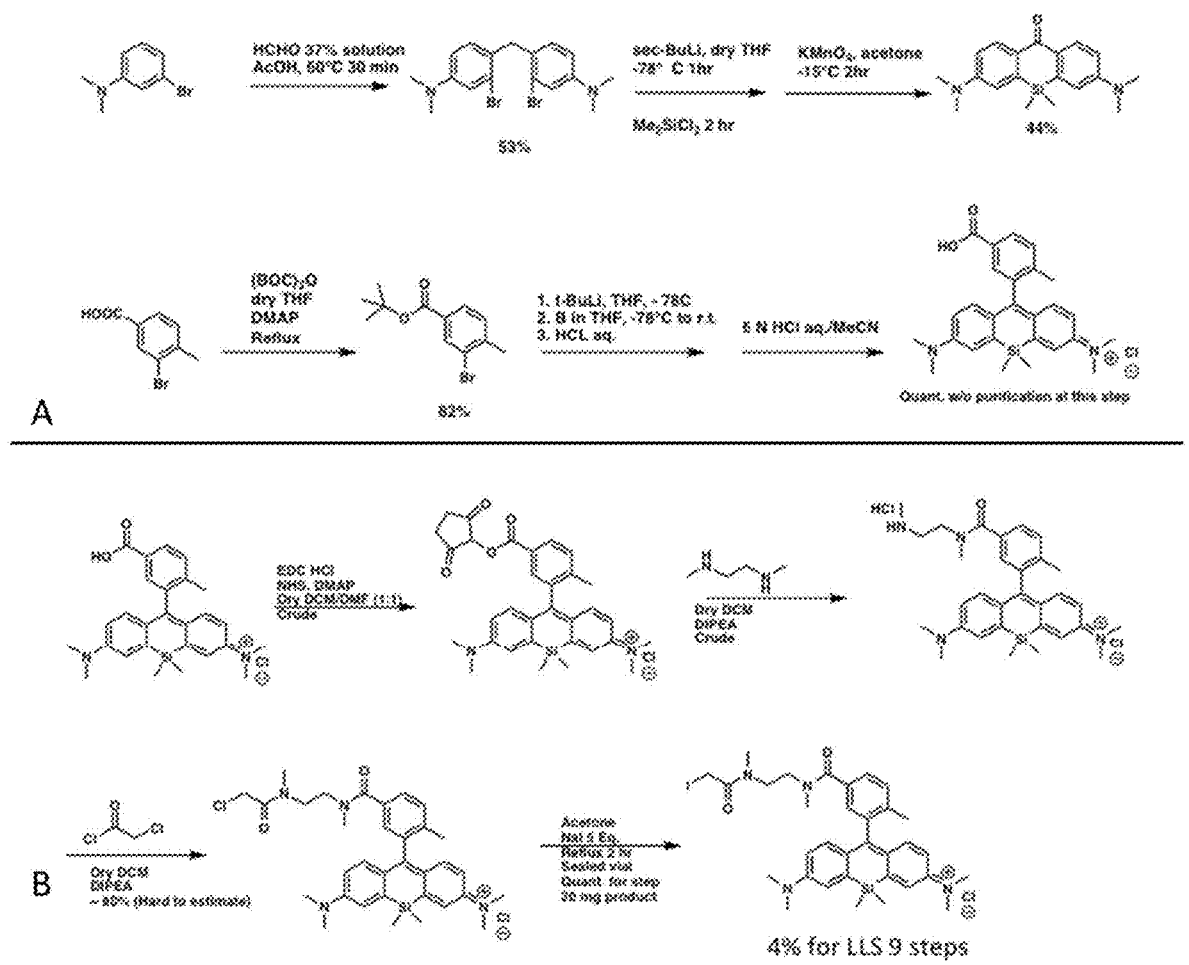

FIGURES 64A-B
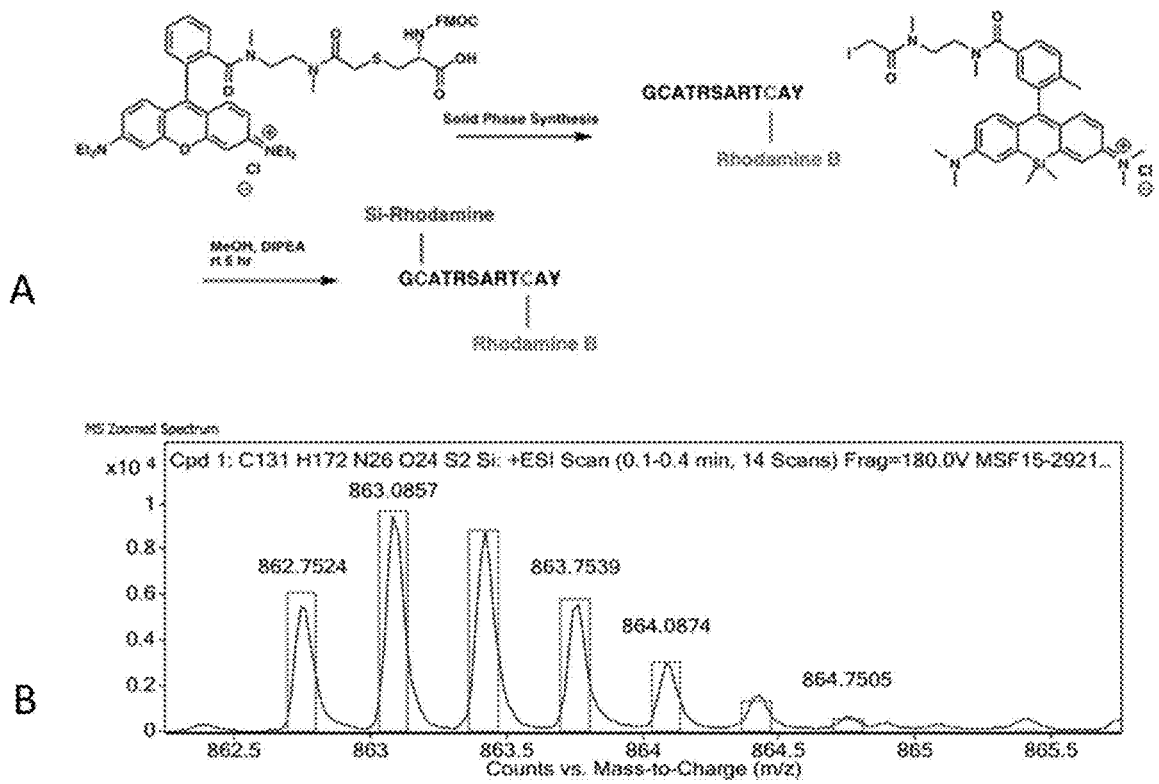
FIGURE 65
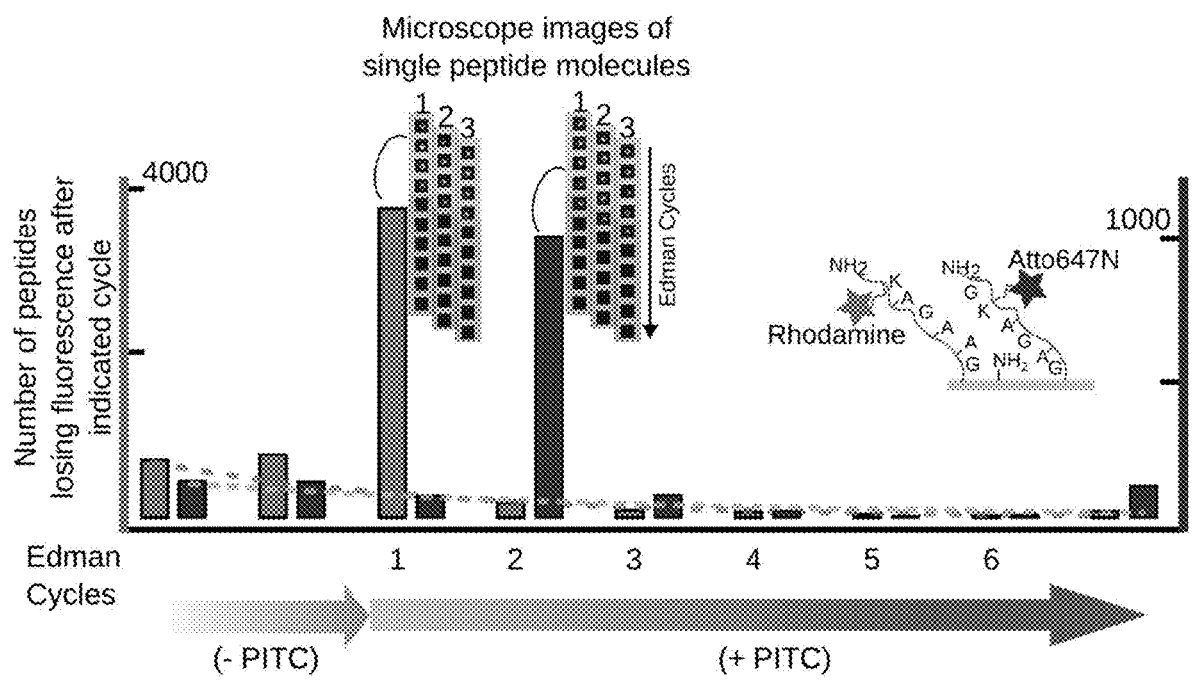

SINGLE MOLECULE PEPTIDE SEQUENCING

This application is a continuation of U.S. patent application Ser. No. 17/491,485, filed on Sep. 30, 2021, which is a continuation of U.S. patent application Ser. No. 16/572,194, filed Sep. 16, 2019, now U.S. Pat. No. 11,162,952, issued on Nov. 2, 2021, which is a continuation of U.S. patent application Ser. No. 15/510,962, filed Mar. 13, 2017, now U.S. Pat. No. 10,545,153, issued on Jan. 28, 2020, which is a National Stage Entry of International Application No. PCT/US15/50099, filed Sep. 15, 2015, which claims the benefit of U.S. Provisional Patent Application No. 62/050,462, filed on Sep. 15, 2014, each of which is entirely incorporated herein by reference.

This application is a continuation-in-part of U.S. patent application Ser. No. 17/384,118, filed Jul. 23, 2021, which is a continuation of U.S. patent application Ser. No. 15/461,034, filed Mar. 16, 2017, now U.S. Pat. No. 11,105,812, issued on Aug. 31, 2021, which is a continuation of U.S. patent application Ser. No. 14/128,247, filed Apr. 18, 2014, now U.S. Pat. No. 9,625,469, issued on Apr. 18, 2017, which is a National Stage Entry of International Application No. PCT/US2012/043769, filed Jun. 22, 2012, which claims the benefit of U.S. Provisional Patent Application No. 61/500,525, filed Jun. 23, 2011, each of which is entirely incorporated herein by reference.

This invention was made with government support under Grant no. GM106408 awarded by the National Institutes of Health and Grant no. N66001-14-2-4051 awarded by the Space and Naval Warfare Systems Center, Pacific. The government has certain rights in the invention.

FIELD OF THE INVENTION

The present invention relates to the field of identifying proteins and peptides, and more specifically large-scale sequencing of single peptides in a mixture of diverse peptides at the single molecule level. The present invention also relates to methods for identifying amino acids in peptides, including peptides comprising unnatural amino acids. In one embodiment, the present invention contemplates labeling the N-terminal amino acid with a first label and labeling an internal amino acid with a second label. In some embodiments, the labels are fluorescent labels. In other embodiments, the internal amino acid is Lysine. In other embodiments, amino acids in peptides are identified based on the fluorescent signature for each peptide at the single molecule level.

BACKGROUND OF THE INVENTION

The development of Next Generation DNA sequencing methods for quickly acquiring genome and gene expression information has transformed biology. The basis of Next Generation DNA sequencing is the acquisition of large numbers (millions) of short reads (typically 35-450 nucleotides) in parallel. While nucleic acid mutations frequently underlie disease, these changes are most readily embodied by proteins expressed in specific bodily compartments (i.e. saliva, blood, urine) that are accessible without invasive procedures such as biopsies. Unfortunately, a similar high-throughput method for the large-scale identification and quantitation of specific proteins in complex mixtures remains unavailable; representing a critical bottleneck in many biochemical, molecular diagnostic and biomarker discovery assays.

The first method for analysis of the N-terminal amino acid of polypeptides was described by Frederick Sanger, who demonstrated that the free unprotonated α-amino group of peptides reacts with 2,4-dinitrofluorobenzene (DNFB) to form yellow 2,4-dinitrophenyl derivatives (FIG. 1). When such a derivative of a peptide, regardless of its length, is subjected to hydrolysis with 6 N HCl, all the peptide bonds are hydrolyzed, but the bond between the 2,4-dinitrophenyl group and the α-amino of the N-terminal amino acid is relatively stable to acid hydrolysis. Consequently, the hydrolyzate of such a dinitrophenyl peptide contains all the amino acid residues of the peptide chain as free amino acids except the N-terminal one, which appears as the yellow 2,4-dinitrophenyl derivative. This labeled residue can easily be separated from the unsubstituted amino acids and identified by chromatographic comparison with known dinitrophenyl derivatives of the different amino acids.

Sanger's method has been largely supplanted by more sensitive and efficient procedures. An example of one such method employs the labeling reagent 1-dimethylaminoaphthalene-5-sulfonyl chloride (dansyl chloride) (FIG. 2). Since the dansyl group is highly fluorescent, dansyl derivatives of the N-terminal amino acid can be detected and measured in minute amounts by fluorimetric methods. The dansyl procedure is 100 times more sensitive that the Sanger method.

The most widely used reaction for the sequential analysis of N-terminal residue of peptides is the Edman degradation method (Edman, et al. "Method for determination of the amino acid sequence in peptides", Acta Chem. Scand. 4: 283-293 (1950) [1], (herein incorporated by reference). Edman degradation is a method of sequencing amino acids in a peptide wherein the amino-terminal residue is labeled and cleaved from the peptide without disrupting the peptide bonds between other amino acid residues (FIG. 3). In the Edman procedure phenylisothiocyanate reacts quantitatively with the free amino group of a peptide to yield the corresponding phenylthiocarbamoyl peptide. On treatment with anhydrous acid the N-terminal residue is split off as a phenylthiocarbamoyl amino acid, leaving the rest of the peptide chain intact. The phenylthiocarbomyl amino acid is then cyclized to the corresponding phenylthiohydantin derivative, which can be separated and identified, usually by gas-liquid chromatography. Alternatively, the N-terminal residue removed as the phenylthiocarbamoyl derivative can be identified simply by determining the amino acid composition of the peptide before and after removal of the N-terminal residue; called the subtractive Edman method. The advantage of the Edman method is that the rest of the peptide chain after removal of the N-terminal amino acid is left intact for further cycles of this procedure; thus the Edman method can be used in a sequential fashion to identify several or even many consecutive amino acid residues starting from the N-terminal end. Edman and Begg have further exploited this advantage by utilizing an automated amino acid "sequenator" for carrying out sequential degradation of peptides by the phenylisothiocyanate procedure (Eur. J. Biochem. 1:80-91, (1967) [2], (herein incorporated by reference). In one embodiment, such automated amino acid sequencers permit up to 30 amino acids to be accurately sequenced with over 99% efficiency per amino acid (Niall et al. "Automated Edman degradation: the protein sequenator". Meth. Enzymol. 27: 942-1010, (1973) [3], (herein incorporated by reference).

A drawback to Edman degradation is that the peptides being sequenced cannot have more than 50 to 60 (more practically fewer than 30) amino acid residues. The sequenced peptide length is typically limited due to the increase in heterogeneity of the product peptides with each Edman cycle due to cyclical derivitization or cleavage failing to proceed to completion on all peptide copies. Furthermore, since Edman degradation proceeds from the N-terminus of the protein, it will not work if the N-terminal amino acid has been chemically modified or if it is concealed within the body of the protein. In some native proteins the N-terminal residue is buried deep within the tightly folded molecule and is inaccessible. Edman degradation typically is performed only on denatured peptides or proteins. Intact, folded proteins are seldom (if at all) subjected to Edman sequencing.

Importantly, the current automated peptide sequencers that perform Edman degradation cannot sequence and identify individual peptides within the context of a mixture of peptides or proteins. What is thus needed is a rapid method for identifying and quantitating individual peptide and/or protein molecules within a given complex sample.

SUMMARY OF THE INVENTION

The present invention relates to the field of identifying proteins and peptides, and more specifically large-scale sequencing of single peptides in a mixture of diverse peptides at the single molecule level. The present invention also relates to methods for identifying amino acids in peptides, including peptides comprising unnatural amino acids. In one embodiment, the present invention contemplates labeling the N-terminal amino acid with a first label and labeling an internal amino acid with a second label. In some embodiments, the labels are fluorescent labels. In other embodiments, the internal amino acid is Lysine. In other embodiments, amino acids in peptides are identified based on the fluorescent signature for each peptide at the single molecule level.

The present invention relates to the field of identifying proteins and peptides, and more specifically large-scale sequencing (including but not limited to partial sequencing) of single intact peptides (not denatured) in a mixture of diverse peptides at the single molecule level by selective labeling amino acids on immobilized peptides followed by successive cycles of labeling and removal of the peptides' amino-terminal amino acids. The methods of the present invention are capable of producing patterns sufficiently reflective of the peptide sequences to allow unique identification of a majority of proteins from a species (e.g. the yeast and human proteomes).

In one embodiment, the present invention provides a massively parallel and rapid method for identifying and quantitating individual peptide and/or protein molecules within a given complex sample.

In one embodiment, the present invention provides a method of labeling of a peptide, comprising, a) providing, i) a peptide having at least one Cysteine amino acid, at least one Lysine amino acid, an N-terminal end, an amino acid having at least one carboxylate side group, a C-terminal end, and at least one Tryptophan amino acid, and ii) a first compound, iii) a second compound, iv) a third compound, v) a fourth compound, and vi) a fifth compound; and b) labeling said Cysteine with said first compound, c) labeling said Lysine with said second compound, d) labeling said N-terminal end with said third compound, e) labeling said carboxylate side group and said C-terminal end with said fourth compound; and f) labeling said Tryptophan with said fifth compound for providing a peptide having specific labels. In one embodiment, steps b-f are sequential in order from b-f. In one embodiment, the labeling in steps b-f is performed in one (a single) solution. In one embodiment, steps b-f are sequential in order from b-f and performed in one solution. In one embodiment, said first compound is iodoacetamide. In one embodiment, said second compound is 2-methylthio-2-imadazoline hydroiodide (MDI). In one embodiment, said third compound is 1-(4,4-dimethyl-2,6-dioxocyclohexylidene)-3-methylbutyl diethyl phosphate (Phos-ivDde). In one embodiment, said fourth compound is selected from the group consisting of benzylamine (BA), 3-dimethylaminopropylamine, and isobutylamine. In one embodiment, said fifth compound is 2,4-dinitrobenzenesulfenyl chloride. In one embodiment, the method further comprises a step of attaching said peptide to a solid support for immobilization of said peptide. In one embodiment, the peptide is attached to said solid support at its C-terminal end. In one embodiment, the method further comprises a step of treating said immobilized peptides under conditions such that each N-terminal amino acid of each peptide is removed by an Edman degradation reaction; and a step of detecting the signal for each peptide at the single molecule level. In one embodiment, said label is attached to a fluorophore by a covalent bond. In one embodiment, said fluorophore and said covalent bond is resistant to degradation effects when incubated in an Edman degradation reaction solvent. It is not meant to limit the fluorophore. In fact, any fluorophore that remains intact and attached to said label during Edman degradation sequencing would find use in the present inventions. Including, but not limited to tetramethylrhodamine, Si-Rhodamine, Rhodamine B, Rhodamine B N, N'-dimethylethylenediamine, Rhodamine B sulfenyl chloride, Alexafluor555, Alexa Fluor 405, Atto647N, (5)6-napthofluorescein, variants and derivations thereof, etc. In one embodiment, said fluorophore is selected from the group consisting of tetramethylrhodamine, Si-Rhodamine, Rhodamine B, Rhodamine B N, N'-dimethylethylenediamine, Rhodamine B sulfenyl chloride, Alexafluor555, Alexa Fluor 405, Atto647N, (5)6-napthofluorescein, variants and derivations thereof.

In one embodiment, the present invention provides a method of solution phase labeling of a peptide, comprising, a) providing, i) a peptide having at least one Cysteine amino acid, ii) a first compound, and b) labeling said Cysteine with said first compound for providing a peptide having a specific label. In one embodiment, said peptide has at least one Lysine amino acid, further providing a second compound, and comprising a step c) labeling said Lysine with said second compound. In one embodiment, said peptide has an N-terminal end, further providing a third compound, and comprising a step d) labeling said N-terminal end with said third compound. In one embodiment, said peptide has an amino acid having at least one carboxylate side group and a C-terminal end, further providing a fourth compound, and comprising a step e) labeling said carboxylate side group and said C-terminal end with said fourth compound. In one embodiment, said peptide has at least one Tryptophan amino acid, further providing a fifth compound, and comprising a step f) labeling said Tryptophan with said fifth compound for providing a peptide having specific labels. In one embodiment, the method further comprises a step of attaching said peptide to a solid support for immobilization of said peptide. In one embodiment, the peptide is attached to said solid support at its C-terminal end. In one embodiment, the method further comprises a step of treating said immobilized peptides under conditions such that each N-terminal amino acid of each peptide is removed by an Edman degradation reaction; and a step of detecting the signal for each peptide at the single molecule level. In one embodiment, said label is attached to a fluorophore by a covalent bond. In one embodiment, said fluorophore and said covalent bond is resistant to degradation effects when incubated in an Edman degradation reaction solvent. It is not meant to limit the fluorophore. In fact, any fluorophore that remains intact and attached to said label during Edman degradation sequencing would find use in the present inventions. Including, but not limited to tetramethylrhodamine, Si-Rhodamine, Rhodamine B, Rhodamine B N, N'-dimethylethylenediamine, Rhodamine B sulfenyl chloride, Alexafluor555, Alexa Fluor 405, Atto647N, (5)6-napthofluorescein, variants and derivations thereof, etc. In one embodiment, said fluorophore is selected from the group consisting of tetramethylrhodamine, Si-Rhodamine, Rhodamine B, Alexafluor555, Alexa Fluor 405, Atto647N, (5)6-napthofluorescein, variants and derivations thereof.

In one embodiment, the present invention provides a method of immobilizing peptides at the C-terminus, comprising, a) providing, i) a peptide having a C-terminus capable of forming a covalent bond and a blocked N-terminus, and ii) a solid support, and b) immobilizing said peptide to said solid support at said C-terminus by said covalent bond. In one embodiment, said peptide does not have a fluorophore label. In one embodiment, said peptide has at least one type of fluorophore label. In one embodiment, said solid support has an amine functional group. In one embodiment, said solid support has a thiol functional group. In one embodiment, said solid support is selected from the group consisting of a resin, a bead and a glass surface. In one embodiment, said solid support is coated with a polyethylene glycol polymer. In one embodiment, said blocked N-terminus is blocked by fluorenylmethoxycarbonyl (fmoc). In one embodiment, said peptides have at least one internal amino acid comprising a side group capable of forming a covalent bond with said solid support. It is not intended to limit said internal amino acid to any particular amino acid. In fact, any internal amino acid whose side group is capable of forming a covalent bond with said solid substrate may find use in this invention, including but not limited to a cysteine, a glutamic acid, an aspartic acid, and the like. In one embodiment, said internal amino acid is selected from the group consisting of a cysteine, a glutamic acid, an aspartic acid. In one embodiment, said fluorophore label is attached to said peptide by a covalent bond. In one embodiment, said fluorophore and said covalent bond is resistant to degradation effects when incubated in an Edman degradation reaction solvent. It is not meant to limit the fluorophore. In fact, any fluorophore that remains intact and attached to said label during Edman degradation sequencing would find use in the present inventions. Including, but not limited to tetramethylrhodamine, Si-Rhodamine, Rhodamine B, Rhodamine B N, N'-dimethylethylenediamine, Rhodamine B sulfenyl chloride, Alexafluor555, Alexa Fluor 405, Atto647N, (5)6-napthofluorescein, variants and derivations thereof, etc. In one embodiment, said fluorophore is selected from the group consisting of tetramethylrhodamine, Si-Rhodamine, Rhodamine B, Alexafluor555, Alexa Fluor 405, Atto647N, (5)6-napthofluorescein, variants and derivations thereof.

In one embodiment, the present invention provides a method of immobilizing peptides at the C-terminus, comprising, a) providing, i) a peptide having a C-terminus capable of forming a covalent bond and a blocked N-terminus, and ii) a solid support comprising a chemically modified surface, and b) immobilizing said peptide to said solid support at said C-terminus under conditions wherein a covalent bond is made with said chemically modified surface. In one embodiment, said chemically modified surface comprises an amine functional group. In one embodiment, the conditions of step b) comprise mixing said solid support and said peptide in the presence of a cross-linking compound. In one embodiment, said cross-linking compound comprises N-hydroxysulfosuccinimide. In one embodiment, the method further comprises a step c) of treating said immobilized peptides under conditions such that each N-terminal amino acid of each peptide is removed by an Edman degradation reaction; and a step d) of detecting the signal for each peptide at the single molecule level. In one embodiment, said fluorophore label is attached to said peptide by a covalent bond. In one embodiment, said fluorophore and said covalent bond is resistant to degradation effects when incubated in an Edman degradation reaction solvent. It is not meant to limit the fluorophore. In fact, any fluorophore that remains intact and attached to said label during Edman degradation sequencing would find use in the present inventions. Including, but not limited to tetramethylrhodamine, Si-Rhodamine, Rhodamine B, Rhodamine B N, N'-dimethylethylenediamine, Rhodamine B sulfenyl chloride, Alexafluor555, Alexa Fluor 405, Atto647N, (5)6-napthofluorescein, variants and derivations thereof, etc. In one embodiment, said fluorophore is selected from the group consisting of tetramethylrhodamine, Si-Rhodamine, Rhodamine B, Alexafluor555, Alexa Fluor 405, Atto647N, (5)6-napthofluorescein, variants and derivations thereof.

In one embodiment, the present invention contemplates a method of treating peptides, comprising: a) providing a plurality of peptides immobilized on a solid support, each peptide comprising an N-terminal amino acid and internal amino acids, said internal amino acids comprising Lysine, each Lysine labeled with a label selected from the group consisting of Alexafluor dyes and Atto dyes, and said label producing a signal for each peptide; b) treating said plurality of immobilized peptides under conditions such that each N-terminal amino acid of each peptide is removed by an Edman degradation reaction; and c) detecting the signal for each peptide at the single molecule level. A variety of Alexafluor dyes, Atto dyes and Rhodamine dye derivatives are contemplated (as well as other dyes used in conjunction with Alexafluor dyes and Atto dyes). In a preferred embodiment, the Alexafluor dye is Alexafluor555. In one embodiment, the Atto dye is Atto647N. In one embodiment, the Atto dye is Atto655. In one preferred embodiment, the Rhodamine dye derivative is tetramethylrhodamine. In one embodiment, the removal of said N-terminal amino acid in step b) is done under conditions such that the remaining peptides each have a new N-terminal amino acid. In one embodiment, the method further comprises the step d) removing the new N-terminal amino acid done under conditions such that the remaining peptides each have a next N-terminal amino acid. In one embodiment, the method further comprises the step e) detecting the next signal for each peptide at the single molecule level. It is not intended that the present invention be limited by the number of times the steps of the method are repeated. In one embodiment, the N-terminal amino acid removing step and the detecting step are successively repeated 10 times, more preferably 20 times, or more (even 50 times or more). It is contemplated that the repetitive detection of signal for each peptide at the single molecule level results in a pattern. It is further contemplated that the pattern is unique to a single-peptide within the plurality of immobilized peptides. In one embodiment, the single-peptide pattern is compared to the proteome of an organism to identify the peptide. In one embodiment, the intensity of said labels are measured amongst said plurality of immobilized peptides. In a preferred embodiment, the peptides are immobilized via Cysteine residues. In a preferred embodiment, the detecting in step c) is done with optics capable of single-molecule resolution. In a specific embodiment, one or more of said plurality of peptides comprises one or more unnatural amino acids. In one embodiment, said unnatural amino acids comprise moieties selected from the group consisting of hydroxycarboxylates, aldehydes, thiols, and olefins. In one embodiment, one or more of said plurality of peptides comprises one or more beta amino acids.

In an alternative embodiment, the present invention contemplates a method of treating peptides, comprising: a) providing a plurality of peptides immobilized on a solid support, each peptide comprising an N-terminal amino acid and internal amino acids, said internal amino acids comprising Lysine, each Lysine labeled with a first label, said first label producing a first signal for each peptide, and said N-terminal amino acid of each peptide labeled with a second label, said second label being different from said first label and selected from the group consisting of Alexafluor dyes and Atto dyes; b) treating said plurality of immobilized peptides under conditions such that each N-terminal amino acid of each peptide is removed by an Edman degradation reaction; and c) detecting the first signal for each peptide at the single molecule level. A variety of Alexafluor dyes and Atto dyes are contemplated (as well as other dyes used in conjunction with Alexafluor dyes and Atto dyes). In a preferred embodiment, the Alexafluor dye is Alexafluor555. In one embodiment, the Atto dye is Atto647N. In one embodiment, the Atto dye is Atto655. In a preferred embodiment, the emission spectrum of said first label do not overlap with the emission spectrum of said second label. In a preferred embodiment, the removal of said N-terminal amino acid in step b) is done under conditions such that the remaining peptides each have a new N-terminal amino acid. In one embodiment, the method further comprises the step d) adding said second label to said new N-terminal amino acids of the remaining peptides. It is contemplated that, among the remaining peptides, the new end terminal amino acid is Lysine. In one embodiment, the method further comprises the step e) detecting the next signal for each peptide at the single molecule level. It is not intended that the present invention be limited to a precise number of repetitions of the steps of the method. However, in one embodiment, the N-terminal amino acid removing step, the detecting step, and the label adding step to a new N-terminal amino acid are successively repeated 10 time, more preferably 20 times or more (even 50 times or more). It is contemplated that the repetitive detection of signal for each peptide at the single molecule level results in a pattern. It is further contemplated that the pattern is unique to a single-peptide within the plurality of immobilized peptides. It is still further contemplated that the single-peptide pattern is compared to the proteome of an organism to identify the peptide. In one embodiment, the intensity of said first and second labels are measured amongst said plurality of immobilized peptides. In a preferred embodiment, the peptides are immobilized via Cysteine residues. In a preferred embodiment, the detecting in step c) is done with optics capable of single-molecule resolution. In one embodiment, one or more of said plurality of peptides comprises one or more unnatural amino acids. A variety of unnatural amino acids are contemplated. In one embodiment, said unnatural amino acids comprises moieties selected from the group consisting of hydroxycarboxylates, aldehydes, thiols, and olefins. In one embodiment, one or more of said plurality of peptides comprises one or more beta amino acids.

The present invention also contemplates in one embodiment, a method of treating peptides, comprising: a) providing i) a plurality of peptides immobilized on a solid support, each peptide comprising an N-terminal amino acid and internal amino acids, said internal amino acids comprising Lysine, each Lysine labeled with a first label, said first label producing a first signal for each peptide, and said N-terminal amino acid of each peptide labeled with a second label, said second label being different from said first label and selected from the group consisting of Alexafluor dyes and Atto dyes, and ii) an optical device capable of detecting said first collective signal for each peptide at the single molecule level; b) treating said plurality of immobilized peptides under conditions such that each N-terminal amino acid of each peptide is removed by an Edman degradation reaction; and c) detecting the first signal for each peptide at the single molecule level with said optical device. In one embodiment, portions of the emission spectrum of said first label do not overlap with the emission spectrum of said second label. In one embodiment, the removal of said N-terminal amino acid in step b) is done under conditions such that the remaining peptides each have a new N-terminal amino acid. In one embodiment, the method further comprises the step d) adding said second label to said new N-terminal amino acids of the remaining peptides. In one embodiment, it is contemplated that, among the remaining peptides, the new end terminal amino acid is Lysine. In one embodiment, the method further comprises the step e) detecting the next signal for each peptide at the single molecule level. It is not intended that the present invention be limited to the precise number of times the steps are repeated. However, in one embodiment, the N-terminal amino acid removing step, the detecting step, and the label adding step to a new N-terminal amino acid are successively repeated 10 times, and more preferably 20 times or more (even 50 times or more). It is preferred that the repetitive detection of signal for each peptide at the single molecule level results in a pattern. It is preferred that the pattern is unique to a single-peptide within the plurality of immobilized peptides. In one embodiment, the single-peptide pattern is compared to the proteome of an organism to identify the peptide. In one embodiment, the intensity of said first and second labels are measured amongst said plurality of immobilized peptides. It is preferred that the peptides are immobilized via Cysteine residues. In one embodiment, one or more of said plurality of peptides comprises one or more unnatural amino acids. A variety of unnatural amino acids are contemplated. In one embodiment, said unnatural amino acids comprises moieties selected from the group consisting of hydroxycarboxylates, aldehydes, thiols, and olefins. In one embodiment, one or more of said plurality of peptides comprises one or more beta amino acids.

The present invention further contemplates in one embodiment a method of identifying amino acids in peptides, comprising: a) providing a plurality of peptides immobilized on a solid support, each peptide comprising an N-terminal amino acid and internal amino acids, said internal amino acids comprising Lysine, each Lysine labeled with a first label, said first label producing a first signal for each peptide, and said N-terminal amino acid of each peptide labeled with a second label, said second label being different from said first label and selected from the group consisting of Alexafluor dyes and Atto dyes, wherein a subset of said plurality of peptides comprise an N-terminal Lysine having both said first and second label; b) treating said plurality of immobilized peptides under conditions such that each N-terminal amino acid of each peptide is removed by an Edman degradation reaction; and c) detecting the first signal for each peptide at the single molecule level under conditions such that said subset of peptides comprising an N-terminal Lysine is identified. It is preferred that the removal of said N-terminal amino acid in step b) is done under conditions such that the remaining peptides each have a new N-terminal amino acid. It is preferred that the peptides are immobilized via Cysteine residues. In one embodiment, one or more of said plurality of peptides comprises one or more unnatural amino acids. A variety of unnatural amino acids are contemplated. In one embodiment, said unnatural amino acids comprise moieties selected from the group consisting of hydroxycarboxylates, aldehydes, thiols, and olefins. In one embodiment, one or more of said plurality of peptides comprises one or more beta amino acids.

The present invention further contemplates in one embodiment, a method of identifying amino acids in peptides, comprising: a) providing a plurality of peptides immobilized on a solid support, each peptide comprising an N-terminal amino acid and internal amino acids, said internal amino acids comprising Lysine, each Lysine labeled with a first label, said first label producing a first signal for each peptide, and said N-terminal amino acid of each peptide labeled with a second label, said second label being different from said first label and selected from the group consisting of Alexafluor dyes and Atto dyes, wherein a subset of said plurality of peptides comprise an N-terminal acid that is not Lysine; b) treating said plurality of immobilized peptides under conditions such that each N-terminal amino acid of each peptide is removed by an Edman degradation reaction; and c) detecting the first signal for each peptide at the single molecule level under conditions such that said subset of peptides comprising an N-terminal amino acid that is not Lysine is identified. It is preferred that the removal of said N-terminal amino acid in step b) is done under conditions such that the remaining peptides each have a new N-terminal amino acid. It is preferred that the peptides are immobilized via Cysteine residues. In one embodiment, one or more of said plurality of peptides comprises one or more unnatural amino acids. A variety of unnatural amino acids are contemplated. In one embodiment, said unnatural amino acids comprises moieties selected from the group consisting of hydroxycarboxylates, aldehydes, thiols, and olefins. In one embodiment, one or more of said plurality of peptides comprises one or more beta amino acids.

The present invention further contemplates in one embodiment a method of screening and sequencing polymers comprising unnatural amino acid monomers, comprising: a) providing a plurality of polymers, each polymer comprising one or more unnatural amino acids; b) exposing said polymers to a target, wherein a portion of said polymers bind to said target; and c) sequencing said polymers which bind to said target. It is preferred that said sequencing comprises the steps set forth in any of the methods of treating peptides described herein.

In one embodiment, the invention relates to a method of treating peptides, comprising: a) providing a plurality of peptides immobilized on a solid support, each peptide comprising an N-terminal amino acid and internal amino acids, said internal amino acids comprising Lysine, each Lysine labeled with a first label, said first label producing a first signal for each peptide, and said N-terminal amino acid of each peptide labeled with a second label, said second label being different from said first label; b) treating said plurality of immobilized peptides under conditions such that each N-terminal amino acid of each peptide is removed; and c) detecting the first signal for each peptide at the single molecule level. In one embodiment, said second label is attached via an amine-reactive dye. In one embodiment, said second label is selected from the group consisting of fluorescein isothiocyanate, rhodamine isothiocyanate or other synthesized fluorescent isothiocyanate derivative. In one embodiment, portions of the emission spectrum of said first label do not overlap with the emission spectrum of said second label. In one embodiment, the removal of said N-terminal amino acid in step b) is done under conditions such that the remaining peptides each have a new N-terminal amino acid. In one embodiment, the method further comprises the step d) adding said second label to said new N-terminal amino acids of the remaining peptides. In one embodiment, among the remaining peptides the new end terminal amino acid is Lysine. In one embodiment, the method further comprises the step e) detecting the next signal for each peptide at the single molecule level. In one embodiment, the N-terminal amino acid removing step, the detecting step, and the label adding step to a new N-terminal amino acid are successively repeated from 1 to 20 times. In one embodiment, the repetitive detection of signal for each peptide at the single molecule level results in a pattern. In one embodiment, the pattern is unique to a single-peptide within the plurality of immobilized peptides. In one embodiment, the single-peptide pattern is compared to the proteome of an organism to identify the peptide. In one embodiment, the intensity of said first and second labels are measured amongst said plurality of immobilized peptides. In one embodiment, the N-terminal amino acids are removed in step b) by an Edman degradation reaction. In one embodiment, the peptides are immobilized via Cysteine residues. In one embodiment, the detecting in step c) is done with optics capable of single-molecule resolution. In one embodiment, the degradation step in which removal of second label coincides with removal of first label is identified. In one embodiment, said removal of the amino acid is measured in step b is measured as a reduced fluorescence intensity.

In one embodiment, the invention relates to a method of treating peptides, comprising: a) providing i) a plurality of peptides immobilized on a solid support, each peptide comprising an N-terminal amino acid and internal amino acids, said internal amino acids comprising Lysine, each Lysine labeled with a first label, said first label producing a first signal for each peptide, and said N-terminal amino acid of each peptide labeled with a second label, said second label being different from said first label, and ii) an optical device capable of detecting said first collective signal for each peptide at the single molecule level; b) treating said plurality of immobilized peptides under conditions such that each N-terminal amino acid of each peptide is removed; and c) detecting the first signal for each peptide at the single molecule level with said optical device. In one embodiment, said second label is attached via an amine-reactive dye. In one embodiment, said second label is selected from the group consisting of fluorescein isothiocyanate, rhodamine isothiocyanate or other synthesized fluorescent isothiocyanate derivative. In one embodiment, portions of the emission spectrum of said first label do not overlap with the emission spectrum of said second label. In one embodiment, the removal of said N-terminal amino acid in step b) is done under conditions such that the remaining peptides each have a new N-terminal amino acid. In one embodiment, the method further comprises the step d) adding said second label to said new N-terminal amino acids of the remaining peptides. In one embodiment, among the remaining peptides the new end terminal amino acid is Lysine. In one embodiment, the method further comprises the step e) detecting the next signal for each peptide at the single molecule level. In one embodiment, the N-terminal amino acid removing step, the detecting step, and the label adding step to a new N-terminal amino acid are successively repeated from 1 to 20 times. In one embodiment, the repetitive detection of signal for each peptide at the single molecule level results in a pattern. In one embodiment, the pattern is unique to a single-peptide within the plurality of immobilized peptides. In one embodiment, the single-peptide pattern is compared to the proteome of an organism to identify the peptide. In one embodiment, the intensity of said first and second labels are measured amongst said plurality of immobilized peptides. In one embodiment, the N-terminal amino acids are removed in step b) by an Edman degradation reaction. In one embodiment, the peptides are immobilized via Cysteine residues. In one embodiment, the degradation step in which removal of second label coincides with removal of first label is identified. In one embodiment, said removal of the amino acid is measured in step b is measured as a reduced fluorescence intensity.

In one embodiment, the invention relates to a method of identifying amino acids in peptides, comprising: a) providing a plurality of peptides immobilized on a solid support, each peptide comprising an N-terminal amino acid and internal amino acids, said internal amino acids comprising Lysine, each Lysine labeled with a first label, said first label producing a first signal for each peptide, and said N-terminal amino acid of each peptide labeled with a second label, said second label being different from said first label, wherein a subset of said plurality of peptides comprise an N-terminal Lysine having both said first and second label; b) treating said plurality of immobilized peptides under conditions such that each N-terminal amino acid of each peptide is removed; and c) detecting the first signal for each peptide at the single molecule level under conditions such that said subset of peptides comprising an N-terminal Lysine is identified. In one embodiment, the removal of said N-terminal amino acid in step b) is done under conditions such that the remaining peptides each have a new N-terminal amino acid. In one embodiment, the N-terminal amino acids are removed in step b) by an Edman degradation reaction. In one embodiment, the peptides are immobilized via Cysteine residues.

In one embodiment, the invention relates to a method of identifying amino acids in peptides, comprising: a) providing a plurality of peptides immobilized on a solid support, each peptide comprising an N-terminal amino acid and internal amino acids, said internal amino acids comprising Lysine, each Lysine labeled with a first label, said first label producing a first signal for each peptide, and said N-terminal amino acid of each peptide labeled with a second label, said second label being different from said first label, wherein a subset of said plurality of peptides comprise an N-terminal acid that is not Lysine; b) treating said plurality of immobilized peptides under conditions such that each N-terminal amino acid of each peptide is removed; and c) detecting the first signal for each peptide at the single molecule level under conditions such that said subset of peptides comprising an N-terminal amino acid that is not Lysine is identified. In one embodiment, the removal of said N-terminal amino acid in step b) is done under conditions such that the remaining peptides each have a new N-terminal amino acid. In one embodiment, the N-terminal amino acids are removed in step b) by an Edman degradation reaction. In one embodiment, the peptides are immobilized via Cysteine residues.

In one embodiment, the present invention contemplates a method of treating peptides, comprising providing a plurality of peptides immobilized on a solid support, each peptide comprising an N-terminal amino acid and internal amino acids, the internal amino acids comprising Lysine, each Lysine labeled with a first label, the first label producing a first signal for each peptide (the strength of which will depend in part on the number of labeled Lysines for any one peptide), and the N-terminal amino acid of each peptide labeled with a second label, the second label being different from the first label; treating the plurality of immobilized peptides under conditions such that each N-terminal amino acid of each peptide is removed; and detecting the first signal for each peptide at the single molecule level.

In one embodiment, the present invention contemplates a method of treating peptides, comprising providing a plurality of peptides immobilized on a solid support, each peptide comprising an N-terminal amino acid and internal amino acids, the internal amino acids comprising Lysine, each Lysine labeled with a first label, the first label producing a first signal for each peptide (the strength of which will depend in part on the number of labeled Lysines for any one peptide), and the N-terminal amino acid of each peptide labeled with a second label, the second label being different from the first label, and an optical device capable of detecting the first collective signal for each peptide at the single molecule level; treating the plurality of immobilized peptides under conditions such that each N-terminal amino acid of each peptide is removed; detecting the first signal for each peptide at the single molecule level with the optical device.

In one embodiment, the present invention contemplates a method of identifying amino acids in peptides, comprising providing a plurality of peptides immobilized on a solid support, each peptide comprising an N-terminal amino acid and internal amino acids, the internal amino acids comprising Lysine, each Lysine labeled with a first label, the first label producing a first signal for each peptide (the strength of which will depend in part on the number of labeled Lysines for any one peptide), and the N-terminal amino acid of each peptide labeled with a second label, the second label being different from the first label, wherein a subset of the plurality of peptides comprise an N-terminal Lysine having both the first and second label; treating the plurality of immobilized peptides under conditions such that each N-terminal amino acid of each peptide is removed; and detecting the first signal for each peptide at the single molecule level under conditions such that the subset of peptides comprising an N-terminal Lysine is identified.

In one embodiment, the present invention contemplates a method of identifying amino acids in peptides, comprising providing a plurality of peptides immobilized on a solid support, each peptide comprising an N-terminal amino acid and internal amino acids, the internal amino acids comprising Lysine, each Lysine labeled with a first label, the first label producing a first signal for each peptide (the strength of which will depend in part on the number of labeled Lysines for any one peptide), and the N-terminal amino acid of each peptide labeled with a second label, the second label being different from the first label, wherein a subset of the plurality of peptides comprise an N-terminal acid that is not Lysine; treating the plurality of immobilized peptides under conditions such that each N-terminal amino acid of each peptide is removed; and detecting the first signal for each peptide at the single molecule level under conditions such that the subset of peptides comprising an N-terminal amino acid that is not Lysine is identified.

In one embodiment, the present invention contemplates a method of treating peptides, comprising providing a plurality of peptides immobilized on a solid support, each peptide comprising an N-terminal amino acid and internal amino acids, the internal amino acids comprising Lysine, each Lysine labeled with a first label, the first label producing a first signal (e.g. green) for each peptide, and the N-terminal amino acid of each peptide labeled with a second label, the second label being different from the first label, the second label providing a second signal (e.g. red) for each peptide, the first and second signals producing a collective signal (e.g. red/green) for each peptide; detecting the second signal (or the collective signal) for each peptide at the single molecule level; treating the plurality of immobilized peptides under conditions such that each N-terminal amino acid of each peptide is removed; and detecting the first signal for each peptide at the single molecule level.

In one embodiment, the present invention contemplates a method of treating peptides, comprising providing a plurality of peptides immobilized on a solid support, each peptide comprising an N-terminal amino acid and internal amino acids, the internal amino acids comprising Lysine, each Lysine labeled with a first label, the first label producing a first signal (e.g. green) for each peptide, and the N-terminal amino acid of each peptide labeled with a second label, the second label being different from the first label, the second label providing a second signal (e.g. red) for each peptide, the first and second signals producing a collective signal (e.g. red/green) for each peptide, and an optical device capable of detecting the first and second signal (i.e. either separately or collectively) for each peptide at the single molecule level; detecting the second signal (or the collective signal) for each peptide at the single molecule level with the optical device; treating the plurality of immobilized peptides under conditions such that each N-terminal amino acid of each peptide is removed; and detecting the first signal for each peptide at the single molecule level with the optical device.

In one embodiment, the present invention contemplates a method of identifying amino acids in peptides, comprising providing a plurality of peptides immobilized on a solid support, each peptide comprising an N-terminal amino acid and internal amino acids, the internal amino acids comprising Lysine, each Lysine labeled with a first label, the first label producing a first signal (e.g. green) for each peptide, and the N-terminal amino acid of each peptide labeled with a second label, the second label being different from the first label, the second label providing a second signal (e.g. red) for each peptide, the first and second signals producing a collective signal (e.g. red/green) for each peptide, wherein a subset of the plurality of peptides comprise an N-terminal Lysine having both the first and second label; detecting the second signal (or the collective signal) for each peptide at the single molecule level; treating the plurality of immobilized peptides under conditions such that each N-terminal amino acid of each peptide is removed; and detecting the first signal for each peptide at the single molecule level under conditions such that the subset of peptides comprising an N-terminal Lysine is identified.

In one embodiment, the present invention contemplates a method of identifying amino acids in peptides, comprising providing a plurality of peptides immobilized on a solid support, each peptide comprising an N-terminal amino acid and internal amino acids, the internal amino acids comprising Lysine, each Lysine labeled with a first label, the first label producing a first signal (e.g. green) for each peptide, and the N-terminal amino acid of each peptide labeled with a second label, the second label being different from the first label, the second label providing a second signal (e.g. red) for each peptide, the first and second signals producing a collective signal (e.g. red/green) for each peptide, wherein a subset of the plurality of peptides comprise an N-terminal acid that is not Lysine; detecting the second signal (or the collective signal) for each peptide at the single molecule level; treating the plurality of immobilized peptides under conditions such that each N-terminal amino acid of each peptide is removed; and detecting the first signal for each peptide at the single molecule level under conditions such that the subset of peptides comprising an N-terminal amino acid that is not Lysine is identified.

In one embodiment, the present invention contemplates a method of sequencing peptides, comprising providing a sample comprising a plurality of peptides, a first label (for example a first fluorescent molecule), and a second label (for example, a second fluorescent molecule); immobilizing the plurality of peptides on a solid support; labeling every residue of a specific amino acid type in the plurality of immobilized peptides with the first label; labeling the N-terminal amino acids of the plurality of immobilized peptides with the second label; removing the N-terminal amino acids of the plurality of immobilized peptides; and detecting the label (for example, measuring the fluorescence intensity of the first and second fluorescent molecules) for single-peptides within the plurality of immobilized peptides. In one embodiment, the labeling and removing steps are successively repeated from 1 to 20 times. In one embodiment, the first and second labels are detected measuring on the plurality of immobilized peptide. In another embodiment, the N-terminal amino acids are removed by an Edman degradation reaction. In another embodiment, the Edman degradation reaction labels the N-terminal amino acids of the immobilized peptides with the second fluorescent molecule. In yet another embodiment, the peptides are immobilized via internal Cysteine residues. In one embodiment, the specific amino acid labeled with the first label is Lysine. In one embodiment, the first and second labels on the single-peptides are measured with optics capable of single-molecule resolution. In another embodiment, the degradation step in which a loss of second label (for example a reduced fluorescence intensity) coincides with a loss of first label (for example reduced fluorescence intensity) is identified. In one embodiment, the pattern of degradation steps that coincide with a reduction of the first label (for example a loss in fluorescence intensity) is unique to a single-peptide within the plurality of immobilized peptides. In one embodiment, the single-peptide pattern is compared to the proteome of an organism to identify the peptide.

In one embodiment, only a single label is used. In this embodiment, the invention relates to a method of treating peptides, comprising: a) providing a plurality of peptides immobilized on a solid support, each peptide comprising an N-terminal amino acid and internal amino acids, said internal amino acids comprising Lysine, each Lysine labeled with a label, and said label producing a signal for each peptide; b) treating said plurality of immobilized peptides under conditions such that each N-terminal amino acid of each peptide is removed; and c) detecting the signal for each peptide at the single molecule level. In one embodiment, said label is a fluorescent label. In one embodiment, the removal in step b) said N-terminal amino acid of each peptide reacted with a phenyl isothiocyanate derivative. In one embodiment, the removal of said N-terminal amino acid in step b) is done under conditions such that the remaining peptides each have a new N-terminal amino acid. In one embodiment, the method further comprises the step d) removing the next N-terminal amino acid done under conditions such that the remaining peptides each have a new N-terminal amino acid. In one embodiment, the method further comprises the step e) detecting the next signal for each peptide at the single molecule level. In one embodiment, the N-terminal amino acid removing step and the detecting step are successively repeated from 1 to 20 times. In one embodiment, the repetitive detection of signal for each peptide at the single molecule level results in a pattern. In one embodiment, the pattern is unique to a single-peptide within the plurality of immobilized peptides. In one embodiment, the single-peptide pattern is compared to the proteome of an organism to identify the peptide. In one embodiment, the intensity of said labels are measured amongst said plurality of immobilized peptides. In one embodiment, the N-terminal amino acids are removed in step b) by an Edman degradation reaction. In one embodiment, the peptides are immobilized via Cysteine residues. In one embodiment, the detecting in step c) is done with optics capable of single-molecule resolution. In one embodiment, the degradation step in which removal of the N-terminal amino acid coincides with removal of the label is identified. In one embodiment, said removal of the amino acid is measured in step b) is measured as a reduced fluorescence intensity.

In one embodiment, the present invention contemplates labeling two or more amino acids. For example, in one embodiment, a triple labeling scheme is contemplated for labeling Cysteine, Lysine and Tryptophan. Thus in one embodiment, the first fluorophore is attached to a structure in a group consisting of a thiol in Cysteine, an amine in Lysine, and an N-terminus, the second fluorophore is attached to a structure selected from the amino acids having carboxylate side chains and/or a free C-terminus. In a further embodiment, a third fluorophore is attached to a Tryptophan. Thus, in one embodiment, the first fluorophore attached to Cysteine is an iodoacetamide. In another embodiment, the first fluorophore attached to Lysine is a 2-methoxy-4,5-dihydro-1H-imidazole. In one embodiment, Cysteine side chains are solution labeled with an iodoacetamide with or without subsequent labeling with a 2-methylthio-2-imadazoline hydroiodide (MDI). In one embodiment, Lysine side chains are solution labeled with a 2-methoxy-4,5-dihydro-1H-imidazole. In one embodiment, Tryptophan side chains are solution labeled with a 2,4-Dinitrobenzenesulfenyl chloride (DBSC).

In one embodiment, the present invention contemplates solution-phase labeling of at least five targets in a peptide is shown in FIG. 43 and described in Example V. Thus in one embodiment, Cys is labeled first, Lys is labeled second, N-terminal labeling third, carboxylates (side chains and C-terminus) are labeled fourth, followed by Trp-labeling fifth. In one embodiment, the first label is selected from the group consisting of iodoacetamide and 2-methylthio-2-imadazoline hydroiodide (MDI). In one embodiment, the second label is 2-methoxy-4,5-dihydro-1H-imidazole. In one embodiment, the third label is 1-(4,4-dimethyl-2,6-dioxocyclohexylidene)-3-methylbutyl diethyl phosphate (Phos-ivDde). In one embodiment, the fourth label is selected from the group consisting of benzylamine (BA), 3-dimethylaminopropylamine, and isobutylamine. In one embodiment, the fifth label is 2,4-dinitrobenzenesulfenyl chloride.

In one embodiment, the present invention contemplates solid-phase labeling of at least three targets in a peptide is shown in FIG. 44 and described in Example V. In one embodiment, Lys is labeled first, carboxylates are labeled second followed by Trp-labeling third. In one embodiment, the first label is 2-methoxy-4,5-dihydro-1H-imidazole. In one embodiment, the second label is (7-Azabenzotriazol-1-yloxy)tripyrrolidinophosphonium hexafluorophosphate (PyAOP). In one embodiment, the third label is 2,4-Dinitrobenzenesulfenyl chloride. In one embodiment, the peptide is attached to hydrazinobenzoyl resin.

Definitions

To facilitate the understanding of this invention a number of terms are defined below. Terms defined herein (unless otherwise specified) have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. As used herein, terms defined in the singular are intended to include those terms defined in the plural and vice versa.

As used herein, the term "amino acid" in general refers to organic compounds that contain at least one amino group, —$NH_2$ which functionalized is —$NH_3^+$, and one carboxyl group, —COOH, which functionalized is —$COO^-$, where the carboxylic acids are deprotonated at neutral pH, having the basic formula of $NH_2CHRCOOH$. An amino acid and thus a peptide has an N (amino)-terminal residue region and a C (carboxy)-terminal residue region. Types of amino acids include at least 20 that are considered "natural" as they comprise the majority of biological proteins in mammals, such as Lysine, Cysteine, Tyrosine; Tyr; Y, Threonine; Thr; T, etc. Amino acids may also be grouped as having carboxylic acid groups (at neutral pH), including aspartic acid or aspartate (Asp; D) and glutamic acid or glutamate (Glu;E); and basic amino acids (at neutral pH), including lysine (Lys;L), arginine (Arg;N), and histidine (His; H).

As used herein, the term "terminal" is referred to as singular terminus and plural termini.

As used herein, the term "side chains" or "R" refers to unique structures attached to the alpha carbon (attaching the amine and carboxylic acid groups of the amino acid) that render uniqueness to each type of amino acid. R groups have a variety of shapes, sizes, charges, and reactivities, such as Charged Polar side chains, either positively or negatively charged, such as lysine (+), arginine (+), Histidine (+), aspartate (−) and glutamate (−), amino acids can also be basic, such as lysine, or acidic, such as glutamic acid; Uncharged Polar side chains have Hydroxyl, Amide, or Thiol Groups, such as Cysteine having a chemically reactive side chain, i.e. a thiol group that can form bonds with another Cysteine, Serine (Ser) and Threonine (Thr), that have hydroxylic R side chains of different sizes; Asparagine (Asn), Glutamine (Gln), and Tyrosine (Tyr); Non-polar hydrophobic amino acid side chains include the amino acid Glycine; Alanine, Valine, Leucine, and Isoleucine having aliphatic hydrocarbon side chains ranging in size from a methyl group for alanine to isomeric butyl groups for Leucine and Isoleucine; Methionine (Met) has a thiol ether side chain, Proline (Pro) has a cyclic pyrrolidine side group. Phenylalanine (with its phenyl moiety) (Phe) and Tryptophan (Trp) (with its indole group) contain aromatic side groups, which are characterized by bulk as well as nonpolarity.

Amino acids can also be referred to by a name or 3-letter code or 1-letter code, for example, Cysteine; Cys; C, Lysine; Lys; K, Tryptophan; Trp; W, respectively.

Amino acids may be classified as nutritionally essential or nonessential, with the caveat that nonessential vs. essential may vary from organism to organism or vary during different developmental stages. Nonessential or conditional amino acids for a particular organism is one that is synthesized adequately in the body, typically in a pathway using enzymes encoded by several genes, as substrates to meet the needs for protein synthesis. Essential amino acids are amino acids that the organism is not unable to produce or not able to produce enough naturally, via de novo pathways, for example Lysine in humans. Humans obtain essential amino acids through their diet, including synthetic supplements, meat, plants and other organisms.

"Unnatural" amino acids are those not naturally encoded or found in the genetic code nor produced via de novo pathways in mammals and plants. They can be synthesized by adding side chains not normally found or rarely found on amino acids in nature. Potential functional groups and side chains for synthesizing unnatural amino acids are described herein and in the Figures.

As used herein, β amino acids, which have their amino group bonded to the β carbon rather than the α carbon as in the 20 standard biological amino acids, are unnatural amino acids. The only common naturally occurring β amino acid is β-alanine.

As used herein, the term the terms "amino acid sequence", "peptide", "peptide sequence", "polypeptide", and "polypeptide sequence" are used interchangeably herein to refer to at least two amino acids or amino acid analogs that are covalently linked by a peptide (amide) bond or an analog of a peptide bond. The term peptide includes oligomers and polymers of amino acids or amino acid analogs. The term peptide also includes molecules that are commonly referred to as peptides, which generally contain from about two (2) to about twenty (20) amino acids. The term peptide also includes molecules that are commonly referred to as polypeptides, which generally contain from about twenty (20) to about fifty amino acids (50). The term peptide also includes molecules that are commonly referred to as proteins, which generally contain from about fifty (50) to about three thousand (3000) amino acids. The amino acids of the peptide may be L-amino acids or D-amino acids. A peptide, polypeptide or protein may be synthetic, recombinant or naturally occurring. A synthetic peptide is a peptide that is produced by artificial means in vitro.

As used herein, the term "subset" refers to the N-terminal amino acid residue of an individual peptide molecule. A "subset" of individual peptide molecules with an N-terminal Lysine residue is distinguished from a "subset" of individual peptide molecules with an N-terminal residue that is not Lysine.

As used herein, the term "fluorescence" refers to the emission of visible light by a substance that has absorbed light of a different wavelength. In some embodiments, fluorescence provides a non-destructive means of tracking and/or analyzing biological molecules based on the fluorescent emission at a specific wavelength. Proteins (including antibodies), peptides, nucleic acid, oligonucleotides (including single stranded and double stranded primers) may be "labeled" with a variety of extrinsic fluorescent molecules referred to as fluorophores. Isothiocyanate derivatives of fluorescein, such as carboxyfluorescein, are an example of fluorophores that may be conjugated to proteins (such as antibodies for immunohistochemistry) or nucleic acids. In some embodiments, fluorescein may be conjugated to nucleoside triphosphates and incorporated into nucleic acid probes (such as "fluorescent-conjugated primers") for in situ hybridization. In some embodiments, a molecule that is conjugated to carboxyfluorescein is referred to as "FAM-labeled".

As used herein, sequencing of peptides "at the single molecule level" refers to amino acid sequence information obtained from individual (i.e. single) peptide molecules in a mixture of diverse peptide molecules. It is not necessary that the present invention be limited to methods where the amino acid sequence information obtained from an individual peptide molecule is the complete or contiguous amino acid sequence of an individual peptide molecule. In some embodiment, it is sufficient that only partial amino acid sequence information is obtained, allowing for identification of the peptide or protein. Partial amino acid sequence information, including for example the pattern of a specific amino acid residue (i.e. Lysine) within individual peptide molecules, may be sufficient to uniquely identify an individual peptide molecule. For example, a pattern of amino acids such as X-X-X-Lys-X-X-X-X-Lys-X-Lys (SEQ ID NO: 1), which indicates the distribution of Lysine molecules within an individual peptide molecule, may be searched against a known proteome of a given organism to identify the individual peptide molecule. It is not intended that sequencing of peptides at the single molecule level be limited to identifying the pattern of Lysine residues in an individual peptide molecule; sequence information for any amino acid residue (including multiple amino acid residues) may be used to identify individual peptide molecules in a mixture of diverse peptide molecules.

As used herein, "single molecule resolution" refers to the ability to acquire data (including, for example, amino acid sequence information) from individual peptide molecules in a mixture of diverse peptide molecules. In one non-limiting example, the mixture of diverse peptide molecules may be immobilized on a solid surface (including, for example, a glass slide, or a glass slide whose surface has been chemically modified). In one embodiment, this may include the ability to simultaneously record the fluorescent intensity of multiple individual (i.e. single) peptide molecules distributed across the glass surface. Optical devices are commercially available that can be applied in this manner. For example, a conventional microscope equipped with total internal reflection illumination and an intensified charge-couple device (CCD) detector is available (see Braslavsky et al., PNAS, 100(7): 3960-4 (2003) [4]. Imaging with a high sensitivity CCD camera allows the instrument to simultaneously record the fluorescent intensity of multiple individual (i.e. single) peptide molecules distributed across a surface. In one embodiment, image collection may be performed using an image splitter that directs light through two band pass filters (one suitable for each fluorescent molecule) to be recorded as two side-by-side images on the CCD surface. Using a motorized microscope stage with automated focus control to image multiple stage positions in the flow cell may allow millions of individual single peptides (or more) to be sequenced in one experiment.

As used herein, the term "collective signal" refers to the combined signal that results from the first and second labels attached to an individual peptide molecule.

As used herein, the term "experimental cycle" refers to one round of single molecule sequencing, comprised of the Edman degradation of a single amino acid residue followed by TIRF measurement of fluorescence intensities.

Attribution probability mass function—for a given fluorosequence, the posterior probability mass function of its source proteins, i.e. the set of probabilities $P(p_i/f_i)$ of each source protein $p_i$, given an observed fluorosequence $f_i$.

BRIEF DESCRIPTION OF THE DRAWINGS

For a more complete understanding of the features and advantages of the present invention, reference is now made to the detailed description of the invention along with the accompanying FIGS.

FIG. 6 depicts a simulation that demonstrates that successive cleavage of N-terminal amino acids results in patterns capable of identifying at least one peptide from a substantial fraction of proteins that comprise the human and yeast proteome.

FIG. 7 depicts a simulation that demonstrates that limiting sequencing to peptides with no more than eight Lysines provides nearly the coverage of the full set of peptides in the yeast proteome.

FIG. 9 depicts the synthesis scheme for producing the isothiocyanate derivatives of cyanine dyes Cy3 and Cy5.

FIG. 19 is a schematic showing one embodiment for the synthesis of 30-mers via olefin metathesis concatenation of 10-mers, and reversal with ethylene. FIG. 19A shows an approach for synthesis where the C terminus is Cysteine. FIG. 19B shows the transition of 30 mers to 10-mers. FIG. 19C shows the preparation for sequencing. FIG. 19D shows a schematic for olefin metathesis.

FIG. 25 shows useful orthogonal dynamic covalent functional groups.

FIG. 26 shows alternative orthogonal reactions.

FIG. 27 shows alternative side chains.

FIG. 28 shows embodiments of unnatural peptides that can be constructed with the dynamic covalent functional groups discussed above.

FIGS. 36A-B show an exemplary select number of fluorophores exhibit fluorescence stability towards Edman solvents. (a) The panel of fluorophores scanning across four fluorescent channels were tested for their percentage change in fluorescence intensity after a 24 hour incubation with trifluoroacetic acid (TFA) or pyridine/PITC in 9:1 (shown as pyridine) at 40° C. The fluorophores demarcated in boxes had a relatively small change (<40%) in fluorescence with the prolonged incubation in the Edman solvents. (b) The panel of bead images are two examples of the fluorescence changes in dyes on the Tentagel® beads with 24 hour TFA and pyridine incubation. The BODIPY-FL and Atto647N dye shows dramatic differences in dye behavior with the Edman solvent incubation. In the case of BODIPY-FL, the fluorescence intensity decreases with TFA incubation while there is a spectral shift with pyridine incubations. The fluorescence intensity is unchanged for the case of Atto647N dye. The terminologies used for the four fluorescence channels are combinations of filter sets described in methods section. The scale bar is 200 μm.

FIGS. 38A-B show exemplary peptides that can be stably and covalently immobilized on amine surfaces using EDC chemistry. The carbodiimide conjugation between the activated carboxylic acid of the peptide—(fmoc)-K*A (where* is the fluorescent tetramethylrhodamine) and amine group on Tentagel® beads occurs by the EDC (Ethyl-(3-dimethylaminopropyl) carbodiimide)/NHS cross-linker (see methods for the EDC coupling protocol). The peripheral fluorescent signal from immobilized peptide is stable with 24 h incubation with TFA or pyridine/PITC (9:1 v/v) solvents as seen in (a). The panel of images of peptide (fmoc-K*A) immobilization on aminosilane coated glass beads in (b)

controls for the effect of other variables involved in the chemistry and the non-covalent binding of Tentagel beads. High density peripheral binding of peptides is observed on amine coated glass beads which verifies that the peptides are covalently immobilized on the amine surface via their carboxylic acid group. Scale bar used is 200 μm.

FIG. 39 shows an exemplary structure of rhodamine variants with the conjugated peptide. The structures of the four peptides with their F-Lysines labeled with the rhodamine dye variant are shown. Peptides A and B was (boc)-K*A labeled with rhodamine B and rhodamine 101 respectively. Peptide C is (fmoc)-K*A labeled with tetramethylrhodamine and peptide D was labeled with a rhodamine B but contains a synthetic N, N'-dimethylethylenediamine (DMEDA) linker.

FIGS. 40A-B show that exemplary fluorescence of rhodamine dyes attached to peptides is affected by the pH of the imaging buffer. (a) Comparison of four different synthetic peptides (fmoc or boc)-K*A, labeled with commercially available rhodamine B, rhodamine 101, tetramethylrhodamine or rhodamine B with DMEDA linker, showed differences in their fluorescence behavior under different pH conditions. While all the rhodamine variants showed enhanced fluorescence under pH 1 imaging buffer, the fluorescence of tetramethylrhodamine and synthesized methyl-rhodamine B was stable across pH 1 to pH 10 imaging buffers. The fluorescence of the rhodamine variants are dramatically reduced under basic conditions due to the formation of spirolactam (see text for reasoning). (b) The panel of images show the fluorescence of napthofluorescein in the CY5 channel under basic conditions while maximum fluorescence of rhodamine 101 dye is observed in acidic conditions. The pH effect on dye fluorescence can be theoretically leveraged to decouple the dye neighborhood interactions (such as FRET). The free electrons in the nitrogen atom in the amide bond formed with the peptide for rhodamine B and rhodamine 101 variants (see FIG. 39 for examples of the structures) causes spirolactam ring formation and quenched fluorescence under basic conditions.

FIGS. 41A-B show exemplary Edman degradation that can be used to determine the positional information of the fluorescently labeled Lysine residues of synthetic peptides using bulk fluorescence measurements. The scale bar shown is 200 μm.

FIGS. 42A-B show exemplary model peptides. (a) KDYWEC (SEQ ID NO: 3) for solution labeling (1) and (b) KDYWE (SEQ ID NO: 4) immobilized on hydrazine benzoyl resin (2).

Figure 43:
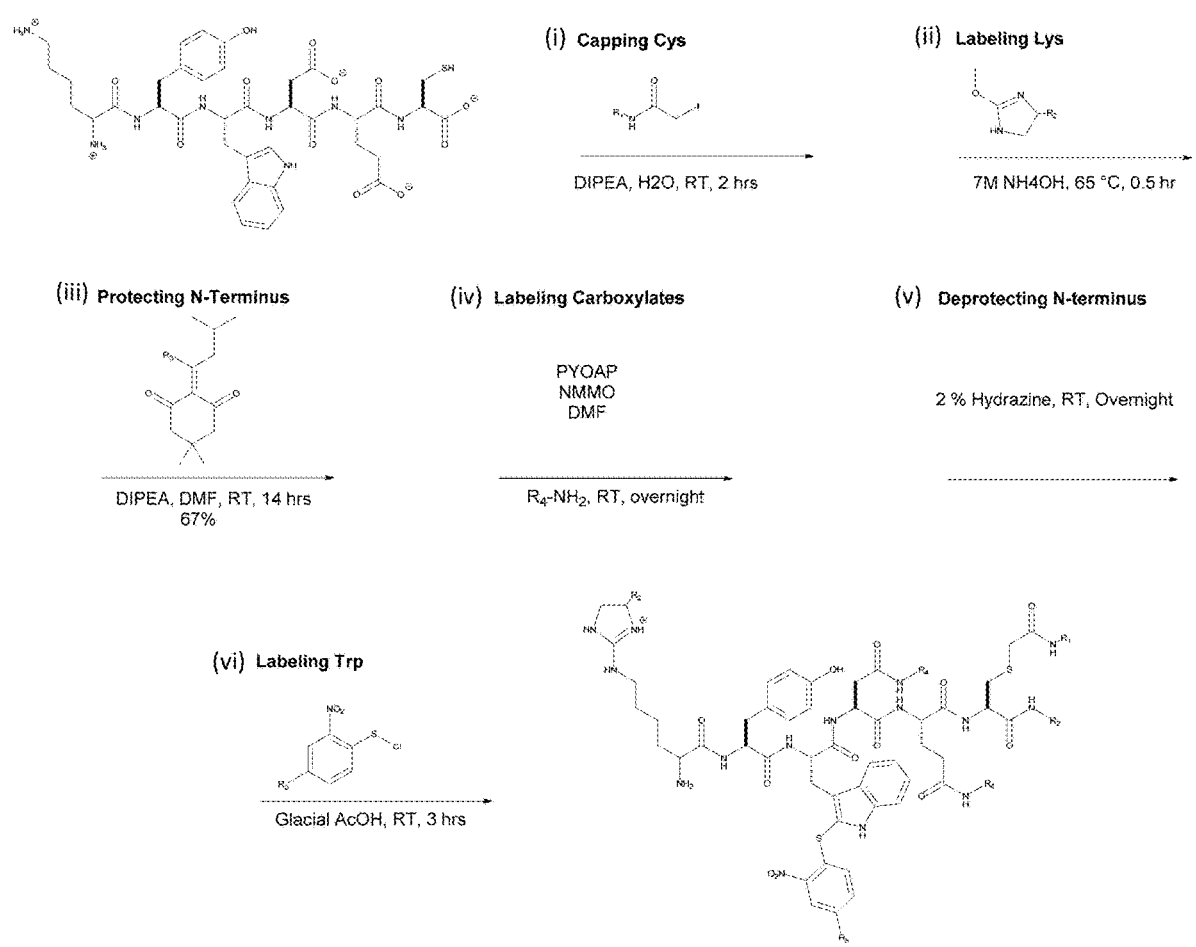

FIG. 43 shows exemplary orthogonal labeling route in solution-phase. (i)-(ii) labeling of Cysteine and Lysine are done consecutively in the same vial. (iii) Labeling of N-terminus occurs with 1-(4,4-dimethyl-2,6-dioxocyclohexylidene)-3-methylbutyl diethyl phosphate (Phos-ivDde) formed in sutu (iv) Labeling of carboxylates were done using three different amines. (v) Deprotecting N-terminus. (vi) Labeling of Tryptophan.

Figure 44:
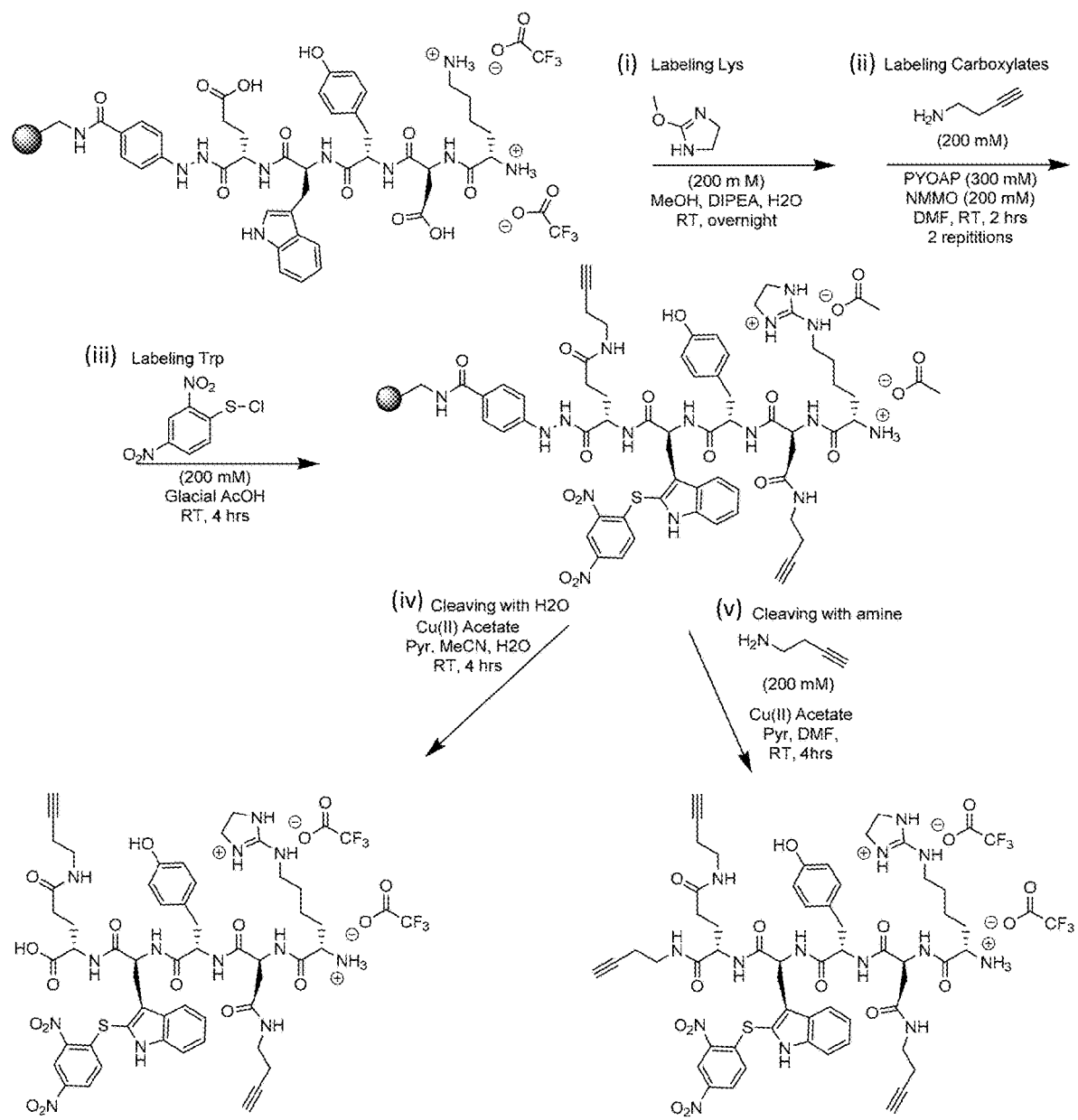

FIG. 44 shows exemplary Solid phase labeling of KDYWE (SEQ ID NO: 4). (i) Labeling for Lysine was done similarly for immobilized KDYWEC (SEQ ID NO: 3). (ii) Repetitions were performed to drive reaction to completion. (iii) Labeling of Tryptophan. (iv) Cleavage with water releases C-terminus as an acid. (v) Cleavage with amine functionalized C-terminus with an alknvne.

FIG. 45 shows exemplary peptide KDYWE (SEQ ID NO: 4) derivatives.

FIGS. 46A-I show exemplary characterization data showing successful orthogonal labeling with model peptide KDYWEC (SEQ ID NO: 3) in solution-phase and KDYWE (SEQ ID NO: 4) in solid-phase. See, Example V. A) Peptide 3, B) Peptide 4, C) Peptide 5, D) Peptide 6, E) Peptide 8, F) Peptide 9, G) Peptide 10, H) Peptide 11 and I) Peptide 12.

Figure 47:
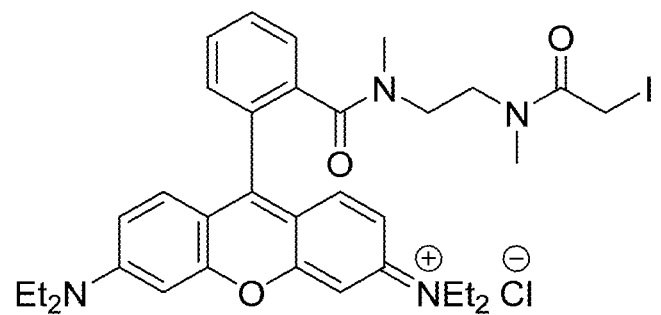

FIG. 47 shows embodiments of a fluorescent pH insensitive (methyl groups on amide Ns) labeling reagent for Cysteine labeling, Rhodamine B iodoacetamide: N-(6-(diethylamino)-9-(2-((2-iodo-N-methylacetamido)ethyl)(methyl)carbamoyl)phenyl)-3H-xanthen-3-ylidene)-N-ethylethanaminium chloride.

FIGS. 48A-C show exemplary Cysteine labeling: Model synthetic peptides containing Cysteine were solution-phase labeled with Rhodamine B iodoacetamide. A) YKTCYTD (SEQ ID NO: 5), B) KCGGYCD (SEQ ID NO: 6), and C) GYCKCTD (SEQ ID NO: 7). This reaction was selective for Cysteine where the Lysine and N-terminus were boc-protected. Purified peptides were confirmed by high resolution mass spectrometry.

FIG. 49 shows embodiments of a model reagent for Tryptophan labeling: 4-(butylcarbamoyl)-2-nitrophenyl hypochlorothioite can be used to label Tryptophan containing peptides. The sulfenyl chloride functional group was synthesized using the procedure from Li, Z.-S.; Wang, W.-M.; Lu, W.; Niu, C.-W.; Li, Y.-H.; Li, Z.-M.; Wang, J.-G. "Synthesis and biological evaluation of nonsymmetric aromatic disulfides as novel inhibitors of acetohydroxyacid synthase." *Bioorg. Med. Chem. Lett.* 2013, 23, 3723-3727.

FIG. 50 shows exemplary Tryptophan labeling: The labeled Tryptophan was stable to Edman degradation in solution.

FIGS. 51A-B show exemplary Lysine labeling: An isothiourea was synthesized as a model reagent for Lysine labeling. A) Reaction of the isothiourea with Lysine dihydrochloride proceeded once. B) Reaction of the isothiourea with peptides proceeds slowly.

FIGS. 52A-B show an exemplary synthesis of a Tryptophan labeling reagent as Rhodamine B sulfenyl chloride. A) Synthesis of a thioether precursor to Rhodamine B sulfenyl chloride. B) Synthesis of Rhodamine B sulfenyl chloride from the thioether precursor.

FIGS. 53A-B show exemplary labeling of a peptide with a tryptophan labeling with the Rhodamine B sulfenyl chloride as shown in FIG. 52. Successful labeling is observed in test reactions with two small peptides, A) Ser-Trp (SW) and B) Ala-Asn-Trp (ANW).

Figure 54:
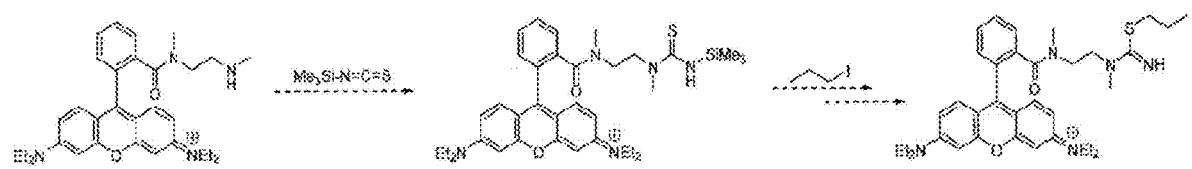

FIG. 54 shows an exemplary synthesis of rhodamine B variants for use with labeling an amino acid. Rhodamine B modified with N,N'-dimethylethylenediamine (first structure) was activated by Me3Si—NHS to form an isothiourea variant (second structure), then reacted in n-Propyl iodide for a third structure, any of these structures may find use in labeling amino acids and peptides.

Figure 55:
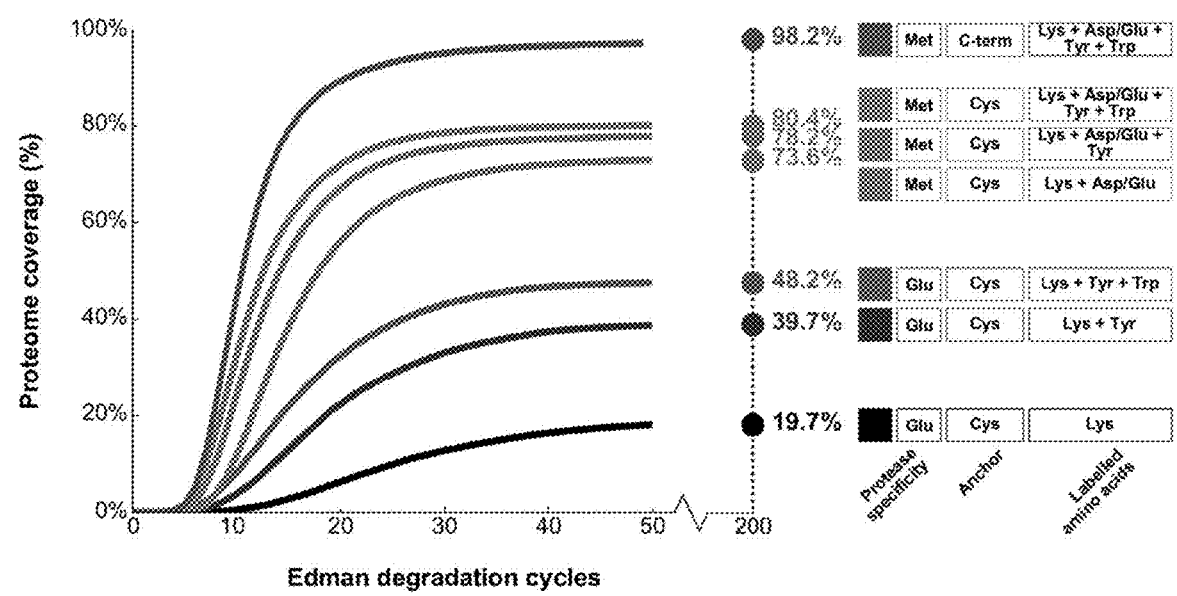

FIG. 55 shows exemplary simulations of ideal experimental conditions that suggest relatively simple labeling schemes are sufficient to identify most proteins in the human proteome. Each curve summarizes the fraction of human proteins uniquely identified by at least one peptide as a function of the number of sequential experimental cycles (a paired Edman degradation reaction and TIRF observation). As used herein, peptides generated by different proteases (e.g. Glu represents cleavage C-terminal to glutamic acid residues by GluC, Met represents cleavage after methionine residues by cyanogen bromide) and under different labeling schemes (e.g. Lys+Tyr indicates Lys and Tyr selectively labeled with two distinguishable fluorophores. Asp/Glu indicates both residues are labeled with identical fluorophores). Peptides are immobilized as indicated, with Cys representing anchoring by cysteines (thus, only cysteine-containing peptides are sequenced) and C-term representing anchoring by C-terminal amino acids. Increasing the number of distinct label types improves identification up to 80% within only 20 experimental cycles even when only Cys-containing peptides are sequenced; near total proteome coverage is theoretically achievable when cyanogen bromide generated peptides are anchored by their C-termini and labeled by a combination of four different fluorophores. Cycle numbers denote upper bounds, since each fluorosequence is not allowed to proceed past the anchoring residue (cysteine or C-terminus). Note also that the peptide length distributions change depending on the enzyme used for cleavage, with median lengths of 26 amino acids for cyanogen bromide, 8 for GluC and 10 for trypsin digests.

FIGS. 56A-D shows exemplary typical proteolytic peptides which have counts of labelable amino acids sufficiently low to sequence. Frequency histograms of amino acids in in silico proteolytic peptides for lysine (A), tyrosine (B), tryptophan (C), and glutamic acid/aspartic acid (D) indicate low median values. Peptide sequences in A-C were generated in silico from the human proteome by GluC digestion, and those in D by cyanogen bromide digestion. Low counts of labelable amino acids per peptide are expected to increase the ability to discriminate removal of one fluorophore amongst many on a peptide.

Figure 57:
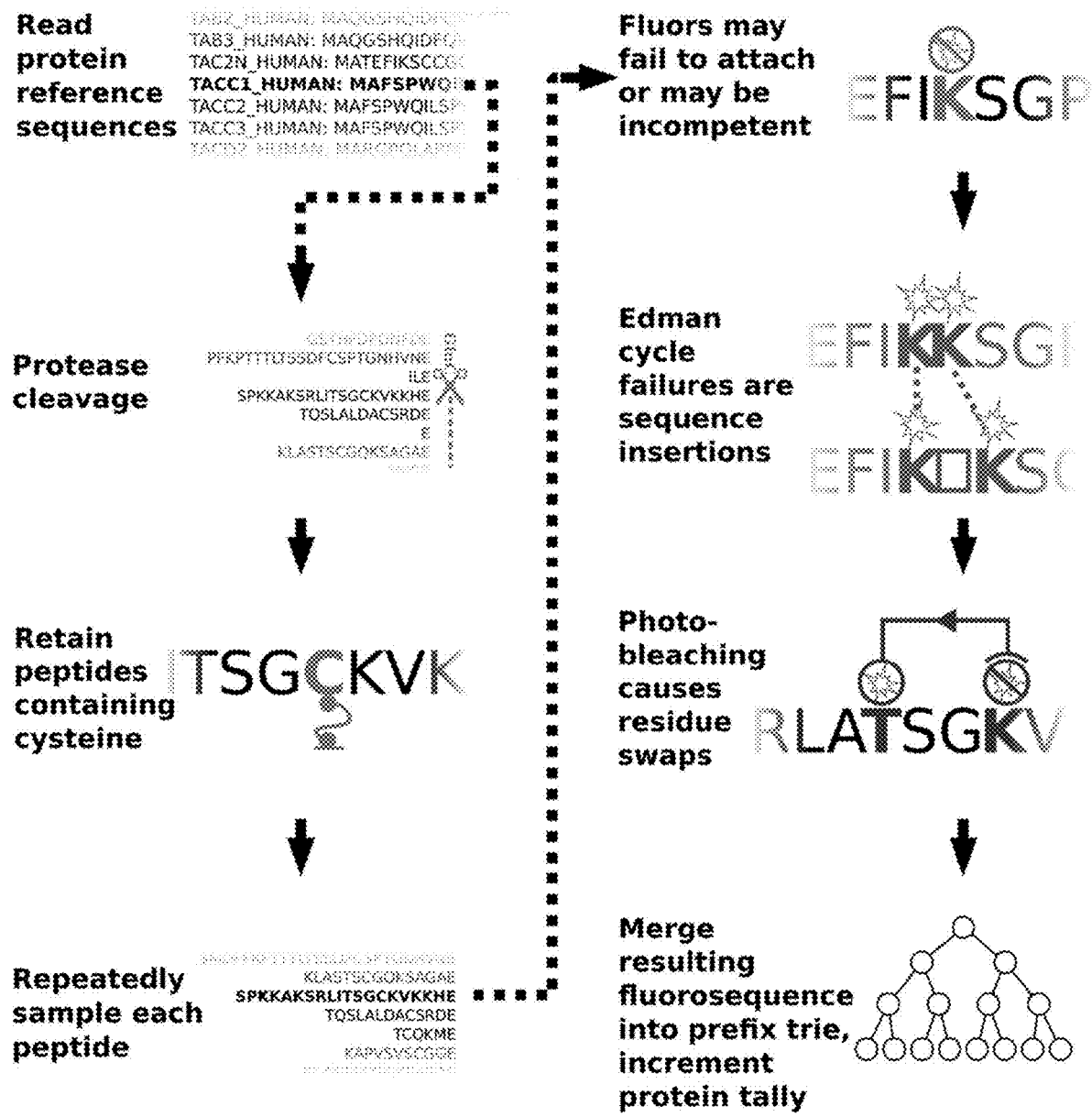

FIG. 57 shows an exemplary overview of a Monte Carlo simulation of fluorosequencing with errors. In detail, protein sequences are read as amino-acid character strings from the UniProt database. For each protein sequence, the subsequent steps are repeated: proteolysis was simulated and peptides lacking the residue for surface attachment (e.g. cysteine) were discarded. All remaining peptides were encoded as fluorosequences and subsequent steps were repeated in accordance to the desired sampling depth: The fluorosequences were altered via random functions modeling experimental errors-(1) labels were removed modeling failed fluorophores or failed fluorophore attachment, (2) positions of the remaining labels were randomly dilated modeling Edman reaction failures, and (3) fluorophores were shifted upstream from their positions, modeling photobleaching. Each resulting fluorosequence was sorted based on its position and label type and merged into a prefix trie to tally the frequencies of observing each fluorosequence from a given source protein.

FIGS. 58A-C show an exemplary simple example of the trie structure for storing and attributing fluorosequences to peptides or proteins. Consider a toy peptide mixture with peptide X (sequence GK*EGC (SEQ ID NO: 9), where K* represents fluorescently-labeled lysine; the sequence can be simplified to (K,2)) and peptide Y (GK*GK*EC (SEQ ID NO: 10); represented as (K,2), (K,4)). Panels (A) and (B) summarize populating the trie with fluorosequences from 500 copies each of Peptide X and Y, respectively. For example, peptide X might generate fluorosequence xK*, incorporated into the trie as a new node (K,2), indicated by the dashed blue lines and arrows in panel (A). (B) Simulations on Peptide Y add additional nodes to the trie. For example, the fluorosequence xK*xK* yields an additional node (K,2), (K,4) after traversing node (K,2). Additional fluorosequences are incorporated into the trie in a similar fashion, along with a tally of the number of observations of each fluorosequence, stored for each trie node along with the source peptide identities. Following the Monte Carlo simulation, the frequency of each source protein or peptide can be calculated for each trie node. To simplify data analysis and visualization, thresholds can be applied (see Example VIII) to identify and count those source proteins most confidently identified by the observed fluorosequences. As shown in FIG. 58C, fluorosequences ((K,2), (K,5)) and ((K,2), (K,4)) confidently identify peptide Y, while Peptide X is less confidently identified by fluorosequences (K,2) or (K,3).

FIGS. 59A-B shows exemplary Monte Carlo sampling that reveals the confidence with which fluorosequences can be attributed to specific source proteins. (A) and (B) represent two example fluorosequences, illustrating opposite extremes in terms of the number of proteins capable of yielding each sequence. In (A), the frequencies with which rival source proteins yield fluorosequence "xxxxExxKxK" (SEQ ID NO: 11) in the Monte Carlo simulations indicates low confidence in attributing that fluorosequence to any one protein. In (B), a single protein is by far the most likely source of fluorosequence "EEEEExxKxK" (SEQ ID NO: 12). (X-axes represent incomplete lists of proteins, ordered by the frequencies with which they are observed to generate the given fluorosequence in the simulations.)

Figure 60:
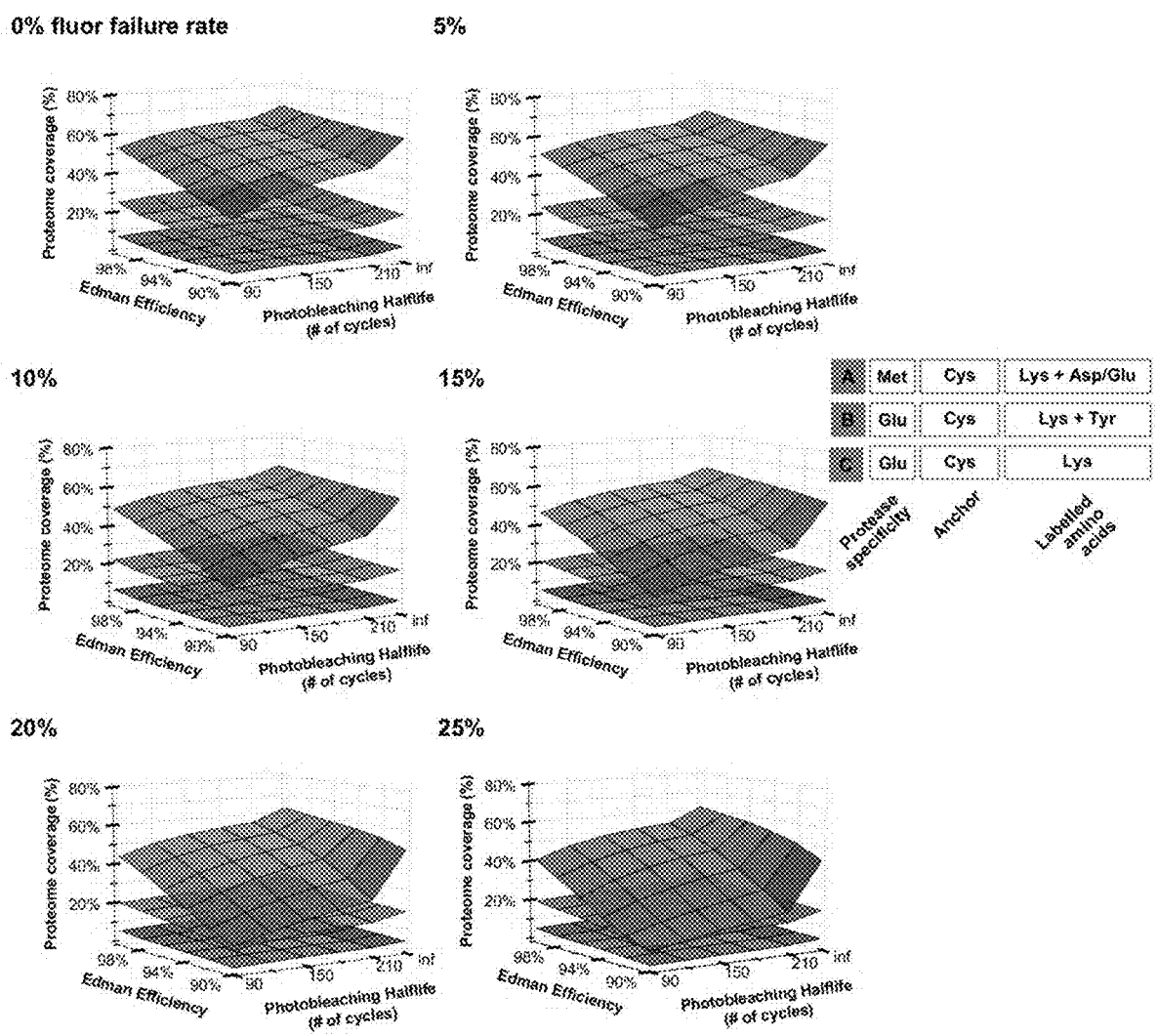

FIG. 60 shows exemplary surface plots illustrate the consequences of differing rates of Edman efficiency, photobleaching, and fluorophore failure rates. Each panel summarizes the consequences of varying rates of photobleaching and Edman failures for a different fixed fluorophore failure rate, ranging from 0% to 25%, as calculated after simulating 30 experimental cycles on the complete human proteome at a simulation depth of 10,000 copies per protein. Photobleaching shows the strongest negative impact on proteome coverage when compared to other errors; increasing the number of distinguishable labels strongly increases proteome coverage. Labeling and immobilization schemes are denoted as in FIG. 38. For comparison, literature evidence suggests that common failure rates of fluorophores may be about 15-20% [18,32], Edman degradation proceeds with about 94% efficiency [33], and the mean photobleaching lifetime of a typical Atto680 dye is about 30 minutes [23], corresponding to 1800 Edman cycles, estimating 1 sec exposure per Edman cycle. Thus, error rates should sufficiently low for effective fluorosequencing. See references numbered in Example IX.

Figure 61:
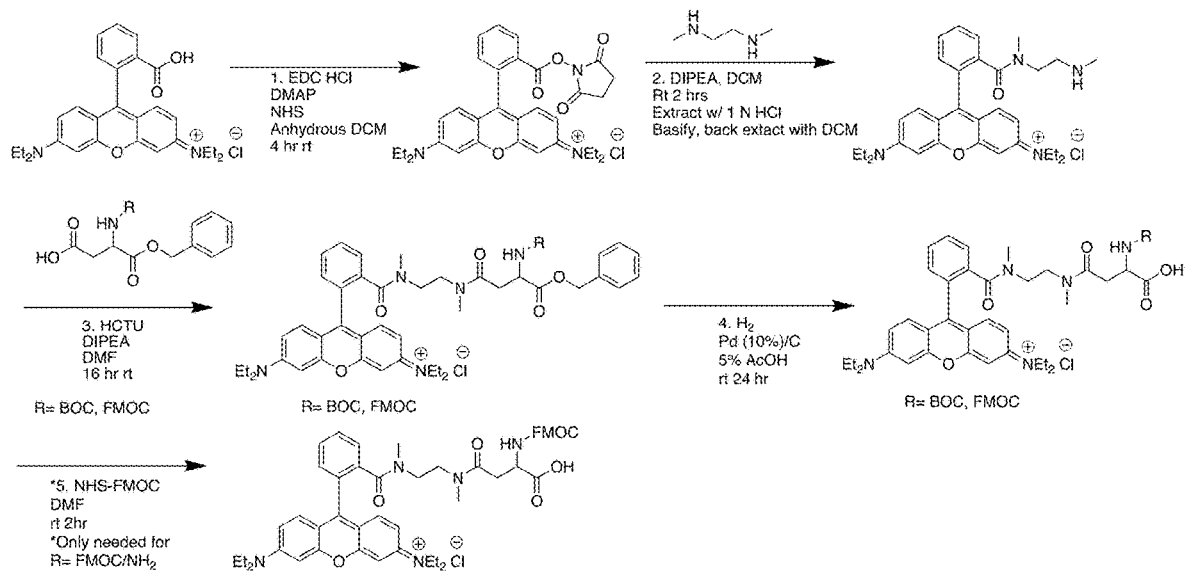

FIG. 61 shows exemplary Boc-Asp-OBzl peptide labeled with Rhodamine B via HCTU (1H-Benzotriazolium 1-[bis (dimethylamino)methylene]-5chloro-,hexafluorophosphate (1-),3-oxide) coupling.

Figure 62:
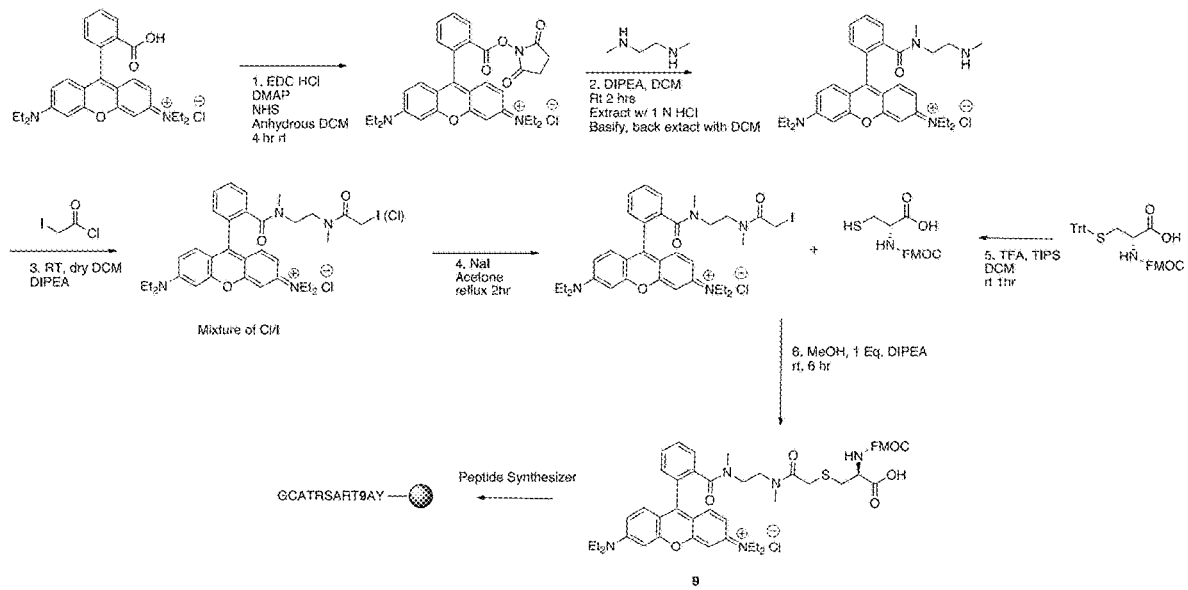

FIG. 62 shows exemplary FMOC-Cys peptide labeled with Rhodamine B via iodoacetamide handle. This Rhodamine B labeled Cys peptide was used for synthesizing a peptide. Another example of using a Rhodamine B labeled Cys used for synthesizing a peptide is shown in FIG. 64.

FIGS. 63A-B show exemplary synthesis of a Rhodamine-based dye containing a Silicon atom replacing the oxygen of the core structure. A) Si-Rhodamine cores structure as reported in literature (Lukinavičius et al. *Nature Chemistry* 5, 132-139 (2013)). B) Inventive synthetic strategies that involve the development of a "handle" i.e. via iodoacetamide, attached to core Si-Rhodamine structure for labeling an amino acid, such as Cysteine, as in FIG. 64.

FIGS. 64A-B shows exemplary two-dye labeling of a peptide. A) Labeling strategy using Rhodamine B and Si-Rhodamine of the present inventions. B) After HPLC purification, this high-resolution mass spectometry confirmed that the 12 amino acid peptide was labeled with 2 different colored dyes.

FIG. 65 shows exemplary results for Single Molecule Peptide Sequencing. Two peptide populations differing in the position of their labeled amino-acid residue were discriminated in a mixture at single-molecule sensitivity using the single-molecule Edman peptide sequencing procedure. Peptide-A labeled orange (left bar, left peptide, lighter color) in the diagram, with sequence (boc)-K*AGAAG (SEQ ID NO: 13) (*Rhodamine=Tetramethylrhodamine); and Peptide B-labeled blue (right bar, right peptide, darker color) in the diagram, with sequence (boc)-GK*[Atto647N]AGAG (SEQ ID NO: 14). Both peptides were labeled via their Lysines with dyes excitable at 561 nm and 647 nm wavelengths, respectively. Both peptide populations were immobilized on a glass slide via their carboxyl terminuses, and the protecting boc groups were removed from their amino termini.

DETAILED DESCRIPTION OF THE INVENTION

The present invention relates to the field of identifying proteins and peptides, and more specifically large-scale sequencing of single peptides in a mixture of diverse peptides at the single molecule level. The present invention also relates to methods for identifying amino acids in peptides, including peptides comprising unnatural amino acids. In one embodiment, the present invention contemplates labeling the N-terminal amino acid with a first label and labeling an internal amino acid with a second label. In some embodiments, the labels are fluorescent labels. In other embodiments, the internal amino acid is Lysine. In other embodiments, amino acids in peptides are identified based on the fluorescent signature for each peptide at the single molecule level.

The fluorophore choices that are amenable to Edman degradation chemistry have an unusual selection criteria, as they were not selectable based upon structure alone. In fact, there is no available literature or method for predicting the ideal choice of fluorophores that could be integrated in the fluorosequencing technique. Such that empirically screening each fluorophore was the method used by the inventors in order to identify Edman reaction stable fluorophores. As described herein, many of the fluorophores in the rhodamine and Atto classes of dyes were stable to the solvents of Edman degradation while others in these classes were not.

The lack of a method for sequential labeling of amino acids and development of orthogonal handles (i.e. chemically reactive labels) to fluorophores represents a unique problem in the field of protein labeling. In a majority of current uses, one class of amino acid residues are typically conjugated to a label without the use of other labeled residues. Attaching linkers to multiple amino acid residues in the same experiment provides a unique challenge and thereby a method for solving the problem. One limitation found in these methods was that low levels of cross reactivity or non-reactivity between the different linkers may complicate the interpretation of the fluorescence signal originating from the peptide molecule.

During the development of the present invention, solutions were discovered to overcome the problem of a lack of a known range of fluorophores resistant to Edman solvents and the ability to attach them orthogonally to different amino acid classes (i.e. lysine, cysteine, tryptophan, aspartic acid and/or glutamic acid). Therefore the methods described herein enable the successful implementation of the fluorosequencing technology through the discovery of numerous fluorophores having a range of fluorescence, and methods for orthogonal labeling of numerous classes of amino acids.

Apart from the importance in fluorosequencing, the addition of labels to proteins or peptides can useful in applications of mass spectrometry based proteomics in the creation of mass labels. For example, labels can be redesigned to incorporate different isotopes and shotgun proteomics involving mass spectrometry can be used for quantitative studies and better identification (similar to SILAC but treated on protein mixtures after extraction). Julka S, Regnier F. Quantification in proteomics through stable isotope coding: a review. J. Proteome Res. 2004; 3: 350-363; Krusemark C J, Frey, B L, Smith L M, Belshaw P J, Complete chemical modification of amine and acid functional groups of peptides and small proteins, In Gel-Free Proteomics, Methods in Molecular Biology, 753 (Eds: Gevaert K, Vandekerckhove J) Humana Press, New York, 2011, pp. 77-91.

The present invention relates to the field of sequencing proteins and peptides, and more specifically large-scale sequencing of single peptides in a mixture of diverse peptides at the single molecule level. In one embodiment, the present application relates to a method to determine protein sequences (including but not limited to partial sequences) in a massively parallel fashion (potentially thousands, and even millions, at a time) wherein proteins are iteratively labeled and cleaved to produce patterns reflective of their sequences. The patterns of cleavage (even of just a portion of the protein) provide sufficient information to identify a significant fraction of proteins within a known proteome, i.e. where the sequences of proteins are known in advance.

I. Protein Sequencing.

While changes in nucleic acids often underlie disease, these changes are amplified and are most readily found in proteins, which are in turn present in compartments (i.e. saliva, blood and urine) that are accessible without invasive procedures such as biopsies. Unfortunately, despite advances in high-throughput DNA sequencing, methods for the large-scale identification and quantitation of specific proteins in complex mixtures remain unavailable. For example, a variety of techniques have been examined for identifying unique tumor biomarkers in serum, including mass spectrometry and antibody arrays. However, these techniques are hampered by a lack of sensitivity and by an inability to provide quantitative readouts that can be interpreted with statistical significance by pattern analysis. This deficiency underlies many biochemical assays and molecular diagnostics and represents a critical bottleneck in biomarker discovery.

In one embodiment, the single-molecule technologies of the present application allow the identification and absolute quantitation of a given peptide or protein in a biological sample. This advancement is greater than five orders of magnitude more sensitive than mass spectrometry (the only major competing technology for identifying proteins in complex mixtures), which cannot always accurately quantify proteins because of differential ionization and desorption into the gas phase. Non-limiting example applications might therefore include single molecule detection of circulating proteins in humans or animals, leading to the determination of specific circulating biomarkers for e.g. tumors, infectious disease, etc.

The sequential identification of terminal amino acid residues is the critical step in establishing the amino acid sequence of a peptide. As noted above, a drawback to Edman degradation is that the peptides being sequenced cannot have more than 50 to 60 (more practically fewer than 30) amino acid residues. Peptide length is typically limited because with each Edman cycle there is an incomplete cleavage of the peptides, causing the reaction to lose synchrony across the population of otherwise identical peptide copies, resulting in the observation of different amino acids within a single sequencing cycle. This limitation would however not be applicable to single molecule Edman sequencing such as the method proposed, because the Edman cycling on each peptide is monitored independently.

Amino acids buried within the protein core may not be accessible to the fluorescent label(s), which may give rise to a misleading pattern of amino acids. In one embodiment of the present invention, such derivitization problems may be resolved by denaturing large proteins or cleaving large proteins or large peptides into smaller peptides before proceeding with the reaction.

It was also noted above that, since Edman degradation proceeds from the N-terminus of the protein, it will not work if the N-terminal amino acid has been chemically modified or if it is concealed within the body of the protein. In some native proteins the N-terminal residue is buried deep within the tightly folded molecule and is inaccessible to the labeling reagent. In one embodiment of the present invention the protein or peptide is denatured prior to proceeding with the Edman reaction; in such cases, denaturation of the protein can render it accessible.

It was also noted that while the standard Edman degradation protocol monitors the N-terminal amino acid liberated at each cycle, in one embodiment the present invention monitors the signal obtained from the remaining peptide.

It was also noted that unlike the Edman sequencing traditionally carried out by automated sequenators or sequencers in which complex mixtures of peptides cannot be analyzed, the current invention is capable of identifying individual peptides within a mixture.

II. Fluorescence.

Fluorosequencing refers to sequencing peptides in a complex protein sample at the level of single molecules. In one contemplated embodiment, millions of individual fluorescently labeled peptides are visualized in parallel, monitoring changing patterns of fluorescence intensity as N-terminal amino acids are sequentially removed, and using the resulting fluorescence signatures (fluorosequences) to uniquely identify individual peptides. In a more specific embodiment, a fluorosequencing method of the present inventions is contemplated to selectively label amino acids on immobilized peptides, followed by successive cycles of removing the peptide's N-terminal residues (by Edman degradation) and imaging the corresponding decrease of fluorescent intensity for individual peptide molecules. The resulting stair-step patterns of fluorescence decreases will provide positional information of the select amino acid residues. This partial pattern is often sufficient to allow unique identification of the peptide by comparison to a reference proteome. One aspect of developing this methodology is to selectively conjugate fluorophores to amino acid residues via the side chain functional group. Another aspect is choosing fluorophores that are spectrally distinct from each other in addition to being inert (i.e. resistant) to the conditions used in Edman degradation chemistry. Therefore, during the development of the present inventions, experiments were done for selectively orthogonally labeling amino acid side chain groups along with experiments for determining which fluorophores would be useful for both selective labeling and those that would survive Edman degradation chemistry by remaining bonded to the selected amino acid or chemistry group and continue to fluoresce at the expected wavelengths.

The development of next-generation DNA and RNA sequencing methods has transformed biology, with current platforms generating >1 billion sequencing reads per run. Unfortunately, no method of similar scale and throughput exists to identify and quantify specific proteins in complex mixtures, representing a critical bottleneck in many biochemical and molecular diagnostic assays. What is needed is a massively parallel method, akin to next-gen DNA sequencing, for identifying and quantifying peptides or proteins in a sample. In principle, single-molecule peptide sequencing is contemplated to achieve this goal, allowing billions of distinct peptides to be sequenced in parallel and thereby identifying proteins composing the sample and digitally quantifying them by direct counting of peptides. As described herein, theoretical considerations of single molecule peptide sequencing are accessed which indicate a possible experimental strategy. Using computer simulations, the strategies are characterized for their potential utility and unusual properties for application to future proteomics technology.

Embodiments of fluorosequencing strategy as described herein, are methods of identifying peptides based on the position of its fluorescently labeled amino acid. This can be achieved by detecting the decrease in the peptide's fluorescence intensity (coinciding with the position of labeled amino acid) through the amino acid cleavage steps of Edman degradation chemistry. The development of this technique includes testing for Edman solvent resistant fluorophores, testing for target side chain or end specific reagents, and determining which reaction steps and/or order of these steps is successful, in addition to some optimization of underlying chemistry procedures for labeling peptides.

Some of these procedures include (a) immobilization of fluorescent peptides on solid supports and (b) performing Edman chemistry to cleave one amino acid at a time from its N-terminus. While Edman degradation on immobilized peptides was developed extensively on solid support [75,87, 117], the use of fluorescently labeled peptides and detecting their fluorescence on solid support as described herein or in solution provides a unique set of new challenges for successful methods of sequencing peptides.

Figure 16:
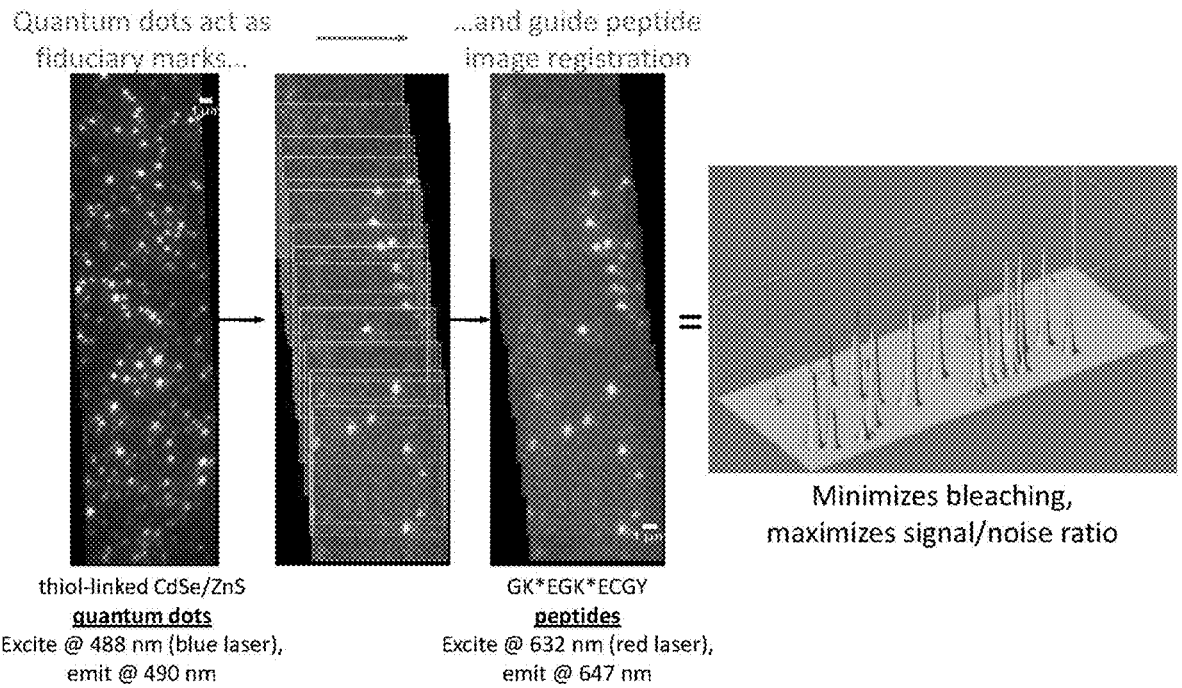
FIG. 16 shows scanning the microscope stage and tiling images to analyze large numbers of peptides wherein quantum dots can serve as guides.

Thus in one embodiment, the first labels utilized in the methods described above is a fluorescent label. In another embodiment, the first and second labels utilized in the methods described above are both fluorescent labels. In the life sciences fluorescence is generally employed as a non-destructive means to track and/or analyze biological molecules since relatively few cellular components are naturally fluorescent (i.e. intrinsic or autofluorescence). Important characteristics of fluorescent peptides are high sensitivity and non-radioactive detection. Fluorescent peptides have been widely used in fluorescence fluorimetry, fluorescence microscopy, fluorescence polarization spectroscopy, time-resolved fluorescence and fluorescence resonance energy transfer (FRET). In general, the preferred fluorescent labels should have high fluorescence quantum yields and retain the biological activities of the unlabeled biomolecules. In one embodiment, a protein can be "labeled" with an extrinsic fluorophore (i.e. fluorescent dye), which can be a small molecule, protein or quantum dot (see FIG. 16). The fluorescent dye may be attached to a peptide at a specific point through a covalent bond, which is stable and not destructive under most physiological conditions. In some embodiments, a functional linker is introduced between the dye and peptide to minimize the alteration of peptide biological activity. Peptide labeling requires attaching the dye at a defined position in the peptide (i.e. N-terminus, C-terminus, or in the middle of sequence). Examples of such embodiments are provided herein.

A. Use of Tentagel® Beads as a Solid Substrate for Peptide Immobilization.

During the development of the present inventions the Edman degradation process was tested on bulk fluorescently labeled peptide attached to beads for indicating success of the method's chemistry steps for fluorosequencing. Given the diversity of functional groups on commercially available beads, Tentagel® beads were chosen as the platform for immobilizing fluorophores or peptides, optimizing the chemistry and by image acquisition and processing, quantitate the fluorescent peptide density (see FIG. 35 for a schematic of an exemplary method). Among the number of other commercially available beads such as controlled pore glass, magnetic beads, polystyrene beads etc., Tentagel® beads have a set of advantages for this study due to their compressibility (suitable for imaging by sandwiching them between glass slides), high peripheral density of functional groups (enables quantitation of bound peptides and discriminating the non-specifically attached peptides) [133] and availability as micron sized beads (facilitating imaging and ability to be retained in many fritted syringes).

Thus several types of tests were done using peptides or fluorophore attached to Tentagel® beads during the development of the present inventions: primarily amine functionalized Tentagel® beads were tested as described herein to shortlist the fluorophore choices contemplated to be successful for performing fluorosequencing; establishing a scheme for immobilizing peptides to the bead via their carboxyl termini and optimizing the Edman degradation procedure to provide information and data for discriminating multiple peptides. In one embodiment, a fluorophore was immobilized on a bead for testing resistance to Edman solvents of said fluorophore. In one embodiment, a peptide comprising Lysine attached to a fluorophore was immobilized on a bead for testing resistance to Edman solvents. In one embodiment, testing was based on the position of certain fluorescently labeled Lysine residues in a peptide.

1. A Small Set of Fluorophores was Found Suitable for Use with Edman Solvents and Fluorophore Labeled Tentagel® Beads.

Since the principle of fluorosequencing involves measuring the decrease in fluorescent intensity due to Edman degradation the fluorescence property of the fluorophores used should not be affected by incubation with solvents used in the chemistry (namely Trifluoroacetic acid (TFA) and pyridine). Such that, a decrease in fluorescent intensity should not be significantly altered by factors, such as the solvents, bleaching, nonspecific binding of (or detachment of) fluorophores (dyes).

Despite the long history of the studies on synthesis of fluorophores, it is not evident whether subjecting the fluorophores (especially some of the commercially available fluorophores such as Atto647N, Alexa680 etc. with their superior quantum yields and publicly unavailable structures) to Edman conditions will alter their inherent photo-physical properties. Although there is precedence for the use of some fluorophores such as fluorescein isothiocyanate (FITC), 4-N, N-dimethylaminoazobenzene 4'-isothiocyanate (DABITC) etc. [129] as Edman reagents, there is no generalizable structural patterns that can be applied to shortlist fluorophores (i.e. develop a list of Edman resistant labels) for successful use in labeling for stable Edman degradation sequencing. Thus, empirically testing the fluorophores for their stability was a necessary and experimentally feasible route to narrow down the list of ideal fluorophores for the fluorosequencing technique, i.e. shortlisting for testing for use in the present inventions.

While Edman degradation was optimized to work with the different amino acid side chains and even glycosylated side chains [132] with relatively high efficiency of >90% [128], testing was necessary to determine whether the presence of bulky and charged fluorophore on the amino acid side chains hinder the reaction. Performing Edman degradation on synthetic peptides with known position of the fluorophores was contemplated for use to determine the efficiency of cleavage of the fluorescently labeled amino acid.

Figure 17:
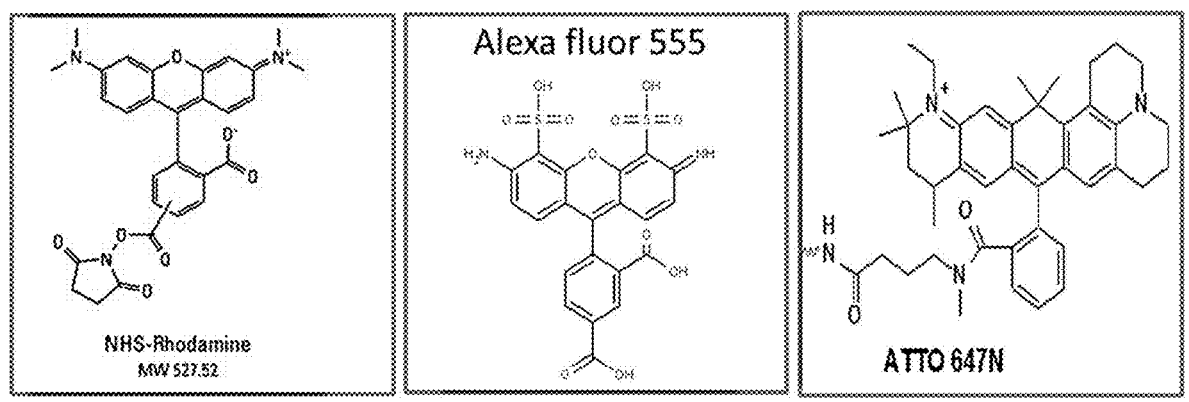
FIG. 17 shows the structure of some particularly stable dyes, i.e. stable to extended incubation with TFA and Pyridine/PITC solvents. The structures of these dyes gives some indication of its stability, primarily due to the lack of any conjugation and the presence of an extended or decorated three ring system.

The single molecule peptide sequencing method described herein involves, in one embodiment, measurement of fluorescent intensity after several cycles of Edman degradation chemistry. Some dyes show good stability in the face of the organic conditions and solvents used. Others do not. In one embodiment, the method involves exposing the peptide (with the fluorophores covalently attached to the side chain) to an incubation in Pyridine/Phenylisothiocyanate (PITC) (9:1 vv) and Trifluoroacetic acid (TFA). While the fluorescence of certain classes of fluorophores are affected by these solvents, a number of fluorophores are relatively stable over the incubation time. Indeed, certain fluorophores like Alexafluor555, Rhodamine-NHS and Atto647N, are inert to these solvents. The structures of these dyes, which have been shown to be very stable to these conditions, Rhodamine, Alexafluor555 and Atto647N are provided in FIG. 17. In another embodiment, a fluorophore was immobilized by an amide linkage to the surface of a bead, i.e. Tentagel bead, for testing resistance to Edman solvents of said fluorophore.

Fluorophores, immobilized on Tentagel beads, were tested for changes in their fluorescence properties under prolonged 24-hour incubation at 40° C. with 9:1 v/v pyridine/PITC (reagent used for coupling reaction) and neat trifluoroacetic acid (reagent used for cleavage reaction) separately. Stability under these extreme conditions ascertains usefulness in shorter experimental cycles. The test on a palette of different classes of commercially available dyes spanning four excitation and emission filter spectra indicated that only a small number of fluorophores were suitable for the study. The fluorescence stability of the dyes after 24 h TFA and PITC/pyridine incubation shortlisted six fluorophores that showed <40% change in fluorescence (see FIG. 36a).

Among the narrowed set of fluorophores in the red and far-red fluorescence channels which showed a stable fluorescence after exposure to Edman solvents were Alexa Fluor 405, Rhodamine B, tetramethyl rhodamine, Alexa Fluor 555, Atto647N and (5)6-napthofluorescein, FIG. 36a. Dyes with rigid core structures such as rhodamine dyes (tetramethyl rhodamine, Alexa Fluor 555), atto dyes (Atto647N) (also shown in FIG. 36b), and the like, were used for further studies as described herein. Due to the commercial availability of cheap dyes and a long history on the study of rhodamine dyes and their functionalization, further studies involved rhodamine dyes. In one preferred embodiment, tetramethylrhodamine is used as a label.

In one embodiment, a peptide comprises Lysine, wherein said Lysine is labeled with tetramethylrhodamine. In one embodiment, a peptide comprises Lysine labeled with tetramethylrhodamine. In one embodiment, a peptide comprises Lysine labeled with tetramethylrhodamine attached to a solid support. In one embodiment, a peptide comprises Lysine labeled with tetramethylrhodamine attached to a Tentagel® bead. In one embodiment, a peptide comprises Lysine labeled with tetramethylrhodamine attached by its C-terminus to a Tentagel bead. In other embodiments, a peptide comprises Lysine, wherein Lysine is labeled with methyl-rhodamineB. In other embodiments, a peptide comprises Lysine, wherein Lysine is labeled with rhodamineB having a DMEDA linker, such that N, N'-dimethylethylenediamine (DMEDA) is a linker between the rhodamineB fluorophore and the aspartic acid side chain of lysine. In other embodiments, a peptide comprises Lysine, wherein Lysine is labeled with rhodamine 101. In other embodiments, a peptide comprises Lysine, wherein Lysine is labeled with silicon-rhodamine (SiR):Si rhodamine B.

Since the fluorescence imaging was performed at neutral pH, it is likely that the fluorescence properties of some of the chemically unstable fluorophores can be modified if the right protonation state is induced. Some dyes like Hilyte-488 and BODIPY-FL showed shifts in their fluorescence spectra after their incubation under acidic conditions and were incapable of reverting back to its original fluorescence profile after solvent washes and incubation with pH 7 buffer (see FIG. 36b for BODIPY-FL example).

While most of the dyes exhibited binding at the periphery, some fluorophores seemed to have high internal binding. Given the highly branched nature of the polystyrene bead matrix and the grafted polyethylene glycol layer, it is possible that the internal fluorescence represents non-specific binding of the dyes to hydrophobic pockets. Many fluorophores, which were added in large excess, could possess different extents of non-specific binding despite the repeated washes with solvents.

The reasons for the chemical instability of certain fluorophores are unclear and broad generalizations cannot be made based on core structure alone. Many commercially available fluorophores such as Hilyte647 (Anaspec, CA, USA) are packaged and sold with TFA salts and yet surprisingly were not found to be acid stable under prolonged incubation. However, some empirical reasoning can explain the lack of stability of some fluorophores containing linear unsaturated bonds (polyenes), such as those found in cyanine or some BODIPY and Alexa Fluor dyes under prolonged TFA incubation. Thus it was contemplated that the protonation of unsaturated bonds under acidic conditions, inducing a cis-trans isomerization reaction, thereby changing the underlying electronics of the fluorescence structure of the dyes [134].

2. Fluorescence of Rhodamine Dyes is pH Dependent.

The fluorescence from rhodamine dyes has been known to be pH dependent [136] requiring efforts to determine the most suitable imaging buffer. The investigation of pH dependence on the fluorescence properties of four different rhodamine labeled peptides (see FIG. 39 for structure and positional nomenclature for rhodamine dyes and the peptides), indicated an environmentally induced variation in their behavior.

The acidic environment of the imaging buffer (pH 1.0) caused the highest fluorescence of the rhodamine labeled peptides (FIG. 40a). However the pH effect was most profound in the case of peptides labeled with rhodamine B (peptide A) and rhodamine 101 (peptide B). This effect did not seem to occur for the case of tetramethylrhodamine labeled peptide (peptide C). The peptides A and B showed pH dependent fluorescence because the amide nitrogen found at the 3' position is closer to the carbon position at 9 (or 1') and results in a 5 membered ring formation. This spirolactam ring is known to quench fluorescence and occurs at a pH higher than 3.1 [137]. This spirolactam formation does not occur for tetramethylrhodamine since the succinate ester is present at the 5'-6' position is not accessible to the central ring. The spironolactone formation, involving a ring formation with the carboxylate oxygen (at 3' position) can potentially quench fluorescence but requires a strong base such as piperidine. To test the hypothesis and prevent spirolactam formation in rhodamine B, an N, N'-dimethylethylenediamine (DMEDA) linker between the rhodamine B fluorophore and the aspartic acid side chain of the peptide was made resulting in the methylated amine at the 3' position (Rhodamine B-DMEDA or mRhodamine B). This prevented ring closure of the rhodamine B variant and was demonstrated by the independence of its fluorescence intensity with different pH imaging buffers.

By exploiting the fluorescence dependence on pH for the different fluorophores, the fluorescence from a dye based on its pH and emission spectra is contemplated for use in the methods of the present inventions. While the highest fluorescence of rhodamine B dye was observed in pH 1 buffer in the TRITC filter channel, the 5, 6-carboxynaphthofluorescein had its highest intensity in the pH 10 buffer in the Cy5 filter channel (FIG. 40b).

This information is contemplated for use in a novel method of isolating two neighboring fluorophores from transferring resonance energy and thus preventing quenching or FRET (Forester Resonance Energy transfer) behavior [37]. In one embodiment rhodamine dyes such as the ones used here would be used for this method. In one embodiment rhodamine dyes such as the ones used here would be used with other dyes, such as 5, 6-carboxynaphthofluorescein, having separate emissions depending upon the pH of the imaging buffer and/or emission spectra.

3. The Amide Bond Formed Between Succinate Ester and Amine Coated Beads is Specific and Occurs at the Bead Periphery.

In addition, it is important that the chemistry linking the dye is also stable. For example, there is good stability of the amide linkage (between the succinimidyl ester group of the dye with the amine group of a bead) and thioether linkage (between the maleimide group of the dye with the thiol group of a bead) after TFA and Pyridine/PITC incubations.

a. Amide Linkage.

The set of fluorophores discovered herein stable to the Edman solvents also highlights the fact that the amide bond formed between the succinimidyl (succinate) ester of the fluorophores and the free amines on the Tentagel bead was chemically inert to the harsh Edman conditions used in the experiment. The specificity of this amide bond formation was tested by comparing it with control experiments involving a carboxyl or a hydrazide functional group on Alexa Fluor 555 dye with the amine coated Tentagel beads (see FIG. 37). Internal binding of the dye was observed in these control experiments, while a clear peripheral binding was observed with the succinimidyl ester variant of the Alexa Fluor 555. The radial profile (shown in the image inset) elucidates the image processing methodology where covalently bound fluorophores are clustered in the periphery of the beads while non-specifically adsorbed fluorophores are trapped within the beads.

However, the isothiocyanate derivative of the tetramethylrhodamine dye did not show specificity for an amide linkage on the surface of the Tentagel beads.

b. Thioether Linkage.

However, even though a thiol-maleimide group linkage to some dyes might be stable to Edman solvents under certain circumstances, in this experiment there were indications of differences between types of linkages at the labeling steps when using Tentagel® beads, as described herein.

Figure 37:
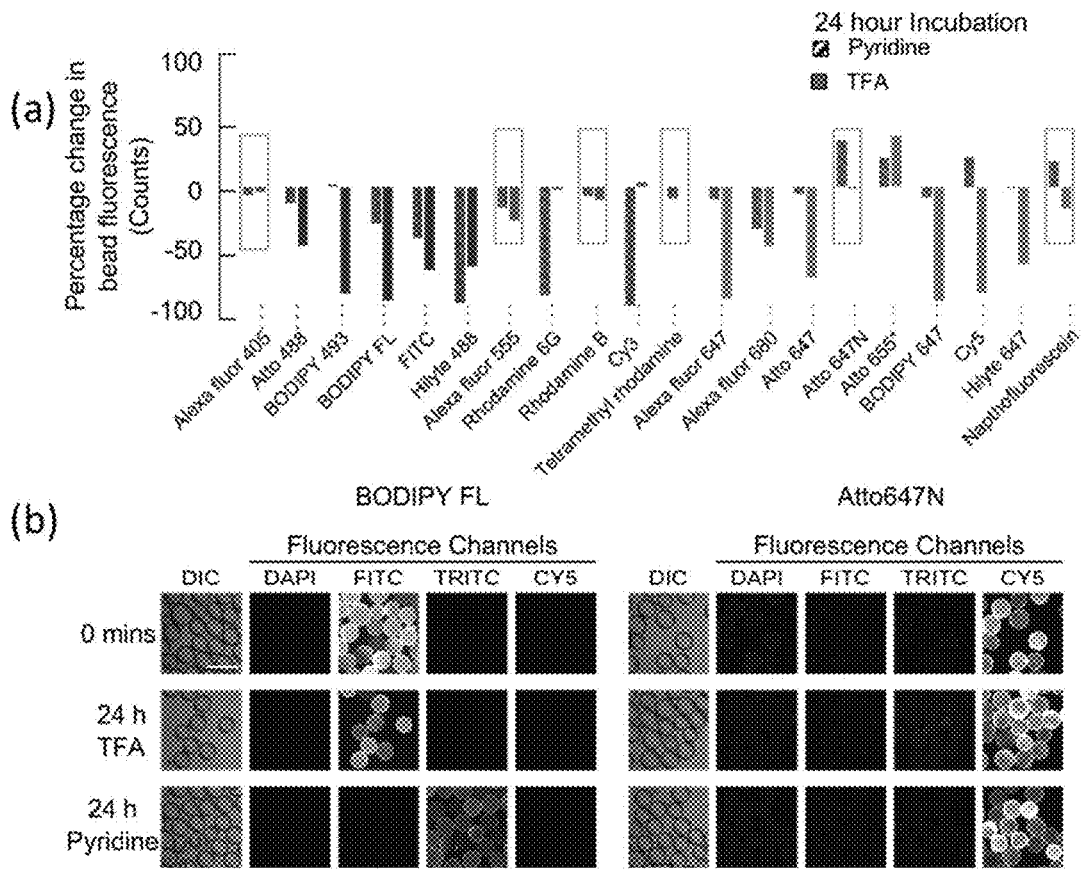
FIG. 37 shows an exemplary amide bond between the dye succinimidyl ester group and the amine surface on Tentagel® beads that results in highly specific peripheral binding. The panel of images shows the differences in binding profile (inset or radial distribution of fluorescence intensity in images) of the Alexa Fluor 555 with its different functional handles and tetramethylrhodamine isothiocyanate dye on amine or thiol grafted Tentagel® beads. The negative control involves where the carboxylate and hydrazide derivatives of the Alexa Fluor 555 did not bind to the bead periphery but bound non-specifically in its interior. The binding nature of maleimide and isothiocyanate variants is unclear. Images are not contrast stretched and the scale bar is 200 μm.

For one example, a thioether linkage between a maleimide variant of Alexa Fluor555 and thio treated Tentagel® beads showed no specific labeling of the bead, FIG. 37, unlike the succinimidyl ester linkage of Alexa Fluor555 to an amine coated Tentagel® bead.

It was contemplated that the failure of the amide linkage of tetramethylrhodamine isothiocyanate and the thioether linkage of the Alexa Fluor555 maleimide might have been due to the poor loading of the fluorophore.

B) N-Terminal Labeling.

Amine-reactive fluorescent probes are widely used to modify peptides at the N-terminal or Lysine residue. A number of fluorescent amino-reactive dyes have been developed to label various peptides, and the resultant conjugates are widely used in biological applications. Three major classes of amine-reactive fluorescent reagents are currently used to label peptides: succinimidyl esters (SE), isothiocyanates and sulfonyl chlorides. Fluorescein isothiocyanate (FITC) is one of the most popular fluorescent labeling dyes and is predominantly used for preparing a variety of fluorescent bioconjugates; however, its low conjugation efficiency and short shelf lifetime of FITC conjugates remain troublesome for some biological applications.

1) Fluorescent Dye Carboxylic Acids.

Succinimidyl esters (SE) are extremely reliable for amine modifications because the amide bonds that are formed are essentially identical to, and as stable as, the natural peptide bonds. These reagents are generally stable and show good reactivity and selectivity with aliphatic amines. For the most part, reactive dyes are hydrophobic molecules and should be dissolved in anhydrous dimethylformamide (DMF) or dimethylsulfoxide (DMSO). The labeling reactions of amines with succinimidyl esters are strongly pH dependent. Amine-reactive reagents react with non-protonated aliphatic amine groups, including the terminal amines of proteins and the e-amino groups of Lysines. Thus amine acylation reactions are usually carried out above pH 7.5. Protein modifications by succinimidyl esters can typically be done at pH 7.5-8.5, whereas isothiocyanates may require a pH 9.0-10.0 for optimal conjugations. Buffers that contain free amines such as Tris and glycine and thiol compounds must be avoided when using an amine-reactive reagent. Ammonium salts (such as ammonium sulfate and ammonium acetate) that are widely used for protein precipitation must also be removed (such as via dialysis) before performing dye conjugations. Most conjugations are done at room temperature. However, either elevated or reduced temperature may be required for a particular labeling reaction.

2) Fluorescent Dye Sulfonyl Chlorides.

Sulfonyl chlorides are highly reactive and are unstable in water, especially at the higher pH required for reaction with aliphatic amines. Molecular modifications by sulfonyl chlorides should be performed at low temperature. Sulfonyl chlorides can also react with phenols (including tyrosine), aliphatic alcohols (including polysaccharides), thiols (such as Cysteine) and imidazoles (such as histidine), but these reactions are not common in proteins or in aqueous solution. SC dyes are generally hydrophobic molecules and should be dissolved in anhydrous dimethylformamide (DMF). Sulfonyl chlorides are unstable in dimethylsulfoxide (DMSO) and should never be used in this solvent. The labeling reactions of amines with SC reagents are strongly pH dependent. SC reagents react with non-protonated amine groups. On the other hand, the sulfonylation reagents tend to hydrolyze in the presence of water, with the rate increasing as the pH increases. Thus sulfonylation-based conjugations may require a pH 9.0-10.0 for optimal conjugations. In general, sulfonylation-based conjugations have much lower yields than the succinimidyl ester-based conjugations. Buffers that contain free amines such as Tris and glycine must be avoided when using an amine-reactive reagent. Ammonium sulfate and ammonium must be removed before performing dye conjugations. High concentrations of nucleophilic thiol compounds should also be avoided because they may react with the labeling reagent to form unstable intermediates that could destroy the reactive dye. Most SC conjugations are performed at room temperature, however reduced temperature may be required for a particular SC labeling reaction.

3) Fluorescent Dye Isothiocyanates.

Isothiocyanates form thioureas upon reaction with amines. Some thiourea products (in particular, the conjugates from α-amino acids/peptides/proteins) are much less stable than the conjugates that are prepared from the corresponding succinimidyl esters. It has been reported that antibody conjugates prepared from fluorescein isothiocyanates deteriorate over time. For the most part, reactive dyes are hydrophobic molecules and should be dissolved in anhydrous dimethylformamide (DMF) or dimethylsulfoxide (DMSO). 2). The labeling reactions of amines with isothiocyanates are strongly pH dependent. Isothiocyanate reagents react with nonprotonated aliphatic amine groups, including the terminal amines of proteins and the e-amino groups of Lysines. Protein modifications by isothiocyanates may require a pH 9.0-10.0 for optimal conjugations. Buffers that contain free amines such as Tris and glycine must be avoided when using an amine-reactive reagent. Ammonium salts (such as ammonium sulfate and ammonium acetate) that are widely used for protein precipitation must also be removed before performing dye conjugations. High concentrations of nucleophilic thiol compounds should also be avoided because they may react with the labeling reagent to form unstable intermediates that could destroy the reactive dye. Isothiocyanate conjugations are usually done at room temperature; however, either elevated or reduced temperature may be required for a particular labeling reaction.

4) Cyanine Dyes.

Cyanine dyes exhibit large molar absorptivities (~150,000-250,000$M^{-1}$ $cm^{-1}$) and moderate quantum yields resulting in extremely bright fluorescence signals. Depending on the structure, they cover the spectrum from infrared (IR) to ultraviolet (UV). Cyanines have many uses as fluorescent dyes, particularly in biomedical imaging, laser technology and analytical chemistry. Cy3 and Cy5 are reactive water-soluble fluorescent dyes of the cyanine dye family. Cy3 dyes fluoresce in the green-yellow spectrum (~550 nm excitation, ~570 nm emission), while Cy5 dyes fluoresce in the far red spectrum (~650 nm excitation, 670 nm emission) but absorb in the orange spectrum (~649 nm). The chemical structure of both Cy3 and Cy5 is provided in FIG. 8. A detailed synthesis scheme for producing isothiocyanate derivatives of these dyes is also provided (FIG. 9). In one embodiment, Cy3 and Cy5 are synthesized with reactive groups on either one or both of their nitrogen side chains so that they can be chemically linked to either nucleic acids or protein molecules. In one embodiment, this facilitates visualization and/or quantification of the labeled molecule(s). A wide variety of biological applications employ Cy3 and Cy5 dyes, including for example, comparative genomic hybridization and in gene chips, label proteins and nucleic acid for various studies including proteomics and RNA localization.

To avoid contamination due to background fluorescence scanners typically use different laser emission wavelengths (typically 532 nm and 635 nm) and filter wavelengths (550-600 nm and 655-695 nm), thereby providing the ability to distinguish between two samples when one sample has been labeled with Cy3 and the other labeled with Cy5. Scanners are also able to quantify the amount of Cy3 and Cy5 labeling in either sample. In some embodiments, Cy3 and Cy5 are used in proteomics experiments so that samples from two sources can be mixed and run together thorough the separation process. This eliminates variations due to differing experimental conditions that are inevitable if the samples were run separately.

C) C-Terminal and Carboxylic Acid Attachment of Peptides.

Among the different immobilization schemes investigated, the knowledge of the stability of the amide bond between the succinate ester and amine surface was used to optimize a crosslinking procedure to immobilize peptides to the amine surface via their carboxyl (C—) termini [135]. Many solid phase Edman reactions have employed the use of EDC chemistry to immobilize peptides onto resin supports [85]. By performing EDC chemistry on amine coated glass beads and Tentagel beads, an exemplary scheme was developed for covalently immobilizing peptides on the solid supports. It is contemplated that the N-terminal amine group of the fluorescently labeled peptide is protected by either boc or fmoc protecting group to prevent the formation of the peptide concatemers. When the amines on the peptide are not protected, then amide bond formation would occur between the carboxyl and the free amine group of peptides in the presence of EDC. Thus, in one embodiment, peptides are covalently immobilized by their carboxyl (C) terminal functional group. As one example, peptides are covalently immobilized to Tentagel-NH2 beads via their C-terminal carboxyl group and blocked by fluorenylmethoxycarbonyl (fmoc) at their N-terminal amines.

In some embodiments, peptides are immobilized via carboxylic acid groups, including glutamic acid. In some embodiments, peptides are immobilized via carboxylic acid groups, aspartic acid. In some embodiments, peptides are immobilized via carboxylic acid groups and aspartic acid. In other embodiments, peptides are immobilized via carboxylic acid groups, including the C-terminus, glutamic acid and aspartic acid. In other embodiments, peptides are immobilized via carboxylic acid groups, including the C-terminus and glutamic acid. In other embodiments, peptides are immobilized via carboxylic acid groups, including the C-terminus and aspartic acid.

1. Amide Bond Stability with Fluorophores.

It was observed herein, that the fluorescence intensity of these immobilized peptides on Tentagel beads was unchanged with 24-hour incubation with the Edman solvents (see FIG. 38a). Owing to the probable presence of hydrophobic pockets between the polymer matrices in Tentagel beads, which may give rise to false interpretation of binding, the EDC test was also done on aminosilane coated glass beads (FIG. 38b). Under conditions prohibiting amide bond formation, there was little to no binding on the glass beads. Thus was demonstrated a strategy to immobilize peptides covalently on amine surface and show the stability of the bonds and surface to incubations with Edman solvents.

2. Edman Degradation Occurs at High Efficiency on Tentagel® Beads.

After determining the stability of the fluorophore and the amide bond between the peptide's carboxyl and the surface's amine groups, the efficiency of Edman chemistry was tested on three different peptides differing in the position of its fluorescently labeled Lysine residue. Four cycles of Edman degradation were performed in parallel on the three peptides with the sequences—(fmoc)-K*A, (fmoc)-GK*A and (fmoc)-K*AK*A (SEQ ID NO: 15) (K* represents the Lysine labeled with tetramethylrhodamine at its c position).

The peptides were immobilized on Tentagel beads via their C-termini and the fmoc protecting group at their N-termini was removed by incubation with 20% Piperidine in DMF for 1 hour prior to Edman degradation. To control for any false enhancements or decreases in fluorescence of beads due to effect of solvents and not the Edman chemistry, the "Mock" degradation scheme of solvent incubation and washes were used. A "Mock" Edman cycle is similar to a regular Edman cycle, but without the reactive phenylisothiocyanate reagent in the coupling solvent. The fluorescence profile of the beads through the Mock and Edman degradation cycles shows a statistically significant step drop coinciding with the position of the labeled Lysine. As shown in FIG. 41, Edman degradation was performed on three rhodamine labeled synthetic peptides (KA, GKA and KAKA (SEQ ID NO: 15)) immobilized to Tentagel-NH2 beads via their C-terminal carboxyl group and blocked by fluorenylmethoxycarbonyl (fmoc) at their N-terminal amines. After deblocking the peptide, the step decrease in fluorescence intensity (in the TRITC channel) for each peptide coincided with the position of the labeled Lysine as shown in the bar chart (a). Any loss of fluorescence occurring due to the use of solvents is controlled by the mock experimental cycle. A 60-70% decrease in the overall intensity after the Edman cycles is observed for all the beads. The panel of images (with the radial profile in the inset) are representative fluorescent images of the beads for each of the peptide used across all the experimental cycles. They provide a visual illustration of the decrease in the fluorescence of the beads that coincides with the position of the labeled Lysine residue. The fluorescent bead images are acquired in the TRITC channel (see methods for filter setup used) at an acquisition of 20 milliseconds under pH 1 imaging buffer.

Thus by tracking the fluorescence intensity decrease with Edman cycle, the positional information of Lysine residues was obtained in the three peptides. The determination of this positional information is the basis for fluorosequencing.

Thus, a protocol used for Edman degradation was adapted and optimized from similar solid phase chemistry [70,78] and showed efficiency of cleavage ranging from 60-90%. Since Tentagel beads are heavily PEGylated (comprising of polyethylene glycol (PEG) polymers), a number of sites are contemplated as available for strong non-specific binding of the hydrophobic peptides. Due to the accumulation of functional groups and thereby covalent peptide binding at the periphery of the bead the true fluorescence intensity of the peptides on the bead was calculated in the area under its radial profile. Due to the unambiguous occurrence of a two-step drop in fluorescence intensity at Edman cycle 2 and 4 for the doubly labeled peptide (fmoc)-K*AK*A (SEQ ID NO: 15) or the presence of a single step drop at Edman cycle 2 for the case of (fmoc)-GK*A, Edman efficiency was estimated to be largely greater than 50%, at least in the preceding steps. A lower efficiency would result in a decay of fluorescence with Edman cycles as opposed to a stepwise drop. The high efficiency of Edman degradation on these fluorescently labeled peptide variants demonstrate the practicality of performing fluorosequencing and Edman degradation on long fluorescently labeled peptides.

D) Side Chain Labeling.

Side chain labeling protocols are used to tag and modify proteins. Mass-labels are routinely employed to understand biological processes such as expression, post-translation modifications, and protein interactions. [1] Missing in these labeling studies is an orthogonal route integrating these standard mass-labeling protocols into a sequential fashion. Additionally missing is the use of modification protocols for labeling amino acid or reactive groups within a peptide with Edman stable fluorophores. Thus, a labeling route taking advantage of corroborated techniques with Edman stable dyes would be a useful approach for protein/peptide mass spectrometry studies. Further, devising a generalized orthogonal labeling route is contemplated to have applications for synthetic peptide design. Additionally, functionalizing different side chains on the same peptide using these orthogonal handles can be employed in the synthesis of novel, unnatural peptides.

Known techniques for modifying side chains have gained widespread use with or without subsequent fluorophore labeling. For example, guanidination kits are commercially available for targeting Cysteine and Lysine. The Cysteine is labeled with an iodoacetamide followed in the same-pot by selective labeling of Lysine using O-methylisourea hemisulfate [2] Acylation and reductive alkylation are also employed to label both $N_\varepsilon$-amines and N-termini. Cross-labeling of Threonine, serine, and tyrosine occur under acylation and alkylating conditions. [4] Recently, amines have been modified via reductive methylation preventing cross-reactivity with alcohol and phenol residues. Once these amines were modified, the Smith group achieved global labeling of aspartate and glutamate via amidation with amine-containing compounds. Furthermore, labeling studies of less abundant side chains have been explored. Horton, Koshland, and Scoffone demonstrated labeling of Tryptophan under acidic conditions using 2-hydroxy-5-nitrobenzyl bromide and dinitrophenylsulfenyl chloride [5-7]. References are shown Example III.

Protein/peptide modifications relate to the selectivity of the reagent for an amino acid. [1] Such that global labeling of amines and carboxylates is contemplated if the appropriate conditions and a sequence of successful derivatization steps are discovered and used.

Similarly, a proper protocol is needed to selectively hit (i.e. specifically label) target side groups by using iodoacetamide, guanidination reagents, and tryptophan labeling reagents. Minimizing cross-reactivity between each step might be achieved if the nucleophilicity, $pK_a$ of each side chain, reactivity of labeling reagent, reactions times, and temperature were considered. Strong nucleophiles like the thiol in Cysteine, or the amine in Lysine, and the N-terminus can be targeted first. Selective labeling of cysteine between pH 7-8 is possible, while labeling of amines is possible at a higher pH. [8]

Thus in one embodiment, the first fluorophore is attached to a structure in a group consisting of a thiol in Cysteine, an amine in Lysine, and an N-terminus, the second fluorophore is attached to a structure selected from the amino acids having carboxylate side chains and/or a free C-terminus. In a further embodiment, a third fluorophore is attached to a Tryptophan. Thus, in one embodiment, the first fluorophore attached to Cysteine is iodoacetamide. In another embodiment, the first fluorophore attached to Lysine is 2-methoxy-4,5-dihydro-1H-imidazole.

Since guanidinating reagents are selective for Lysine, distinguishing between the $N_\varepsilon$-amine and $\alpha$-amine was explored herein. Labeling of the remaining amines is necessary before subsequent labeling steps. So, a different labeling reagent is required for labeling the N-termini. Once the most nucleophilic sites are labeled, the carboxylate side chains would then be targeted, followed by modification of the Tryptophan. Therefore, experiments described herein were designed to test this strategy. References are shown in Example V. Thus in one embodiment, target side chain labeling and/or end labeling will allow the attachment of specific fluorophores for fluorosequencing, such as described herein.

As described herein, a series of orthogonal labeling steps, using the steps as described above, for labeling KDYWEC (1 (SEQ ID NO: 3)) was achieved (FIG. 42). Labeling studies were initially performed in solution-phase for ease of identification and purification. Once orthogonal labeling was achieved in solution phase, labeling studies were transitioned to the solid phase using model peptide KDYWE (2 (SEQ ID NO: 4)). Examples and references are shown in section IV below and Examples IV and V.

Solution-phase labeling of at least five targets in a peptide is shown in FIG. 43 and described in Examples IV and V. Thus in one embodiment, Cys is labeled first, Lys is labeled second, N-terminal labeling third, carboxylates (side chains and C-terminus) are labeled fourth, followed by Trp. labeling fifth. In one embodiment, the first label is selected from the group consisting of iodoacetamide and 2-methylthio-2-imadazoline hydroiodide (MDI). In one embodiment, the second label is 2-methoxy-4,5-dihydro-1H-imidazole. In one embodiment, the third label is 1-(4,4-dimethyl-2,6-dioxocyclohexylidene)-3-methylbutyl diethyl phosphate (Phos-ivDde). In one embodiment, the fourth label is selected from the group consisting of benzylamine (BA), 3-dimethylaminopropylamine, and isobutylamine. In one embodiment, the fifth label is 2,4-dinitrobenzenesulfenyl chloride.

Solid-phase labeling of at least three targets in a peptide is shown in FIG. 44 and described in IV below and Examples IV and V. In one embodiment, Lys is labeled first, carboxylates are labeled second followed by Trp. labeling third. In one embodiment, the first label is 2-methoxy-4,5-dihydro-1H-imidazole. In one embodiment, the second label is (7-Azabenzotriazol-1-yloxy)tripyrrolidinophosphonium hexafluorophosphate (PyAOP). In one embodiment, the third label is 2,4-Dinitrobenzenesulfenyl chloride. In one embodiment, the peptide is attached to a resin, such as a hydrazinobenzoyl resin.

The exemplary labels named herein are not meant to limit the scope of the inventions. Any label that selectively targets an amino acid side chain or reactive group as described above may be used in these labeling methods.

III. Single-Molecule Peptide Identification And Quantitation.

As described herein, the invention provides (1) a method for developing orthogonal functional fluorophore linkers that selectively labels a plurality of classes of amino acids and/or targets on amino acids (lysine, cysteine, carboxylic acid and tryptophan residues) (2) a method describing the sequence of labeling conditions, as a series of steps with increasing nucleophilicity, to selectively target the side chains of amino acid residues and (c) a screening method and compilation of select number of fluorophores inert to solvents used in Edman degradation. Additionally, dyes are chemically modified in order to prevent effects of pH on their fluorescence.

The fluorophores along with the sequential chemistry of orthogonal conjugation to amino acid residues is contemplated as a component of the fluorosequencing technology. In turn, the success of the fluorosequencing technology is contemplated to benefit the field of proteomics.

In one embodiment, the present application relates to a method to determine protein sequences (typically sequence information for a portion of the protein) in a massively parallel fashion (thousands, and optimally millions at a time) wherein proteins (or fragments/portions thereof) are iteratively labeled and cleaved to produce patterns reflective of their sequences. It is not intended that the present invention be limited to the precise order of certain steps. In one embodiment, the proteins (or peptide fragments thereof) are first labeled and then immobilized, and subsequently treated under conditions such that amino acids are cleaved/removed. As one example, a strategy for single-molecule peptide sequencing is shown schematically in FIG. 5B. Proteins are extracted and digested into peptides by a sequence-specific endo-peptidase. All occurrences of particular amino acids are selectively labeled by fluorescent dyes (e.g., yellow for tyrosine, green for tryptophan, and blue for lysine residues), and the peptides are surface immobilized for single-molecule imaging (e.g. by anchoring via cysteine). The peptides are subjected to cycles of Edman degradation; in each cycle, a fluorescent Edman reagent (pink trace) couples to and removes the most N-terminal amino acid. The step drop of fluorescent intensity indicates when labeled amino acids are removed, which in combination with the Edman cycle completion signal, gives the resulting fluorosequence (e.g., "WKKxY . . . " (SEQ ID NO: 16) i.e. W-K-K-x-Y-x (SEQ ID NO: 2) etc.). Matching this partial sequence to a reference protein database identifies the peptide.

Figure 8:
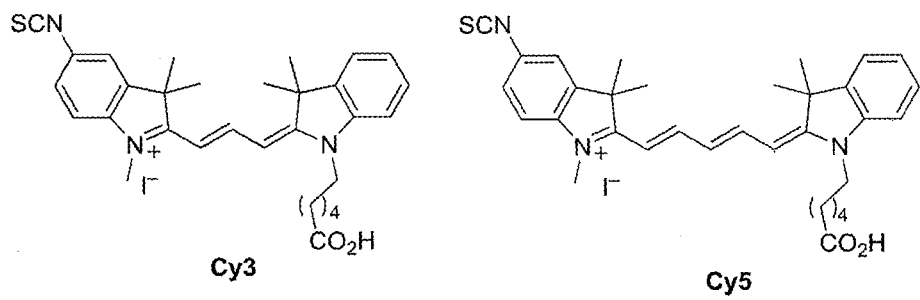
FIG. 8 depicts the structures of cyanine dyes Cy3 and Cy5.

In another embodiment, acquiring information about the sequences of single proteins involves two related methods (FIG. 8). Peptides or proteins are first immobilized on a surface (e.g., via internal Cysteine residues) and then successively labeled, pieces of the peptides are then cleaved away using either chemical, photochemical or enzymatic degradation. In either case, the patterns of cleavage provide sufficient information to identify a significant fraction of proteins within a known proteome. Given the extraordinary amount of DNA information that has already been accumulated via NextGen DNA sequencing, the sequences of many proteomes are known in advance.

A) Immobilization and Labeling.

In one embodiment, peptides or proteins are first immobilized on a surface (via internal Cysteine residues), and successively labeled and cleaved away pieces of the peptides based on either chemical or enzymatic degradation (the two variations on the common theme). It is not intended that the present invention be limited to which amino acids are labeled. However, in a preferred embodiment, the chemical methodology entails labeling the lysyl residues of a peptide or protein with a single dye ("green" in FIG. 8). The Edman degradation method is then used to successively cleave amino acid residues away from the amino terminus of the immobilized peptide. In a preferred embodiment, the present application contemplates the use of a modified fluorescent derivative of the Edman reagent in order to successively label each newly exposed residue on the protein ("red" in FIG. 9). This successive labeling permits the efficiency of the reaction to be determined and also "counts" the number of reaction cycles a given immobilized peptide has undergone. Determining when in the "red" count there occurs a coincident loss of "green" residues from a single peptide molecule provides sequence information about that specific peptide. Sequence information resulting from such analysis may be of the form X-X-X-Lys-X-X-X-X-Lys-X-Lys (SEQ ID NO: 1) (for example). In another embodiment, rather than using a fluorescent second label ("red" in FIG. 5), a non-fluorescent Edman reagent such as PITC can be employed instead; in this case, the rounds of Edman cycling are simply counted as they are applied rather than monitoring each optically using the second label.

In a preferred embodiment, the carboxylate side chains of glutamyl/aspartyl residues may be labeled with a third fluorescent molecule (i.e. third color) to further increase the amount of sequence information derived from each reaction. Informatic analyses indicate that performing 20 cycles of Edman degradation in this method is sufficient to uniquely identify at least one peptide from each of the majority of proteins from within the human proteome. For descriptions and Examples, see above Section D, Side Chain Labeling, Section V, below, Solution-phase and Solid-phase labeling, and Examples V and VI.

In a preferred embodiment, the surface coating is engineered for Edman chemistry and single molecule peptide imaging. The surface, in one embodiment, is optically transparent across the visible spectra, has a refractive index between 1.3 and 1.6, a thickness between 10 to 50 nm, and is chemically resistant to organic solvents and neat trifluoroacetic acid. A large range of substrates (like fluoropolymers (Teflon-AF(Dupont), Cytop® (Asahi Glass, Japan)), aromatic polymers (polyxylenes (Parylene,Kisco, CA), polystyrene, polymethmethylacrytate) and metal surfaces (Gold coating)), coating schemes (spin-coating, dip-coating, electron beam deposition for metals, thermal vapor deposition and plasma enhanced chemical vapor deposition) and functionalization methodologies (polyallylamine grafting, use of ammonia gas in PECVD, doping of long chain end-functionalized fluorous alkanes etc) are all contemplated as approaches to obtain a useful surface. In one embodiment, a 20 nm thick, optically transparent fluoropolymer surface made of Cytop can be used. This surface can be further derivatized with a variety of fluoroalkanes that will sequester peptides for sequencing and modified targets for selection. In another embodiment, aminosilane modified surfaces are employed.

In other embodiments, peptides are immobilized on the surface of beads, resins, gels, or combinations thereof, quartz particles, glass beads, and the like. For examples, peptides are immobilized on the surface of Tentagel® beads, Tentagel® resins and the like. In some embodiments, the surface is coated with a polymer, such as polyethylene glycol. In some embodiments, the surface is amine functionalized. In some embodiments, the surface is thiol functionalized.

B) Cleavage.

In another embodiment, the present application contemplates labeling proteins prior to immobilization followed by the addition of a series of proteases that cleave very specifically between particular amino acid dimers to release the labels. The sequence information obtained by this method may be in the form of patterns such as Lys-[Protease site 1]-Lys-[Protease site 2]-Lys (for example). While it is possible that multiple (or zero) protease sites may exists between given labels, the presence of multiple (or zero) protease sites is also information that can be used to identify a given peptide. As with the Edman degradation reaction, discussed above, informatic analyses reveal that proteases with approximately 20 different dimeric specificities are sufficient to uniquely identify at least one peptide from a substantial fraction of proteins from within the human proteome. In one embodiment, proteases with defined specificities may be generated using directed evolution methods.

C) Identification.

A single molecule microscope capable of identifying the location of individual, immobilized peptides is used to "read" the number of fluorescent molecules (i.e. dyes) on an individual peptide in one-dye increments. The level of sensitivity is comparable to that available on commercial platforms, and should allow these subtractive approaches to be successful over several iterations. As indicated previously, the resulting data does not provide a complete peptide sequence, but rather a pattern of amino acids (e.g. X-X-X-Lys-X-X-X-X-Lys-X-Lys (SEQ ID NO: 1)) that can be searched against the known proteome sequences in order to identify the immobilized peptide. These patterns sometimes match to multiple peptide sequences in the proteome and thus are not always sufficiently information-rich to unambiguously identify a peptide, although by combining information from multiple peptides belonging to the same protein, the unique identification of proteins could be substantially higher. The present method relies on the fact that potentially millions or billions of immobilized peptides may be sequenced in an analysis (for comparison, current single molecule Next-Gen DNA sequencing can sequence approx. 1 billion reads per run), and thus that a very large proportion of these can be uninformative while still providing sufficient information from the interpretable fraction of peptide patterns to identify and quantify proteins unambiguously. See Example IX for a computer simulation (Monte Carlo) of an embodiment of this method.

D) Quantitation.

The ability to perform single molecule, high-throughput identification of peptides from complex protein mixtures represents a profound advancement in proteomics. In addition to identifying a given peptide or protein, in one embodiment the present methods also permit absolute quantification of the number of individual peptides from a mixture (i.e. sample) at the single molecule level. This represents an improvement to mass spectrometry, which is greater than 5 orders of magnitude less sensitive and which cannot always accurately quantify proteins because of differential ionization and desorption into the gas phase.

E) Biomarkers.

While other techniques have been used to identify unique tumor biomarkers in serum, including mass spectrometry and antibody arrays, these techniques have been greatly hampered by a lack of sensitivity and by an inability to provide quantitative readouts that can be interpreted with statistical significance by pattern analysis. In one embodiment, the present application contemplates the identification of biomarkers relevant to cancer and infectious diseases. While changes in nucleic acids often underlie disease, these changes become typically amplified and are most readily found in proteins. These aberrant proteins are often present in discrete locations throughout the body that are accessible without invasive procedures such as biopsies, including for example, saliva, blood and urine. In one embodiment, a single molecule detection assay for circulating proteins may be performed in a particular animal model of disease (e.g., human proteins from xenografts implanted in mice) to identify unique biomarkers. In a preferred embodiment, such assays may provide the foundation for identifying protein patterns in humans that are indicative of disease. For example, comparing the protein pattern in serum samples from cancer patients versus normal individuals.

Thus, specific compositions and methods of identifying peptides at the single molecule level have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

IV. Single Molecule Sequencing.

Figure 1:
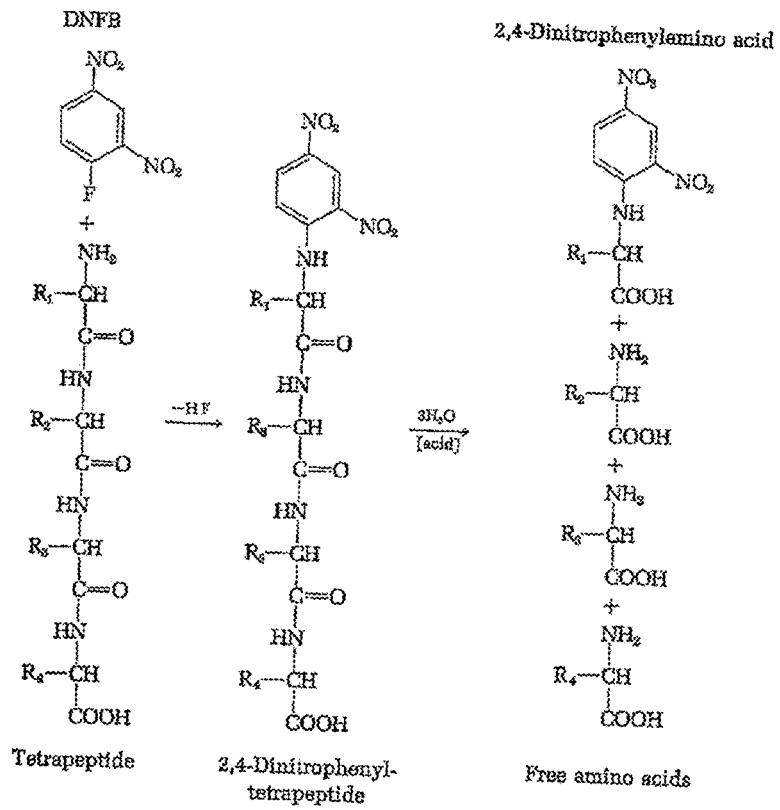
FIG. 1 depicts the identification of the N-terminal amino acid residue of a tetrapeptide by means of the Sanger reaction.
Figure 2:
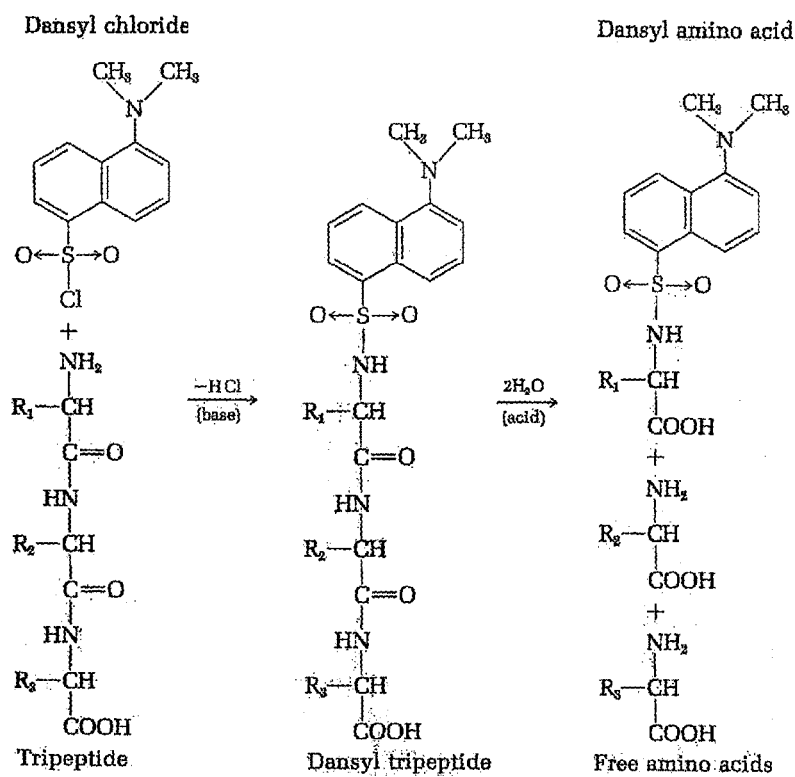
FIG. 2 depicts the identification of the N-terminal residue of a tetrapeptide as the dansyl derivative.
Figure 3:
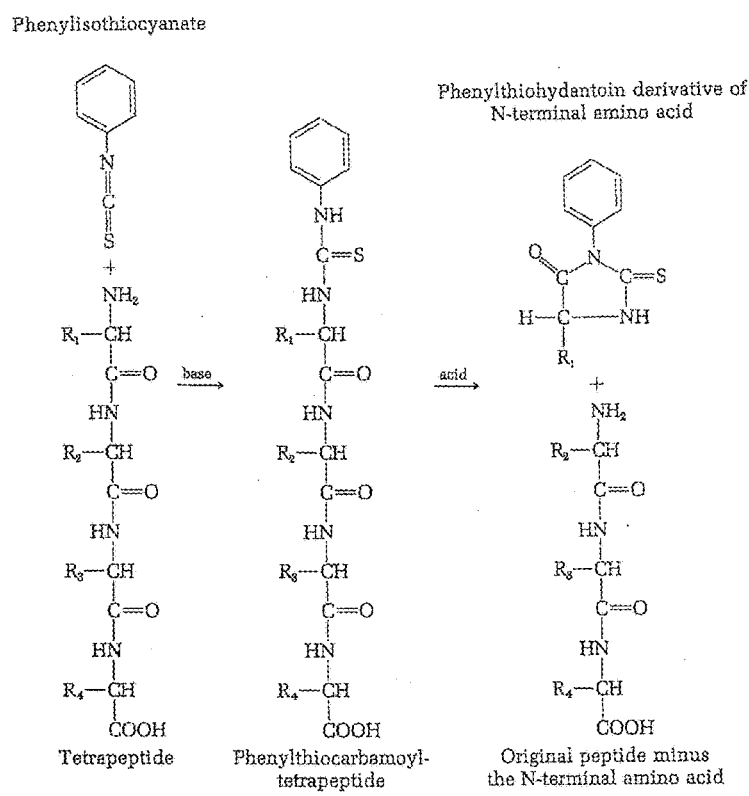
FIG. 3 depicts the identification of the N-terminal amino acid residue by Edman degradation.
Figure 4:
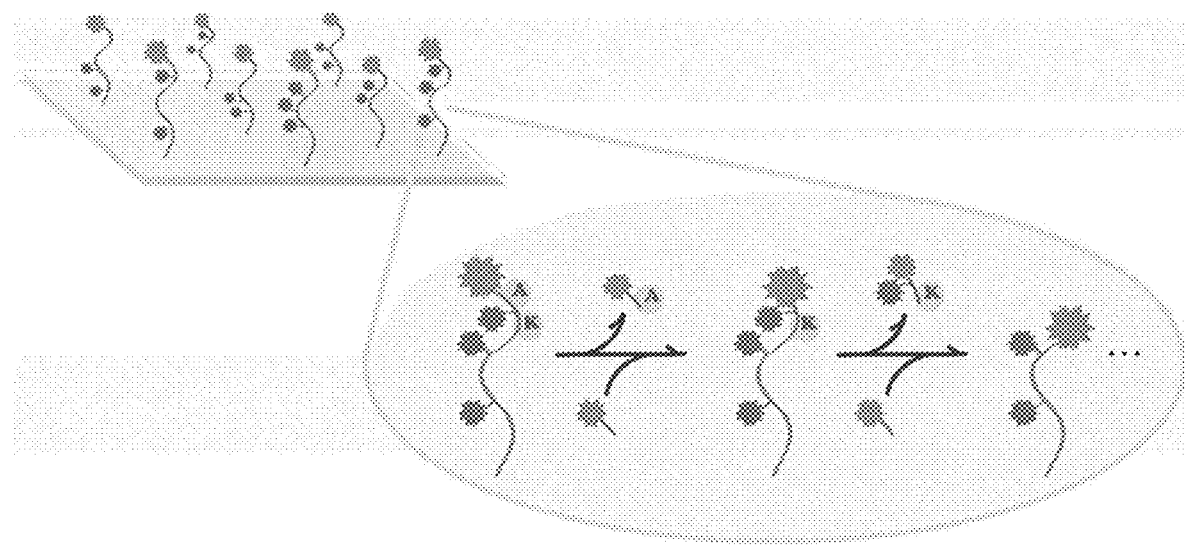
FIG. 4 depicts one embodiment of a single molecule peptide sequencing scheme of the present invention.
Figure 5A:
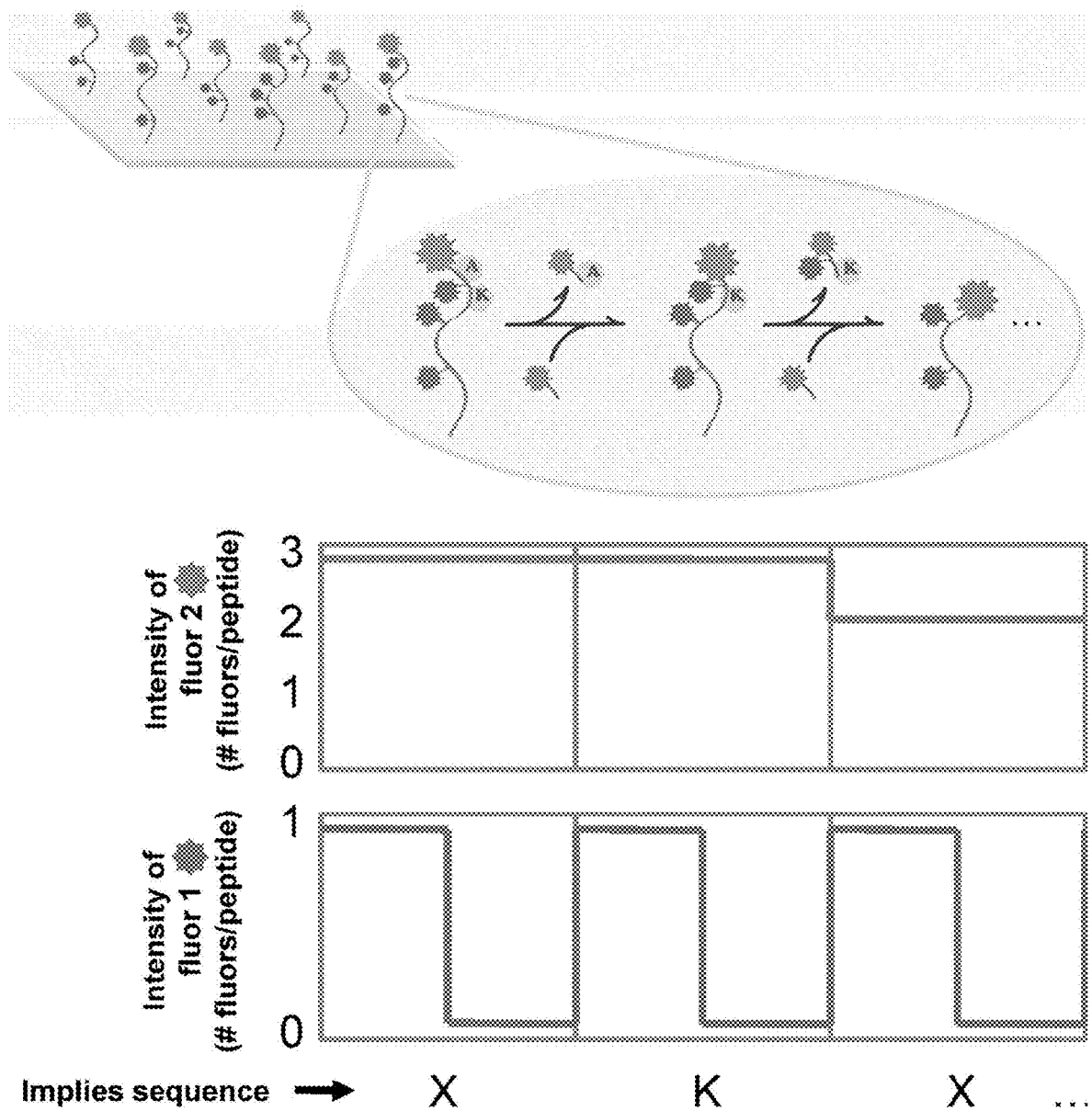
FIG. 5A depicts one embodiment of the selective labeling of immobilized peptides followed by successive cycles of N-terminal amino acid labeling and removal to produce unique patterns that identify individual peptides.

FIG. 4 depicts one embodiment of the single-molecule peptide sequencing method. Briefly, selective labeling of amino acids on immobilized peptides followed by successive cycles of labeling and removal of the peptides' amino-terminal amino acids is capable of producing patterns sufficiently reflective of their sequences to allow unique identification of a majority of proteins in the yeast and human proteomes. FIG. 5 shows the simplest scheme with 2 fluorescent colors (i.e. "fluors" or "labels"), in which fluor 2 (red star) labels the peptide amino termini (N-termini) over successive cycles of removal of the N-terminal amino acids and re-labeling of the resulting new N-termini, and fluor 1 (green star) labels Lysine (K) residues. The immobilization of fluor 2 on a peptide serves as an indicator that the Edman reaction initiated successfully; its removal following a solvent change indicates that the reaction completed successfully. Fluor 2 thus serves as an internal error check—i.e., indicating for each peptide which Edman cycles have initiated and completed successfully—and gives a count of amino acids removed from each peptide, as well as reporting the locations of all peptides being sequenced. Fluor 1 serves to indicate when Lysines are removed, which, in combination with the reporting of each Edman cycle by fluor 2, gives the resulting sequence profile (e.g. . . . XKX . . . below) that will be used to identify the peptide by comparison with a database of possible protein sequences from the organism being sequenced. In another embodiment, a second fluorescent label is not used; instead, a non-fluorescent version of the reagent which labels and removes the amino termini in successive cycles is employed; in this embodiment, cycles are simply counted, resulting in the same sequence patterns (e.g. . . . XKX . . . ) as in the above embodiment but without providing an internal error check for the successful initiation/completion of each Edman reaction cycle. See Example IX for a computer simulation (Monte Carlo) of an embodiment of this method.

A) Identification of Proteins in Yeast and Human Proteomes.

FIG. 6 demonstrates that selective labeling of amino acids on immobilized peptides followed by successive cycles of labeling and removal of their amino-terminal amino acids is capable of producing patterns sufficiently reflective of their sequences to allow unique identification of a majority of proteins in the yeast and human proteomes. Plotted curves show results of computer simulation of successive cleavage of single N-terminal amino acids from all proteolytic peptides derived from the complete human or yeast proteome, top and bottom plots respectively. This FIG. 6 depicts the results of various cutting ("Cut") and labeling ("Label") scenarios. For example, "Cut E" indicates that all human proteins were proteolyzed with the peptidase GluC in order to cut each protein after glutamate ("E") residues. Similarly, "Label" simulates the results of initially labeling different subsets of amino acid residues. For example, "Label K" indicates that only Lysine ("K") amino acid residues carry a detectable label (e.g. a fluorescent molecule observable by single molecule fluorescence microscopy). The sequencing reaction is not allowed to proceed beyond the Cysteine ("C") residue since they are used to anchor the peptide sequence. FIG. 5 demonstrates that labeling schemes employing only two or three amino acid-specific fluorescent labels can provide patterns capable of uniquely identifying at least one peptide from a substantial fraction of the human or yeast proteins. Given that only one peptide is required to identify the presence of an individual protein in a protein mixture, and further given that the peptide may be observed repeatedly and the number of observations counted, FIG. 6 demonstrates that this approach may both identify and quantify a large proportion of proteins in highly complex protein mixtures. This capability requires that the genomic sequence of the organism being analyzed is available to serve as a reference for the observed amino acid patterns. As indicated above, the complete human and yeast genomes are available to match against patterns of amino acid labels (e.g. "XXXKXXXKXXXTX . . . C . . . E" (SEQ ID NO: 17)).

B) Lysine Content.

FIG. 7 demonstrates that the numbers of Lysines per peptide are sufficiently low to monitor their count based on fluorescence intensity. The present method requires the ability to distinguish (i.e. resolve) different numbers of fluorescent molecules based on fluorescence intensity; however, resolution naturally decreases as the number of Lysines in a single peptide increase. For example, while distinguishing 3 Lysines from 2 Lysines only requires detecting a 33% decrease in fluorescence intensity, high Lysine counts would require detecting proportionally smaller changes in fluorescence intensity (e.g. only 5% for the case of 21 Lysines versus 20 Lysines). Fortunately, the natural distribution of Lysine residues in peptides tends to be small (top plot, shown for the yeast proteome), and therefore within the capacity of current fluorescent microscopes. The simulations depicted in FIG. 7 demonstrate that limiting sequencing to peptides with no more than eight Lysines nearly provides coverage for the full set of peptides in the yeast proteome (bottom plot, shown for the case of labeling K, cutting at E with GluC, anchoring by C).

V. Two-Color Single-Molecule Peptide Sequencing Reaction.

Proteins may be analyzed from natural or synthetic sources collected using standard protocols. For example, proteins may be isolated from human cells obtained from blood samples, tumor biopsies or in vitro cell cultures. In one embodiment, the present invention contemplates a two-color single molecule peptide sequencing reaction. In other embodiments, protein sequencing protocols may include more than two fluorescent molecules (e.g. covalently labeling a third fluorescent molecule with an additional type of amino acid) to provide greater protein sequence and/or protein profile information.

A) Cell Sample Preparation.

Isolated cells are resuspended in a standard lysis buffer that includes a reducing agent such as Dithiothreitol (DTT) to denature proteins and break disulphide linkages and a protease inhibitor cocktail to prevent further protein degradation. Cells are lysed by homogenization or other lysis technique and the lysate centrifuged to obtain soluble cytosolic proteins (supernatant) and insoluble membrane bound proteins (pellet). Samples may be further fractionated, e.g. by chromatography, gel electrophoresis, or other methods to isolate specific protein fractions of interest. The protein mixtures are denatured in a solution containing, for example, urea or trifluoroethanol (TFE) and the disulfide bonds are reduced to free thiol group via the addition of reducing agents such as tris(2-carboxyethyl)phosphine (TCEP) or DTT.

B) Protein Digestion, Labeling and Anchoring.

Protein preparations are then digested by specific endopeptidases (e.g. GluC), which selectively cleave the peptide bonds' C-terminal to glutamic acid residue. The resulting peptides are labeled by a fluorescent Edman reagent (label 1) such as fluorescein isothiocyanate (FITC), rhodamine isothiocyanate or other synthesized fluorescent isothiocyanate derivative (e.g., Cy3-ITC, Cy5-ITC). Considerations in choosing the first fluorescent Edman reagent (label 1) include 1) good reactivity towards available amine groups on Lysine residues and the N-terminus, 2) high quantum yield of the fluorescent signal, 3) reduced tendency for fluorescent quenching, and 4) stability of the fluorescent molecule across the required range of pH.

Labeled peptides are then anchored to an activated glass or quartz substrate for imaging and analysis. In one embodiment, the substrate is glass coated with a low density of maleimide, which is chemically reactive to available sulfydryl groups (SH—) on the Cysteine residues in a subset of the peptide molecules. In a preferred embodiment, the substrate is glass coated with a layer of N-(2-aminoethyl)-3-aminopropyl trimethoxy silane and then passivated with a layer of methoxy-poly(ethylene glycol) doped with 2-5% maleimide-poly(ethylene glycol), the latter of which is chemically reactive to available sulfhydryl groups (SH—) on the cysteine residues in a subset of the peptide molecules. In this embodiment only peptides that contain Cysteine residues are anchored to the solid surface; peptides that do not contain Cysteine residues are washed away in successive steps. In a preferred embodiment, peptides are preferably anchored with a surface density that is low enough to permit the resolution of single molecules during subsequent microscopy steps. In one embodiment, the order of the labeling and anchoring steps may be reversed, for example if required by the coupling—decoupling rate of the Edman reagent and its ability to produce thioazolinone N-terminal amino acid derivatives.

C) Edman Sequencing in a Microscope Flow Cell.

Figure 10:
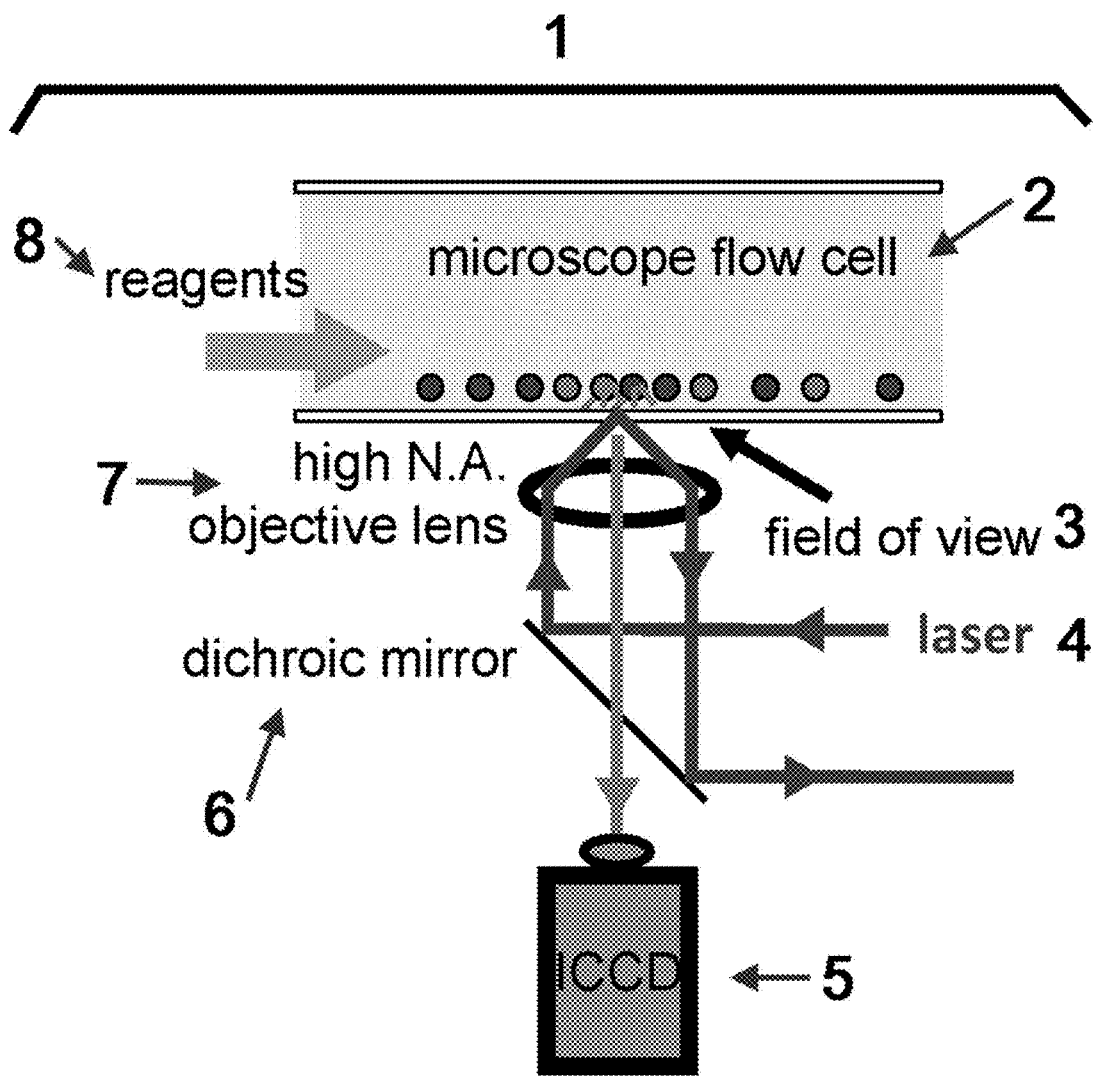
FIG. 10 shows one diagram of a total internal reflectance fluorescence (TIRF) microscopy setup (1) that can be used in one embodiment of sequence analysis. In such a setup is a microscope flow cell (2) wherein the fluorescence of the labeled proteins can be observed through the field of view (3). The laser (4) is directed against the dichroic mirror (6) through the high numerical aperture objective lens (7) through the field of view (3). An intensified charge-couple device (ICCD) (5) observes the fluorescent signal from the labeled peptides.
Figure 11:
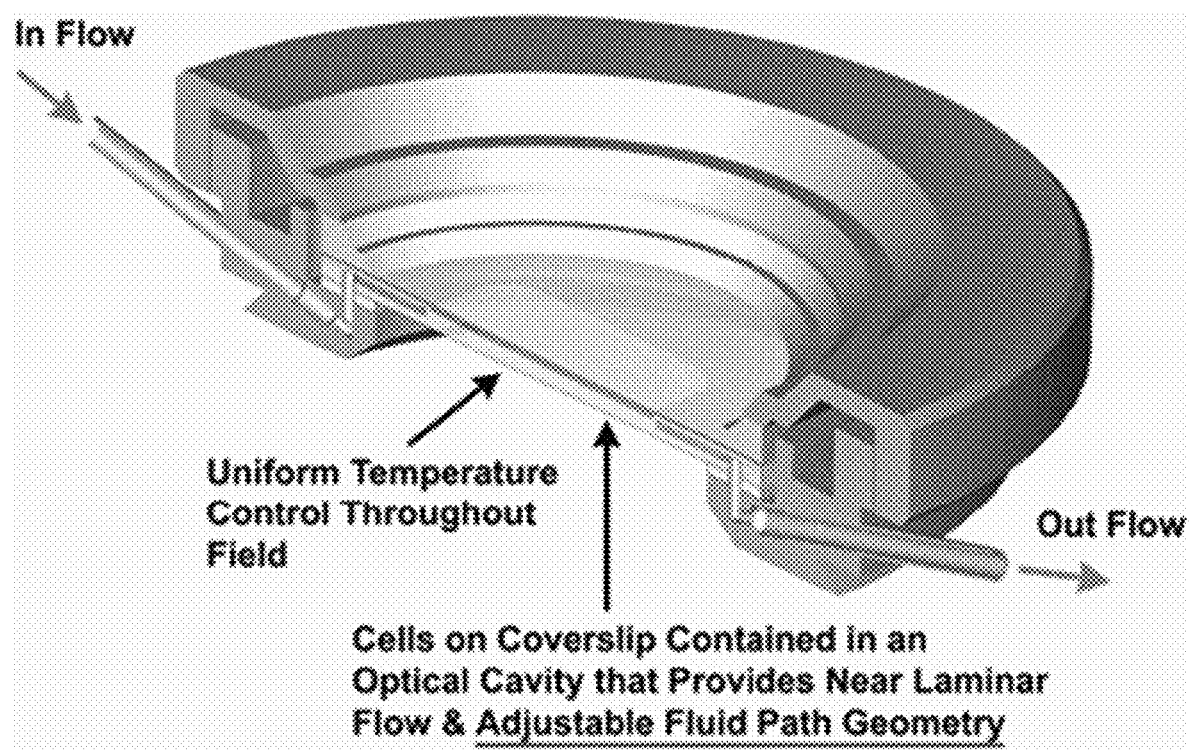
FIG. 11 shows a cross-sectional view of one embodiment of a closed perfusion chamber flow cell. Modifications to this commercial flow cell are to the materials employed for the lower gasket, for which many materials have been tested and are currently using Teflon in order to be resistant to the solvents used for the Edman procedure, and to the surface of the glass slide, which we modify chemically in order to immobilize the peptides.
Figure 12A:
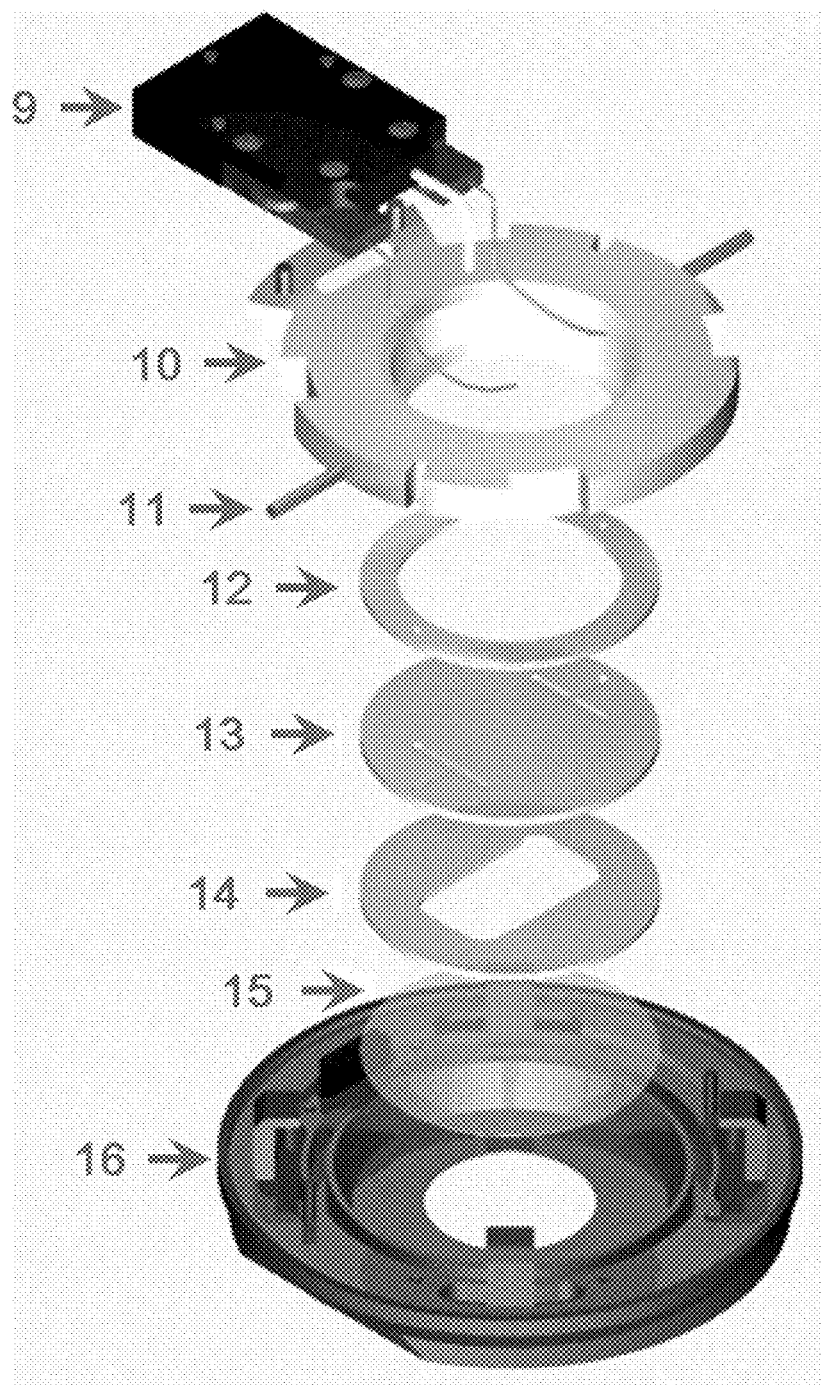
FIG. 12A shows an exploded view of one embodiment of a closed imaging chamber. In this embodiment, the closed imaging chamber includes: Electrical Enclosure (9) which can be detached to sterilize the perfusion tubes an contains temperature sensor and heater contacts; flow cell chamber top (10)—Designed to assure parallel uniform closure, eliminate leaks, and broken coverslips and contains the perfusion tubes; Perfusion Tubes (11) For fluid flow; Upper gasket (12); Flow Control/Microaqueduct Slide (13)—An optical surface which integrates perfusion and temperature control, High-volume laminar flow, Koehler illumination, and electronically conductive coating for temperature control; Lower Gasket (14)—Provides a seal between the flow cell coverslip and flow control slide. This gasket can have any internal geometry one desires. Standard thicknesses from 0.1 mm to 1.0 mm are contemplated. This allows one to define the volume and flow characteristics of the chamber. Modifications to this commercial flow cell are to the materials employed for the lower gasket (14), for which many materials have been tested and are currently using Teflon in order to be resistant to the solvents used for the Edman procedure, and to the surface of the glass slide, which we modify chemically in order to immobilize the peptides; Coverslip (15); and flow cell stage adapter base (16)—Temperature controlled and contains a dovetail to lock into stage adapter for stability. In one non-limiting implementation, a Teflon lower gasket is preferably employed (14) in order to allow for the use of organic solvents in the flow cell.
Figure 12B:
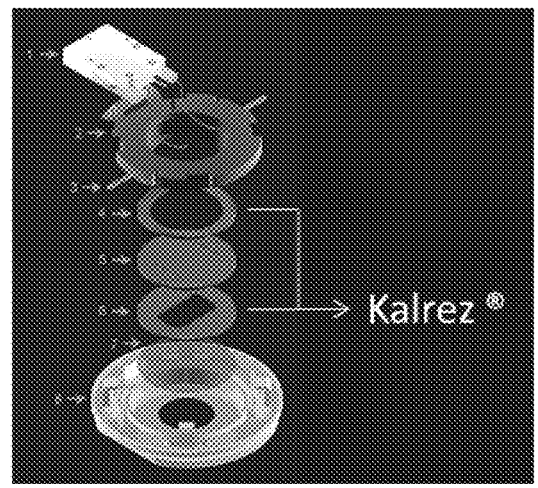
FIG. 12B shows an exploded view of a second embodiment of a closed imaging chamber. The lower and upper rubber gaskets on the commercially available perfusion chamber (FCS2 closed chamber system, Bioptechs Inc, Butler, Pa.) were substituted with a perfluoroelastomer, Kalrez (Dupont). This material has the same resistivity of PTFE (Teflon®) and a compressibility similar to nitrile rubbers, thereby ensuring an oxygen free environment necessary for high efficiency Edman chemistry. Other fluoroelastomers are also contemplated.
Figure 12C:
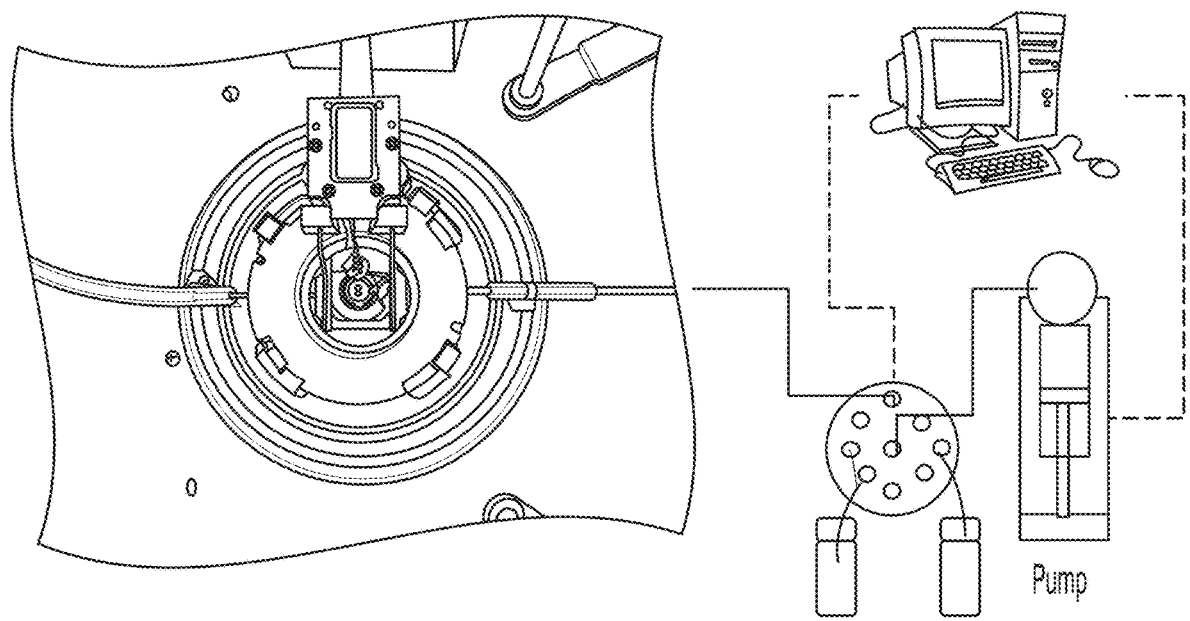
FIG. 12C shows the chamber of FIG. 12B connected to a valve and pumping system. The cycles of fluid exchanges between aqueous and organic solvents can be optimized and computer controlled through this a pump and valve system.

Following labeling and anchoring of the peptides the substrate (e.g., glass slide) is introduced into a flow cell in a fluorescence microscope equipped with total internal reflection illumination, which reduces background fluorescence. The flow cell is washed with purified water to clean the surface. Steps 2 and 3 correspond to the Edman coupling steps, which are performed repeatedly with fluorescence microscopy images collected twice in each cycle—once after cleavage and once after re-labeling. FIG. 10 is a diagram showing one embodiment of the working principle of a total internal reflectance fluorescence (TIRF) microscopy setup that can be used in sequence analysis. Other embodiments of the microscopy setup include the use of a scanning confocal microscope for visualizing the single molecules or a dove prism for performing TIRF. Using a motorized microscope stage with automated focus control to image multiple stage positions in the flow cell may allow millions of individual single peptides (or more) to be sequenced in one experiment (see FIG. 10, FIG. 11, and FIG. 12).

In the cleavage step trifluoroacetic acid (TFA) is introduced into the flow cell and incubated to complete the cleavage reaction. The liberated thiazolinone N-terminal amino acid derivative and residual TFA is washed away with an organic solvent such as -ethyl acetate. In a preferred embodiment, other solvents may be used to ensure that side products produced are effectively removed. In the re-labeling step the N-terminus of the anchored peptides is re-labeled with a second Edman fluorescent reagent (label 2) under mildly basic conditions. Considerations in choosing the second Edman fluorescent reagent (label 2) include limiting fluorescence bleedthrough (spectral crossover) with label 1 by selecting fluorophores having well-separated absorption and emission spectra such that the fluors can be independently observed via microscopy, and having an efficient rate of decoupling from the labeled N-terminal amino acid. In one embodiment, portions of the emission spectrum of said first label do not overlap with the emission spectrum of said second label. The cleavage and re-labeling steps (steps 2 and 3, respectively) are then repeated in cycles (i.e., treating peptides to the successive rounds of Edman chemistry, involving TFA wash, vacuum dry, etc.) with fluorescence microscopy imaging at each step, as described below, until sufficient data is collected (e.g., 20 or 30 cycles).

D) Single Molecule Fluorescence Microscopy.

In one embodiment, a conventional microscope equipped with total internal reflection illumination and an intensified charge-couple device (CCD) detector may be used for imaging. (For an example of such a scope appropriate for single molecule imaging, see Braslavsky et al., PNAS, 100(7): 3960-4 (2003) [4], (herein incorporated by reference). Depending on the absorption and emission spectra of the two fluorescent Edman labels employed, appropriate filters (for example, a central wavelength of 515 nm for FITC and 630 nm for a rhodamine-ITC derivative) are used to record the emission intensity of the two labels. Imaging with a high sensitivity CCD camera allows the instrument to simultaneously record the fluorescent intensity of multiple single peptide molecules distributed across the glass surface. In one embodiment, image collection is performed using an image splitter that directs light through two band pass filters (one suitable for each fluorescent molecule) to be recorded as two side-by-side images on the CCD surface. FIG. 10 is a diagram showing one embodiment of a total internal reflectance fluorescence (TIRF) microscopy setup that can be used in sequence analysis. Using a motorized microscope stage with automated focus control to image multiple stage positions in the flow cell may allow millions of individual single peptides (or more) to be sequenced in one experiment (see FIG. 10, FIG. 11, and FIG. 12). By way of comparison, current generation single molecule DNA sequencers (e.g., available from Helicos) can sequence approximately 1 billion single DNA molecules per experiment.

As described above, for each Edman cycle the fluorescence intensity of label 1 will be recorded after each cleavage step. After the very first round of removal of label 1 (which corresponds to removing the labeled N-terminal amino acid), this label will exclusively label Lysine residues in the immobilized peptides, with a fluorescence intensity proportional to the count of Lysines in a given peptide. The loss and uptake of label 2 measured after each cleavage step and coupling step, respectively, serves as 1) a counter for the number of amino acid residues removed, and 2) an internal error control indicating the successful completion of each round of Edman degradation for each immobilized peptide.

E) Bioinformatic Analysis.

Following image processing to filter noise and identify the location of peptides, as well as to map the locations of the same peptides across the set of collected images, intensity profiles for label 1 and label 2 are associated with each peptide as a function of Edman cycle. The label 1 intensity profile of each error free peptide sequencing reaction (determined by the cycling of label 2) is transformed into a binary sequence (e.g., 00010001100) in which a "1" precedes a drop in fluorescence intensity of label 1 and its location (i.e. position within the binary sequence) identifies the number of Edman cycles performed. This sequence, termed the binary intensity profile, represents a simplified version of the experimentally derived peptide sequence.

Figure 13:
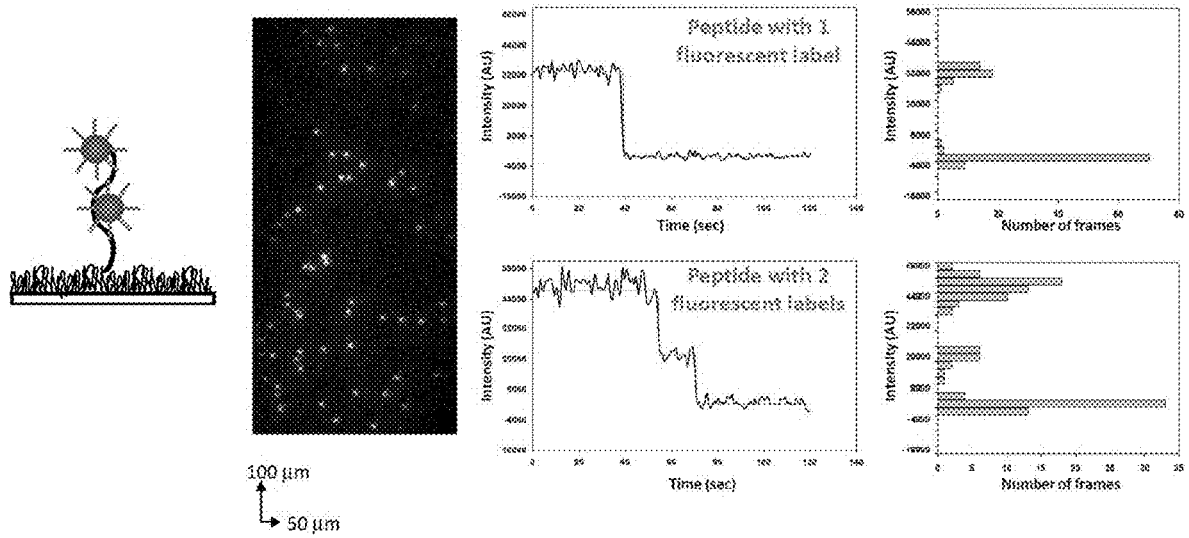
FIG. 13 shows one embodiment of peptides with labeled Lysines (i.e. labeled with the amine-reactive dye HiLyte 647), said peptides attached by Cysteines to maleimide-PEG quartz surface. The different pattern of fluorescence intensity with the different labeled Lysine content. HiLyte Fluor™ 647 succidinimyl ester is a amine-reactive fluorescent labeling dye that generates the conjugates that are slightly red-shifted compared to those of Cy5 dyes, resulting in an optimal match to filters designed for Cy5 dye. Its conjugate may have better performance than Cy5 for fluorescence polarization-based assays.
Figure 14:
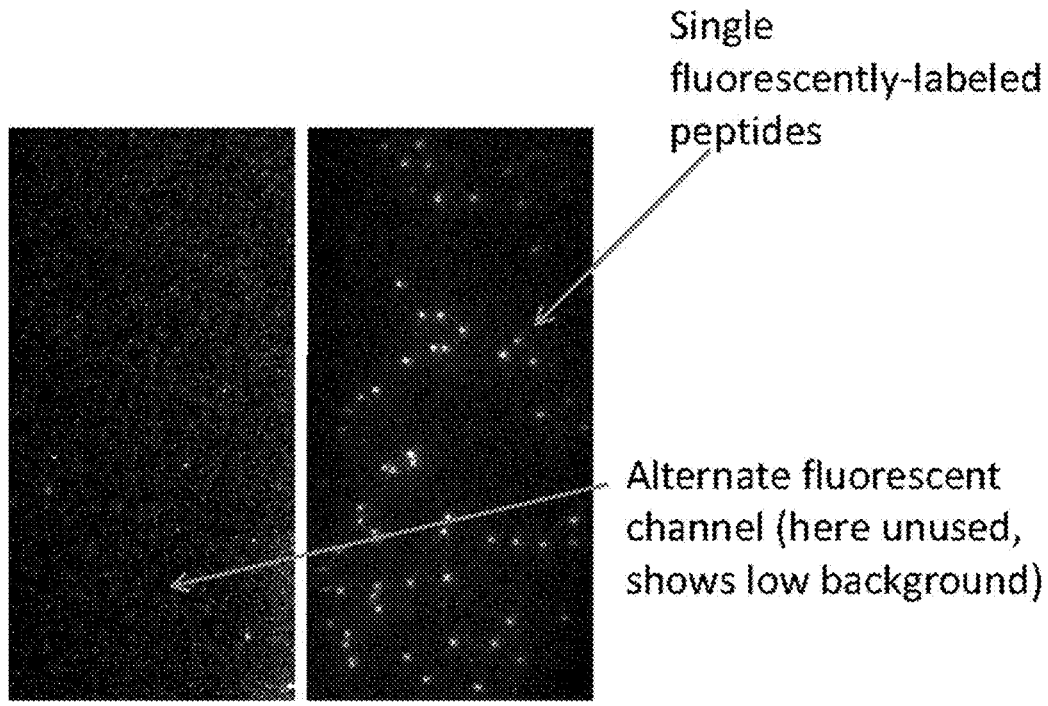
FIG. 14 shows a comparison of single fluorescently-labeled peptides, Hilyte647-NHS dye in the 647 channel. The alternate channel revealing low background fluorescence is a 561 channel.
Figure 15:
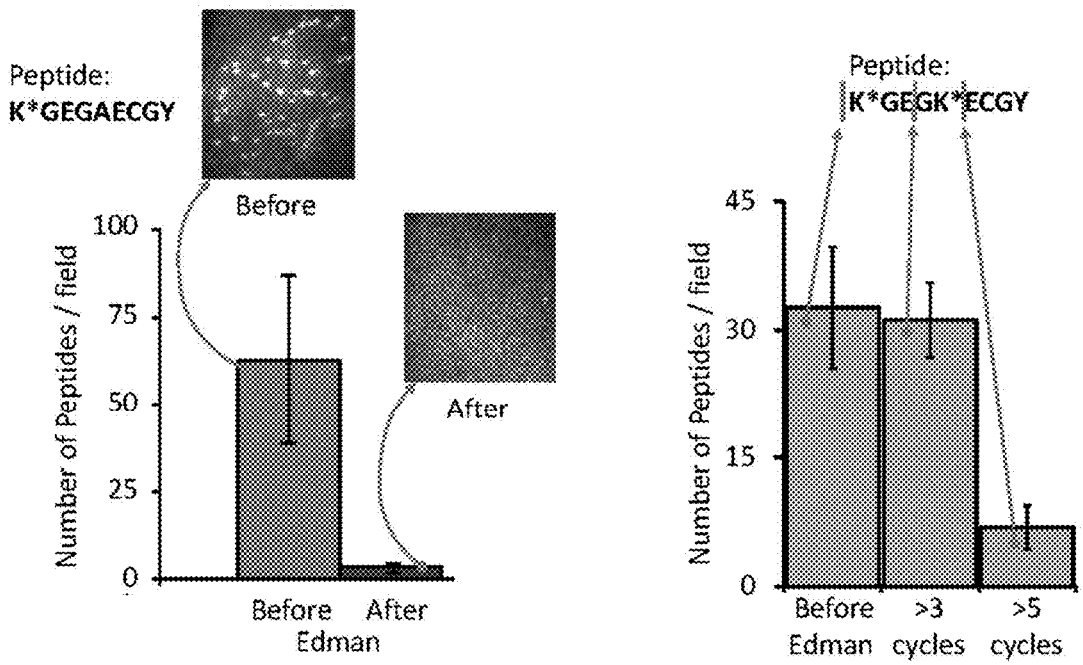
FIG. 15 shows the difference in the Edman degradation of the labeled single peptide molecules between a peptide that contains one versus two labeled Lysines. The fluorescence signal, Hilyte647 dye (excited by the 647 channel), drops when the labeled Lysine is removed. Only fluorescence signal is found with labeled Lysines.

The method has the ability to identify the location of peptides as well as the ability to follow these peptides after a number of steps. FIG. 13 shows one embodiment of labeled Lysines (amine-reactive dye HiLyte 647) attached by Cysteines to maleimide-PEG quartz surface. The different pattern of fluorescence intensity with the different labeled Lysine content is revealed. The reactive dye used, HiLyte Fluor™ 647 succidinimyl ester, is an amine-reactive fluorescent labeling dye that generates the conjugates that are slightly red-shifted compared to those of Cy5 dyes, resulting in an optimal match to filters designed for Cy5 dye. Its conjugate may have better performance than Cy5 for fluorescence polarization-based assays. FIG. 14 shows a comparison of single fluorescently-labeled peptides and alternate channel revealing low background fluorescence. When analyzing the peptides, one can observe the difference in the Edman degradation of the labeled single peptide molecules between a peptide that contains one versus two labeled Lysines (see FIG. 15). The fluorescence signal drops when the labeled Lysine is removed. Only fluorescence signal is found with labeled Lysines. One can also use quantum dots as a guide in analysis of large numbers of peptides from by scanning the microscope and tiling images (see FIG. 16).

A database of predicted potential proteins for the organism under investigation is used as a reference database. For example, in one embodiment the human protein database, compiled from the UniProt protein sequence database and containing 20,252 translated protein sequences, may be used as the reference dataset. A list of potential peptides is generated by simulating the proteolysis, labeling and anchoring approach used in the experiment. In the example provided above, this corresponds to cutting by GluC, labeling of Lysines and anchoring of peptides via Cysteines. Each unique peptide generated in this simulation may be transformed to its corresponding binary sequence (e.g. 0001000110), retaining its mapping to the protein sequence and ID from which it was formed. This creates a lookup database indexing potential binary sequences derived from that organism's proteome to unique protein IDs.

The binary intensity profile of each peptide, as generated from the single molecule microscopy, is then compared to the entries in the simulated peptide database (step 3). This provides the protein ID, if available, from which the peptide is uniquely derived. Performing this lookup over all measured profiles results in the identification of the set of proteins composing the complex protein mixture. Many binary intensity profiles may not have a unique match in the database. In one embodiment, advanced bioinformatics analyses could consider the multiplicity of matches and infer the most likely proteins present. In another embodiment, a simple approach is to just ignore all of these cases and rely only upon uniquely matching cases to build evidence for proteins being present. Quantitation is then accomplished by counting peptides derived from each protein observed. Since this approach is intrinsically digital, the count of peptides from each protein should be proportional to the abundance of the protein in the mixture. In another embodiment, the efficiencies of the reaction steps, including the labeling, Edman reagent coupling, and Edman reagent cleavage reactions can be measured or estimated and then incorporated in the computational search of the proteome sequences in order to provide a probabilistic estimate of the identification of a particular peptide or protein in the database.

F) Variations.

Variants to the above protocol are contemplated. In one embodiment, to improve signal to noise during single molecule imaging, oxygen- and free radical-scavenging and triple quenching components are included in the solution (e.g., see Harris et al., Science 320, 106 (2008) [5], (herein incorporated by reference). In another embodiment, the surface of the solid support can be modified chemically, such as by coating with polyethylene glycol, in order to suppress nonspecific adsorption to the surface and thus improve the signal to noise ratio for the fluorescent detection of peptides. In another embodiment, more than two fluorescent molecules may be used to label additional amino acids. Such an approach might involve, for example, covalently labeling Lysines with a fluorescent Edman reagent prior to sequencing (as described above) and also covalently labeling amino acids with carboxylate side chains (e.g., glutamate, aspartate) with a second fluorescent molecule (chosen for spectral compatibility), then proceeding with Edman degradation cycles using an Edman reagent labeled with a third fluorescent molecule. This method would provide more information-rich sequence profiles for identifying many more peptides. In another embodiment, an alternate imaging strategy involves the use of scanning confocal microscopy. In yet another embodiment, the cleavage/re-labeling steps of the Edman reaction are replaced with a protocol in which the re-labeling is performed using the Edman label 2 (as above), but then the cleavage step is performed using an aminopeptidase enzyme to remove the labeled amino-terminal amino acid. This would allow all reactions to be performed in aqueous solvent and simplify the apparatus by decreasing the need for organic solvents. In this embodiment, the aminopeptidase would be selected such that it requires and tolerates the presence of label 2 on the amino-terminal amino acid, therefore it would likely have to be optimized using in vitro evolution techniques to be suitable for use in sequencing.

In yet another embodiment, the successful removal of amino acids occurs from the carboxy terminus of the peptide, thereby revealing C-terminal sequences instead of N-terminal sequences. In a preferred embodiment, this approach employs, for example, engineered carboxypeptidases or small molecule reagents reacting analogous to the N-terminal Edman chemistry but operating from the C-terminus of the peptide.

VI. Exemplary Labeling of Amino Acids with Two Different Fluorophore Prior to Solid Phase Peptide Synthesis and General Peptide Synthesis.

This Example (and in Example VIII) describes the creation and use of a building block and/or control peptide for use in solid phase peptide synthesis. Thus in one embodiment, eliminating the need to create more than one orthogonal dye label. The main criteria for the building block peptide was that it could be created in fairy large quantity (2-5 g) for use on the peptide synthesizer, such large amounts were required to account for the inefficiency of the solid phase synthesis.

A. Boc-Asp-OBzl Peptide Labeled with Rhodamine B Via HCTU Coupling. See, FIG. 61.

In this embodiment of the method, one of either BOC or FMOC Asp-OBzl was used to generate a building block. The majority of the synthesis proceeded without purification (other than step 2). This series of reactions can also be done on 5 g scale. Step 5 (see FIG. 61) is needed in the instance where R=FMOC. In this case, the basic conditions of step 3 (DIPEA) can de-FMOC the Asp, which needs to be protected before use on the surface. The use of a BOC protecting group on the amine makes this synthesis straightforward because there are no de-protection steps, however, it is labeled under the same conditions as a Wang resin. On any peptide where a BOC protecting group is present, it should be the final amino acid added.

B. FMOC-Cys Peptide Labeled with Rhodamine B Via Iodoacetamide Handle. See, FIG. 62.

Fmoc-Cys(Trt)-OH can be easily de protected in one step with a quantitative yield. The rhodamine B iodoacetamide should be prepared on a several gram scale.

In a reaction solution, combining the FMOC-Cys with the Rhodamine B iodoacetamide goes to completion within 6 hours, with very little by-product, requiring no purification. The FMOC protected amino acid can be placed in any location along the peptide sequence.

NHS Activation steps in A. and B., above, are generally described in Chen et al. *Dyes and Pigments* 94, 296-303 (2012).

C. Making a Peptide that is Labeled with Two Different Dyes.

In this dye sequencing scheme, two different color dyes are used to label two different Cys moieties on a peptide. Using a building block that was synthesized, Cyst-Rhodamine B (See B above, as shown in FIG. 62) another dye containing an iodoacetamide handle needs to be synthesized for use as a second label.

There are literature reports of a rhodamine-based dye containing a Silicon atom replacing the oxygen of the core structure of the dye. This atom replacement shifts the wavelength of emission from ~550 nm to ~640 nm, a distance spectrally resolve enough to limit FRET pairing (A). Synthesis of the core structure is a literature report procedure (Lukinavicˇius et al. *Nature Chemistry* 5, 132-139 (2013)).

The synthetic strategies for using Si-Rhodamine involve the development of a "handle" attached to and using the core Si-Rhodamine structure designed during the development of the present inventions. The method here for labeling Cyst with Si-Rhodamine is the same as in B) above, for labeling the Cys with a rhodamine B dye using a iodoacetamide handle. From the 9 linear steps for producing Si-Rhodamine as a label (see FIG. 63), the overall yield is 4% with column chromatography purification at the final step.

Labeling strategy: In brief, starting with the building block made in B above, then treating it to solid phase peptide synthesis to make a peptide having a Cyst amino acid labeled with Rhodamine B was accomplished. In this case a 12 amino acid peptide was made having a Cys-Rhodamine B.

Following the general steps to remove a peptide from a resin and wash it, this peptide was then reacted, without purification, with the Si-Rhodamine iodoacetamide as described herein. In slightly basic conditions, the 2 position Cys was labeled by the SN2 of the iodine atom. Following HPLC purification, the high-resolution Mass Spectrometry confirmed that the 12 amino acid peptide was labeled with 2 different colored dyes. See, FIG. 64.

D. Exemplary methods for peptide synthesis are described herein. In brief, peptides in general were synthesized using a standard automated solid-phase peptide synthesizer, and purified using high-performance liquid chromatography (HPLC) or $C_{18}$ solid phase extraction. Examples of resins used for solid-based peptide synthesis include but are not limited to Fmoc-Cys(Trt)-Wang resin (100-200 mesh), 4-Fmoc-hydrazinobenzoyl resin AM Novagel™, Tentagel Thiol Resin, and the like. See FIG. 18 as an example.

VII. Solution-Phase and Solid-Phase Labeling.

A sequential and orthogonal scheme of common mass-labeling reactions, first solution and then solid, was developed as described herein, for modifying peptides. In particular, solution-phase labeling orthogonal labeling of side chains in synthesized peptide KDYWEC (SEQ ID NO: 3) with solid-phase in synthesized peptide KDYWE (SEQ ID NO: 4) is demonstrated. In other examples, solution phase labeling is on synthesized model peptides: peptides containing Cysteine (A) YKTCYTD (SEQ ID NO: 5), B) KCGGYCD (SEQ ID NO: 6), and C) GYCKCTD (SEQ ID NO: 7)), FIG. 47 and model peptides containing Lysine (K), and Tryptophan (W) (KCTWGCD (SEQ ID NO: 18), WGCTKWD (SEQ ID NO: 19)).

A. Orthogonal Labeling in Solution-Phase of the Target Side Chains in Peptide KDYWEC (SEQ ID NO: 3).

The majority of the side chains, N-terminus, and C-terminus were labeled. No additional heating was required to label N-terminal amine with ivDde when using Phos-ivDde. Thus, in one embodiment, Cysteine side chains are solution labeled with iodoacetamide with or without subsequent labeling with 2-methylthio-2-imadazoline hydroiodide (MDI). In one embodiment, Lysine side chains are solution labeled with 2-methoxy-4,5-dihydro-1H-imidazole. In one embodiment, Tryptophan side chains are solution labeled with 2,4-Dinitrobenzenesulfenyl chloride (DBSC).

In one embodiment, carboxylate side chains are solution labeled with Benzylamine (BA). In one embodiment, carboxylate side chains are solution labeled with 3-dimethylaminopropylamine (DMAPA). In one embodiment, carboxylate side chains are solution labeled with isobutylamine. In one embodiment, carboxylate side chains are solution labeled with 3-dimethylaminopropylamine.

In one embodiment, the N-terminus of a peptide is solution labeled with 1-(4,4-dimethyl-2,6-dioxocyclohexylidene)-3-methylbutyl diethyl phosphate (Phos-ivDde).

In one embodiment, the C-terminus of a peptide is solution labeled with Benzylamine (BA). In one embodiment, the C-terminus of a peptide is solution labeled with 3-dimethylaminopropylamine (DMAPA). In one embodiment, the C-terminus of a peptide is solution labeled with isobutylamine. In one embodiment, the C-terminus of a peptide is solution labeled with 3-dimethylaminopropylamine.

B. Orthogonal Labeling in Solid-Phase Studies for Peptide KDYWE (SEQ ID NO: 4).

Labeling all target side chains was possible while omitting the labeling of the α-amine. Oxidative cleavage of the resin provided flexibility to choose between releasing labeled or unlabeled C-terminus. The use of 1-amino-3-butyne as the carboxylate-labeling reagent introduced further functionality that is contemplated for use in other reaction embodiments. Such an approach can have many applications for peptide labeling studies and novel synthetic peptide design. Other labels, like fluorescent probes, can be designed to have the same functional handles as described herein.

In one embodiment, Lysine side chains are solid-phase labeled, wherein the peptide is attached to a solid material, with 2-methoxy-4,5-dihydro-1H-imidazole. In one embodiment, Cysteine side chains are solid-phase labeled with 2-methylthio-2-imadazoline hydroiodide (MDI). For solid-phase labeling, a different method was described in the examples than used for solution phase labeling Cysteine, of as described above. Further, solid-phase orthogonal labeling of Cysteine as described herein, showed surprising results compared to published descriptions, see, Example V as an example for details. In one embodiment, Tryptophan side chains were solid-phase labeled with 2,4-Dinitrobenzenesulfenyl chloride (DBSC). In one embodiment, Tryptophan side chains were solid-phase labeled with 1-amino-3-butyne (AB).

In one embodiment, carboxylate side chains are solid-phase labeled with 1-amino-3-butyne (AB).

C. Orthogonal Labeling in Solution-Phase of the Target Side Chains in Peptides Containing Cysteine, Lysine and Tryptophan.

One, two, and at least three different amino acids can be labeled depending on the (orthogonal) reaction conditions. Thus, in one embodiment, solution phase fluorophore labeling, i.e. one up to three types of amino acids of model peptides, is intended for C-terminal immobilization and sequencing. In particular, this method describes embodiments for labeling Lysines using an isothiourea method and labeling tryptophan in addition to using Rhodamine B iodoacetamide for Cysteine labeling; Rhodamine B or Si Rhodamine B for Tryptophan. See, Example VII.

Model peptides were synthesized containing Cysteine and Lysine: A) YKTCYTD (SEQ ID NO: 5), B) KCGGYCD (SEQ ID NO: 6), and C) GYCKCTD (SEQ ID NO: 7)), FIG. 48. Additional model peptides were synthesized containing Cysteine, Lysine and Tryptophan (KCTWGCD (SEQ ID NO: 18), WGCTKWD (SEQ ID NO: 19)) and peptides Serine-Tryptophan (Ser-Trp;SW) and Alanine-Aspatate and Tryptophan (Ala-Asn-Trp;ANW). Peptides were synthesized on a microwave peptide synthesizer.

A: An Example of Solution Phase Labeling of Model Peptides for C-Terminal Immobilization and Sequencing.

1. For Cysteine Labeling.

Figure 48:
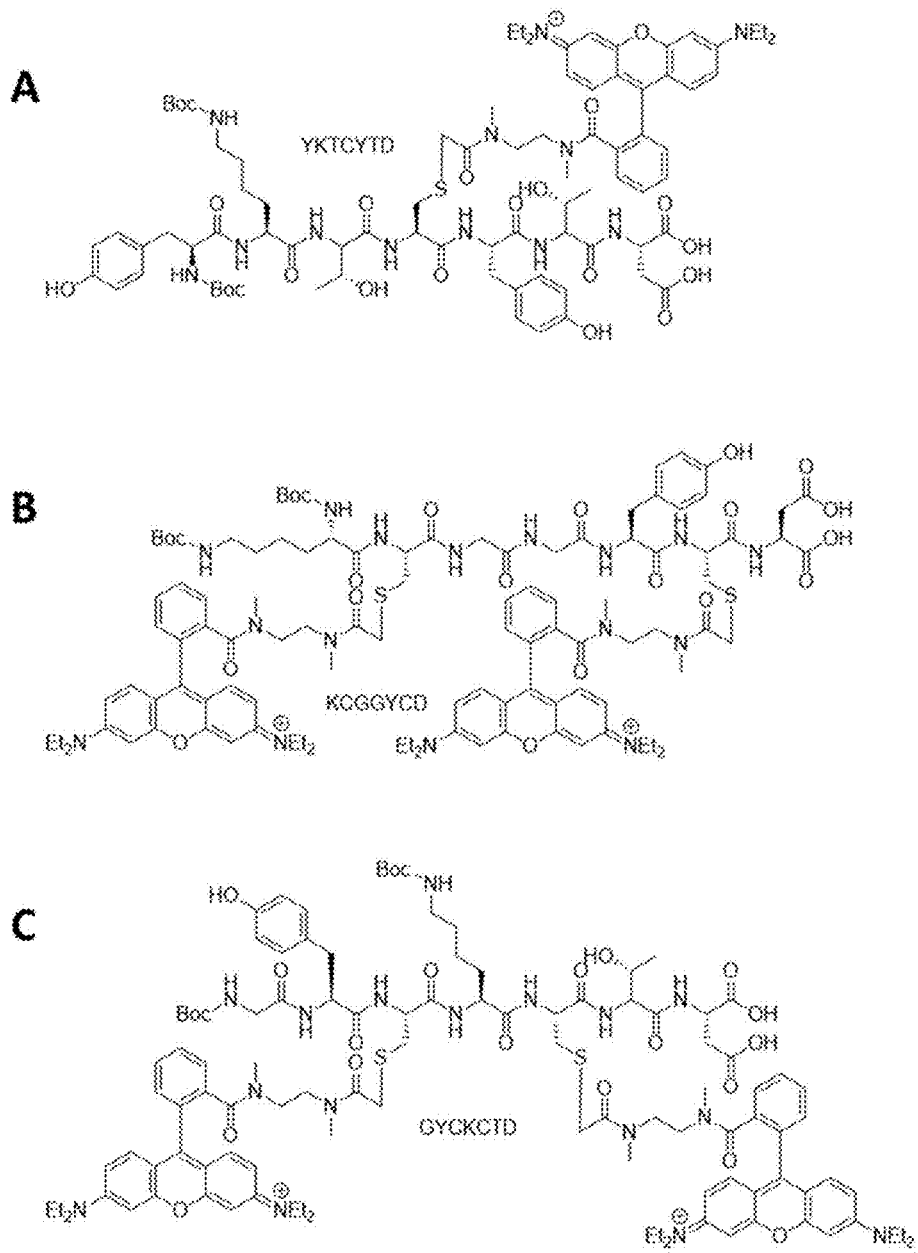

Rhodamine B iodoacetamide: N,N'-dimethylethylenediamine was used to label Cysteine in a solution-phase method. This reaction was selective for Cysteine where the Lysine and N-terminus were boc-protected. Purified peptides were confirmed by high-resolution mass spectrometry. FIG. 48.

2. For Tryptophan Labeling.

A model reagent, 4-(butylcarbamoyl)-2-nitrophenyl hypochlorothioite, see FIG. 48 for an exemplary structure, was made to label Tryptophan containing peptides. For this example, see model peptides above containing Tryptophan. The labeled Tryptophan was stable to Edman degradation in solution. FIG. 49.

3. For Lysine Labeling.

An isothiourea was synthesized as a model reagent for Lysine labeling. FIG. 51A. Reaction of the isothiourea with Lysine dihydrochloride proceeded once. FIG. 51A. Reaction of the isothiourea with peptides proceeds slowly. FIG. 51B.

This method of synthesis is an alternative to labeling lysine residues in that it does not include the use of the o-methyl isourea. Further, this method selectively labels Lysine over the N-terminus.

B: An Example of Solution Phase Labeling, One to Two Types of Amino Acids of Model Peptides Containing Lysine and Tryptophan for C-Terminal Immobilization and Sequencing.

1. For Lysine Labeling.

Contemplated amino acid specific labels, such as for Lysine, are Rhodamine B and Si Rhodamine B (separately) for solution phase labeling of the first of two amino acids with two differently colored dyes. For example, Lysine labeled with Si Rhodamine B was contemplated for use with Tryptophan labeled with Rhodamine B.

2. For Tryptophan Labeling.

A Rhodamine B sulfenyl chloride was synthesized, as describe above for use in labeling Tryptophan. The synthesis is described above and in FIG. 52.

Two small peptides with Trp (W) amino acids were labeled with the Rhodamine B sulfenyl chloride. The expected product from this tryptophan reaction with the Rhodamine B sulfenyl chloride is observed in test reactions with two small peptides, Ser-Trp (SW) and Ala-Asn-Trp (ANW). See, FIGS. 53A and 53B, respectively. The Rhodamine B label is attached to the Trp in FIG. 53A. The Rhodamine B label is attached to the Trp in FIG. 53B.

C. An Example of Solution Phase Labeling, One, Two or Three Types of Amino Acids of Model Peptides Containing Cysteine, Lysine and Tryptophan for C-Terminal Immobilization and Sequencing.

1. For Cysteine Labeling.

In some embodiments, Cysteine labeling is as described herein for Lysine.

2. For Lysine Labeling.

Contemplated amino acid specific labels, such as for Lysine, are Rhodamine B and Si Rhodamine B (separately) for solution phase labeling of the first of two amino acids with two differently colored dyes. In particular, this labeling is contemplated as an alternative to labeling Lysine residues that does not include the use of the o-methyl isourea. For example, in one embodiment, Lysine is labeled with Si Rhodamine B. This labeled Lysine was contemplated for use with Tryptophan labeled with Rhodamine B. In another embodiment, Lysine is labeled with Rhodamine B or a Rhodamine B derivative (variant). Additionally, as shown in FIG. 53A, this method selectively labels lysine over the N-terminus.

VIII. Demonstrating Single Molecule Peptide Sequencing of Fluorescently Labeled Peptides at the Single-Molecule Level.

This example shows exemplary tracking of single peptide molecules through Edman cycles and determining the position of the labeled amino acid. Specifically, two peptide populations differing in the position of their labeled amino-acid residue were discriminated in a mixture at single-molecule sensitivity using a single-molecule Edman peptide sequencing procedure. FIG. 65 shows a summary of these experimental results.

Peptide A—labeled orange (lighter left bar and left peptide) in the diagram, with sequence (boc)-K*AGAAG (SEQ ID NO: 13), where* (Rhodamine=Tetramethylrhodamine); and Peptide B—labeled blue (daker right bar and right peptide) in the diagram, with sequence (boc)-GK*[Atto647N]AGAG (SEQ ID NO: 14).

Peptides A and B were labeled via their Lysines with dyes excitable at 561 nm (Rhodamine) and 647 nm (Atto647N) wavelengths, respectively. Both peptide populations were immobilized on a glass slide via their carboxyl terminuses, and the protecting boc groups were removed from their amino terminuses. Then, the peptides were observed via total internal reflection (TIRF) microscopy through several cycles of Edman degradation. Thousands of labeled peptides across multiple fields of view were individually tracked in parallel, and their fluorescence after every cycle recorded. As a control, the first two cycles did not include the critical Edman reagent phenyl isothiocyanate (PITC) that is needed to cleave an amino acid: i.e., these were "mock" reactions to confirm that there was no loss of fluorophores merely due to any of the other chemical solvents or photobleaching. The subsequent eight cycles included PITC, allowing removal of amino acids. The number of fluorescent peptides in the 561 nm channel decreased dramatically after the first full Edman cycle, in accordance with the position of the 561 nm label on the first amino acid of Peptide A. Likewise, the number of fluorescent peptides in the 647 nm channel decreased after the second Edman cycle, in accordance with the position of the 647 nm label on the second amino acid of Peptide B.

Peptide A: (boc)-K*[Tetramethylrhodamine]AGAAG (SEQ ID NO: 13) and Peptide B: (boc)-GK*[Atto647N] AGAG (SEQ ID NO: 14) were synthesized by Thermo Fisher Scientific (IL, USA) with a purity of >95% and validated by mass spectrometry. The fluorophores was covalently attached to the F-amine of the lysine residue Aminosilane slide coating.

Forty mm #1 thick glass coverslips (Bioptechs Inc., PA, USA), were placed vertically in a custom made Teflon rack, and cleaned by washes and sonication with 5% Alconox (detergent), acetone, 90% Ethanol and finally 1 M Potassium hydroxide (KOH). Between each of the different solvent washes, the slides were thoroughly washed with de-ionized water. The aminosilane coating step was carried out by incubating the slides for 20 minutes in 1% Aminopropyltriethoxy silane (Cat #SIA0610, Gelest Inc., PA, USA) dissolved in the acidified 5% v/v of acetic acid/methanol solvent. The slides were sonicated intermittently for 1 minute to dislodge any adsorbed silane molecules. After incubation, the slides were rinsed thoroughly with methanol and water. It was then dried with nitrogen and stored under vacuum until use. The slides were imaged in water and methanol prior to peptide or fluorophore immobilization to check for presence of fluorescing impurities.

Solvents.

Highest purity and mostly spectrophotometry grade solvents of Methanol (Cat #494437, Sigma), Ethylacetate (Cat #270989, Sigma), Acetonitrile (Cat #34967, Sigma), trifluoroacetic acid (Cat #T6508, Sigma), Pyridine (Cat #270970, Sigma), Dimethylformamide (DMF, Cat #270547, Sigma), phenylisothiocyanate (PITC, Cat #P1034-10x1 ml, Sigma) and water (Cat #5140, Thermo Scientific) was used for all the experiments. Coupling solvent, comprising of 9:1 v/v of pyridine: PITC, was freshly prepared before use. The coupling solvent and the free-basing solvent consisting of 10:3:2:1 v/v of acetonitrile:pyridine:triethylamine:water was flushed with nitrogen for 5 minutes and maintained under nitrogen atmosphere by piercing the septum with a nitrogen filled balloon. The cleavage solvent used was 90% TFA in water. The glass vials fitted with a sealable Teflon-silicone septum (Cat #27022, Sigma) used was rinsed with acetone and the solvent with which it is stored. The FEP tubing from the valves were pierced through the septum and the entire system was maintained under anoxic condition.

Fluidics System.

The aminosilane coated glass coverslip housed in a microfluidic chamber was adapted from the FCS2 perfusion chamber (Bioptechs Inc., PA, USA). The vendor supplied upper and the lower gaskets was replaced with 0.03" perfluoroelastomer Kalrez®-0040 material (DuPont Inc., local vendor—Austin Seals company, TX, USA) and a diamond shape was cut in the lower gasket (die Number—452458, cut by Bioptechs Inc.). The shape ensured complete fluid exchanges when compared with a rectangular cut. The Kalrez material had ideal compressibility with a shore durometer A of 70 and had chemical inertness to trifluoroacetic acid.

DESCRIPTION OF PREFERRED EMBODIMENTS

The peptide sequencing technologies described above may be useful not only for analyzing biological samples, but for the development of a novel polymer synthesis and sequencing schema. In one embodiment, the present invention contemplates a method for selecting sequence-specific, functional polymers, including polymers comprising non-natural amino acid derivatives as monomers.

In one embodiment, polymers are synthesized, sequenced, screened and selected. A variety of screening is contemplated, including assays that detect the binding to specific targets and assays that detect catalysts for specific reactions. In one embodiment, the present invention contemplates identifying the individual sequence components of binders or catalysts.

The nature of the platform will assist with the identification of the highest affinity molecules and the fastest catalysts. This is because one can carry out screens and selections at the single molecule level, directly on the platform used for sequencing. Molecular populations can be introduced directly into the same flow cell used for sequencing. The surface of the flow cell will have been previously derivatized or modified with target molecules. A cyclic flow will be established such that the population is allowed to thoroughly equilibrate with the targets. The cyclic path will then be opened for washing, allowing molecules that do not bind tightly enough to their targets to be successively washed away. This is, in essence, a $k_{off}$ selection, and it has been previously employed to great effect to sieve large libraries, such as libraries of aptamers. The progress of the selection can be directly monitored by the simple expedient of attaching dyes to the library, and periodically inquiring of the surface how many single molecules are present. This method also allows tuning of the stringency of selection, both in advance of the selection proper and during the winnowing of the pool.

In one embodiment, competitive (affinity) or non-competitive (passivation) molecules can also be introduced into the flow stream. Control of selection at the single molecule level should allow for selection of a few thousand molecules (for sequencing out of hundreds of thousands, to millions to even billions of molecules.

In one embodiment, the present invention contemplates selection for binders to important or useful targets. For example, the present invention contemplates synthesis, selection and sequencing of individual polymers that can bind to phosphoryl fluorides (diethylchlorophosphate and diethylfluorophosphate) or other toxic substances. In one embodiment, binders to other targets are made, selected and sequenced, including but not limited to synthesizing and selecting individual polymers that bind to hen egg white lysozyme, ovalbumin, maltotriose, lanatoside C, erlose, and the like.

Selection for catalysis can be performed in a similar manner. In one embodiment, catalysts for reactions that degrade toxins are contemplated. For example, in one embodiment, catalysts for the hydrolysis of organophosphonic di- and mono-chlorides will be sought. In another embodiment, the present invention contemplates catalysts for phosphoaryl fluoride (a toxic gas) hydrolysis, including gas phase alkaline hydrolysis. In one embodiment, catalysts are selected that release themselves from interactions with their ligand, only to be carried into the chamber for single molecule sequencing. Following sequencing, additional rounds of screening or selection can be carried out by resynthesis of the population, focusing on validated binding or catalytic species, and then once again winnowing the pool within the flow cell on the surface of the device.

Single molecule resolution provides important advantages for advancing polymer characterization. By taking into account the extent of aggregation on the surface, one can quickly determine soluble compositions, and by determining the volume of wash solution required for removal of a given fluorescent pixel, it should be possible to readily calculate the $K_d$ of the underlying binding species.

The protein sequencing methods described herein are enabling for unnatural polymer discovery. That is to say, the same method described herein to sequence peptides/proteins using the 20-natural amino acids can be used to sequence peptides/proteins made from unnatural amino acids, potentially including beta amino acids, and will provide a platform for future advances, such as deconvoluting 'chemically translated' nucleic acid libraries. While to our knowledge Edman degradation has never been applied to beta amino acids, the intramolecular cyclization reaction would form a 6-membered ring, and therefore should occur rapidly. β amino acids have their amino group bonded to the β carbon rather than the α carbon as in the 20 standard biological amino acids.

Figure 18:
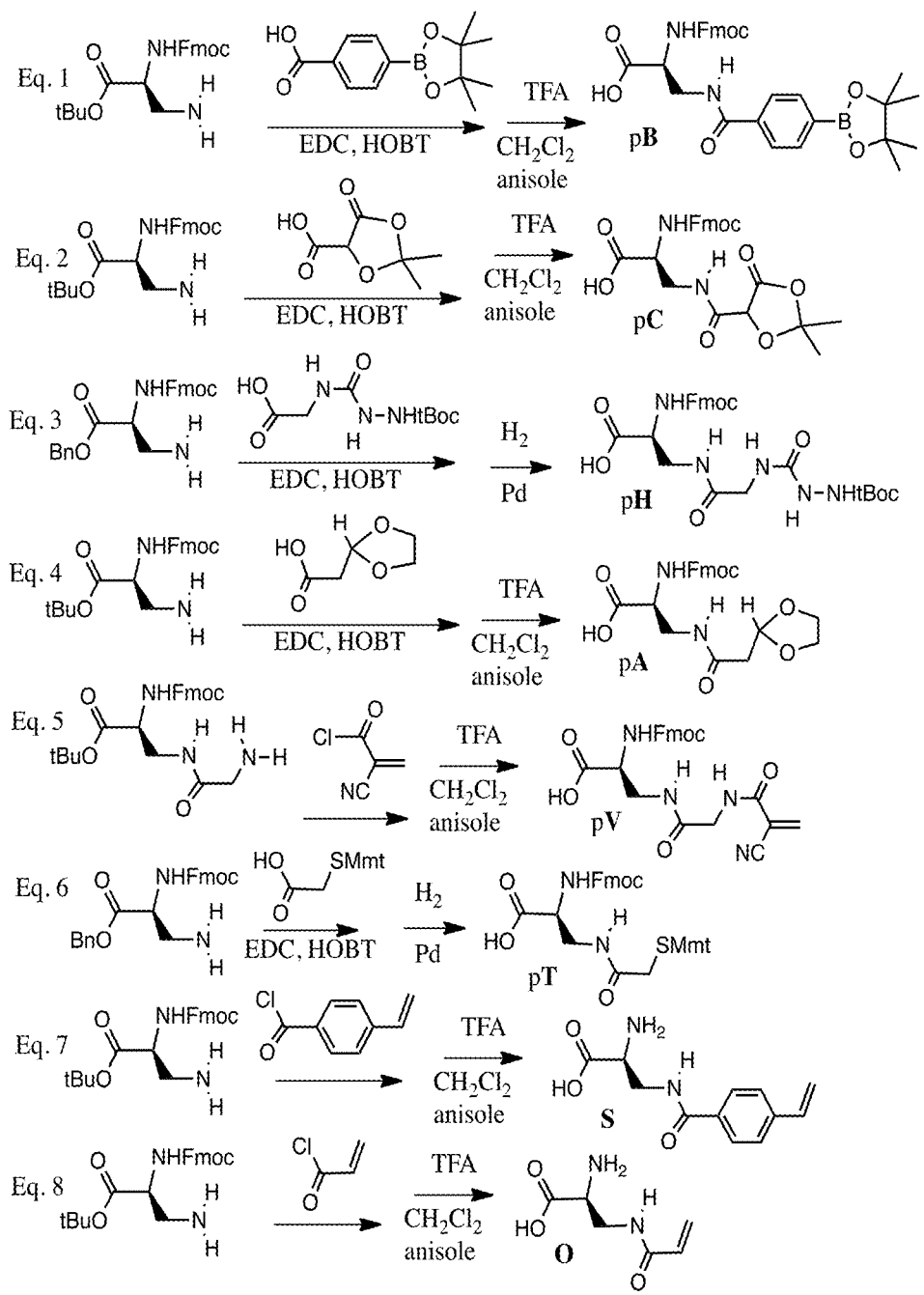
FIG. 18 shows synthetic pathways for a group of contemplated exemplary monomers in a protected form to be used in Fmoc-based solid phase synthesis.

It is not intended that the present invention be limited to the precise nature of the unnatural polymers. Therefore, it is also not intended that the present invention be limited by the nature of the monomers used to make the unnatural polymers. However, by way of example, FIG. 18 shows synthetic pathways for a group of contemplated monomers in a protected form to be used in Fmoc-based solid phase synthesis. The protected amino acids are designated with a "p," such as pB and pV. All the syntheses start with two different versions of a protected amino acid. When the protecting group on the side chain is acid stable (such as with pB, pC, pA, pV, pS, and pO), the carboxylate of the amino acid will initially be a tBu-ester, that can be deprotected with TFA in the presence of the carbocation trap anisole. Alternatively, when the side chain-protecting group is acid labile, one can start with a benzyl protected carboxylate of the amino acid, which can be deprotected by hydrogenation (pH and pT). In addition, because the solid-phase synthesis routine, in one embodiment, will use Fmoc-chemistry, the side chains of the amino acids used during peptide synthesis must all be stable to basic conditions. The side chains carry therefore acetals, t-Boc groups, or mono-methoxytrityl (Mmt) for final deprotection with acid, as in standard solid phase peptide synthesis. The syntheses are simple enough that it is likely that all monomers can be made in gram (or larger) quantities for library screening and eventually for large-scale polymer synthesis.

In one embodiment, peptide synthesis will proceed from the protected amino acid monomers discussed above. In one embodiment, the polymer starts with a Cys followed by eight random amino acids from the group [B,C,H, and A] followed by O (FIG. 19A). Because Edman degradation starts from the N-terminus and incrementally removes each amino acid one at a time toward the C-terminus, the last amino acid in each decamer chain can be Cys to fix the peptide on the microscope slide surface. If we add a pre-synthesized Cys-S dimer via olefin metathesis, one can build another library of 7 unnatural amino acids finished with an S to make the second 10-mer ("=" in FIG. 19A represents an alkene created from metathesis). The third 10-mer can start with Cys-S but can be followed by a random 8-mer.

Olefin metathesis is high yielding, and readily reversible by adding Grubbs catalyst and ethylene, thereby clipping the 30-mer into three 10-mers for immobilization for single molecule sequencing (FIGS. 19B and C). Additionally, the placements of O and S act as markers to identify whether the 10-mers were the C-terminal, the central, or the N-terminal peptides. Finally, in order to monitor libraries and individual polymers on surfaces and in solution, fluorescent conjugates to terminal amines or Cysteine residues will be prepared using the cognate dyes shown in FIG. 17.

The present invention contemplates using monomers to create combinatorial libraries of polymers. In one embodiment, the present invention contemplates a combinatorial library of B, H, V, and S, with 10% C as should create a globular macromolecule that is on average 10% cross-linked and possesses boronic acids, super-nucleophiles, conjugate acceptors, and hydrophobic side chains. Conversely, of course, the monomers could be primarily "short monomers" (C, A, T, and O) and potentially 20% S. Now the unnatural 30-mers would carry hydroxycarboxylates, aldehydes, thiols, and olefins (alkenes), and the extent of crosslinking would depend upon the addition of Grubbs catalyst and the concentration of added ethylene. The proper mixture of amino acids will need to be determined empirically to keep the libraries highly water soluble while retaining binding characteristics.

In one embodiment, one surface immobilizes polymers of via C-terminal Cysteine residues, and carries out rounds of subtractive Edman degradation in which individual amino acids (and corresponding dyes) are removed. Polymers can initially be immobilized in situ by the inclusion of fluorous maleimide during the Cytop coating of the slide. During selections, polymers can be captured by including a fluorous thiol in the coating and shifting to oxidizing conditions.

Figure 20:
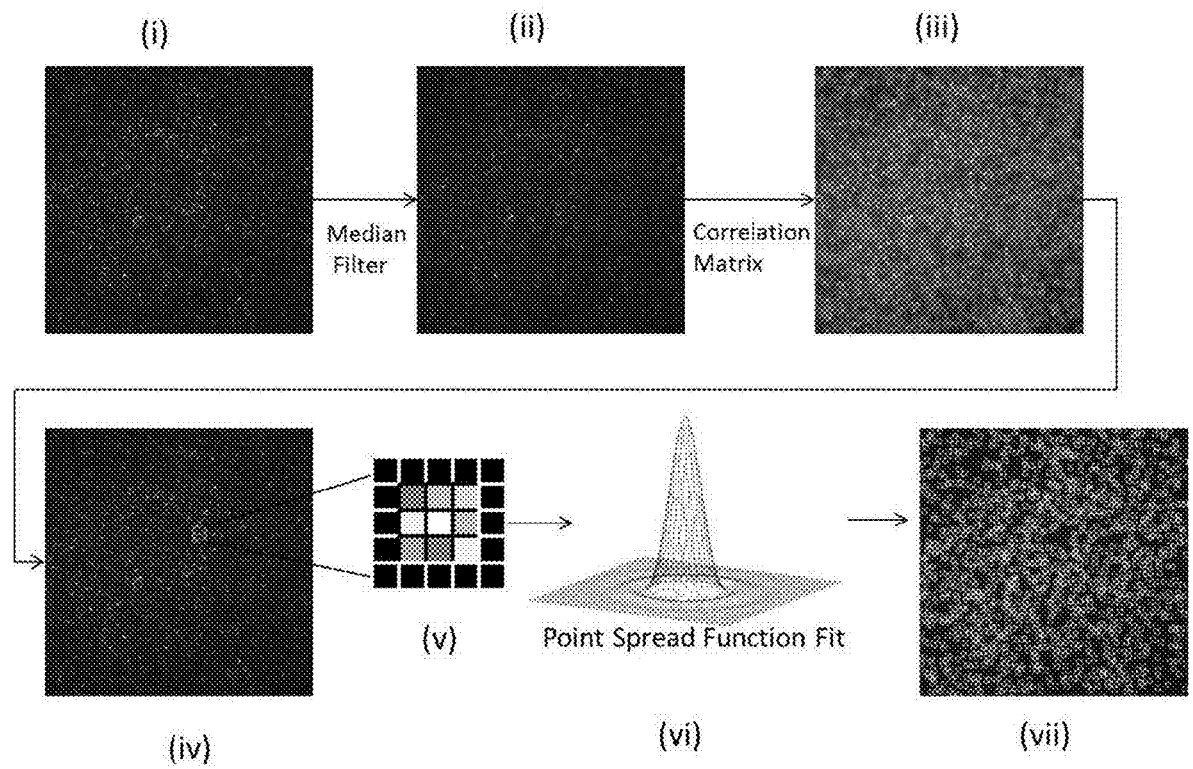
FIG. 20 depicts an automated computational pipeline for peak identification. To the acquired raw image (i), a box median filter is applied to remove the background noise. A correlation matrix sweeps across this 2D processed image to detect candidate peaks that fits a defined criterion. The coordinates of the candidate peaks from this image (iii) are mapped to the raw image (iv). To illustrate how the peak is identified, assume a 5×5 pixel region (v) in the image that contains the candidate peak. To the central 3×3 pixel, a point spread function (vi) is fitted on its intensity values. The background intensity is the average of the intensity values of the squares surrounding the central 3×3 pixel region. It is considered as true peak if the $R^2$ value of the fit is greater than 0.7. By iterating through all the candidate peaks and applying the filter, we identify all the peaks (as denoted in image vii) in our acquired image.

In parallel, the present invention contemplates a computational infrastructure required for the interpretation of single molecule imaging data. For peptide sequencing, a pipeline for rapid image analysis by modeling of a subpixel resolved point spread function for every peptide and estimating its intensity has been developed (FIG. 20). After aligning the images after each Edman cycle we will track the fluorescent intensity of every single polymer molecule.

Dyes illuminated for a considerable period of time may photobleach, although the microscope setup, the photostable dyes, and the imaging buffers used have made this a less serious concern. Image analysis should statistically separate true degradation versus false losses of molecules or emission. We start with simple statistical methods like moving average that can indicate a step-drop of intensity with cycle and help deconvolute a fluorescent pattern for every molecule. The acquired images processed will be in multidimensional parameter space, wherein every single polymer will be assigned a spatial coordinate along with its intensity profiles for every color channel over time. A computational infrastructure for parallelized image processing and database structure can be implemented. Integrating the statistical and image alignment packages into a computational pipeline will enable tracking the intensity profile of every single polymer as a function of Edman cycle.

EXPERIMENTAL

The following are examples that further illustrate embodiments contemplated by the present invention. It is not intended that these examples provide any limitations on the present invention.

In the experimental disclosure that follows, the following abbreviations apply: eq. or eqs. (equivalents); M (Molar); M (micromolar); N (Normal); mol (moles); mmol (millimoles); mol (micromoles); nmol (nanomoles); pmoles (picomoles); g (grams); mg (milligrams); g (micrograms); ng (nanogram); vol (volume); w/v (weight to volume); v/v (volume to volume); L (liters); ml (milliliters); μL (microliters); cm (centimeters); mm (millimeters); μm (micrometers); nm (nanometers); C (degrees Centigrade); rpm (revolutions per minute); DNA (deoxyribonucleic acid); kDal (kilodaltons).

I. Single Molecule Sequencing.

FIG. 4 depicts one embodiment of the single-molecule peptide sequencing method. Briefly, selective labeling of amino acids on immobilized peptides followed by successive cycles of labeling and removal of the peptides' amino-terminal amino acids is capable of producing patterns sufficiently reflective of their sequences to allow unique identification of a majority of proteins in the yeast and human proteomes. FIG. 5 shows the simplest scheme with 2 fluorescent colors (i.e. "fluors" or "labels"), in which fluor 2 (red star) labels the peptide amino termini (N-termini) over successive cycles of removal of the N-terminal amino acids and re-labeling of the resulting new N-termini, and fluor 1 (green star) labels Lysine (K) residues. The immobilization of fluor 2 on a peptide serves as an indicator that the Edman reaction initiated successfully; its removal following a solvent change indicates that the reaction completed successfully. Fluor 2 thus serves as an internal error check—i.e., indicating for each peptide which Edman cycles have initiated and completed successfully—and gives a count of amino acids removed from each peptide, as well as reporting the locations of all peptides being sequenced. Fluor 1 serves to indicate when Lysines are removed, which, in combination with the reporting of each Edman cycle by fluor 2, gives the resulting sequence profile (e.g. . . . XKX . . . below) that will be used to identify the peptide by comparison with a database of possible protein sequences from the organism being sequenced. In another embodiment, a second fluorescent label is not used; instead, a non-fluorescent version of the reagent which labels and removes the amino termini in successive cycles is employed; in this embodiment, cycles are simply counted, resulting in the same sequence patterns (e.g. . . . XKX . . . ) as in the above embodiment but without providing an internal error check for the successful initiation/completion of each Edman reaction cycle.

A) Identification of Proteins in Yeast and Human Proteomes.

FIG. 6 demonstrates that selective labeling of amino acids on immobilized peptides followed by successive cycles of labeling and removal of their amino-terminal amino acids is capable of producing patterns sufficiently reflective of their sequences to allow unique identification of a majority of proteins in the yeast and human proteomes. Plotted curves show results of computer simulation of successive cleavage of single N-terminal amino acids from all proteolytic peptides derived from the complete human or yeast proteome, top and bottom plots respectively. This FIG. 6 depicts the results of various cutting ("Cut") and labeling ("Label") scenarios. For example, "Cut E" indicates that all human proteins were proteolyzed with the peptidase GluC in order to cut each protein after glutamate ("E") residues. Similarly, "Label" simulates the results of initially labeling different subsets of amino acid residues. For example, "Label K" indicates that only Lysine ("K") amino acid residues carry a detectable label (e.g. a fluorescent molecule observable by single molecule fluorescence microscopy). The sequencing reaction is not allowed to proceed beyond the Cysteine ("C") residue since they are used to anchor the peptide sequence. FIG. 5 demonstrates that labeling schemes employing only two or three amino acid-specific fluorescent labels can provide patterns capable of uniquely identifying at least one peptide from a substantial fraction of the human or yeast proteins. Given that only one peptide is required to identify the presence of an individual protein in a protein mixture, and further given that the peptide may be observed repeatedly and the number of observations counted, FIG. 6 demonstrates that this approach may both identify and quantify a large proportion of proteins in highly complex protein mixtures. This capability requires that the genomic sequence of the organism being analyzed is available to serve as a reference for the observed amino acid patterns. As indicated above, the complete human and yeast genomes are available to match against patterns of amino acid labels (e.g. "XXXKXXXKKXXXTX . . . C . . . E" (SEQ ID NO: 17)).

B) Lysine Content.

FIG. 7 demonstrates that the numbers of Lysines per peptide are sufficiently low to monitor their count based on fluorescence intensity. The present method requires the ability to distinguish (i.e. resolve) different numbers of fluorescent molecules based on fluorescence intensity; however, resolution naturally decreases as the number of Lysines in a single peptide increase. For example, while distinguishing 3 Lysines from 2 Lysines only requires detecting a 33% decrease in fluorescence intensity, high Lysine counts would require detecting proportionally smaller changes in fluorescence intensity (e.g. only 5% for the case of 21 Lysines versus 20 Lysines). Fortunately, the natural distribution of Lysine residues in peptides tends to be small (top plot, shown for the yeast proteome), and therefore within the capacity of current fluorescent microscopes. The simulations depicted in FIG. 7 demonstrate that limiting sequencing to peptides with no more than eight Lysines nearly provides coverage for the full set of peptides in the yeast proteome (bottom plot, shown for the case of labeling K, cutting at E with GluC, anchoring by C).

II. Two-Color Single-Molecule Peptide Sequencing Reaction.

Proteins may be analyzed from natural or synthetic sources collected using standard protocols. For example, proteins may be isolated from human cells obtained from blood samples, tumor biopsies or in vitro cell cultures. In one embodiment, the present invention contemplates a two-color single molecule peptide sequencing reaction. In other embodiments, protein sequencing protocols may include more than two fluorescent molecules (e.g. covalently labeling a third fluorescent molecule with an additional type of amino acid) to provide greater protein sequence and/or protein profile information.

A) Cell Sample Preparation.

Isolated cells are resuspended in a standard lysis buffer that includes a reducing agent such as Dithiothreitol (DTT) to denature proteins and break disulphide linkages and a protease inhibitor cocktail to prevent further protein degradation. Cells are lysed by homogenization or other lysis technique and the lysate centrifuged to obtain soluble cytosolic proteins (supernatant) and insoluble membrane bound proteins (pellet). Samples may be further fractionated, e.g. by chromatography, gel electrophoresis, or other methods to isolate specific protein fractions of interest. The protein mixtures are denatured in a solution containing, for example, urea or trifluoroethanol (TFE) and the disulfide bonds are reduced to free thiol group via the addition of reducing agents such as tris(2-carboxyethyl)phosphine (TCEP) or DTT.

B) Protein Digestion, Labeling and Anchoring.

Protein preparations are then digested by specific endopeptidases (e.g. GluC), which selectively cleave the peptide bonds' C-terminal to glutamic acid residue. The resulting peptides are labeled by a fluorescent Edman reagent (label 1) such as fluorescein isothiocyanate (FITC), rhodamine isothiocyanate or other synthesized fluorescent isothiocyanate derivative (e.g., Cy3-ITC, Cy5-ITC). Considerations in choosing the first fluorescent Edman reagent (label 1) include 1) good reactivity towards available amine groups on Lysine residues and the N-terminus, 2) high quantum yield of the fluorescent signal, 3) reduced tendency for fluorescent quenching, and 4) stability of the fluorescent molecule across the required range of pH.

Labeled peptides are then anchored to an activated glass or quartz substrate for imaging and analysis. In one embodiment, the substrate is glass coated with a low density of maleimide, which is chemically reactive to available sulfydryl groups (SH—) on the Cysteine residues in a subset of the peptide molecules. In a preferred embodiment, the substrate is glass coated with a layer of N-(2-aminoethyl)-3-aminopropyl trimethoxy silane and then passivated with a layer of methoxy-poly(ethylene glycol) doped with 2-5% maleimide-poly(ethylene glycol), the latter of which is chemically reactive to available sulfhydryl groups (SH—) on the cysteine residues in a subset of the peptide molecules. In this embodiment only peptides that contain Cysteine residues are anchored to the solid surface; peptides that do not contain Cysteine residues are washed away in successive steps. In a preferred embodiment, peptides are preferably anchored with a surface density that is low enough to permit the resolution of single molecules during subsequent microscopy steps. In one embodiment, the order of the labeling and anchoring steps may be reversed, for example if required by the coupling—decoupling rate of the Edman reagent and its ability to produce thioazolinone N-terminal amino acid derivatives.

C) Edman Sequencing in a Microscope Flow Cell.

Following labeling and anchoring of the peptides the substrate (e.g., glass slide) is introduced into a flow cell in a fluorescence microscope equipped with total internal reflection illumination, which reduces background fluorescence. The flow cell is washed with purified water to clean the surface. Steps 2 and 3 correspond to the Edman coupling steps, which are performed repeatedly with fluorescence microscopy images collected twice in each cycle—once after cleavage and once after re-labeling. FIG. 10 is a diagram showing one embodiment of the working principle of a total internal reflectance fluorescence (TIRF) microscopy setup that can be used in sequence analysis. Other embodiments of the microscopy setup include the use of a scanning confocal microscope for visualizing the single molecules or a dove prism for performing TIRF. Using a motorized microscope stage with automated focus control to image multiple stage positions in the flow cell may allow millions of individual single peptides (or more) to be sequenced in one experiment (see FIG. 10, FIG. 11, and FIG. 12).

In the cleavage step trifluoroacetic acid (TFA) is introduced into the flow cell and incubated to complete the cleavage reaction. The liberated thiazolinone N-terminal amino acid derivative and residual TFA is washed away with an organic solvent such as -ethyl acetate. In a preferred embodiment, other solvents may be used to ensure that side products produced are effectively removed. In the re-labeling step the N-terminus of the anchored peptides is re-labeled with a second Edman fluorescent reagent (label 2) under mildly basic conditions. Considerations in choosing the second Edman fluorescent reagent (label 2) include limiting fluorescence bleedthrough (spectral crossover) with label 1 by selecting fluorophores having well-separated absorption and emission spectra such that the fluors can be independently observed via microscopy, and having an efficient rate of decoupling from the labeled N-terminal amino acid. In one embodiment, portions of the emission spectrum of said first label do not overlap with the emission spectrum of said second label. The cleavage and re-labeling steps (steps 2 and 3, respectively) are then repeated in cycles (i.e., treating peptides to the successive rounds of Edman chemistry, involving TFA wash, vacuum dry, etc.) with fluorescence microscopy imaging at each step, as described below, until sufficient data is collected (e.g., 20 or 30 cycles).

D) Single Molecule Fluorescence Microscopy.

In one embodiment, a conventional microscope equipped with total internal reflection illumination and an intensified charge-couple device (CCD) detector may be used for imaging. (For an example of such a scope appropriate for single molecule imaging, see Braslavsky et al., PNAS, 100(7): 3960-4 (2003) [4], (herein incorporated by reference). Depending on the absorption and emission spectra of the two fluorescent Edman labels employed, appropriate filters (for example, a central wavelength of 515 nm for FITC and 630 nm for a rhodamine-ITC derivative) are used to record the emission intensity of the two labels. Imaging with a high sensitivity CCD camera allows the instrument to simultaneously record the fluorescent intensity of multiple single peptide molecules distributed across the glass surface. In one embodiment, image collection is performed using an image splitter that directs light through two band pass filters (one suitable for each fluorescent molecule) to be recorded as two side-by-side images on the CCD surface. FIG. 10 is a diagram showing one embodiment of a total internal reflectance fluorescence (TIRF) microscopy setup that can be used in sequence analysis. Using a motorized microscope stage with automated focus control to image multiple stage positions in the flow cell may allow millions of individual single peptides (or more) to be sequenced in one experiment (see FIG. 10, FIG. 11, and FIG. 12). By way of comparison, current generation single molecule DNA sequencers (e.g., available from Helicos) can sequence approximately 1 billion single DNA molecules per experiment.

As described above, for each Edman cycle the fluorescence intensity of label 1 will be recorded after each cleavage step. After the very first round of removal of label 1 (which corresponds to removing the labeled N-terminal amino acid), this label will exclusively label Lysine residues in the immobilized peptides, with a fluorescence intensity proportional to the count of Lysines in a given peptide. The loss and uptake of label 2 measured after each cleavage step and coupling step, respectively, serves as 1) a counter for the number of amino acid residues removed, and 2) an internal error control indicating the successful completion of each round of Edman degradation for each immobilized peptide.

E) Bioinformatic Analysis.

Following image processing to filter noise and identify the location of peptides, as well as to map the locations of the same peptides across the set of collected images, intensity profiles for label 1 and label 2 are associated with each peptide as a function of Edman cycle. The label 1 intensity profile of each error free peptide sequencing reaction (determined by the cycling of label 2) is transformed into a binary sequence (e.g., 00010001100) in which a "1" precedes a drop in fluorescence intensity of label 1 and its location (i.e. position within the binary sequence) identifies the number of Edman cycles performed. This sequence, termed the binary intensity profile, represents a simplified version of the experimentally derived peptide sequence.

The method has the ability to identify the location of peptides as well as the ability to follow these peptides after a number of steps. FIG. 13 shows one embodiment of labeled Lysines (amine-reactive dye HiLyte 647) attached by Cysteines to maleimide-PEG quartz surface. The different pattern of fluorescence intensity with the different labeled Lysine content is revealed. The reactive dye used, HiLyte Fluor™ 647 succidinimyl ester, is an amine-reactive fluorescent labeling dye that generates the conjugates that are slightly red-shifted compared to those of Cy5 dyes, resulting in an optimal match to filters designed for Cy5 dye. Its conjugate may have better performance than Cy5 for fluorescence polarization-based assays. FIG. 14 shows a comparison of single fluorescently-labeled peptides and alternate channel revealing low background fluorescence. When analyzing the peptides, one can observe the difference in the Edman degradation of the labeled single peptide molecules between a peptide that contains one versus two labeled Lysines (see FIG. 15). The fluorescence signal drops when the labeled Lysine is removed. Only fluorescence signal is found with labeled Lysines. One can also use quantum dots as a guide in analysis of large numbers of peptides from by scanning the microscope and tiling images (see FIG. 16).

A database of predicted potential proteins for the organism under investigation is used as a reference database. For example, in one embodiment the human protein database, compiled from the UniProt protein sequence database and containing 20,252 translated protein sequences, may be used as the reference dataset. A list of potential peptides is generated by simulating the proteolysis, labeling and anchoring approach used in the experiment. In the example provided above, this corresponds to cutting by GluC, labeling of Lysines and anchoring of peptides via Cysteines. Each unique peptide generated in this simulation may be transformed to its corresponding binary sequence (e.g. 0001000110), retaining its mapping to the protein sequence and ID from which it was formed. This creates a lookup database indexing potential binary sequences derived from that organism's proteome to unique protein IDs.

The binary intensity profile of each peptide, as generated from the single molecule microscopy, is then compared to the entries in the simulated peptide database (step 3). This provides the protein ID, if available, from which the peptide is uniquely derived. Performing this lookup over all measured profiles results in the identification of the set of proteins composing the complex protein mixture. Many binary intensity profiles may not have a unique match in the database. In one embodiment, advanced bioinformatics analyses could consider the multiplicity of matches and infer the most likely proteins present. In another embodiment, a simple approach is to just ignore all of these cases and rely only upon uniquely matching cases to build evidence for proteins being present. Quantitation is then accomplished by counting peptides derived from each protein observed. Since this approach is intrinsically digital, the count of peptides from each protein should be proportional to the abundance of the protein in the mixture. In another embodiment, the efficiencies of the reaction steps, including the labeling, Edman reagent coupling, and Edman reagent cleavage reactions can be measured or estimated and then incorporated in the computational search of the proteome sequences in order to provide a probabilistic estimate of the identification of a particular peptide or protein in the database.

F) Variations.

Variants to the above protocol are contemplated. In one embodiment, to improve signal to noise during single molecule imaging, oxygen- and free radical-scavenging and triple quenching components are included in the solution (e.g., see Harris et al., Science 320, 106 (2008) [5], (herein incorporated by reference). In another embodiment, the surface of the solid support can be modified chemically, such as by coating with polyethylene glycol, in order to suppress nonspecific adsorption to the surface and thus improve the signal to noise ratio for the fluorescent detection of peptides.

In another embodiment, more than two fluorescent molecules may be used to label additional amino acids. Such an approach might involve, for example, covalently labeling Lysines with a fluorescent Edman reagent prior to sequencing (as described above) and also covalently labeling amino acids with carboxylate side chains (e.g., glutamate, aspartate) with a second fluorescent molecule (chosen for spectral compatibility), then proceeding with Edman degradation cycles using an Edman reagent labeled with a third fluorescent molecule. This method would provide more information-rich sequence profiles for identifying many more peptides. In another embodiment, an alternate imaging strategy involves the use of scanning confocal microscopy. In yet another embodiment, the cleavage/re-labeling steps of the Edman reaction are replaced with a protocol in which the re-labeling is performed using the Edman label 2 (as above), but then the cleavage step is performed using an aminopeptidase enzyme to remove the labeled amino-terminal amino acid. This would allow all reactions to be performed in aqueous solvent and simplify the apparatus by decreasing the need for organic solvents. In this embodiment, the aminopeptidase would be selected such that it requires and tolerates the presence of label 2 on the amino-terminal amino acid, therefore it would likely have to be optimized using in vitro evolution techniques to be suitable for use in sequencing.

In yet another embodiment, the successful removal of amino acids occurs from the carboxy terminus of the peptide, thereby revealing C-terminal sequences instead of N-terminal sequences. In a preferred embodiment, this approach employs, for example, engineered carboxypeptidases or small molecule reagents reacting analogous to the N-terminal Edman chemistry but operating from the C-terminus of the peptide.

Example I: Photolithography on Aminosilane Slides

This example describes one embodiment for preparing a surface, involving the steps of cleaning of the slides, aminosilane deposition, and attachment of fluorophores.

Cleaning of slides: The 40 mm glass coverslips (Bioptechs Inc, Butler, Pa., USA) was cleaned by sonicating the coverslips at maximum power for twenty minutes with 10% Alconox (detergent), followed by acetone, 90% Ethanol and finally 1 M Potassium hydroxide (KOH). Between each of the different solutions, the slips were thoroughly rinsed with deionised water and sonicated in water for 5 minutes. The slides were dried at 110 C for 2 h in an oven. To completely clean these glass coverslip and hydroxylate the surface, oxygen plasma was performed. The clean-dried coverslips were placed on the platform of oxygen plasma equipment in the Center for Nano and Materials Science (CNM) facility clean room (March Plasma CS170IF RIE etching system). The operating conditions for cleaning the slides were—Power-120 W; Base Pressure-90 mTorr; Time-120 secs and 30% Oxygen.

Aminosilane deposition: Slides were incubated with aminosilane solvent (1% vv of 99% pure aminopropyltriethoxysilane (APTES) was mixed with Methanol, acidified with 5% vv glacial acetic acid) for 30 mins with a 1-minute sonication to remove physioadsorbed polymer. The self-assembled polymer layer forms a hydrophilic coating of the glass surface and provides for a surface exposed amine functional group.

Positive photoresist (S18-18) was deposited by spin coating on the slides (1000 rpm for 1 min). It was then soft baked at 110 C for 5 mins. Square shaped patterns of 20 um was created on the photoresist by using Suss Mask Aligner (at the CNM facility) with a UV350 nm illumination. The unpolymerised photoresist was removed by developer solvent (MF-319) and the aminosilane interspersed between the square patterns were etched away by oxygen plasma using the March Plasma equipment at the CNM facility. The unetched photoresist was removed by acetone solvent wash and sonication. This process generates a glass slide with pillars of 20 um squares of aminosilane interspersed with clean and unfunctionalized glass.

Fluorophore attachment: 2 uM of Alexa fluor 555-NHS in PBS was incubated on the patterned aminosilane slide for 2 hours. Non-specifically bound fluorophores were removed by washes of wash buffer (PBS with 1% Triton, 1% SDS and 0.1% Tween) and DMF. The slide was housed in the FCS2 fluidic chamber (Bioptechs Inc) altered with a Kalrez® (Dupont Inc) gasket material. Images were acquired at 200 ms on an xIon-X3 camera (Andor, Belfast, UK) cooled to −70 C.

Figure 21:
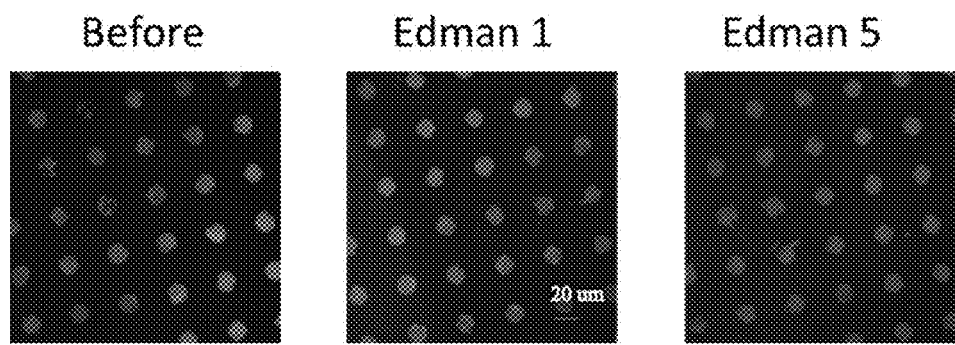
FIG. 21 demonstrates that Alexafluor-NHS immobilized on patterned aminosilane glass slide is stable through cycles of Edman degradation. The Alexafluor555 dye immobilized on the square patterned aminosilane glass slide is stable to 5 Edman cycles. The dye is not quenched and the amide bond is not destroyed during the process.
Figure 22:
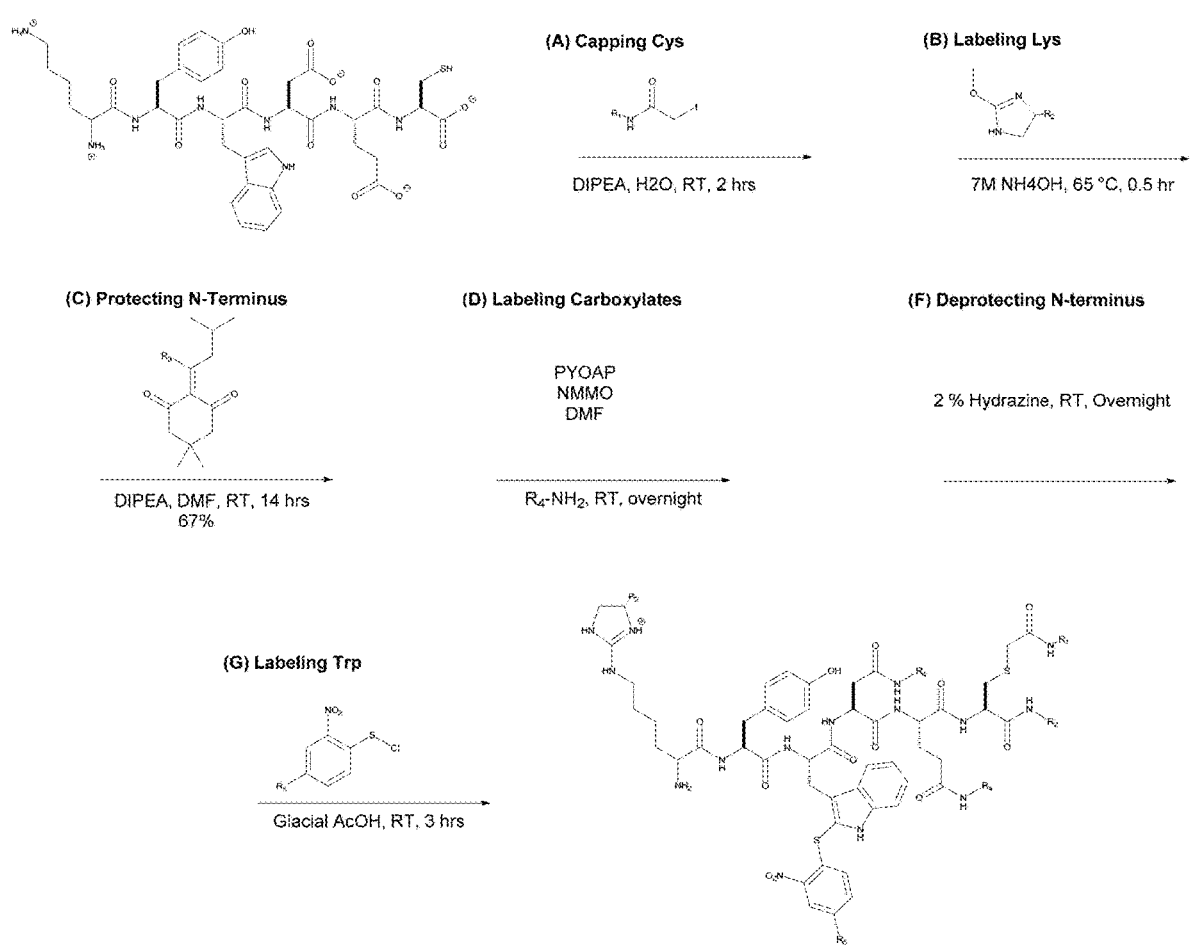
FIG. 22 shows one embodiment of a sequence of derivitization reactions that allows for the labeling of the side chains of various amino acids in an orthogonal and step-by-step fashion. In particular, the N-terminus is deprotonated for use in future Edman degradation.
Figure 23:
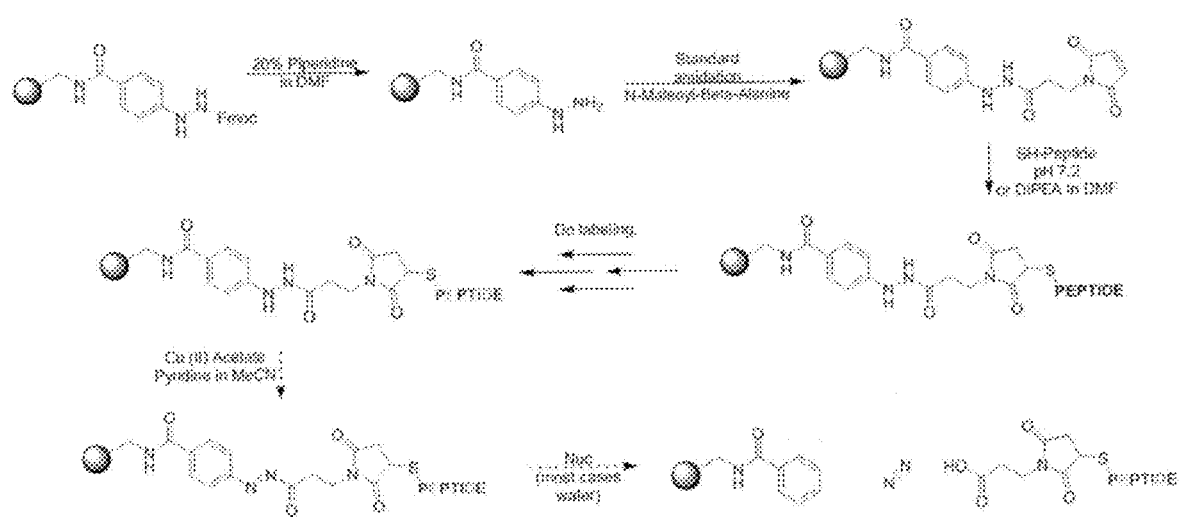
FIG. 23 shows one embodiment of a method of immobilizing peptides via Cysteine using a resin, followed by labeling steps, and then freeing the peptides with a carboxylic acid on the end.
Figure 24:
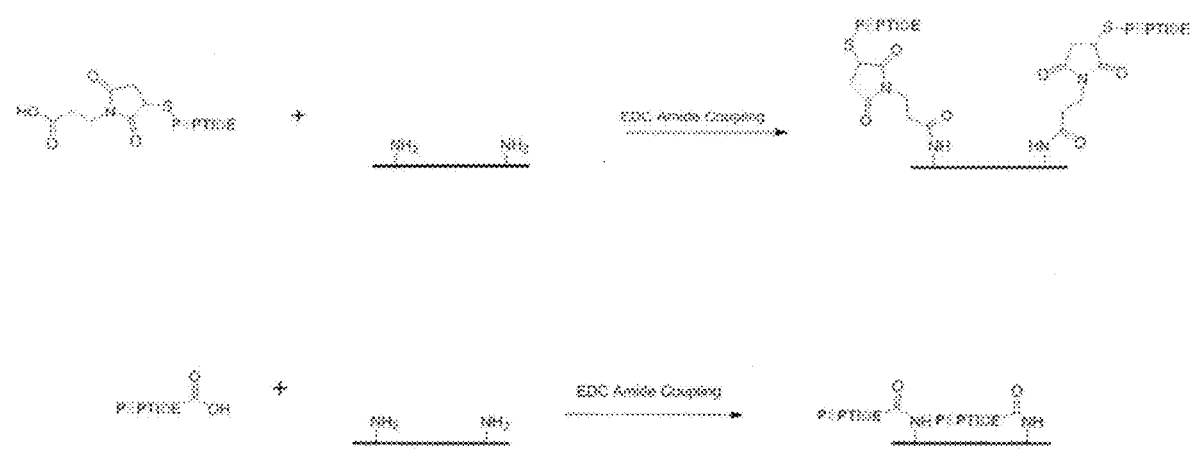
FIG. 24 shows one embodiment wherein, once the peptide is labelled, they are immobilized for the sequencing.
Figure 29:
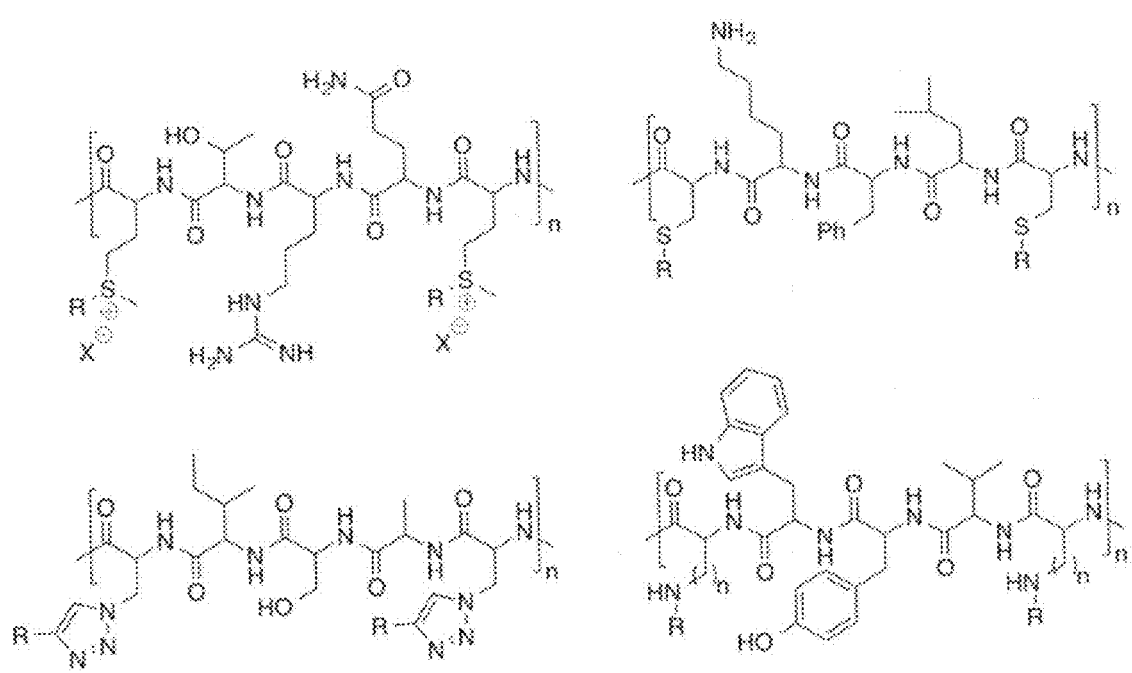
FIG. 29 shows embodiments of polymer wherein functional groups on the side chains are introduced during synthesis.
Figure 30:
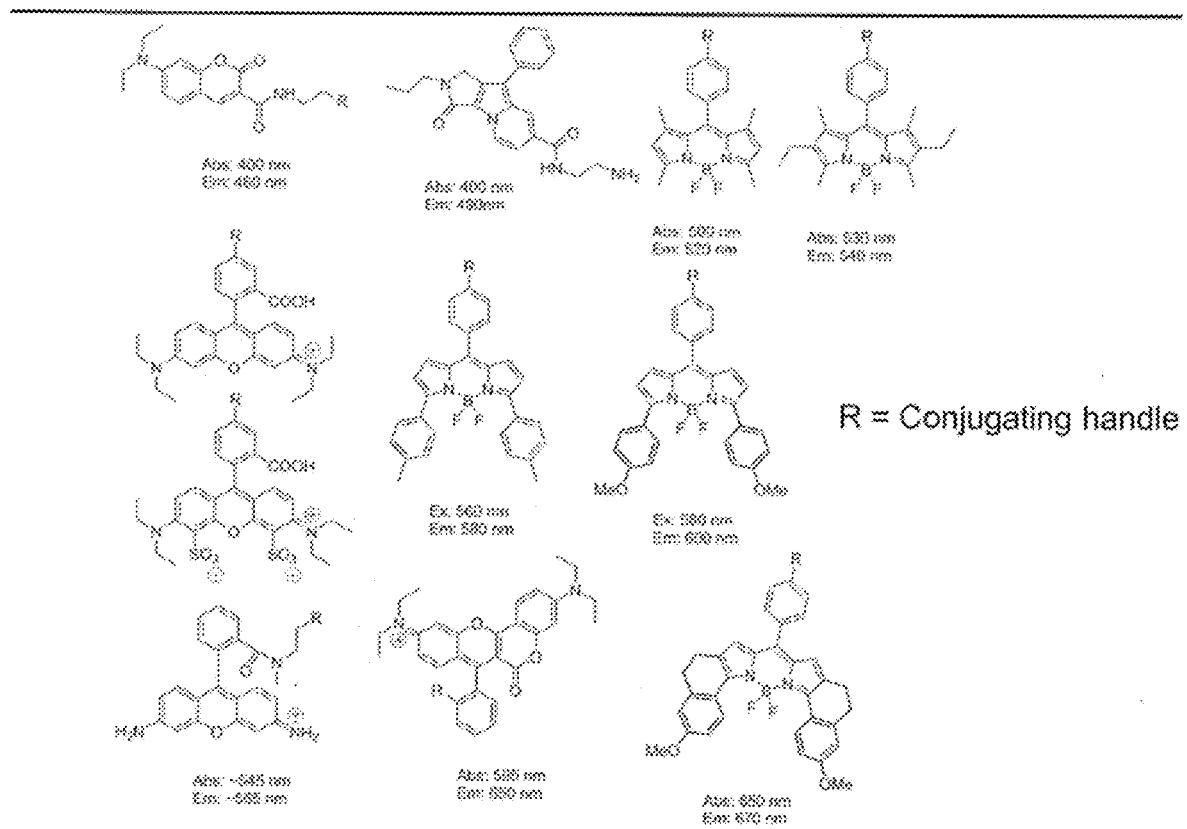
FIG. 30 shows embodiments of fluorophores, including BODIPY derivatives.
Figure 31:
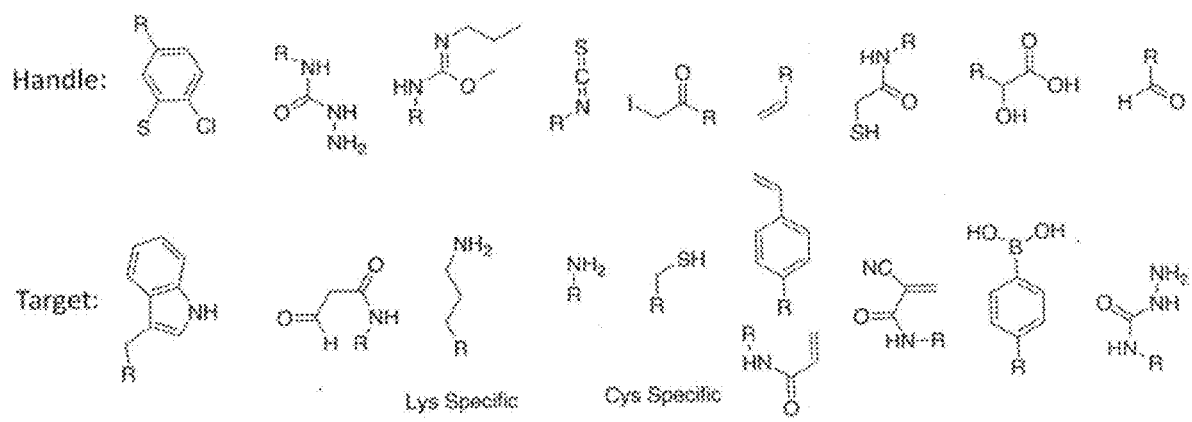
FIG. 31 shows embodiments of chemical pairs for side chains and labeling units.
Figure 32:
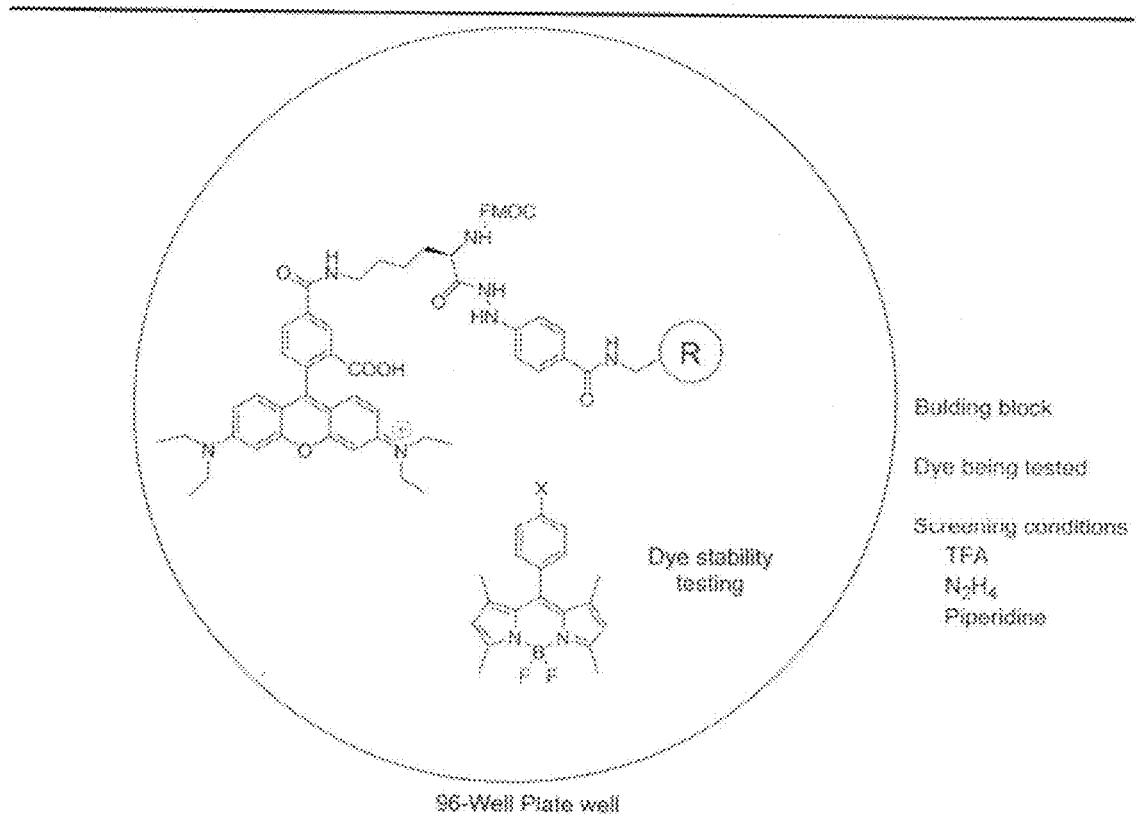
FIG. 32 shows one embodiment of a screening method to test all dyes and linkages to the various chemical conditions need in synthesis and sequencing.
Figure 33:
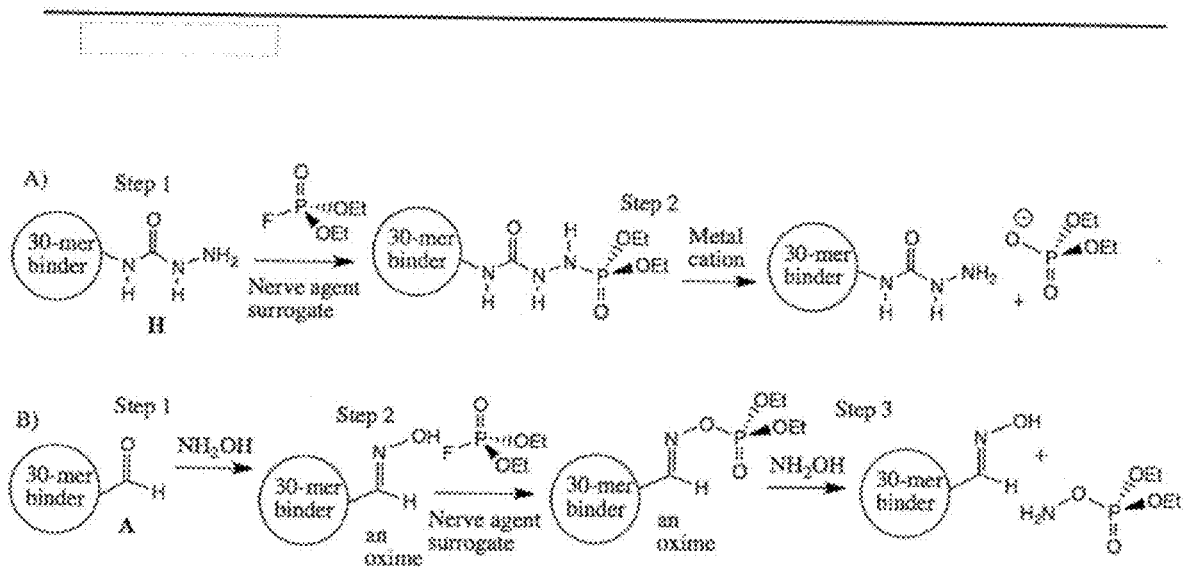
FIG. 33 shows embodiments of methods for taking the oligomers and creating nerve agent degrading agents.
Figure 34:
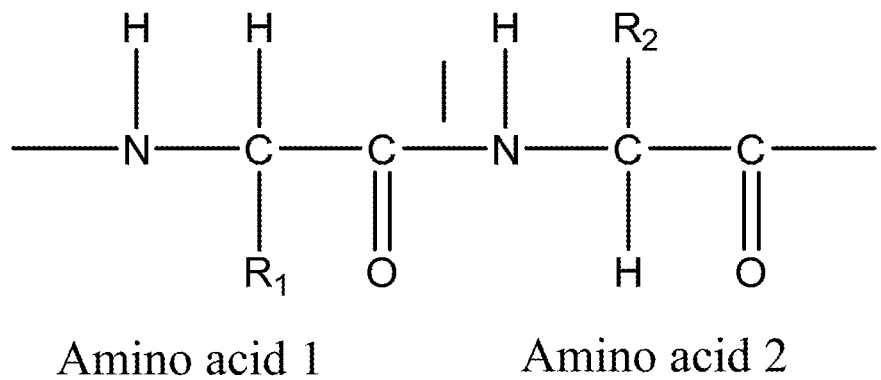
FIG. 34 depicts polypeptide cleavage sites for a number of proteases. Methods and Peptide bonds cleaved, respectively, Trypsin: Amino acid 1=Lys or Arg; Chymotrypsin: Amino acid 1=Phe, Trp or Tyr; Pepsin: Amino acid 1=Phe, Trp, Tyr and several others; Thermolysin: Amino acid 2=Leu, Ile, or Val; and Cyanogen bromide: Amino acid 1=Met.

Five cycles of Edman degradation was performed on the patterned aminosilane slide. As shown in FIG. 21, the dye and bond are stable to this chemistry.

REFERENCES INCLUDING BACKGROUND

1. Edman et al. (1950) Method for determination of the amino acid sequence in peptides, *Acta Chem. Scand.* 4, 283-293.
2. Edman and Begg, (1967) A Protein Sequenator, *Eur. J. Biochem.* 1(1), 80-91.
3. Niall, (1973) Automated Edman degradation: the protein sequenator, *Methods Enzymol.* 27, 942-1010.
4. Braslavsky, et al. (2003) Sequence information can be obtained from single DNA molecules, *Proc. Natl. Acad. Sci. U. S. A* 100(7), 3960-3964.
5. Harris, et al. (2008) Single-Molecule DNA Sequencing of a Viral Genome, *Science* 320(5872), 106-109.

Example II: Exemplary Methods and Materials Used for Example III

Amine Coating on Beads.

The commercially available 100 μm TentagelS-NH2 resin beads (Cat #04773, Chem-Impex International Inc., IL, USA), made of amine functionalized PEG chains grafted on polystyrene beads, was used as such for the experiments. For the preparation of 100 μm glass beads (Cat #4649, Sigma Aldrich, MO, USA) with an amine functionalized surface, the beads were loaded into syringe with frit (Cat #NC9214213, Thermo Fisher) and first cleaned by repeated washes of 5% Alconox (detergent), followed by acetone, 90% Ethanol and finally 1 M Potassium hydroxide (KOH). Between each of the different solutions, the beads were thoroughly washed with de-ionized water. The aminosilane coating step was carried out by gently shaking the cleaned beads for 1 h at room temperature in a solution of 10% Aminopropyltriethoxysilane (Cat #SIA0610.1 Gelest Inc., PA, USA) in the acidified 5% v/v of acetic acid/methanol solvent. The beads were washed with methanol and water before vacuum drying.

Peptides Used in the Study.

The sequences and modifications of the custom peptides (provided by Dr. Eric Anslyn) are (a) (fmoc)-K[TMR]A, (b) (fmoc)-GK[TMR]A, (c) (boc)-K[rhodamine 101]A, (d) (boc)-K[rhodamine B]A, (e) (boc)-K[rhodamine B-DMEDA]A and (f) (fmoc)-K[TMR]AK[TMR]A (SEQ ID NO: 15). Expansions of the abbreviations are—fmoc: fluorenylmethyloxycarbonyl, boc: butyloxycarbonyl, TMR: tetramethylrhodamine. The structures of the four rhodamine variants used are shown in FIG. 39. Peptides were synthesized using a standard automated solid-phase peptide synthesizer, and purified using high-performance liquid chromatography (HPLC) or $C_{18}$ solid phase extraction.
Peptide Immobilization.

For immobilizing peptide via the carboxyl group of the C-terminal amino acid, EDC chemistry [135] was used. About 40 nano-mole of the peptide, with the blocked amine at its N-terminal amino acid, was incubated with MES coupling buffer, comprising 6 mM EDC(1-ethyl-3-(3-dimethylaminopropyl)carbodiimide hydrochloride; Cat #22980, Thermo Scientific), 5 mM NHS (N-hydroxysulfosuccinimide; Cat #24599, Thermo Scientific) in 0.1 M MES buffer (pH 4.3; Cat #28390, Thermo Scientific), for 1 h at room temperature. After appropriately diluting the activated peptides with 2 mM Sodium bicarbonate buffer (pH 8.2; Cat #S233-3, Fisher Scientific), ~20 mg of amine functionalized beads were mixed and incubated for 16 h at room temperature.
Fluorophore Immobilization.

The fluorophores used were either commercially purchased (from a number of distributors and vendors, predominantly Life Technologies, Sigma and Pierce) as a succinimidyl ester or chemically derivatized into that reactive form. The fluorophores, dissolved in dimethylformamide (DMF), were diluted in 2 mM Sodium bicarbonate solution (pH 8.2) to the appropriate concentration and incubated with Tentagel or glass beads for 16 hours prior to use.
Edman Degradation Procedure.

The peptide functionalized beads were added into the syringes with frit, washed with DMF, dichloromethane (DCM) and methanol and dried under vacuum for 20 minutes. 20% Piperidine in DMF or 90% TFA in water was used to deprotect the fmoc or boc derivatized peptides respectively. In brief, the Edman reaction of the deprotected peptides on beads comprised of incubating the beads in 20% phenylisothiocyanate (v/v in pyridine) for 30 minutes at 40° C. for the coupling condition, followed by incubating in TFA for 30 minutes at 40° C. for the cleavage of the N-terminal amino acid from the peptide backbone. After the coupling and cleavage condition, the beads were washed with Ethyl acetate solution for 5 minutes with constant shaking. Following the Edman reaction and before imaging, the beads were washed thoroughly with DMF, DCM and methanol. Solvents used were reagent grade solvents purchased from Sigma Aldrich (MO, USA). For Mock experimental cycle, the entire Edman reaction was performed but PITC was not added to the coupling reagent.
Imaging of Beads.

A tiny portion (~0.5 mg) of the solvent washed and vacuum dried beads, which was added to 50 µL of pH 1 (0.1M KCl/HCl buffer) or other imaging buffers, was spotted on a clean glass slide. The beads were sandwiched with a coverslip and its sides were taped. The DIC and epifluorescence images of the beads were obtained using a Nikon Eclipse TE2000-E inverted microscope (Nikon Inc., Japan). The images of the beads were acquired at different exposure times with a Cascade II 512 camera (Photometrics, AZ, USA) on a Nikon Apo 10x/NA 0.45 objective. A combination of excitation filters DAPI—AT350/50 (340-380 nm), FITC—ET490/20 (465-495 nm), TRITC—ET555/25 (528-553 nm) and Cy5—ET670 (590-640 nm) and emission filters DAPI—ET460/50 (435-485 nm), FITC—ET525/36 (515-555 nm), TRITC—ET605/52 (590-650 nm) or Cy5—ET700/60 (640-730 nm) were used (Chroma Technology Corp, VT, USA). The use of corresponding excitation and emission filter set for the experiments described is represented by their filter name like DAPI, FITC, TRITC and Cy5 in the experiments. The Sutter Lambda 10-3 lter wheels (Sutter Instrument, CA, USA), motorized stage (Prior Scientific Inc. MA, USA) and image acquisition were driven by Nikon NIS Elements Imaging Software.
Image Analysis of Beads.

For image processing and analysis, the circular outline of the beads was first identified by Hough algorithm. For a given fluorescent channels, the radial profile of every bead (normalized with its radius) was shape corrected with a negative bead profile (the radial profile of the control bead with only adsorbed fluorophores). This profile was averaged across the beads under the experimental condition and area under the curve was calculated using the trapezoid method. For a different mode of image processing, when the peptide binding is not always on the periphery, masks were created for the identified bead in the DIC channel and the count density (i.e. intensity/pixel) under the masks were calculated for the fluorescent channels. Scripts were written in python using different publicly available image processing library such as openCV [138].

Example III: Tentagel® Beads as a Platform for Immobilizing Fluorophores and Peptides and Effects of pH on Imaging Buffers This example demonstrates embodiments for using beads, including optimizing the chemistry, i.e. by image acquisition and processing and quantitating the fluorescent peptide density (see FIG. 35) for immobilizing fluorophores and peptides.

Among the number of other commercially available beads such as controlled pore glass, magnetic beads, polystyrene beads etc., Tentagel beads have a set of advantages for this study due to their compressibility (suitable for imaging by sandwiching them between glass slides), high peripheral density of functional groups (enables quantitation of bound peptides and discriminating the non-specifically attached peptides) [McAlpine S R, Schreiber S L. Visualizing Functional Group Distribution in Solid-Support Beads by Using Optical Analysis. Chem—A Eur J. 1999; 5: 3528-3532.] and availability as micron sized beads (facilitating imaging and ability to be retained in many fritted syringes). As shown herein, amine functionalized Tentagel beads were shortlisted to fluorophore choices contemplated for performing fluorosequencing, establishing the scheme for immobilizing peptides to the bead via their carboxyl termini and by optimizing the Edman degradation procedure, then test for discriminating between multiple peptides based on the position of their fluorescently labeled Lysine residues.

Figure 35:
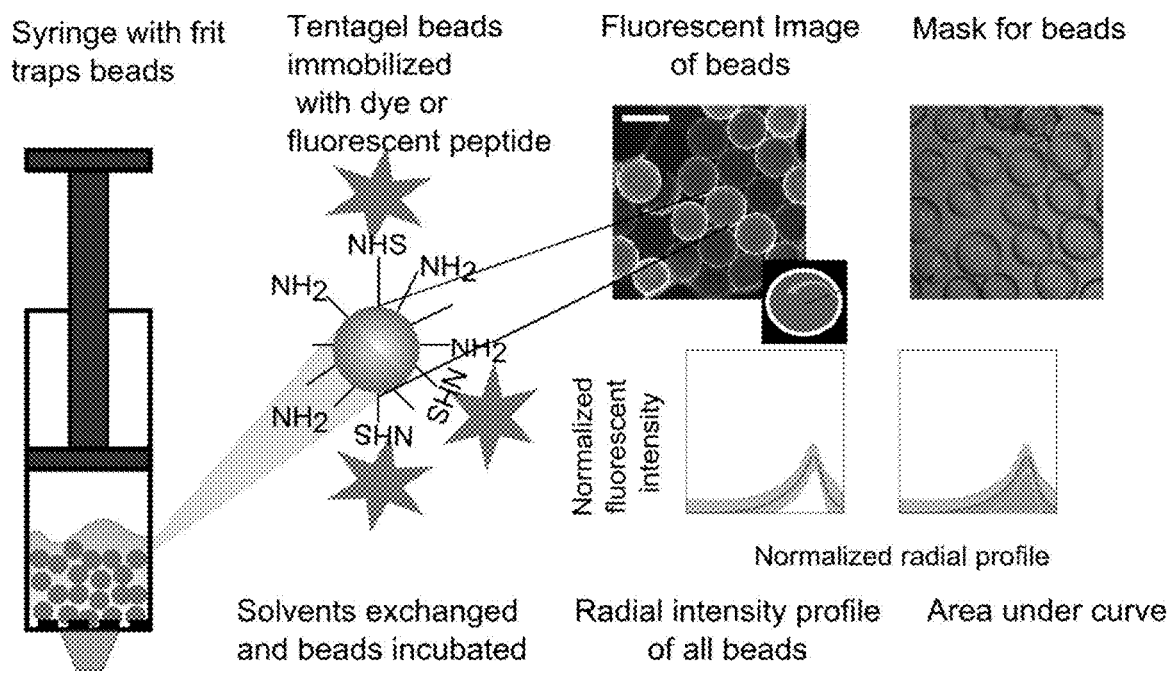
FIG. 35 shows that exemplary specific binding of fluorophores to functionalized Tentagel beads occurs at the periphery and density can be measured by image processing. The 100 μm amine functionalized Tentagel beads is incubated with the succinimidyl ester form of dye or peptide to form the stable amide bond. Repeated solvent washes remove the majority of non-specifically bound dyes or peptides resulting in abundant fluorescent signal at the bead periphery. A mask of every bead is generated and a radial intensity sweep for the fluorescent channel across each bead is performed. The radial intensity profile for a bead is normalized and shape corrected using a non-specifically bound dye on bead as a control. The area under the normalized radial intensity across all beads for an experiment is the density of the truly bound fluorophore or fluorescently labeled peptide on the bead. The scale bar shown in the fluorescent image is 200 μm.

As shown in a schematic and bead imaging overview in FIG. 35, specific binding of fluorophores to functionalized Tentagel beads occurs at the periphery and density was measured by image processing. In brief, 100 µm amine functionalized Tentagel beads is incubated with the succinimidyl ester form of dye or peptide to form the stable amide bond. Repeated solvent washes remove the majority of non-specifically bound dyes or peptides resulting in abundant fluorescent signal at the bead periphery. A mask of every bead is generated and a radial intensity sweep for the fluorescent channel across each bead is performed. The radial intensity profile for a bead is normalized and shape corrected using a non-specifically bound dye on bead as a control. The area under the normalized radial intensity across all beads for an experiment is the density of the truly bound fluorophore or fluorescently labeled peptide on the bead. The scale bar shown in the fluorescent image is 200 μm.

A: Discovering a Set of Fluorescent Dyes Resistant to Edman Degradation Solvents.

Fluorophores, immobilized on Tentagel beads, were tested for changes in their fluorescence properties under prolonged 24 hour incubation at 40° C. with 9:1 v/v pyridine/PITC (reagent used for coupling reaction) and neat trifluoroacetic acid (reagent used for cleavage reaction) separately. Stability under these extreme conditions ascertains usefulness in shorter experimental cycles. The test on a palette of different classes of commercially available dyes spanning four excitation and emission filter spectra indicated that only a small number of fluorophores were suitable for the study. The fluorescence stability of the dyes after 24 h TFA and PITC/pyridine incubation shortlisted six fluorophores that showed <40% change in fluorescence (see FIG. 36a).

Among the narrowed set of fluorophores in the red and far-red fluorescence channels which showed a stable fluorescence, the dyes with rigid core structures such as rhodamine dyes (tetramethyl rhodamine, Alexa Fluor 555) and atto dyes (such as Atto647N, shown in FIG. 36b) were used for further studies. Since the fluorescence imaging was performed at neutral pH, it is likely that the fluorescence properties of some of the chemically unstable fluorophores can be modified if the right protonation state is induced. Some dyes like Hilyte-488 and BODIPY-FL showed shifts in their fluorescence spectra after their incubation under acidic conditions and were incapable of reverting back to its original fluorescence profile after solvent washes and incubation with pH 7 buffer (see FIG. 36b for BODIPY-FL example).

While most of the dyes exhibited binding at the periphery, some fluorophores seemed to have high internal binding. Given the highly branched nature of the polystyrene bead matrix and the grafted polyethylene glycol layer, it is possible that the internal fluorescence represents non-specific binding of the dyes to hydrophobic pockets. Many fluorophores, which were added in large excess, could possess different extents of non-specific binding despite the repeated washes with solvents.

The reasons for the chemical instability of certain fluorophores are unclear and broad generalizations cannot be made based on core structure alone. Many commercially available fluorophores such as Hilyte647 (Anaspec, CA, USA) are packaged and sold with TFA salts and yet surprisingly were not found to be acid stable under prolonged incubation. However, some empirical reasoning can explain the lack of stability of some fluorophores containing linear unsaturated bonds (polyenes), such as those found in cyanine or some BODIPY and Alexa Fluor dyes under prolonged TFA incubation. It is hypothesized that the protonation of unsaturated bonds under acidic conditions, induces a cis-trans isomerization reaction, thereby changing the underlying electronics of the fluorescence structure of the dyes [134]. Due to the commercial availability of cheap dyes and a long history on the study of rhodamine dyes and their functionalization, further studies involved rhodamine dyes, especially tetramethylrhodamine.

B: The Amide Bond Formed Between Succinate Ester and Amine Coated Beads is Specific and Occurs at the Bead Periphery.

The set of fluorophores discovered herein stable to the Edman solvents also highlights the fact that the amide bond formed between the succinimidyl (succinate) ester of the fluorophores and the free amines on the Tentagel bead was chemically inert to the harsh Edman conditions used in the experiment. The specificity of this amide bond formation was tested by comparing it with control experiments involving a carboxyl or a hydrazide functional group on Alexa Fluor 555 dye with the amine coated Tentagel beads (see FIG. 37). Internal binding of the dye was observed in these control experiments, while a clear peripheral binding was observed with the succinimidyl ester variant of the Alexa Fluor 555. It was not clear whether the nature of binding between a maleimide variant of Alexa Fluor 555 with the thiol Tentagel beads and the isothiocyanate derivative of the tetramethylrhodamine dye was specific. This might have been due to the poor loading of the fluorophore. The radial profile (shown in the image inset) elucidates the image processing methodology where covalently bound fluorophores are clustered in the periphery of the beads while non-specifically adsorbed fluorophores are trapped within the beads.

C: Peptides can be Covalently Immobilized by their Carboxyl Functional Group.

Among the different immobilization schemes investigated, the knowledge of the stability of the amide bond between the succinate ester and amine surface was used to optimize a crosslinking procedure to immobilize peptides to the amine surface via their carboxyl termini [135]. Many solid phase Edman reactions have employed the use of EDC chemistry to immobilize peptides onto resin supports [85]. By performing EDC chemistry on amine coated glass beads and Tentagel beads, an exemplary scheme was developed for covalently immobilizing peptides on the solid supports. It is contemplated that the N-terminal amine group of the fluorescently labeled peptide protected by either boc or fmoc protecting group prevents the formation of the peptide concatemers. If the amines on the peptide are not protected, then amide bond formation would occur between the carboxyl and the free amine group of peptides in the presence of EDC.

It was observed that the fluorescence intensity of these immobilized peptides on Tentagel beads was unchanged with 24 hour incubation with the Edman solvents (see FIG. 38a). Owing to the probable presence of hydrophobic pockets between the polymer matrices in Tentagel beads, which may give rise to false interpretation of binding, the EDC test was also done on aminosilane coated glass beads (FIG. 38b). Under conditions prohibiting amide bond formation, there was little to no binding on the glass beads. Thus was demonstrated a strategy to immobilize peptides covalently on amine surface and show the stability of the bonds and surface to incubations with Edman solvents.

D: Fluorescence of Rhodamine Dyes is pH Dependent.

The fluorescence from rhodamine dyes has been known to be pH dependent [136] requiring efforts to determine the most suitable imaging buffer. The investigation of pH dependence on the fluorescence properties of four different rhodamine labeled peptides (see FIG. 39 for structure and positional nomenclature for rhodamine dyes and the peptides), indicated an environmentally induced variation in their behavior.

The acidic environment of the imaging buffer (pH 1.0) caused the highest fluorescence of the rhodamine labeled peptides (FIG. 40a). However the pH effect was most profound in the case of peptides labeled with rhodamine B (peptide A) and rhodamine 101 (peptide B). This effect did not seem to occur for the case of tetramethylrhodamine labeled peptide (peptide C). The peptides A and B showed pH dependent fluorescence because the amide nitrogen found at the 3' position is closer to the carbon position at 9 (or 1') and results in a 5 membered ring formation. This spirolactam ring is known to quench fluorescence and occurs at a pH higher than 3.1 [137]. This spirolactam formation does not occur for tetramethylrhodamine since the succinate ester is present at the 5'-6' position is not accessible to the central ring. The spironolactone formation, involving a ring formation with the carboxylate oxygen (at 3' position) can potentially quench fluorescence but requires a strong base such as piperidine. To test the hypothesis and prevent spirolactam formation in rhodamine B, we added an N, N'-dimethylethylenediamine (DMEDA) linker between the rhodamine B fluorophore and the aspartic acid side chain of the peptide resulting in the methylated amine at the 3' position. This prevented ring closure of the rhodamine B variant and was demonstrated by the independence of its fluorescence intensity with different pH imaging buffers.

By exploiting the fluorescence dependence on pH for the different fluorophores, the fluorescence from a dye based on its pH and emission spectra is contemplated for use in the methods of the present inventions. While the highest fluorescence of rhodamine B dye was observed in pH 1 buffer in the TRITC filter channel, the 5, 6-carboxynaphthofluorescein had its highest intensity in the pH 10 buffer in the Cy5 filter channel (FIG. 40b).

This information is contemplated for use in a novel method of isolating two neighboring fluorophores from transferring resonance energy and thus preventing quenching or FRET (Forester Resonance Energy transfer) behavior [37]. In one embodiment rhodamine dyes such as the ones used here would be used for this method.

E. Edman Degradation Occurs at High Efficiency on Tentagel Beads.

After determining the stability of the fluorophore and the amide bond between the peptide's carboxyl and the surface's amine groups, we tested the efficiency of Edman chemistry on three different peptides differing in the position of its fluorescently labeled Lysine residue. Four cycles of Edman degradation were performed in parallel on the three peptides with the sequences—(fmoc)-K*A, (fmoc)-GK*A and (fmoc)-K*AK*A (SEQ ID NO: 15) (K* represents the Lysine labeled with tetramethylrhodamine at its c position). The peptides were immobilized on Tentagel beads via their C-termini and the fmoc protecting group at their N-termini was removed by incubation with 20% Piperidine in DMF for 1 hour prior to Edman degradation. To control for any false enhancements or decreases in fluorescence of beads due to effect of solvents and not the Edman chemistry, the "Mock" degradation scheme of solvent incubation and washes were used. A "Mock" Edman cycle is similar to a regular Edman cycle, but without the reactive phenylisothiocyanate reagent in the coupling solvent. The fluorescence profile of the beads through the Mock and Edman degradation cycles shows a statistically significant step drop coinciding with the position of the labeled Lysine. As shown in FIG. 41, Edman degradation was performed on three tetramethylrhodamine labeled synthetic peptides (K*A, GK*A and K*AK*A (SEQ ID NO: 15)) immobilized to Tentagel-NH2 beads via their C-terminal carboxyl group and blocked by fluorenylmethoxycarbonyl (fmoc) at their N-terminal amines. After deblocking the peptide, the step decrease in fluorescence intensity (in the TRITC channel) for each peptide coincided with the position of the labeled Lysine as shown in the bar chart (a). Any loss of fluorescence occurring due to the use of solvents is controlled by the mock experimental cycle. A 60-70% decrease in the overall intensity after the Edman cycles is observed for all the beads. The panel of images (with the radial profile in the inset) are representative fluorescent images of the beads for each of the peptide used across all the experimental cycles. They provide a visual illustration of the decrease in the fluorescence of the beads that coincides with the position of the labeled Lysine residue. The fluorescent bead images are acquired in the TRITC channel (see methods for filter setup used) at an acquisition of 20 milliseconds under pH 1 imaging buffer.

Thus by tracking the fluorescence intensity decrease with Edman cycle, the positional information of Lysine residues in the three peptides is obtained. The determination of this positional information is the basis for fluorosequencing.

Thus, a protocol used for Edman degradation was adapted and optimized from similar solid phase chemistry [70,78] and showed efficiency of cleavage ranging from 60-90%. Since Tentagel beads are heavily PEGylated (comprising of polyethylene glycol (PEG) polymers), a number of sites are contemplated as available for strong non-specific binding of the hydrophobic peptides. Due to the accumulation of functional groups and thereby covalent peptide binding at the periphery of the bead the true fluorescence intensity of the peptides on the bead was calculated in the area under its radial profile. Due to the unambiguous occurrence of a two-step drop in fluorescence intensity at Edman cycle 2 and 4 for the doubly labeled peptide (fmoc)-K*AK*A (SEQ ID NO: 15) or the presence of a single step drop at Edman cycle 2 for the case of (fmoc)-GK*A, Edman efficiency eas estimated to be largely greater than 50%, at least in the preceding steps. A lower efficiency would result in a decay of fluorescence with Edman cycles as opposed to a stepwise drop. The high efficiency of Edman degradation on these fluorescently labeled peptide variants demonstrate the practicality of performing fluorosequencing and Edman degradation on long fluorescently labeled peptides.

75. Laursen R A. Solid-Phase Edman Degradation. An Automatic Peptide Sequencer. Eur J Biochem. 1971; 20: 89-102.

85. Herbrink P, Tesser G I, Lamberts J J M. Solid phase Edman degradation. High yield attachment of tryptic protein fragments to aminated supports. FEBS Lett. 1975; 60: 313-316.

87. Previero A, Derancourt J, Coletti-Previero M-A, Laursen R A. Solid phase sequential analysis: Specific linking of acidic peptides by their carboxyl ends to insoluble resins. FEBS Lett. 1973; 33: 135-138.

117. Doolittle L R, Mross G A, Fothergill L A, Doolittle R F. A simple solid-phase amino acid sequencer employing a thioacetylation stepwise degradation procedure. Anal 128. Thoma R S, Smith J S, Sandoval W, Leone J W, Hunziker P, Hampton B, et al. The ABRF Edman Sequencing Research Group 2008 Study: investigation into homopolymeric amino acid N-terminal sequence tags and their effects on automated Edman degradation. J Biomol Tech. 2009; 20: 216-25.

129. Jin S-W, Shan-Zhen X, Xiu-Lan Z, Tian-Bou T. Study on New Edman-type Reagents. In: Wittmann-Liebold B, editor. Methods in Protein Sequence Analysis. Berlin, Heidelberg: Springer Berlin Heidelberg; 1989. pp. 34-41.130. Fredkin E. Trie memory. Commun ACM. ACM; 1960; 3: 490-499.

132. Gooley A A, Classon B J, Marschalek R, Williams K L. Glycosylation sites identified by detection of glycosylated amino acids released from Edman degradation: The identification of Xaa-Pro-Xaa-Xaa as a motif for Thr-O-glycosylation. Biochem Biophys Res Commun. 1991; 178: 1194-1201.

133. McAlpine S R, Schreiber S L. Visualizing Functional Group Distribution in Solid-Support Beads by Using Optical Analysis. Chem—A Eur J. 1999; 5: 3528-3532.
134. Valeur B. Molecular Fluorescence: Principles and Applications. Wiley-VCH; 2002.
135. Hermanson G T. Bioconjugate Techniques. Bioconjugate Techniques. Elsevier; 2013.
136. Czaplyski W L, Purnell G E, Roberts C A, Allred R M, Harbron E J. Substituent effects on the turn-on kinetics of rhodamine-based fluorescent pH probes. Org Biomol Chem. The Royal Society of Chemistry; 2014; 12: 526-33.
137. Yuan L, Lin W, Feng Y. A rational approach to tuning the pKa values of rhodamines for living cell fluorescence imaging. Org Biomol Chem. Royal Society of Chemistry; 2011; 9: 1723-6.
138. Bradski G. OpenCV. Dr Dobb's J Softw Tools. 2000

Example IV: Exemplary Materials and Methods Used for Example V

A. General Peptide Synthesis.

For automated, Fmoc amino solid-phase peptide synthesis, OtBu (Asp, Glu), Boc (Lys, Trp), tBu (Tyr) were used. Fmoc-protected amino acids were purchased from Novabiochem (USA) and AAPPTec (USA). Fmoc-Cys(Trt)-Wang resin (100-200 mesh) and 4-Fmoc-hydrazinobenzoyl resin AM Novagel™ was purchased from Novabiochem (USA). Tentagel Thiol Resin was purchased from ChemImpex International Incorporated (USA). Other chemicals used for automated, solid-phase peptide synthesis were purchased from Fisher Scientific and Sigma-Aldrich. Reagents used for orthogonal labeling studies were iodoacetamide (IA), 2-methylthio-2-imadazoline hydroiodide (MDI), sodium methoxide, diethylchlorophosphate, 2-(3-Methylbutyryl)-5,5-dimethyl-1,3-cyclohexandione, benzylamine (BA), isobutylamine, 3-dimethylaminopropylamine (DMAPA), 1-amino-3-butyne (AB), (7-Azabenzotriazol-1-yloxy)tripyrrolidinophosphonium hexafluorophosphate (PyAOP), N-methylmorpholine (NMMO), and 2,4-Dinitrobenzenesulfenyl chloride (DBSC). Chemicals were purchased from Sigma-Aldrich.

A Prelude peptide synthesizer (Protein Technologies, Inc.) was used for automated-solid phase synthesis. Preparative HPLC purification of peptides was performed using an Agilent Zorbax SB-$C_{18}$ Prep HT column 21.2×250 mm. Analytical HPLC characterization of peptides was performed using an Agilent Zorbax column 4.6×250 mm; 1 ml/min, 5-95% MeCN (0.1% TFA) in 40 min (RT). An Agilent Technologies 6530 Accurate Mass QTofLC/MS was used for high-resolution mass spectra of purified peptides. Solvents used were HPLC grade.

KDYWEC (SEQ ID NO: 3) was synthesized using Fmoc-Cys(Trt)-Wang Resin by sequential coupling of Na-Fmoc-amino acid (0.1 M) in DMF in the presence of N,N,N,N-Tetramethyl-O-(1H-benzotriazol-1-yl)uronium hexafluorophosphate (HBTU, 0.15 M) and DIPEA (0.2 M) with a reaction time of 30 minutes at room temperature. A total of three repetitions were performed for each amino acid building block. DMF (3 ml, 3 min, 3×) and DCM (3 ml, 3 min, 3×) washes were done before each repetition. Post synthesis, resin was washed with glacial AcOH (5 ml, 3×), DCM (5 ml, 3×), and MeOH (5 ml, 3×). The resin was placed under vacuum overnight. Peptide was cleaved from resin using trifluoroacetic acid (TFA), triisopropylsilane, 1,2-ethanedithiol (EDT), and nanopure water (94:1.0:2.5:2.5), and precipitated with diethyl ether at 0° C. No further purification of the crude peptide was necessary. KDYWE (SEQ ID NO: 4) was synthesized using 4-Fmoc-hydrazinobenzoyl resin AM Novagel™. Synthesis of peptides, resin washing, and solvent removal was done as described. TFA, TIS, and nanopure water were used (95:2.5:2.5) to deprotect the side chains, and the peptide remained immobilized on the solid support.

B. Solution-Phase Labeling Studies of KDYWEC (SEQ ID NO: 3).

Labeling of Cysteine with iodoacetamide. Peptide 1 (75 μmole) was dissolved in 0.4 ml of nanopure water. A solution consisting of 0.37 mL of MeOH/Pyr/TEA/nanopure $H_2O$ (7/1/1/1) (v/v/v/v) was introduced (adjusting to pH 8), followed by addition of iodoacetamide (97 μmole). The reaction was incubated for 2 hrs at RT.

Labeling of Lysine with 2-methoxy-4,5-dihydro-1H-imidazole (3). In the same pot, 0.5 ml of a 7 N solution of NH$_4$OH was added, followed by introduction of MDI (SI) (750 μmole). The reaction mixture was incubated for 24 mins at 65° C., followed by introduction of TFA (0.3 ml) at 0° C. The crude peptide was prepared for preparative HPLC using an Extract Clean™ $C_{18}$ 500 mg/4 ml solid phase extraction column (SI). The peptide was purified using preparative HPLC, and the organic solvent in the peptide fraction was removed via rotary evaporation. Aqueous remnants were frozen at −78° C. and lyophilized overnight. Purified yield: (29 μmole) 38%. High-res MS: found m/z 968.39360, calcd. 968.39310 (M+H)$^+$; found m/z 966.37880, calcd. 966.37850 (M−H)$^-$ Labeling the N-terminus with 1-(4,4-dimethyl-2,6-dioxo-cyclohexylidene)-3-methylbutyl diethyl phosphate (Phos-ivDde) (4). Peptide 3 (12 μmole) was dissolved in 0.1 ml of nanopure water, followed by dilution with 0.2 ml of MeCN. To the solution, 0.12 ml of 7/2/1 MeOH/TEA/H$_2$O (v/v/v) was introduced. A solution of Phos-ivDde (SI) (18 μmole) was introduced. The solution was incubated overnight at RT. The peptide was purified using preparative HPLC. Organic solvent in peptide fraction was removed via rotary evaporator. Aqueous remnants were frozen at −78° C. and lyophilized overnight. Purified yield: (8 μmole) 67%. High-res MS: found m/z 1174.52380, calcd. 1174.52380 (M+H)$^+$; found m/z 1172.50750, calcd. 1172.50920 (M−H)$^-$.

Labeling the carboxylate side chains and C-terminus with benzylamine (BA) (5). Peptide 4 (51 μmole) was dissolved in 0.2 ml of 3/1 MeOH/H$_2$O (v/v). In a separate vial, benzylamine (1.3 mmole) was dissolved in 0.1 ml of MeCN, followed by addition of NMMO (1.0 mmole). The BA/NMMO solution was introduced to the peptide solution, followed by addition of solid PyAOP (0.51 mmole) and anhydrous HOBt (0.56 mmole). 0.1 ml of MeCN was introduced to improve the solubility of PyAOP/HOBt. Benzylamine (1.3 mmole) and PyAOP (0.51 mmole) was added after 15 mins of incubation at RT. The solution was incubated for a total of 4 hrs at RT. The peptide was purified using preparative HPLC. The organic solvent in peptide fraction was removed via rotary evaporation. Aqueous remnants were frozen at −78° C. and lyophilized overnight. Purified yield: (15 μmole) 29%. High-res MS: found m/z 1441.71230, calcd. 1441.71260 (M+H)$^+$; found m/z 1439.69600, calcd. 1439.69800 (M−H)$^-$.

Labeling the carboxylate side chains and C-terminus with 3-dimethylaminopropylamine (6). Peptide 4 (11 μmole) was dissolved in 0.2 ml of dry DMF. DMAPA (1.6 mmole) and NMMO (1.4 mmole) were combined in a separate vial. The amine/NMMO solution was introduced to the peptide solution, followed by addition of solid PyAOP (1.9 mmole). The solution was incubated for 24 hrs at RT. The sample was placed in a centrifugal evaporator for 21 hrs at 35° C. The resulting oil was dissolved in 1.5 ml of 2/1 H$_2$O/DMF (v/v), and purified by prep HPLC. The organic solvent in the peptide fraction was removed via rotary evaporation. Aqueous remnants were frozen at −78° C. and lyophilized overnight. Purified yield: (2.4 µmole) 23%. High-res MS: found m/z 812.91050, calcd. 812.91000 (M+2H)$^{+2}$; found m/z 1439.69600, calcd. 1439.69800 (M−H)$^−$.

Labeling the carboxylate side chains and C-terminus with isobutylamine (7). Isobutylamine and NMMO were combined in a separate vial with 0.1 ml DMF. Amine/NMMO solution was introduced to peptide 4 (20 µmole), followed by introduction of solid PyAOP. The solution was incubated for 3 hrs at RT, following quenching with 1 ml of H$_2$O. The solution was placed in centrifugal evaporator for 14 hrs at 35° C. The residual oil was dissolved in 1.5 ml of 1/1 H$_2$O/MeCN (v/v) and purified via prep HPLC. An impurity and desired compound eluted at the same time. The peptide was therefore subjected to subsequent labeling of Tryptophan directly.

Labeling Tryptophan in peptide 6 (8). Peptide 6 (19 µmole) was dissolved in 1 ml of glacial acetic acid, followed by introduction of 2,4-dinitrobenzenesulfenyl chloride (57 µmole). The reaction was shaken for 4 hrs at RT. Glacial acetic acid was removed by rotary evaporation. The residual film was dissolved in 1/1 MeCN/H$_2$O (v/v), and purified via preparative HPLC. The organic solvent in the peptide fraction was removed via rotary evaporation. Aqueous remnants were frozen at −78° C. and lyophilized overnight. Purified yield: (6.4 µmole) 32%. High-res MS: found m/z 812.91050, calcd. 812.91000 (M+2H)$^{2+}$; found m/z 1622.79650, calcd. 1622.79810 (M−H)$^−$.

Labeling Tryptophan in peptide 7 (9). Peptide 7 (6.2 µmole) was dissolved in 1 ml of glacial acetic acid, followed by introduction of 2,4-dinitrobenzenesulfenyl chloride (19 µmole). The reaction was shaken for 4 hrs at RT. The peptide was purified using preparative HPLC. The organic solvent in the peptide fraction was removed via rotary evaporator. Aqueous remnants were frozen at −78° C. and lyophilized overnight. Purified yield: (6.4 µmole) 49%. High-res MS: found m/z 769.37050, calcd. 769.37020 (M+2H)$^{2+}$; found m/z 1535.71420, calcd. 1535.71850 (M−H)$^−$.

C. Solid-Phase Labeling Studies of KDYWE (SEQ ID NO: 4).

Before and after each labeling step, the resin was washed with DMF and DCM (3 mL, 3 mins, 3×). Resins where placed under high vacuum overnight before cleavage at each step. Copper acetate (0.3 mmole) was dissolved in 3 ml 45/45/10 MeCN/H$_2$O/Pyr (v/v/v). The copper acetate solution was introduced to the dried resin and incubated for 4 hrs at RT. This solution was removed from the resin and collected, followed by washing with 1/1 MeCN/H$_2$O (v/v) (1 ml, 3 mins, 3×); washes were collected.

Labeling the Lysine with 2-methoxy-4,5-dihydro-1H-imidazole in (2). Resin (130 mg, 0.66 mmole g$^{−1}$). To the swollen resin, 3 ml of a 200 mM solution of 2-methoxy-4,5-dihydro-1H-imidazole in 7/2/1 MeOH/DIPEA/H$_2$O (v/v/v) was added. The resin was incubated overnight at RT. The peptide was cleaved from the resin using copper acetate solution, and the. MeCN and pyridine were removed by rotary evaporation. The remaining aqueous solution was frozen at −78° C. and lyophilized overnight. The resulting solid was dissolved in 1.5 ml of 1/1 MeCN/H$_2$O (v/v) and purified by prep HPLC. Organic solvent in peptide fraction was removed via rotary evaporator. Aqueous remnants were frozen at −78° C. and lyophilized overnight. Purified yield: (1.4 µmole) 2%. High-res MS: found m/z 910.45740, calcd. 910.45700 (M+H)$^+$; found m/z 908.44300, calcd. 908.44240 (M−H)$^−$.

Labeling the carboxylates and c-terminus (10). 1-Amino-3-butyne (0.61 mmole) was dissolved in NMMO (0.45 mmole), and the mixture was diluted with 1 ml of DMF. PyAOP (0.40 mmole) was separately dissolved in 2 ml DMF. The amine/NMMO solution was introduced to the resin, followed by introduction of the PyAOP solution. The resin was incubated overnight at RT, followed rinsing with MeOH (3 ml, 3 mins, 3×). The peptide was cleaved with 55 µmole of Cu(OAc)$_2$, and the MeCN and pyridine were removed by rotary evaporation. The remaining aqueous solution was frozen at −78° C. and lyophilized overnight. The solid was dissolved in 1.5 ml of 1/1/MeCN/H2O (v/v) and purified by prep HPLC. The organic solvent in the peptide fraction was removed via rotary evaporation, and aqueous remnants were frozen at −78° C. and lyophilized overnight. Purified yield: (1.4 µmole) 2%. High-res MS: found m/z 910.45740, calcd. 910.45700 (M+H)$^+$; found m/z 908.44300, calcd. 908.44240 (M−H)$^−$.

Tryptophan labeling of immobilized peptide (11). Immobilized peptide 10 was prepared as described using 193 mg of the same resin. 2,4-Dinitrobenzenesulfenyl chloride (0.30 mmole) was dissolved in 3 ml of glacial acetic acid. This solution was introduced to the swollen resin, and incubated for 4 hrs at RT. The solution was removed from the resin, and 6 ml of DMF was continuously passed through the resin. The peptide was cleaved from the resin using copper acetate solution, and MeCN and pyridine were removed by rotary evaporation. Remaining aqueous solution was frozen at −78° C. and lyophilized overnight. The solid was dissolved in 1.5 ml of 1/1/MeCN/H2O (v/v) and purified by prep HPLC, and the organic solvent in peptide fraction was removed via rotary evaporator. The aqueous remnants were frozen at −78° C. and lyophilized overnight. Purified yield: (5.4 µmole) 4%. High-res MS: found m/z 1108.42840, calcd. 1108.43050 (M+H)$^+$; found m/z 1106.41400, calcd. 1106.41600 (M−H)$^−$.

Cleavage of peptide 11 from hydrazinobenzoyl resin using H$_2$O. Cleavage of the peptide was performed as described with copper acetate (0.3 mmole) dissolved in 3 ml of 45/45/10 MeCN/H$_2$O/Pyr (v/v/v). MeCN and pyridine were removed by rotary evaporation, and the remaining aqueous solution was frozen at −78° C. and lyophilized overnight. The solid was dissolved in 1.5 ml of 1/1/MeCN/H2O (v/v) and purified by prep HPLC. The organic solvent in the peptide fraction was removed via rotary evaporation. Aqueous remnants were frozen at −78° C. and lyophilized overnight. Purified yield: (5.4 µmole) 4%. High-res MS: found m/z 1108.42840, calcd. 1108.43050 (M+H)$^+$; found m/z 1106.41400, calcd. 1106.41600 (M−H)$^−$.

Cleavage of peptide 12 from hydrazinobenzoyl resin. Copper acetate (0.33 mmole) was dissolved in 3 ml of 9/8.3/1.6 MeCN/Pyr/1-amino-3-butyne (v/v/v). Solution was introduced to swollen resin. The resin was incubated for 4 hrs at RT, Followed by filtration to collect the solution. MeCN and pyridine were removed by rotary evaporation. Washes of the resin with DMF (3 ml, 3 mins, 3×) were used, to improve the solubility of the peptide. The solvent was removed by centrifugal evaporation (35° C., 24 hrs). The solid was dissolved in 1.5 ml of 1/1/MeCN/H2O (v/v) and purified by prep HPLC. The organic solvent in the peptide fraction was removed via rotary evaporation and the aqueous remnants were frozen at −78° C. and lyophilized overnight. Purified yield: (5 µmole) 5%. High-res MS: found m/z 1159.47250, calcd. 1159.47780 (M+H)⁺; found m/z 1157.46220, calcd. 1157.46330 (M−H)⁻.

D: Preparation of Labeling Reagents.

2-Methoxy-4,5-dihydro-1H-imidazole was prepared following a literature protocol. (Peters E C, Horn D M, Tully D C, Brock A. A novel multifunctional labeling reagent for enhanced protein characterization with mass spectrometry. *Rapid Commun. Mass Spectrom.* 2001; 15: 2387-2392.

1-(4,4-dimethyl-2,6-dioxocyclohexylidene)-3-methylbutyl diethyl phosphate was prepared by dissolving of 2-(3-methylbutyryl)-5,5-dimethyl-1,3-cyclohexandione (17 µmole) in 0.5 ml of dry MeCN under argon. Solution was placed in ice bath. DIEA (20 µmole) was introduced, followed by slow introduction of diethylchlorophosphate (22 µmole). Reaction was stirred overnight at RT. Yield: quantitative. Low-res MS: found m/z 457.0, calcd. 457.2 (M+H)⁺. (Adapted from Zhang, H. A process for the preparation of the intermediate of β-methyl carbapenem. WO 2007104219 A1, Sep. 20, 2007.)

E: Desalting of Peptide 4.

Crude peptide was prepared for preparative HPLC using an Extract Clean™ C₁₈ 500 mg/4 ml solid phase extraction column. Column was flushed with 6 ml of 90/10 MeOH/H₂O with 0.1% TFA (v/v/v) at a flow rate of 1 drop sec⁻¹ (RT), followed by equilibration with 3 ml of 0.1% TFA in water (v/v) at a flow rate of 1 drop sec⁻¹. Acidified peptide solution was loaded on the column 1 drop sec⁻¹ (RT). Peptide was eluted with 1 ml 5% MeOH/Water with 0.1% TFA (v/v/v). Residually bound peptide was eluted with 50/50 MeCN/Water with 0.1% TFA (v/v/v).

Example V: Demonstrates Exemplary Solution-Phase and Solid-Phase (Resin) Orthogonal Labeling of Side Chains in KDYWEC (SEQ ID NO: 3) and KDYWE (SEQ ID NO: 4)

This Example describes in general: (i) labeling Cysteine residues with iodoacetamide (ii) Lysine residues with a guanidylating handle (iii) labeling carboxylic acid residues with benzylamine and other variants and (iv) Tryptophan by sulfenylchloride variants. For the solid phase labeling, Cysteine was not labeled. Instead the solid-phase procedure began with labeling Lysine residues.

A: Solution-Phase Orthogonal Labeling.

The order of steps in FIG. 43 took into consideration the nucleophilicity and acid/base-dependent reactivity of the target side chains in KDYWEC (SEQ ID NO: 3). This peptide was synthesized to contain the most reactive natural amino acids. The sulfhydryl group in Cysteine is the most nucleophilic, and is prone to oxidation and disulfide bond formation. To ensure selectivity in future labeling steps, Cysteine was first alkylated with iodoacetamide, forming a stable thioether. Maintaining a pH between 7-8 ensured the amines remained protonated, thus limiting the possibility of undesired alkylation. Subsequently, the pH was raised to 11 and 2-methylthio-2-imidazoline hydroiodide (MDI) was introduced. Labeling of the N_ε-amine occurred in 24 minutes when heated to 50° C. Longer reaction times increased the extent of N-terminal labeling. The two labeling steps were performed in one-pot. The yield of peptide 3 after purification was 38% and starting material was not observed. Because the Lysine was labeled while heating under highly basic conditions, the thioester and guanidinium group were considered to be stable in future derivatization steps.

Of the remaining nucleophilic sites, the N-terminus was first targeted. Protection of the N-terminus was required previous to labeling of aspartate, glutamate, and C-terminus. If not, concatenation of peptides could occur during amidation. The labeling conditions of the N-terminus also required a group compatible to both basic and acidic conditions in subsequent derivatization steps. Literature accounts have reported using 1-(4,4-dimethyl-2,6-dioxocyclohexylidene)-3-methylbutyl for protecting amines in peptide synthesis. The protecting group is stable to highly basic and acidic conditions, and is removed under hydrazinolysis conditions (Eq. 1). [9]

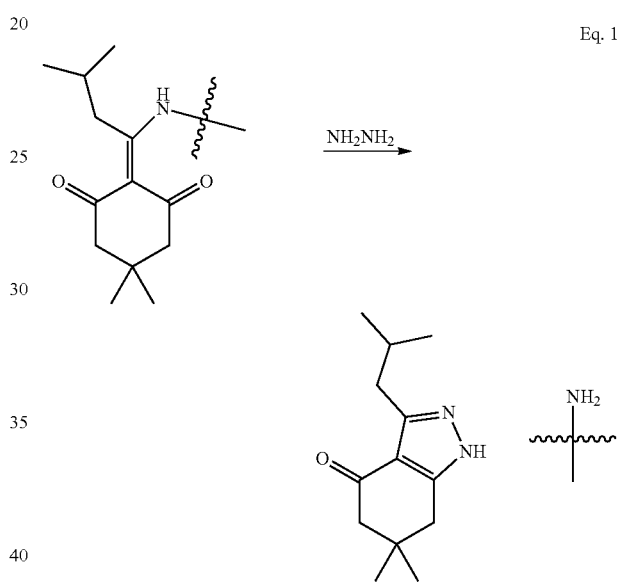

Eq. 1

However, refluxing overnight to efficiently add the protecting group is common. Heating overnight was undesired so as to minimize unwanted degradation. Thus, 1-(4,4-dimethyl-2,6-dioxocyclohexylidene)-3-methylbutyl diethyl phosphate was utilized as an alternative. Diethyl phosphate was anticipated to be a better leaving group, thereby facilitating the reaction (Eq. 2). This compound was formed with chloro diethyl phosphate in situ, followed by incubation with a basic solution of peptide 3 overnight. Post-purification the yield of peptide 4 was 67%.

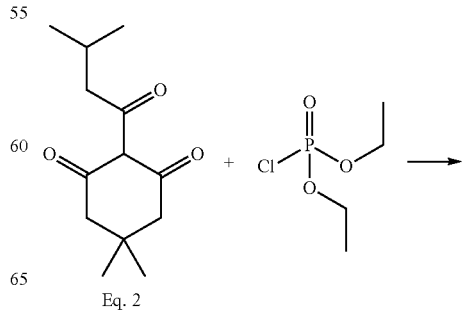

Eq. 2

-continued

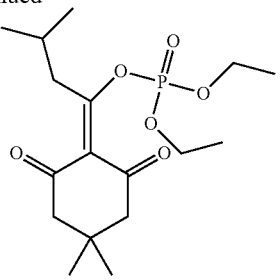

After the nucleophiles in the model peptide were labeled, the carboxyl groups were targeted. Amidation has been used for derivatization of aspartate, glutamate, and the C-terminus. [10] Unlike the labeling of Lysine, distinguishing among these target side chains was not possible. Also, because there were three sites for reaction, an efficient labeling approach was necessary. Highly efficient, global labeling using (7-azabenzotriazol-1-yloxy)tripyrrolidinophosphonium hexafluorophosphate (PyAOP) and n-methylmorpholine (NMMO) has been reported. [4] Using these amidation reagents, dimethylaminopropylamine (DMAPA), benzylamine (BA), and isobutylamine were used for labeling. Peptide 5 dissolved in MeCN/H$_2$O mixtures, and purification of peptide was possible. Yields for peptide 5 and 6 were 29% and 23%, respectively. Isobutylamine was explored as a mass label believed to be an intermediate hydrophobic compound when compared to BA and DMAPA. Desired product was not isolated during HPLC purification. Peptide 6 readily dissolved in MeCN/H$_2$O mixtures, but coeluted with an impurity characterized by LCMS as m/z 313.4 The impurity was removed after synthesizing peptide 8.

Tryptophan was the remaining target. As a less abundant amino acid in nature, the ability to label this side chain can be informative for determining the protein origin of peptides in proteomic studies. [11] In synthetic peptide design, incorporating an additional site for derivatization increases the repertoire of side chains to modify. Therefore, devising an orthogonal labeling strategy incorporating modification of Tryptophan was seen as important. Cysteine reacting with sulfenyl chlorides has been reported. [12] Competition between the Tryptophan and Cysteine was minimized when glacial acetic acid was used as the solvent. Under acidic conditions Tryptophan was selectively labeled in the presence of unprotected N-terminus and Lysine. Thus, considering the high selectivity of sulfenyl chlorides for Tryptophan, this labeling step theoretically could have been the first one. The advantage to labeling the Tryptophan last was the relative ease of the reaction. Peptides 5 and 6 readily dissolved in glacial acetic acid, and the reaction occurred in 4 hrs at RT. 2,4-Dinitrobenzenesulfenyl chloride (DBSC) was a chromophore and peptides could also be monitored at 330 nm. Yields were 32% and 49% for peptides 8 and 9, respectively.

B: Solid-Phase Orthogonal Labeling.

Efforts to label on solid phase supports were explored once the target side chains were successfully modified in solution. Synthetic peptides have been commonly modified when immobilized on a solid support, usually at reactive side chains such as Lysine. [13] Requirements for successful solid-phase reactions include making sure reaction is highly specific. Further, the reagents must be able to diffuse into the resin to reach sites for reaction. A high concentration of starting material in the bulk solution ensures a concentration gradient is formed for reactants to diffuse. [14] Inherent in this study was devising an approach that selectively labeled target side chains in a sequential fashion. Therefore, a requirement for specificity was met. Literature and the work presented here, have demonstrated excess reagent can be used while maintaining that selectivity. The final requirement for solid-phase studies was using a resin that would not cleave with acid or base. 4-Fmoc-hydrazinobenzoyl resin AM was selected, because literature accounts describe the stability towards strong acids and bases. Peptides immobilized on this resin were only isolated after oxidative cleavage with Cu(II) and base. [15-16] The pH of the solution could not be reliably controlled without the use of buffers or aqueous mixtures. Thus, for solid-phase studies, Cysteine was not labeled, reactions were kept at room temperature, and organic solvents were used. The rest of the targeted side chains studied in solution were also present for solid-phase labeling.

FIG. 44 summarizes the labeling reaction performed on the solid support for peptide KDYWE (SEQ ID NO: 4). The first side chain targeted was the Lysine. Two changes were made from the solution approach. The reaction time was longer, and the immobilized peptide was incubated overnight with MDI. A solution of MeOH/DIPEA/H$_2$O (7:2:1) (v/v/v) was used instead of a solution of NH$_4$OH. Overnight incubation and the use of DIPEA have been reported in the literature. [17] The doubly labeled peptide was not observed with an overnight reaction at RT, however, the reaction time was extended to 48 hrs, formation of doubly labeled peptide occurred.

Selectivity for the N$_\epsilon$-amine can be explained due to inductive and steric effects. Since the N$_\epsilon$ amine in Lysine is part of a hydrocarbon chain and not adjacent to an electron-withdrawing amide group, the amine has greater electron density. Thus, the Lysine side chain amine is more nucleophilic than the α-amine. Furthermore, the N-terminal amine is closer to the amide backbone, impeding MDI due to sterics. The same inductive and steric affects played a role when labeling KDYWEC (SEQ ID NO: 3) in solution phase. However, lowering the reaction temperature from 60° C. to RT made these affects more pronounced.

A protection step of the N-terminus was not performed. One reason was to discover whether in the presence of excess amine, the carboxylates would be labeled without concatenation to this terminal amine. A second goal was to check if the number of labeling steps could be reduced, leaving the terminal-amine unlabeled for future reactions. The end result would be a shortening of time required for modifying synthetic peptides. This approach could provide synthetic flexibility by diversifying the kinds of reactions performed at the N-terminus once the peptide is cleaved from the resin. The loading of the resin would need to be relatively small. Higher resin loading meant one peptide could encounter another peptide, increasing the probability of concatenation. A loading of 0.66 mmole/g was suitable, but neared the upper limit for efficient solid-phase reactions. [14] A loading higher than the one used was considered too high and ineffective for peptide synthesis or labeling studies.

The amine used in the solid-phase synthesis differed from that of the solution-phase studies. 1-Amino-3-butyne had an alkyne group that could also provide sites for derivatization via Huigen-Sharpless. The same coupling reactants PyAOP and NMMO were employed for solid-phase studies. Two repetitions ensured all carboxylates were labeled. Cleavage of the peptide was performed using a catalytic amount of Cu(II) and a mixture of MeCN/H$_2$O/Pyr. To a different batch of resin, the Lysine and carboxylates were also labeled. Tryptophan was labeled in a similar fashion as in solution, four hours at RT. [18]

Two different cleavage conditions were tested for the model peptide after target side chains were labeled. The first condition was water, liberating a carboxylate at the C-terminus. Peptide 11 was isolated with a 4% yield. Additionally, a nonaqueous condition in the presence of a nucleophile could also be employed to cleave the peptide. 1-Amino-3-butyne was the nucleophile used, liberating peptide 12 with a purified yield of 5%. The peptide could also have been cleaved with a different nucleophile diversifying the functional groups, further differentiating between the C-terminus and carboxylate side chains. Isolating peptide 12 required extra washes with DMF, because solubility in a $H_2O$/MeCN was reduced once an alkyne was introduced at the C-terminus. Initially, the peptide was rinsed with MeCN and LCMS data of the crude did not indicate presence of desired product. Once rinsed with DMF and the solvent removed, peptide 12 was observed.

Exemplary characterization data showing successful orthogonal labeling with model peptide KDYWEC (SEQ ID NO: 3) in solution-phase and KDYWE (SEQ ID NO: 4) in solid-phase. Exemplary peptide target compound screening reports for Peptides 3-6, 8-12 are shown in FIG. 46.

1. Julka S, Regnier F. Quantification in proteomics through stable isotope coding: a review. *J. Proteome Res.* 2004; 3: 350-363.
2. Cockrill S L, Foster K L, Wildsmith J, Goodrich A R, Dapron J G, Hassel T C, Kappel W K, Scott G B I. Efficient micro-recovery and guanidination of peptides directly from MALDI target spots. *Biotech.* 2005; 38: 301-304.
3. Frey B L, Ladror D T, Sondalle S B, Krusemark C J, Jue A L, Coon J J, Smith L M. Chemical derivatization of peptide carboxyl groups for highly efficient electron transfer dissociation. *J. Am. Mass Spectrom.* 2013; 24: 1710-1721.
4. Krusemark C J, Frey, B L, Smith L M, Belshaw P J, Complete chemical modification of amine and acid functional groups of peptides and small proteins, In *Gel-Free Proteomics, Methods in Molecular Biology*, 753 (Eds: Gevaert K, Vandekerckhove J) Humana Press, New York, 2011, pp. 77-91.
5. Horton H R, Koshland D E. A highly reactive colored reagent with selectivity for the Tryptophan residue in proteins. 2-Hydroxy-5-nitrobenzyl bromide. *J. Am. Chem. Soc.* 1965; 87:1126-1132.
6. Scoffone E, Fontana A, Rocchi R. Sulfenyl halides as modifying reagents for polypeptides and proteins. i. modification of Tryptophan residues. *Biochem.* 1968; 7: 971-979.
7. Kuyama H, Watanabe M, Toda C, Ando E, Tanaka K, Nishimura O. An approach to quantitative proteome analysis by labeling Tryptophan residues. *Rapid Commun. Mass Spectrom.* 2003; 17: 1642-1650.
8. Chalker J M, Bernardes G J L, Lin Y A, Davis B G. Chemical modification of proteins at Cysteine: opportunities in chemistry and biology. Chem. Asian J. 2009; 4: 630-640.
9. Isidro-Llobet A, Alvarez M, Albericio F. Amino acid-protecting groups. *Chem. Rev.* 2009; 109: 2455-2504.
10. Ko B J, Brodbelt J S. Enhanced Electron Transfer Dissociation of Peptides Modified at C-terminus with Fixed Charges. *J. Am. Soc. Mass Spectrom.* 2012; 23: 1991-2000.
11. Moffet J R, Namboodiri M A. Tryptophan and the immune response. *Immunol. Cell Biol.* 2003; 81: 247-265.
12. Scoffone E, Fontana A, Rocchi R. Selective modification of the Tryptophan residue in peptides and proteins using sulfenyl halides. *Biochem. Biophys. Res. Commun.* 1966; 25: 170-174.
13. Wittman V, Seeberger S. Combinatorial solid-phase synthesis of multivalent cyclic neoglycopeptides. *Angew. Chem. Int. Ed.* 2000; 39: 4348-4352.
14. Tulla-Puche J, Albericio F. The (classic concept of) solid support. In *The power of functional resins in organic synthesis* (Eds: Tulla-Pucha J, Albericio F) Wiley, Weinheim, 2008, pp. 3-14.
15. Millington C R, Quarell R, Lowe G. Aryl hydrazides as linkers for solid phase synthesis which are cleavable under mild oxidative conditions. *Tett. Lett.* 1998; 39: 7201-7204.
16. Rosenbaum C, Waldmann H. Solid phase synthesis of cyclic peptides by oxidative cyclative cleavage of an aryl hydrazide linker-synthesis of stylostatin 1. *Tett. Lett.* 2001; 42: 5677-5680.
17. Keough T, Lacey M P, Yongquist R S. Derivatization procedures to facilitate de novo sequencing of Lysine-terminated tryptic peptides using postsource decay matrix-assisted laser desorption/ionization mass spectrometry. *Rapid Commun. Mass Spectrom.* 2000; 14: 2348-2356.
18. Zervas L, Borovas D, Gazis E. New methods in peptide synthesis. i. tritylsulfenyl and o-nitrophenylsulfenyl groups as N-protecting groups. *J. Am. Chem. Soc.* 1963; 85: 3660-3666.

Example VI: Exemplary Synthesis of Fluorophores and Modification for Having Specific Amino Acid Linkages In general, dyes (Fluorophores) synthesized by the inventors, such as tetramethylrhodamine and Si-Rhodamine B, were modified to have an amino linker or as a succinimidyl ester variant. Dyes having the amino acid specific linker were modified with iodoacetamide for targeting a thiol group, in particular for use with targeting Cysteines. Dyes modified to having a succinimidyl ester 'handle' bind to amine groups. Purchased dyes were also modified to provide these variants. Commercial sources of Fluorophores/dyes included Sigma (for Atto dyes), Invitrogen (for Alexa dyes), Thermo (Rhodamine dyes). Additional dyes were modified to have other types of reactivates to selectively target multiple amino acid residue classes and minimizing cross reactivity.

The following is an exemplary description for synthesizing rhodamineB-DMEDA, Rhodamine B-NHS, Rhodamine B iodoacetamide, Si-rhodamine, Si-rhodamine sulfenyl chloride and 4-(butylcarbamoyl)-2-nitrophenyl hypochlorothioite.

Rhodamine B-DMEDA (mRhodamineB): Rhodamine B from a commercial source was modified by adding a N,N'-dimethylethylenediamine to the carboxylate end of the rhodamine B dye to prevent pH dependence of its fluorescence. Further, the attached linker provided another free amine for further modification. As an example, mRhodamineB would be a lysine-labeling handle, or a tryptophan labeling handle. See, the first structure in FIG. 54.

Rhodamine B-NHS: As one example, NHS-activated versions of the Rhodamine B dyes were made for attaching to a diamine linker, such as DMEDA, See, the second structure in FIG. 54.

Rhodamine B iodoacetamide: Rhodamine B was modified to Rhodamine B iodoacetamide. More specifically, Rhodamine B was modified with N,N'-dimethylethylenediamine followed by chloroacetyl chloride and sodium iodide to yield fluorescent labeling reagent N-(6-(diethylamino)-9-(2-((2-iodo-N-methylacetamido)ethyl)(methyl)carbamoyl)phenyl)-3H-xanthen-3-ylidene)-N-ethylethanaminium chloride. The variant with methyl groups on the amide nitrogens made the dye to be pH insensitive. FIG. 47.

Rhodamine B variants: Another variant of Rhodamine B shows an exemplary synthesis for use with labeling an amino acid. Rhodamine B modified with N,N'-dimethylethylenediamine (first structure, as described above) then was activated by Me3Si—NHS to form an isothiourea variant (second structure), then reacted in n-Propyl iodide for a third structure, any of these structures may find use in labeling amino acids and peptides. FIG. 54.

Silicon Rhodamine: Si-rhodamine was synthesized in part using methods described in (1) Kode Y, Urano Y et. al. 2012. Development of NIR fluorescent dyes based on Si-rhodamine for in vivo imaging. JACS. 134: 5029 and (2) Lukinavicius G et.al. 2013. A near-infrared fluorophore for live-cell super-resolution microscopy of cellular proteins. Nature Chemistry. 5: 132 and (3) PCT/JP2014/050088 (WO 2014106957 A1) Asymmetrical Si Rhodamine And Rhodol Synthesis (in Japanese).

Silicon Rhodamine-DMEDA: In some embodiments the Si-Rhodamine dye made during the development of the present inventions was linked to N,N'-dimethylethylenediamine (DMEDA). In some embodiments Si-Rhodamine dye was further modified for other handles as needed. As one example, NHS-activated versions of Si Rhodamine dyes were made to attach to a diamine linker, such as DMEDA. Si-Rhodamine dye is contemplated to serve as an amine reactive dye, however lacks specificity of any kind until a handle such as described herein becomes part of the dye.

Rhodamine B sulfenyl chloride: The thioether precursor to the Rhodamine B sulfenyl chloride was synthesized from Rhodamine B in three steps, See, FIG. 52A.

The procedure for thioether synthesis was modified from Li, Z.-S.; Wang, W.-M.; Lu, W.; Niu, C.-W.; Li, Y.-H.; Li, Z.-M.; Wang, J.-G. Synthesis and biological evaluation of nonsymmetrical aromatic disulfides as novel inhibitors of acetohydroxyacid synthase. *Bioorg. Med. Chem. Lett.* 2013, 23, 3723-3727. No intermediate purification was performed. The Rhodamine B sulfenyl chloride was synthesized from the thioether precursor by treatment with a slight excess of sulfuryl chloride in trifluoroacetic acid. FIG. 52B.

The sulfenyl chloride was not observed directly because it is highly reactive, but the major product observed by LCMS (Liquid Chromatography Mass Spectrometry) was the product of reaction with methanol, the solvent used for LCMS analysis.

4-(butylcarbamoyl)-2-nitrophenyl hypochlorothioite: The sulfenyl chloride functional group was synthesized using the procedure from Li, Z.-S.; Wang, W.-M.; Lu, W.; Niu, C.-W.; Li, Y.-H.; Li, Z.-M.; Wang, J.-G. "Synthesis and biological evaluation of nonsymmetric aromatic disulfides as novel inhibitors of acetohydroxyacid synthase." *Bioorg. Med. Chem. Lett.* 2013, 23, 3723-3727.

Example VII: Exemplary Solution Phase Labeling for Peptides Containing Cysteine, Lysine and Tryptophan One, two, or three different amino acids can be labeled depending on the (orthogonal) reaction conditions. Thus, in one embodiment, solution phase fluorophore labeling, i.e. one to three types of amino acids of model peptides, is intended for C-terminal immobilization and sequencing. In particular, this method describes embodiments for labeling Lysines using an isothiourea method and labeling tryptophan in addition to using Rhodamine B iodoacetamide for Cysteine labeling; Rhodamine B or Si Rhodamine B for Tryptophan Model peptides were synthesized containing Cysteine and Lysine: A) YKTCYTD (SEQ ID NO: 5), B) KCGGYCD (SEQ ID NO: 6), and C) GYCKCTD (SEQ ID NO: 7)), FIG. 48.

Additional model peptides were synthesized containing Cysteine, Lysine and Tryptophan (KCTWGCD (SEQ ID NO: 18), WGCTKWD (SEQ ID NO: 19)) and peptides Serine-Tryptophan (Ser-Trp;SW) and Alanine-Aspatate and Tryptophan (Ala-Asn-Trp;ANW). Peptides were synthesized on a microwave peptide synthesizer.

A: An Example of Solution Phase Labeling of Model Peptides for C-Terminal Immobilization and Sequencing.

1. For Cysteine Labeling.

Rhodamine B iodoacetamide: N,N'-dimethylethylenediamine was used to label Cysteine in a solution-phase method. This reaction was selective for Cysteine where the Lysine and N-terminus were boc-protected. Purified peptides were confirmed by high-resolution mass spectrometry. FIG. 48.

2. For Tryptophan Labeling.

A model reagent, 4-(butylcarbamoyl)-2-nitrophenyl hypochlorothioite, see FIG. 48 for an exemplary structure, was made to label Tryptophan containing peptides. For this example, see model peptides above containing Tryptophan. The labeled Tryptophan was stable to Edman degradation in solution. FIG. 49.

3. For Lysine Labeling.

An isothiourea was synthesized as a model reagent for Lysine labeling. FIG. 51A.

Reaction of the isothiourea with Lysine dihydrochloride proceeded once. FIG. 51A. Reaction of the isothiourea with peptides proceeds slowly. FIG. 51B.

This method of synthesis is an alternative to labeling lysine residues in that it does not include the use of the o-methyl isourea. Further, this method selectively labels Lysine over the N-terminus.

B: An Example of Solution Phase Labeling, One to Two Types of Amino Acids of Model Peptides Containing Lysine and Tryptophan for C-Terminal Immobilization and Sequencing.

1. For Lysine Labeling.

Contemplated amino acid specific labels, such as for Lysine, are Rhodamine B and Si Rhodamine B (separately) for solution phase labeling of the first of two amino acids with two differently colored dyes. For example, Lysine labeled with Si Rhodamine B was contemplated for use with Tryptophan labeled with Rhodamine B. 2. For Tryptophan labeling.

A Rhodamine B sulfenyl chloride was synthesized, as describe above for use in labeling Tryptophan. Its synthesis is described above and in FIG. 52.

Two small peptides with Trp (W) amino acids were labeled with the Rhodamine B sulfenyl chloride. The expected product from this tryptophan reaction with the Rhodamine B sulfenyl chloride is observed in test reactions with two small peptides, Ser-Trp (SW) and Ala-Asn-Trp (ANW). See, FIGS. 53A and 53B, respectively. The Rhodamine B label is attached to the Trp in FIG. 53A. The Rhodamine B label is attached to the Trp in FIG. 53B.

C. An Example of Solution Phase Labeling, One, Two or Three Types of Amino Acids of Model Peptides Containing Cysteine, Lysine and Tryptophan for C-Terminal Immobilization and Sequencing.

1. For Cysteine Labeling.

In some embodiments, Cysteine labeling is as described herein for Lysine.

2. For Lysine Labeling.

Contemplated amino acid specific labels, such as for Lysine, are Rhodamine B and Si Rhodamine B (separately) for solution phase labeling of the first of two amino acids with two differently colored dyes. In particular, this labeling is contemplated as an alternative to labeling Lysine residues that does not include the use of the o-methyl isourea. For example, in one embodiment, Lysine is labeled with Si Rhodamine B. This labeled Lysine was contemplated for use with Tryptophan labeled with Rhodamine B. In another embodiment, Lysine is labeled with Rhodamine B or a Rhodamine B derivative (variant). Additionally, as shown in FIG. 53A, this method selectively labels lysine over the N-terminus.

Example VIII: Exemplary Labeling of Amino Acids with Two Different Fluorophore Prior to Solid Phase Peptide Synthesis This Example describes the creation and use of a building block and/or control peptide for use in solid phase peptide synthesis. Thus in one embodiment, eliminating the need to create more than one orthogonal dye label. The main criteria for the building block peptide was that it could be created in fairy large quantity (2-5 g) for use on the peptide synthesizer, such large amounts were required to account for the inefficiency of the solid phase synthesis.

A. Boc-Asp-OBzl Peptide Labeled with Rhodamine B Via HCTU Coupling. See, FIG. 61.

In this method, one of either BOC or FMOC Asp-OBzl was used to generate a building block. The majority of the synthesis proceeded without purification (other than step 2). This series of reactions can also be done on 5 g scale. Step 5 (see FIG. 61) is needed in the instance where R=FMOC. In this case, the basic conditions of step 3 (DIPEA) can de-FMOC the Asp, which needs to be protected before use on the surface. The use of a BOC protecting group on the amine makes this synthesis straightforward because there are no de-protection steps, however, it is labeled under the same conditions as a Wang resin. On any peptide where a BOC protecting group is present, it should be the final amino acid added.

B. FMOC-Cys Peptide Labeled with Rhodamine B Via Iodoacetamide Handle. See, FIG. 62.

Fmoc-Cys(Trt)-OH can be easily de protected in one step with a quantitative yield. The rhodamine B iodoacetamide should be prepared on a several gram scale. In a reaction solution, combining the FMOC-Cys with the Rhodamine B iodoacetamide goes to completion within 6 hours, with very little by-product, requiring no purification. The FMOC protected amino acid can be placed in any location along the peptide sequence.

NHS Activation steps in A. and B., above, are generally described in Chen et al. *Dyes and Pigments* 94, 296-303 (2012).

C. Making a Peptide that is Labeled with Two Different Dyes.

In this dye sequencing scheme, two different color dyes are used to label two different Cys moieties on a peptide. Using a building block that was synthesized, Cyst-Rhod-amine B (See B above, as shown in FIG. 62) another dye containing an iodoacetamide handle needs to be synthesized for use as a second label.

There are literature reports of a rhodamine-based dye containing a Silicon atom replacing the oxygen of the core structure of the dye. This atom replacement shifts the wavelength of emission from ~550 nm to ~640 nm, a distance spectrally resolve enough to limit FRET pairing (A). Synthesis of the core structure is a literature report procedure (Lukinavic̆ius et al. *Nature Chemistry* 5, 132-139 (2013)).

The synthetic strategies for using Si-Rhodamine involve the development of a "handle" attached to and using the core Si-Rhodamine structure designed during the development of the present inventions. The method here for labeling Cyst with Si-Rhodamine is the same as in B) above, for labeling the Cys with a rhodamine B dye using a iodoacetamide handle. From the 9 linear steps for producing Si-Rhodamine as a label (see FIG. 63), the overall yield is 4% with column chromatography purification at the final step.

Labeling strategy: In brief, starting with the building block made in B above, then treating it to solid phase peptide synthesis to make a peptide having a Cyst amino acid labeled with Rhodamine B was accomplished. In this case a 12 amino acid peptide was made having a Cys-Rhodamine B.

Following the general steps to remove a peptide from a resin and wash it, this peptide was then reacted, without purification, with the Si-Rhodamine iodoacetamide as described herein. In slightly basic conditions, the 2 position Cys was labeled by the SN2 of the iodine atom. Following HPLC purification, the high-resolution Mass Spectrometry confirmed that the 12 amino acid peptide was labeled with 2 different colored dyes. See, FIG. 64.

Example IX: An Exemplary Simulation for Implementing a Single-Molecule Sequencing Technology Based on Edman Degradation This Example describes a contemplated practical approach that would in principle be capable of generating partial peptide sequences in a highly parallel fashion. Further contemplated is a sequencing method scalable to entire proteomes. These methods are contemplated to have broad applications across biology and medicine, for example, as PCR is for nucleic acid research this method would be used for protein research. From a theoretical perspective, the features that data generated by such an approach would have, along with how such data might be interpreted and how sensitive the process might be to potential errors, which we model using Monte Carlo simulations.

Figure 5B:
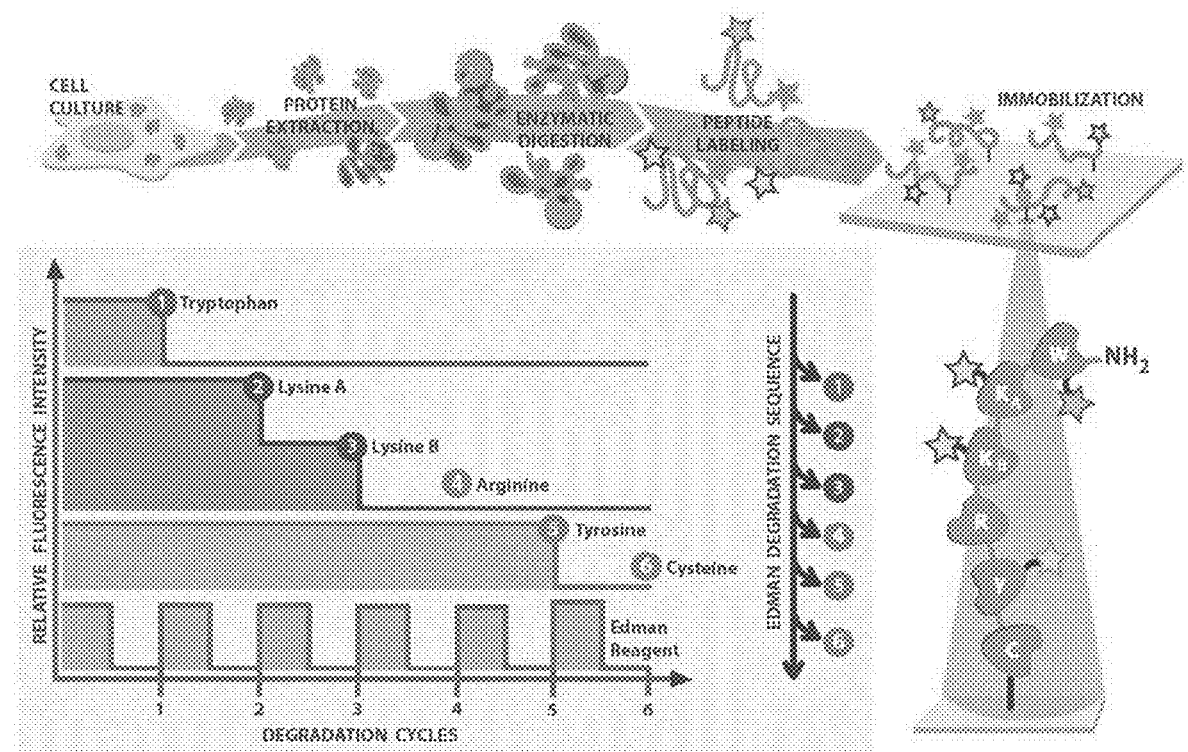
FIG. 5B shows the general scheme of one embodiment of the method. Proteins are extracted and digested by specific endo-peptidases. All occurrences of the particular amino acids (e.g. Lysines, Tryptophan, Arginine in this case) on the peptides are selectively labeled by dyes (blue, green and yellow stars respectively) and surface immobilization for single molecule imaging. The peptides are subjected to a fluorescent Edman reagent coupling and removing the terminal amino acid at the end of every cycle. This works as an internal error check to ensure the successful completion of an Edman cycle and gives the count of amino acids removed. Dye indicates when the specific amino acid is removed which in combination with dye2 signal gives the resulting pattern (W-K-K-x-Y-x (SEQ ID NO: 2)). This pattern identifies the peptide in the reference database.

In one embodiment, a strategy for implementing single molecule peptide sequencing, FIG. 5B, illustrates a proposed scheme for single molecule peptide sequencing. The method is to selectively fluorescently label amino acids on immobilized peptides, followed by successive cycles of removing peptides' N-terminal residues (by Edman degradation) and imaging the corresponding decreases of fluorescence intensity for individual peptide molecules. The resulting stair-step patterns fluorescence decreases will often be sufficiently reflective of their sequences to allow unique identification of the peptides by comparison to a reference proteome.

Briefly, proteins in a complex mixture are first proteolytically digested into peptides using an endo-peptidase of known cleavage specificity. Select amino acid types (e.g. lysine, tryptophan or tyrosine) are covalently labeled with spectrally distinguishable fluorophores, each being specific (by reactivity) to the given amino acid side chain. Labeled peptides are immobilized on a glass surface, as for example via the formation of a stable thioether linkage between a maleimide functionalized surface and the thiol group on cysteine residues [13]. The choice of peptidase, labeled amino acids, and anchor all convey information about the identity of a peptide and thus can be optimized for maximum effect. Using techniques such as Total Internal Reflection Fluorescence (TIRF) microscopy, individual peptide molecules can be imaged on such a surface, and the fluorescence intensity across all fluorophore channels can be determined for each peptide on a molecule-by-molecule basis. By monitoring decreases in fluorescence intensity following cycles of Edman degradation, the relative positions of labeled amino acids in the peptides can be determined, and thereby obtain a partial peptide sequence. This scheme might be improved by using a fluorescent Edman reagent whose coupling and decoupling can be observed, enabling the successful completion of each Edman cycle to be monitored for every single peptide, providing an additional error check. We term the pairing of an Edman degradation cycle and the subsequent observation for changes in fluorescence an experimental cycle (see Definitions). The observed sequence of luminosity drops in fluorescence across experimental cycles is a fluorosequence; the technique itself is thus fluorosequencing. For the example shown in FIG. 5B, the fluorosequence is "WKKxY" (SEQ ID NO: 16). Mapping the partial sequence back to a reference proteome of potential proteins, such as might be derived from a genome sequence, would determine if the fluorosequence uniquely identifies a peptide, and ultimately, its parent protein.

Commercially available TIRF microscopes can easily monitor fluorescence changes for millions of individual peptide molecules [14] and are not dissimilar to early variants of next-generation DNA sequencers [2]. By increasing peptide density and acquiring TIRF images over a large surface area, one could in principle obtain fluorosequences for millions or billions of peptides in parallel. Critically, this approach would be intrinsically quantitative and digital, based on counting repeat peptide observations, in much the same way NextGen RNA sequencing is for identifying and quantifying RNA transcripts.

Under Ideal Conditions, Even Partial Amino Acid Sequences are Informative.

Computer simulations of variations of this scheme confirm that fluorosequences can be quite information-rich; even relatively simple labeling schemes, employing only 1 to 4 amino acid-specific fluorescent labels, can yield patterns capable of uniquely identifying at least one peptide from most of the known human proteins (FIG. 55). For these simulations, only labeling schemes were considered based on known differences in side-chain reactivity and available amino acid-specific targeting chemistry [15], such as the reactivity of diazonium groups for tyrosines [16].

Many of the above labeling schemes (anchoring peptides via internal cysteine residues) fail to achieve 100% coverage of the template proteome even after many experimental cycles under ideal conditions. The reason is two-fold: (a) Edman reactions cannot continue past the cysteine anchor or (b) the proteome contains paralogs and protein families differing at unlabeled amino acids that are hence indistinguishable. When simulations were repeated for the case of anchoring cyanogen bromide cleaved peptides, not just cysteine-containing ones, by their C-termini, the coverage of the four-label scheme rose from 80% to 98% of the proteome (FIG. 55, top curve). Moreover, when simulations were performed for the case of no proteolysis and anchoring each full-length protein at its C-terminus, four of the tested multiple-label schemes (including schemes with only 2 label types) achieved over 96% coverage of the proteome within 200 experimental cycles. The remaining proteins were unidentified due to protein families being indistinguishable by the labeling schemes employed. These simulations thus confirm that single molecule fluorosequencing is intrinsically capable of identifying a majority of proteins in a proteome even when the number of label types is small.

Figure 56:
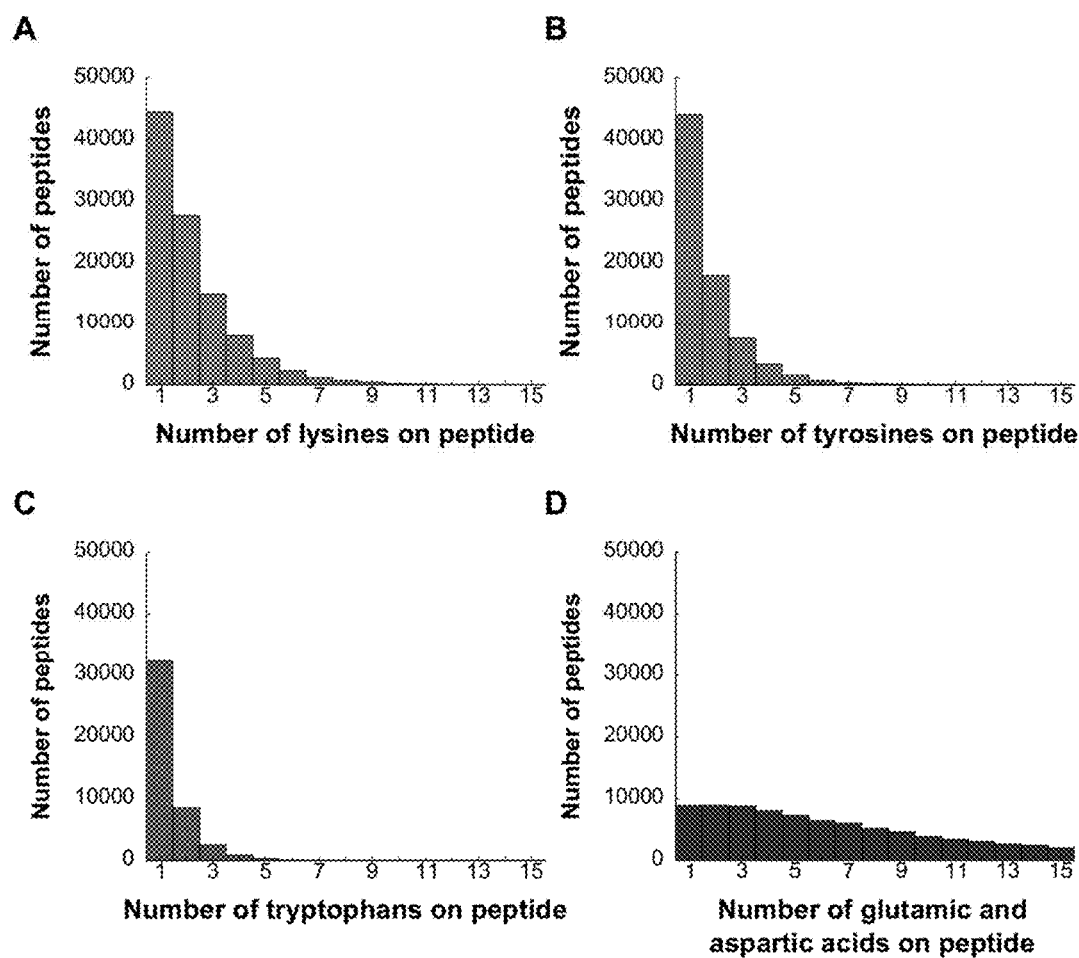

It is also worth considering whether the linear scaling and dynamic range of photon detection by existing cameras might place a limit on the ability to discriminate luminosity drops in fluorescent intensity per peptide. For example, while it might be easy to discriminate a reduction from 5 to 4 fluorophores on a peptide, discriminating a reduction from 25 to 24 fluorophores could be difficult. However, the median count of labelable amino acids per peptide is often small. For example, when considering peptides generated by the protease GluC, this count ranges from approximately 2 (for lysines) to 7 (for glutamic acid/aspartic acid residues, which were considered indistinguishable by reactivity for labeling purposes) (FIG. 56). This range is well within the capacity of most modern cameras, since, in practice, TIRF microscopes equipped with CCD camera variants can count up to at least 13 fluorophores; that is, up to at least 13 copies of a given fluorophore per single molecule can be quantitatively distinguished [17]. Thus, peptides from typical proteomes should not be problematic in this regard.

Anticipating the Inevitable Failures of Dyes and Edman Chemistry.

Being a physico-chemical process, there are potential sources of error for an experimental implementation of the scheme. With errors, an observed fluorosequence would not reflect the true sequence of fluorescently labeled amino acids. Three of the most probable error sources are as follows:

(a) Failure of fluorophore attachment or emission causing apparent substitutions. Steric constraints of peptides or reaction kinetics of fluorophore labeling chemistry might result in specific amino acid(s) not being covalently labeled. This scenario is equivalent to correctly coupled but non-emitting fluorophores, such as those observed in defective fluoro-phores [18]. In both circumstances, the position of a labelable amino acid would be misinterpreted as containing a non-labelable amino acid, e.g. the peptide "GK*EGK*" (SEQ ID NO: 20) (where K* represents a labeled lysine) would mistakenly yield a fluorosequence "xxxxK" (SEQ ID NO: 21) instead of "xKxxK" (SEQ ID NO: 22), for a dye failure at the first lysine.

(b) Photobleaching of labeled fluorophores causing apparent coupled double substitutions ("residue swaps"). The permanent photochemical destruction of dyes could also complicate the analysis. In this scenario, a labeled residue at one position is misinterpreted as an unlabeled residue because the label is lost by photobleaching, while another residue upstream in the peptide (typically unlabeled) is misinterpreted as being labeled because the photobleaching fluorophore loss coincides with that particular experimental cycle. This would shift the apparent position of the label upstream in the fluorosequence. For example, peptide GK*EGK* (SEQ ID NO: 20) might be observed as xKKxx (SEQ ID NO: 23) when the dye on the lysine at the fifth position photobleaches during the third imaging cycle. This situation reduces the ability to (i) reliably count the number of fluors lost during an experimental cycle, (ii) distinguish whether a change in luminosity results from fluorophore loss due to a genuine Edman degradation step or photobleaching, and (iii) identify which downstream fluorophore was extinguished if the loss is indeed due to photobleaching. Although fluorophore half-lives can be extended by use of oxygen scavenging systems [19], synthesis of stable dyes [20] or even surface modification [21], photobleaching is still a stochastic process and accounting for loss of fluorophores erroneously coincident with upstream Edman degradations would be critical to identification. Currently, there are many photo-stable dyes on the market. A recent study on the effects on dyes by oxygen radicals found that the half-life of Atto647 was roughly 3 minutes (corresponding to 180 experimental cycles at 1 second/cycle exposure) [22], while Atto655 showed a mean photobleaching lifetime of 8-20 minutes [23], corresponding to many hundreds of experimental cycles. However, incubation in Edman solvent eventually destroyed the dye.

(c) Inefficiency of Edman degradation chemistry causing apparent insertions.

Optimization of Edman degradation over the past sixty years has resulted in efficiencies of >95% [24]. Nonetheless, failed cycles are expected at some non-zero rate and would yield an observation corresponding to no fluorescence change, even if there was a labeled amino acid in position to be removed. This corresponds to an apparent insertion of a non-labeled amino acid into the fluorosequence. Note that the use of a fluorescing Edman reagent (e.g., DABITC or FITC [25]) would enable direct monitoring of every coupling and decoupling step of the chemistry, providing an internal error check for successful completion of the Edman cycle as in FIG. 5B. Nonetheless, non-fluorescent Edman reagents such as phenylisothiocyanate are more commonly used, so dye was investigated as a parameter.

A Framework for Modeling Single-Molecule Sequencing Under Non-Ideal Conditions.

To analyze how peptide sequencing efficiency is affected by the above three types of errors and to map fluorosequences to source proteins, a modeling framework was developed in order to simulate the process. Unlike the ideal case where fluorosequences are faithful to their source peptides, and hence mapping to the reference proteome is trivial, accounting for errors such as the three previously highlighted complicates mapping. For example, the fluorosequence "xKxxK" (SEQ ID NO: 22) cannot be uniquely attributed to the "GK*EGK*" (SEQ ID NO: 20) peptide, since Edman failure at the first position of peptide "K*EGK*" (SEQ ID NO: 24) or a fluorophore failure on the first lysine of "K*K*EGK*" (SEQ ID NO: 25) could also yield the same pattern. While errors arising from the inefficiency of Edman chemistry and fluorophore failure are tractable by analytical solutions, the non-Markovian nature of photobleaching events forces us to employ a Monte Carlo approach.

A Monte Carlo procedure to simulate thousands of copies of each of the 20,252 proteins in the human proteome being subjected in silico to fluorosequencing in order to obtain a random sample of the fluorosequences produced for a specified set of error rates. FIG. 57 details the simulation steps; the Methods provide more complete descriptions of the error models and pseudo-code for the overall procedure.

Each sample observation generated by the Monte Carlo simulation is a sequence of luminosity drops yielded by one individual peptide subjected to in silico Edman cycles. Conservatively it was contemplated that the absolute number of fluorophores labeling a peptide would not be observed or estimated, but that we can monitor and statistically discriminate whether, after each attempted Edman cycle, there has been a decrease in luminosity in each fluorescent channel, consistent with signals previously shown to be discernable for single molecules [17]. For the purpose of the simulation, we make the simplifying assumptions that different fluorophores have fully distinguishable signals, do not exhibit fluor-to-fluor interactions or Förster resonance energy transfer, nor exhibit channel bleed-over.

The fluorosequences (observed reads) from the simulations are next collated into a prefix trie [26], as illustrated for a simple example in FIG. 58. Each fluorosequence is linked in the trie to its source protein(s) and associated count(s) of observations over the course of the simulation, thereby empirically estimating the fluorosequence's source protein probability distribution. FIG. 59 illustrates two extreme cases of protein probability distributions for a given fluorosequence. Importantly, modeling the frequency of source proteins for fluorosequences is equivalent to obtaining (within sample error) the posterior probability mass functions—i.e. the set of probabilities $P[p_j|f_i]$ such that given an observed fluorosequence f i, the probability that protein p j is its source (henceforth called the attribution probability mass function (p.m.f)). Notably, by sidestepping problems associated with developing algorithms for inverting fluoro sequences to their source peptides, and the peptides' own derivation from source proteins, we make the strategy amenable for incorporating additional experimental parameters, including fluorophore spectral channel bleed-over or protease inefficiencies. Thus, the attribution p.m.f.'s provide a natural framework both for modeling errors and for directly mapping actual experimentally observed fluorosequences to proteins in the proteome. Based on the properties of this distribution, a fluorosequence can be associated with the protein most likely to yield it, for example applying a confidence threshold (see Methods below).

In future applications using attribution p.m.f.'s to interpret fluorosequencing data from real samples, one might also wish to model realistic numbers of copies per protein processed through the simulation pipeline, since the Monte-Carlo based deconvolution of fluorosequences to source proteins will be affected by protein abundance dynamic range as well as simulation depth. For example, high simulation depth would not only reduce the sampling errors, but also accurately attribute low abundance proteins from confounding high abundance proteins that generate the same fluorosequence by a low probability event. In another aspect, simulating protein copies based on their prior known abundances [27] might significantly reduce Monte-Carlo simulation computational resources. The version of the simulation described here makes no such assumptions about protein abundance, and thus corresponds to a Bayesian flat prior expectation on protein abundance, applicable to any sample.

More Amino Acid Colors Compensate for Photobleaching and Poor Edman Efficiency.

Using the Monte Carlo scheme, sequencing the human proteome was simulated to a simulation depth of 10,000 copies per protein, performing a parametric sweep of 216 experimental parameter combinations (corresponding to six values for each of the three error parameters). FIG. 60 illustrates the effects for three alternate labeling schemes of varying Edman efficiency and fluorophore half-life on the percentage of proteins identified after 30 Edman cycles, given fluorophore failure rates ranging between 0 and 25%. As in FIG. 55, diversifying the labels offers the greatest improvement in proteome coverage, even with relatively poor process efficiencies.

The number of proteins identified is reasonably robust to changes in fluorophore failure rates. For example, a 25% increase in failure rate causes only a 0.8%-6.4% reduction (range includes all parameter combinations) in proteome coverage for schemes B and C (see FIG. 60 for scheme descriptions). However for scheme A, a 25% increase in fluorophore failure rate causes a 19% reduction in proteome coverage under moderate estimates of photo-bleaching and Edman efficiency. Scheme A is less robust vis-à-vis all simulated errors because the boost in the positional information stemming from abundant aspartates and glutamates is rapidly undermined by experimental errors, as there are higher chances for fluorescently indistinguishable peptides to confound the fluorosequence.

Notably, the photobleaching half-life has the greatest effect of any of the tested parameters on protein identification, causing up to 50% loss in proteome coverage (under scheme A). The steepest decrease in the number of proteins identified occurs when photobleaching is considered (comparing half-lives of infinity to 210 cycles) and tapers with lower half-life. Although photobleaching shows the strongest impact of any of the errors considered, it is worth noting that the half-lives of commercially-available fluorophores are sufficiently longer than those simulated. Hence, we anticipate that this error source will not derail a real implementation of fluorosequencing. For example, the widely used Atto680 dye has a mean photobleaching lifetime of about 30 minutes [23], corresponding to 1800 Edman cycles, assuming 1 second exposure per Edman cycle. Oxygen-scavenging systems are also widely used in single molecule imaging experiments to reduce the effects of photobleaching [19]. Thus, the most critical error rates appear to fall within acceptable ranges, supporting the feasibility of fluorosequencing.

Determining the Positional Information of Amino Acids as a General Principle for Next-Generation Protein Sequencing.

Fluorosequencing relies on the positional information of specific subsets of amino acids within peptide sequences. The scheme can be generalized as a framework fulfilling two conditions—(a) an observable event 'e', which occurs by detection of a known single amino acid or a class of amino acids, and (b) a sequential analytical process, which increments or decrements the sequence in a known direction and by constrained number of amino acids. Using detection of fluorescently labeled amino acids as the event, other modalities might be considered, such as detecting voltage changes or reactivity of monitored amino acids. Besides Edman degradation, other valid sequential processes could include sequential treatment with known sequence specific peptidases or directional protein translocation through a nanopore channel [9] at a defined translocation rate. The monitoring of sequenced detection events gives information-rich patterns (such as "x-e-e-x . . . " (SEQ ID NO: 8) where 'x' is one or more non-identifiable amino acids) capable of being mapped back to a reference proteome. The nature of this information lies between the extremes of information content, wherein either every amino acid corresponds to a distinct event or there is no observable event associated with the process (as, for example, a peptide translocating through a channel but not generating a detectable signal). In principle, many event-process strategies might be suitable for peptide sequencing and interpretation using a scheme similar to the one described herein.

Conclusions.

A strategy for the parallel identification of proteins in a complex mixture based on the positional information of amino acids in peptides is contemplated. The integration of a 60-year-old, highly optimized Edman chemistry [11] with recent advances in single-molecule microscopy [28] and stable synthetic fluorophore chemistry [29] makes this strategy particularly amenable for experimental execution in the near future. Modeling of experimental errors suggests this strategy can be reasonably expected to identify a high percentage of the proteome, comparable to mass spectrometry, and potentially brings the advantages of single molecule sensitivity and—if next-generation single molecule sequencing is a reasonable proxy-throughputs of hundreds of millions or billions of molecules sequenced per run. Monte-Carlo simulations provide a framework to accommodate the inevitable experimental errors and probabilistically identify proteins from the observed fluorescent patterns. Successful experimental execution of the proposed strategy will not only lead to progress in proteomics, but enable progress in engineering and chemistry to enable the technology.

Exemplary Methods Used for this Example.

Datasets.

The UniProtKB/Swiss-Prot complete *H. sapiens* proteome (manually reviewed) was downloaded on May 29th 2013 and used for all simulations, comprising 20,252 protein sequences and ignoring alternatively spliced isoforms.

Monte Carlo Simulations.

Simulations were programmed in Python using Mersenne Twister [28] as the source of randomness, and implemented in parallel using the Texas Advanced Computing Center. For the purposes of simulation, the proteome can be considered dictionary pairs of protein identifiers and amino acid sequences. The simulations began with 10,000 copies of each protein sequence. The first two steps in the simulation split each amino acid sequence string at residue(s) corresponding to the protease specificity (e.g. E for the GluC protease) and then discard sub-strings that lack the anchor residue (e.g. substrings not containing C). Alternating Edman degradation steps and TIRF observations on the resulting peptides provide temporal ordering for luminosity drops, resulting in an observed fluorosequence for each peptide. In the simulation, fluorosequences were initialized from amino acid substrings' correct fluorophore positions, and experimental errors were then introduced sequentially, modifying the fluorosequences in accordance with each type of error's appropriate probability distribution.

Three experimental sources of error sources were modeled in the Monte Carlo simulation as follows:

1. Inefficient dye labeling—The probability of an amino acid not being labeled with its intended label or being labeled with a nonfunctional dye (i.e. a dye that attaches but is incapable of fluorescence) is modeled as a Bernoulli variable. For each label prepared for the experimental procedure, there is a probability u that the fluor will never be observed.

2. Edman degradation is represented as an attempt to remove one amino acid residue per cycle. These attempts are modeled as a Bernoulli process, since every experimental cycle is independent of the preceding cycle. The probability of the N-terminus amino acid being successfully cleaved off is assigned a parameter p and the corresponding failure follows as q=1−p. Failure of Edman chemistry delays the removal of a downstream labeled amino acid by one experimental cycle, and thus dilates the inter-label intervals in the fluorosequence. Using this model, the probability that an inter-label interval d requires d+e experimental cycles before the subsequent label is removed is $(d-1+e/d-1)p^d q^e$. A random number is drawn from this distribution to indicate the dilation for each interval. Edman chemistry is contemplated to stop at the first cysteine from the N-terminus.

3. Photobleaching is the irreversible photo-induced destruction of a fluorophore. The photo-bleaching process can be best described as a stochastic phenomenon and modeled by an exponential decay function [30]. Every fluorophore has a defined half-life based on solvent conditions and laser operating conditions [31]. The periodic laser excitation has an additive effect on the fluorophore's half-life: exciting a fluorophore once for thirty seconds and, after an arbitrary delay, again for a further thirty seconds will photobleach the fluorophore with the same probability as a continuous excitation for one minute. A constant period of laser exposure per experimental cycle was used. To model whether labeled amino acids have been cleaved, the probability of a fluorophore still on the peptide surviving k experimental cycles can be modeled as an exponential decay $e^{-bk}$, where b is an experimentally-determined characteristic constant of the fluor being used, k is the number of experimental cycles performed, and e is Euler's constant. Labels were shifted to earlier experimental cycles based on random numbers drawn from this exponential decay.

For a given simulation, all simulated fluorosequences were collated into a prefix trie whose keys were the sequences of luminosity drops and associated values represented the counts of source proteins yielding those fluorosequences. One trie was generated for each given choice of error rates, protease and labels, based upon simulating 30 Edman cycles of fluorosequencing 10,000 copies of each protein in the human proteome. For each fluorosequence in the resulting trie, its source proteins were counted, allowing proteome coverage to be calculated.

The simulation can be summarized as pseudo-code:
INITIALIZE result trie as an empty prefix trie.
FOR protein IN proteome:
peptides←Proteolyse protein at the carboxyl side of a given amino acid corresponding to the protease used.
  FOR peptide IN peptides:
  Discard peptide if it does not contain at least one occurrence of the amino acid for anchoring to the surface.
  FOR peptide IN peptides REPEAT 10000 TIMES:
  Attach labels to amino acids with a given probability. Labeling probability is uniform and mutually independent for all amino acids.
  Adjust positions of labeled amino acids to reflect possible Edman failures.
    All Edman reactions for each individual peptide have a uniform probability of success specified by a given parameter, and are mutually independent. The Edman reaction is cannot proceed past the first amino acid anchored to the surface.
  Adjust positions of labeled amino acids to reflect potential photobleaching. Fluors' survival functions are mutually independent exponential decays characterized by a given photobleaching constant.
  Collate final sequence of tuples (fluorosequence) for this peptide into the result trie.
TRAVERSE THE TRIE. For each node, find the most frequent source protein yielding that fluorosequence. For the purposes of data visualization, if the most frequent protein yielded the fluorosequence at least ten times, and all other source proteins for that fluorosequence combined are responsible for less than 10% of all observations, then that fluorosequence is considered to be uniquely attributed to the protein.
RETURN the set of proteins that have at least one uniquely attributed fluorosequence. More detailed pseudo-code is also provided in the supporting S1 Text.

A parameter sweep was performed for the three labeling schemes as in FIG. 60 at a simulation depth of $10^4$ copies per protein, sweeping 216 experimental parameter combinations (testing six values for each of the three error parameters described) spanning fluorophore failure rates of 0%, to 25%, photobleaching half-lives from 90 minutes to infinity (i.e., no photobleaching), and Edman degradation efficiencies from 90% to 100%.

Text S1: Detailed pseudo-code describing the algorithm employed for the simulation.

Definitions and Input of Experimental Parameters proteome is the set of all protein species. Each protein is a sequence of amino acids represented as a sequence of tuples ($aa_i$, $s_i$) where $aa_i$ is the amino acid at position $s_i$. The tuples are sequenced and positions are indexed from the N- to the C-terminuses of the protein, with the first amino acid having position 1.

Amino acid cleave indicating site at which protease is active. Proteolysis takes place at the carboxyl side of the amino acid. Example: For cyanogen bromide, cleave=Met.

Mapping labels from set of amino acids to dyes used to label them
Example: labels={Lys: red, Tyr: green} indicates lysines are labeled using a red dye and tyrosines are labeled with a green dye
Amino acid attachment indicating which amino acid is used to functionalize peptides to the slide Example: attachment=Cys indicates peptides are functionalized via cystines
Probability $u \in [0, 1]$ of unsuccessfully labeling an amino acid. This occurs when an amino acid intended to be labeled per labels fails to covalently bond to its dye, or the dye that bonds is defective before the experiment begins. u is constant across all labels.
Probability $p \in [0, 1]$ of the Edman cycle successfully cleaving off the N-terminal amino acid from a peptide.
Photobleaching constant $b \in [0, \infty)$ indicating the photobleaching half-life of all fluors.
Number of experimental cycles the sample will be subjected to.
Function random( ) is provided by the system and yields random floating point numbers in [0, 1].
Function binomial(x, y) is provided by the system and returns the binomial coefficient e is Euler's constant.
Function sort( ) sorts tuples ($aa_i$, $s_i$) in by $s_i$ in ascending order
Each protein is sampled a simulation_depth number of times.

---

Algorithm section 1: Definition of prefix trie used to collate simulation results and associated utility functions.
Definitions:
  A node in the trie stores three items:
  1. tuple ($aa_i$, $s_i$)

-continued 2. references to all children nodes by their tuples ($aa_i$, $s_i$); for simplicity, we omit the creation of child nodes in this pseudocode and assume they all exist
3. counters for all proteins, i.e. a mapping from the proteome to the set of integers, notated by counter[protein]; all counters are initialized to 0
The root node stores only references to all children nodes
Each sequence of tuples ($aa_i$, $s_i$) uniquely maps to a node in the trie by walking the trie starting from the root node, with each successive tuple($aa_i$, $s_i$) indicating the child node to visit next. The sequence is mapped to the last node the walk arrives at. See function increment_counter below for an illustration.
Functions:
    FUNCTION increment_counter(sequence of tuples ($aa_i$, $s_i$), protein):
current_node ← root node
        FOR tuple ($aa_i$, $s_i$) IN sequence of tuples:
current_node ← child ($aa_i$, $s_i$) of current node
            #current_node is now the node that the sequence of tuples maps uniquely
            onto counter[protein] ← counter[protein] + 1
FUNCTION recursive_traverse(node):
list_of_nodes ← (node) #list of all child nodes including self
FOR node IN children nodes:
list_of_nodes ← list_of_nodes + recursive_traverse(node)
RETURN list_of_nodes
Algorithm section 2: Experiment initialization.
peptides[protein] = NULL
    #this will store all peptides proteolysed from protein that are hybridized to the
    #surface
FOR protein IN proteome:
peptides ← proteolyze protein using cleave
    #peptides is the set of all subsequences of the protein
    #partitioned after tuples with $aa_i$=cleave; for example,
    #((K, 1) (M, 2)(C, 3)(M,4)) would yield the set
    #{ ((K, 1), (M,2)), ((C, 3), (M, 4)) }
FOR peptide IN peptides:
IF attachment NOT IN peptide:
        discard peptide #peptides not having attachment cannot attach to the
        surface and are #washed away
FOR peptide IN peptides:
FOR tuple ($aa_i$, $s_i$) IN peptide:
IF $aa_i$ NOT IN labels:
discard tuple from peptide #ignore unlabeled amino acids
peptides[protein] ← peptides
Algorithm section 3: Monte Carlo simulation.
    FUNCTION simulate(peptide, protein):
    #the sequence of tuples in peptide is copied for every call of this function and is
    manipulated below
sequence ← copy(peptide)
simulate fluor label failure
FOR tuple ($aa_i$, $s_i$) IN sequence:
IF random( ) < u:
discard ($aa_i$, $s_i$) from the sequence
end of fluor label failure section
simulate Edman failure
    cumulative_delay = 0 #temporary variable keeping track of total Edman failures
FOR tuple ($aa_i$, $s_i$) IN sequence:
d ← $s_i$ IF this is the first tuple in the sequence ELSE $s_i - s_{i-1}$
        #distance between consecutive labels
        delay_sample = random( ) #generate random point for delay probability
        distribution delay = 0 #keep track of delays for interval between ($aa_i$, $s_i$) and ($aa_i - 1$, $s_i - 1$)
accumulator = 0 #temporary variable for accumulating delay probabilities
map delay onto [0, 1] via its probability distribution
WHILE:
binomial_pdf = 0 #binomial probability density function
IF random_delay = 0:
binomial_pdf ← p d
ELSE:
binomial_pdf ← binomial(d - 1, d - 1 + delay)$*p^d *(1 - p)^{delay}$ -
binomial(d - 1, d - 2 + delay)$*p^d *(1 - p)^{delay - 1}$
accumulator ← accumulator + binomial_pdf
test if this was the delay chosen by delay_sample
IF accumulator ≥ delay_sample:
BREAK
ELSE:
delay ← delay + 1
cumulative_delay ← cumulative_delay + delay
($aa_i$, $s_i$) ← (aa i, $s_i$ + cumulative_delay)
        #delay $aa_i$ in fluoro sequence due to all prior Edman failures

```
#simulation assumes Edman cannot proceed past the first amino acid hybridized to the surface
IF aa_i = attachment:
        #although Edman cannot reach them, the delay still affects fluors after attachment
            due to
#photobleaching
FOR (aa_j, s_j) IN sequence:
IF j > i:
(aa_j, s_j) ← (aa_j, s_j + cumulative_delay)
BREAK
###end of Edman failure section
    ###simulate photobleaching
    #first loop photobleaches fluors before the first attachment, because
    # Edman cannot proceed past it
    #second loop (further below) photobleaches fluors after first attachment
    FOR (aa_i, s_i) IN sequence:
#this IF statement stops the first loop at the first attachment
IF aa_i = attachment:
BREAK
photobleach_sample = random( )
        #random point for photobleaching probability distribution
        accumulator = 0 #temporary variable for accumulating photobleaching
        probabilities
          exposures = cycles + 1 IF cycles < s_i ELSE s_i #number of exposures for the fluor
FOR k FROM 0 TO exposures − 1:
accumulator ← accumulator + e −bk
IF accumulator * (1 − e−b) ≥ photobleach_sample:
(aa_i, s_i) ← (aa_i, k + 1)
BREAK
    #second loop photobleaches fluors after first attachment
    FOR (aa_i, s_i) IN sequence:
#this IF statement ignores all fluors before the first attachment
IF aa_i = attachment:
CONTINUE
photobleach_sample = random( )
        #random point for photobleaching probability distribution
        accumulator = 0 #temporary variable for accumulating photobleaching
        probabilities exposures = cycles #number of exposures for these fluor is always all
        cycles
FOR k FROM 0 TO exposures − 1:
accumulator ← accumulator + e^{−bk}
IF accumulator * (1 − e^{−b}) ≥ photobleach_sample:
(aa_i, s_i) ← (aa_i ,k + 1)
BREAK
###end of photobleaching section
#sort sequence by final observations and collate result into trie
sequence ← sort(sequence)
increment_counter(sequence, protein)
#main simulation loop
FOR protein IN proteome:
FOR k FROM 0 to simulation_depth:
FOR peptide IN peptides[protein]:
simulate(peptide, protein)
Algorithm section 4: Count identified proteins.
    identified_proteins = { } #set of all proteins considered classified
    FOR node in recursive_traverse(root node): total_source_proteins = 0 #calculate total
number of times the fluoro sequence mapping to this node #has been observed
    FOR protein IN counters:
total_source_proteins ← total_source_proteins + counters[protein]
    FOR protein IN counters:
        IF counters[protein] > 10 AND counters[protein]/total_source_proteins> 0.90:
identified_proteins ← identified_proteins + protein
    RETURN identified_proteins
```

Attributing Fluorosequences to Peptides and Proteins.

For more efficient use of computer memory, trie structures were calculated separately for multiple subsets of the proteome and the resulting tries merged before analysis by traversing all fluorosequences in each trie and adding each fluorosequence along with its protein counts into a master trie for that simulation. Then, the counts of each fluorosequence and affiliated peptides were analyzed to calculate a frequency distribution of the number of times peptides from a given source protein generated a given fluorosequence. For the purposes of summarizing the data, two criteria were applied to this distribution to attribute a fluorosequence uniquely to the protein: (a) its primary source protein yielded the fluorosequence at least 10 times out of a $10^4$ simulation depth, and (b) the summation of frequency from all other source proteins were responsible for less than 10% of that fluorosequence's occurrences. While the former criterion addresses sample error, the latter addresses confounding from other proteins.

The Monte Carlo simulation Python script and C module can be accessed from github: https://github.com/marcotte-lab/FluorosequencingSimulation.git

REFERENCES

1. Eid, et al., (2009) Real-time DNA sequencing from single polymerase molecules. Science 323: 133-138.

2. Braslavsky, et al., (2003) Sequence information can be obtained from single DNA molecules. Proc Natl Acad Sci USA 100: 3960-3964.
3. Sawyers, (2008) The cancer biomarker problem. Nature 452: 548-552.
4. Romond, et al., (2005) Trastuzumab plus adjuvant chemotherapy for operable HER2-positive breast cancer. N Engl J Med 353: 1673-1684.
5. Haab, (2006) Applications of antibody array platforms. Curr Opin Biotechnol 17: 415-421.
6. Ingolia, et al., (2009) Genome-wide analysis in vivo of translation with nucleotide resolution using ribosome profiling. Science 324: 218-223.
7. Thakur, et al., (2011) Deep and highly sensitive proteome coverage by LC-MS/MS without prefractionation. Mol Cell Proteomics 10: M110.003699.
8. Hanay, et al., (2012) Single-protein nanomechanical mass spectrometry in real time. Nat Nanotechnol 7: 602-608.
9. Nivala, et al., (2013) Unfoldase-mediated protein translocation through an α-hemolysin nanopore. Nat Biotechnol 31: 247-250.
10. Zhao, et al., (2014) Single-molecule spectroscopy of amino acids and peptides by recognition tunnelling. Nat Nanotechnol 9: 466-473.
11. Edman, (1949) A method for the determination of amino acid sequence in peptides. Arch Biochem 22: 475.
12. Han, et al., (1985) Current developments in stepwise edman degradation of peptides and proteins. Int J Biochem 17: 429-445.
13. MacBeath, et al., (1999) Printing Small Molecules as Microarrays and Detecting Protein-Ligand Interactions en Masse. J Am Chem Soc 121: 7967-7968.
14. Axelrod, (1981) Cell-substrate contacts illuminated by total internal reflection fluorescence. J Cell Biol 89: 141-145.
15. Baslé, et al., (2010) Protein chemical modification on endogenous amino acids. Chem Biol 17: 213-227.
16. Pieroni, et al., (1975) Reaction of diazonium salt with tyrosine residues in polypeptides. Die Makromol Chemie 176: 3201-3209.
17. Cannon, et al., (2013) A dual-mode single-molecule fluorescence assay for the detection of expanded CGG repeats in Fragile X syndrome. Mol Biotechnol 53: 19-28.
18. Ulbrich and Isacoff, (2007) Subunit counting in membrane-bound proteins. Nat Methods 4: 319-321.
19. Aitken, et al., (2008) An oxygen scavenging system for improvement of dye stability in single-molecule fluorescence experiments. Biophys J 94: 1826-1835.
20. Altman, et al., (2012) Enhanced photostability of cyanine fluorophores across the visible spectrum. Nat Methods 9: 428-429.
21. Cang, et al., (2013) Giant Suppression of Photobleaching for Single Molecule Detection via the Purcell Effect. Nano Lett 13: 5949-5953.
22. Zheng, et al., (2014) The contribution of reactive oxygen species to the photobleaching of organic fluorophores. Photochem Photobiol 90: 448-454.
23. Wang, et al., (2014) The covalent trimethoprim chemical tag facilitates single molecule imaging with organic fluorophores. Biophys J 106: 272-278.
24. Smith, (2001) Peptide Sequencing by Edman Degradation. In: Encyclopedia of Life Sciences. MacMillan Publishers Ltd, Nature Publishing Group, www.els.net.
25. Jin, et al., (1989) Study on New Edman-type Reagents. In: Wittmann-Liebold B, editor. Methods in Protein Sequence Analysis. Berlin, Heidelberg: Springer Berlin Heidelberg. pp. 34-41.
26. Fredkin, (1960) Trie memory. Commun ACM 3: 490-499.
27. Nagaraj, et al., (2011) Deep proteome and transcriptome mapping of a human cancer cell line. Mol Syst Biol 7: 548.
28. Joo, et al., (2008) Advances in single-molecule fluorescence methods for molecular biology. Annu Rev Biochem 77: 51-76.
29. Zheng, et al., (2014) Ultra-stable organic fluorophores for single-molecule research. Chem Soc Rev 43: 1044-1056.
30. Song, et al., (1995) Photobleaching kinetics of fluorescein in quantitative fluorescence microscopy. Biophys J 68: 2588-2600.
31. Hoebe, et al., (2007) Controlled light-exposure microscopy reduces photobleaching and phototoxicity in fluorescence live-cell imaging. Nat Biotechnol 25: 249-253.
32. Garcia-Parajo, et al., (2001) The nature of fluorescence emission in the red fluorescent protein DsRed, revealed by single-molecule detection. Proc Natl Acad Sci USA 98: 14392-14397.
33. Thoma, et al., (2009) The ABRF Edman Sequencing Research Group 2008 Study: investigation into homopolymeric amino acid N-terminal sequence tags and their effects on automated Edman degradation. J Biomol Tech 20: 216-225.

Example X: Demonstrating Single Molecule Peptide Sequencing of Fluorescently Labeled Peptides at the Single-Molecule Level This example shows exemplary tracking single peptide molecules through Edman cycles and determining the position of the labeled amino acid. Specifically, two peptide populations differing in the position of their labeled amino-acid residue were discriminated in a mixture at single-molecule sensitivity using a single-molecule Edman peptide sequencing procedure. FIG. 65 shows a summary of these experimental results.

Peptide A— labeled orange (lighter left bar and left peptide) in the diagram, with sequence (boc)-K*AGAAG (SEQ ID NO: 13), where* (Rhodamine=Tetramethylrhodamine); and Peptide B— labeled blue (daker right bar and right peptide) in the diagram, with sequence (boc)-GK*[Atto647N]AGAG (SEQ ID NO: 14).

Peptides A and B were labeled via their Lysines with dyes excitable at 561 nm (Rhodamine) and 647 nm (Atto647N) wavelengths, respectively. Both peptide populations were immobilized on a glass slide via their carboxyl terminuses, and the protecting boc groups were removed from their amino terminuses. Then, the peptides were observed via total internal reflection (TIRF) microscopy through several cycles of Edman degradation. Thousands of labeled peptides across multiple fields of view were individually tracked in parallel, and their fluorescence after every cycle recorded. As a control, the first two cycles did not include the critical Edman reagent phenyl isothiocyanate (PITC) that is needed to cleave an amino acid: i.e., these were "mock" reactions to confirm that there was no loss of fluorophores merely due to any of the other chemical solvents or photobleaching. The subsequent eight cycles included PITC, allowing removal of amino acids. The number of fluorescent peptides in the 561 nm channel decreased dramatically after the first full Edman cycle, in accordance with the position of the 561 nm label on the first amino acid of Peptide A. Likewise, the number of fluorescent peptides in the 647 nm channel decreased after the second Edman cycle, in accordance with the position of the 647 nm label on the second amino acid of Peptide B.

Peptide A: (boc)-K*[Tetramethylrhodamine]AGAAG (SEQ ID NO: 13) and Peptide B: (boc)-GK*[Atto647N] AGAG (SEQ ID NO: 14) were synthesized by Thermo Fisher Scientific (IL, USA) with a purity of >95% and validated by mass spectrometry. The fluorophores was covalently attached to the ε-amine of the lysine residue Aminosilane slide coating. Forty mm #1 thick glass coverslips (Bioptechs Inc., PA, USA), were placed vertically in a custom made Teflon rack, and cleaned by washes and sonication with 5% Alconox (detergent), acetone, 90% Ethanol and finally 1 M Potassium hydroxide (KOH). Between each of the different solvent washes, the slides were thoroughly washed with de-ionized water. The aminosilane coating step was carried out by incubating the slides for 20 minutes in 1% Aminopropyltriethoxy silane (Cat #SIA0610, Gelest Inc., PA, USA) dissolved in the acidified 5% v/v of acetic acid/methanol solvent. The slides were sonicated intermittently for 1 minute to dislodge any adsorbed silane molecules. After incubation, the slides were rinsed thoroughly with methanol and water. It was then dried with nitrogen and stored under vacuum until use. The slides were imaged in water and methanol prior to peptide or fluorophore immobilization to check for presence of fluorescing impurities.

Solvents.

Highest purity and mostly spectrophotometry grade solvents of Methanol (Cat #494437, Sigma), Ethylacetate (Cat #270989, Sigma), Acetonitrile (Cat #34967, Sigma), trifluoroacetic acid (Cat #T6508, Sigma), Pyridine (Cat #270970, Sigma), Dimethylformamide (DMF, Cat #270547, Sigma), phenylisothiocyanate (PITC, Cat #P1034-10x1 ml, Sigma) and water (Cat #5140, Thermo Scientific) was used for all the experiments. Coupling solvent, comprising of 9:1 v/v of pyridine: PITC, was freshly prepared before use. The coupling solvent and the free-basing solvent consisting of 10:3:2:1 v/v of acetonitrile:pyridine:triethylamine:water was flushed with nitrogen for 5 minutes and maintained under nitrogen atmosphere by piercing the septum with a nitrogen filled balloon. The cleavage solvent used was 90% TFA in water. The glass vials fitted with a sealable Teflon-silicone septum (Cat #27022, Sigma) used was rinsed with acetone and the solvent with which it is stored. The FEP tubing from the valves was pierced through the septum and the entire system was maintained under anoxic condition.

Fluidics System.

The aminosilane coated glass coverslip housed in a microfluidic chamber was adapted from the FCS2 perfusion chamber (Bioptechs Inc., PA, USA). The vendor supplied upper and the lower gaskets was replaced with 0.03" perfluoroelastomer Kalrez®-0040 material (DuPont Inc., local vendor—Austin Seals company, TX, USA) and a diamond shape was cut in the lower gasket (die Number—452458, cut by Bioptechs Inc.). The shape ensured complete fluid exchanges when compared with a rectangular cut. The Kalrez material had ideal compressibility with a shore durometer A of 70 and had chemical inertness to trifluoroacetic acid.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed. Various modifications and variations of the described compositions and methods of the invention will be apparent to those skilled in the art without departing from the scope and spirit of the invention. Although the invention has been described in connection with specific preferred embodiments, it should be understood that the invention should not be unduly limited to such specific embodiments. Indeed, various modifications of the described modes for carrying out the invention which are obvious to those skilled in biochemistry, protein chemistry, physics, cell biology, or related fields are intended to be within the scope of the present invention and the following Claims.

What is claimed:

1. A method for analyzing a polypeptide, comprising:
    (a) providing said polypeptide immobilized to a support, wherein said polypeptide comprises at least one labeled internal amino acid;
    (b) detecting at least one signal or signal change from said polypeptide immobilized to said support to identify at least a portion of a sequence of said polypeptide; and
    (c) subjecting said polypeptide to conditions sufficient to remove at least one amino acid from said polypeptide.

2. The method of claim 1, wherein said at least one amino acid is removed from an N-terminus of said polypeptide.

3. The method of claim 1, wherein, subsequent to (c), said at least one labeled internal amino acid becomes a labeled terminal amino acid.

4. The method of claim 1, wherein said at least one labeled internal amino acid is from a plurality of labeled amino acids, and wherein said at least one signal or signal change comprises a collective signal from said plurality of labeled amino acids.

5. The method of claim 4, wherein said plurality of labeled amino acids comprise amino acids with different labels.

6. The method of claim 5, wherein said different labels generate signals with different signal patterns.

7. The method of claim 1, wherein said at least one labeled internal amino acid comprises one or more members selected from the group consisting of lysine, glutamate, and aspartate.

8. The method of claim 1, wherein said at least one labeled internal amino acid comprises an amino acid having a label covalently attached thereto, which label generates said at least one signal or signal change.

9. The method of claim 1, wherein said at least one labeled internal amino acid comprises an amino acid having a dye coupled thereto, which dye generates said at least one signal or signal change.

10. The method of claim 1, wherein said at least one signal or signal change is an optical signal.

11. The method of claim 1, wherein said at least one signal or signal change comprises a plurality of signals of different intensities.

12. The method of claim 1, wherein said at least one signal or signal change comprises a plurality of signals of different frequencies or frequency ranges.

13. The method of claim 1, wherein said at least one amino acid is removed from said polypeptide by a degradation reaction.

14. The method of claim 13, wherein said degradation reaction is Edman degradation.

15. The method of claim 1, wherein said polypeptide is a protein.

16. The method of claim 1, wherein said polypeptide is part of a protein.

17. The method of claim 1, wherein said at least one signal or signal change is detected with an optical detector having single-molecule sensitivity.

18. The method of claim 1, further comprising processing said at least said portion of said sequence of said polypeptide against a reference sequence to identify said polypeptide or a protein from which said polypeptide is derived.

19. The method of claim 1, further comprising, subsequent to (c), (i) identifying said at least said portion of said sequence of said polypeptide to identify said polypeptide, and (ii) using said polypeptide identified in (i) to quantify said polypeptide or a protein from which said polypeptide was derived.

20. The method of claim 1, wherein in (a), less than all amino acids of said polypeptide are labeled.

21. The method of claim 1, further comprising (i) repeating (b) and (c) to detect at least one additional signal or signal change from said polypeptide immobilized to said support and (ii) using (1) said at least one signal or signal change and (2) said at least one additional signal or signal change to identify said at least said portion of said sequence of said polypeptide.

* * * * *

SEQUENCE LISTING

```
<160> NUMBER OF SEQ ID NOS: 25

<210> SEQ ID NO 1
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 1

Xaa Xaa Xaa Lys Xaa Xaa Xaa Xaa Lys Xaa Lys
1               5                   10
```

```
<210> SEQ ID NO 2
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 2

Trp Lys Lys Xaa Tyr Xaa
1               5

<210> SEQ ID NO 3
<211> LENGTH: 6
<212> TYPE: PRT
<213> ORGANISM: Artificial sequence
<220> FEATURE:
<223> OTHER INFORMATION: Synthetic peptide

<400> SEQUENCE: 3

Lys Asp Tyr Trp Glu Cys
1               5

<210> SEQ ID NO 4
<211> LENGTH: 5
<212> TYPE: PRT
<213> ORGANISM: Artificial sequence
<220> FEATURE:
<223> OTHER INFORMATION: Synthetic peptide

<400> SEQUENCE: 4

Lys Asp Tyr Trp Glu
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic peptide

<400> SEQUENCE: 5

Tyr Lys Thr Cys Tyr Thr Asp
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic peptide

<400> SEQUENCE: 6

Lys Cys Gly Gly Tyr Cys Asp
1               5

<210> SEQ ID NO 7
<211> LENGTH: 7
<212> TYPE: PRT
<213> ORGANISM: Artificial sequence
<220> FEATURE:
```

```
<223> OTHER INFORMATION: Synthetic peptide

<400> SEQUENCE: 7

Gly Tyr Cys Lys Cys Thr Asp
1               5

<210> SEQ ID NO 8
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 8

Xaa Glu Glu Xaa
1

<210> SEQ ID NO 9
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: fluorescently-labeled lysine

<400> SEQUENCE: 9

Gly Lys Glu Gly Cys
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: fluorescently-labeled lysine
<220> FEATURE:
<221> NAME/KEY: MISC_FEATURE
<222> LOCATION: (4)..(4)
<223> OTHER INFORMATION: fluorescently-labeled lysine

<400> SEQUENCE: 10

Gly Lys Gly Lys Glu Cys
1               5

<210> SEQ ID NO 11
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
```

```
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 11

Xaa Xaa Xaa Xaa Glu Xaa Xaa Lys Xaa Lys
 1               5                   10

<210> SEQ ID NO 12
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 12

Glu Glu Glu Glu Glu Xaa Xaa Lys Xaa Lys
 1               5                   10

<210> SEQ ID NO 13
<211> LENGTH: 6
<212> TYPE: PRT
<213> ORGANISM: Artificial sequence
<220> FEATURE:
<223> OTHER INFORMATION: Synthetic peptide

<400> SEQUENCE: 13

Lys Ala Gly Ala Ala Gly
 1               5

<210> SEQ ID NO 14
<211> LENGTH: 6
<212> TYPE: PRT
<213> ORGANISM: Artificial sequence
<220> FEATURE:
<223> OTHER INFORMATION: Synthetic peptide

<400> SEQUENCE: 14

Gly Lys Ala Gly Ala Gly
 1               5

<210> SEQ ID NO 15
<211> LENGTH: 4
<212> TYPE: PRT
<213> ORGANISM: Artificial sequence
<220> FEATURE:
<223> OTHER INFORMATION: Synthetic peptide

<400> SEQUENCE: 15

Lys Ala Lys Ala
 1

<210> SEQ ID NO 16
<211> LENGTH: 5
<212> TYPE: PRT
<213> ORGANISM: Artificial sequence
<220> FEATURE:
<223> OTHER INFORMATION: Synthetic peptide
```

```
<220> FEATURE:
<221> NAME/KEY: misc_feature
<222> LOCATION: (4)..(4)
<223> OTHER INFORMATION: Xaa can be any naturally occurring amino acid

<400> SEQUENCE: 16

Trp Lys Lys Xaa Tyr
1               5

<210> SEQ ID NO 17
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 17

Xaa Xaa Xaa Lys Xaa Xaa Xaa Lys Lys Xaa Xaa Xaa Thr Xaa Cys Glu
1               5                   10                  15

<210> SEQ ID NO 18
<211> LENGTH: 7
<212> TYPE: PRT
<213> ORGANISM: Artificial sequence
<220> FEATURE:
<223> OTHER INFORMATION: Synthetic peptide

<400> SEQUENCE: 18

Lys Cys Thr Trp Gly Cys Asp
1               5

<210> SEQ ID NO 19
<211> LENGTH: 7
<212> TYPE: PRT
<213> ORGANISM: Artificial sequence
<220> FEATURE:
<223> OTHER INFORMATION: Synthetic peptide

<400> SEQUENCE: 19

Trp Gly Cys Thr Lys Trp Asp
1               5

<210> SEQ ID NO 20
<211> LENGTH: 5
<212> TYPE: PRT
<213> ORGANISM: Artificial sequence
<220> FEATURE:
<223> OTHER INFORMATION: Synthetic peptide

<400> SEQUENCE: 20

Gly Lys Glu Gly Lys
1               5
```

```
<210> SEQ ID NO 21
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(4)
<223> OTHER INFORMATION: Xaa can be any naturally occurring amino acid

<400> SEQUENCE: 21

Xaa Xaa Xaa Xaa Lys
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 22

Xaa Lys Xaa Xaa Lys
1               5

<210> SEQ ID NO 23
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 23

Xaa Lys Lys Xaa Xaa
1               5

<210> SEQ ID NO 24
<211> LENGTH: 4
<212> TYPE: PRT
<213> ORGANISM: Artificial sequence
<220> FEATURE:
<223> OTHER INFORMATION: Synthetic peptide

<400> SEQUENCE: 24

Lys Glu Gly Lys
1

<210> SEQ ID NO 25
<211> LENGTH: 5
<212> TYPE: PRT
<213> ORGANISM: Artificial sequence
<220> FEATURE:
<223> OTHER INFORMATION: Synthetic peptide
```

```
<400> SEQUENCE: 25

Lys Lys Glu Gly Lys
1               5
```